(12) United States Patent
Shelton, IV et al.

(10) Patent No.: US 12,137,906 B2
(45) Date of Patent: Nov. 12, 2024

(54) SURGICAL SYSTEMS COMPRISING A CONTROL CIRCUIT

(71) Applicant: Cilag GmbH International, Zug (CH)

(72) Inventors: Frederick E. Shelton, IV, Hillsboro, OH (US); Daniel J. Mumaw, Liberty Township, OH (US); Jason L. Harris, Lebanon, OH (US); Jerome R. Morgan, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/381,878

(22) Filed: Oct. 19, 2023

(65) Prior Publication Data

US 2024/0041455 A1 Feb. 8, 2024

Related U.S. Application Data

(63) Continuation of application No. 17/012,241, filed on Sep. 4, 2020, now Pat. No. 11,896,222, which is a
(Continued)

(51) Int. Cl.
*A61B 17/072* (2006.01)
*A61B 90/00* (2016.01)
(Continued)

(52) U.S. Cl.
CPC ........ *A61B 17/07207* (2013.01); *A61B 90/06* (2016.02); *A61B 2017/00017* (2013.01); *A61B 2017/0023* (2013.01); *A61B 2017/00398* (2013.01); *A61B 2017/00407* (2013.01); *A61B 2017/0046* (2013.01); *A61B 2017/00473* (2013.01); *A61B 2017/00477* (2013.01); *A61B 2017/00734* (2013.01); *A61B 2017/07257* (2013.01); *A61B 2017/07271* (2013.01); *A61B 2017/07278* (2013.01); *A61B 2017/07285* (2013.01); *A61B 2017/2927* (2013.01); *A61B 2017/2933* (2013.01);
(Continued)

(58) Field of Classification Search
CPC ........ A61B 17/07207; A61B 17/07271; A61B 17/07278; A61B 17/07285; A61B 17/00398
USPC ....................................... 227/180.1
See application file for complete search history.

(56) References Cited

U.S. PATENT DOCUMENTS 7,011,657 B2   3/2006   Truckai et al.
7,464,847 B2   12/2008  Viola et al.
(Continued)

*Primary Examiner* — Jacob A Smith

(57) ABSTRACT

A surgical system comprising an end effector, a clamp driver, a motor, and a control circuit is disclosed. The end effector comprises a first jaw and a second jaw moveable relative to the first jaw toward a closed configuration. The clamp driver is movable toward a closure end position. The motor is operably coupled to the clamp driver. The control circuit comprises a processor and a memory, and the control circuit is to: advance, by the motor, the clamp driver to the closure end position; determine a distance between the first jaw and the second jaw in the closed configuration, wherein the closure end position corresponds to the closed configuration; receive a signal indicative of at least one of a staple cartridge identity, type, or characteristic from a corresponding staple cartridge; and detect that the distance is acceptable for staple firing by the end effector based on the received signal.

20 Claims, 89 Drawing Sheets

Related U.S. Application Data continuation of application No. 15/843,704, filed on Dec. 15, 2017, now Pat. No. 10,779,826.

(51) Int. Cl.
  *A61B 17/00* (2006.01)
  *A61B 17/29* (2006.01)
  *H01M 10/42* (2006.01)
  *H01M 50/213* (2021.01)

(52) U.S. Cl.
  CPC . *A61B 2017/2948* (2013.01); *A61B 2090/034* (2016.02); *A61B 2090/061* (2016.02); *A61B 2090/064* (2016.02); *A61B 2090/067* (2016.02); *A61B 2090/0808* (2016.02); *A61B 2090/0811* (2016.02); *A61B 2090/0813* (2016.02); *A61B 2090/0814* (2016.02); *H01M 10/425* (2013.01); *H01M 50/213* (2021.01); *H01M 2220/30* (2013.01)

(56) References Cited

U.S. PATENT DOCUMENTS

| | | |
|---|---|---|
| 7,789,283 B2 | 9/2010 | Shah |
| 7,942,303 B2 | 5/2011 | Shah |
| 8,292,158 B2 | 10/2012 | Sapienza |
| 8,893,949 B2 | 11/2014 | Shelton, IV et al. |
| 9,060,770 B2 | 6/2015 | Shelton, IV et al. |
| 9,072,535 B2 | 7/2015 | Shelton, IV et al. |
| 9,113,880 B2 | 8/2015 | Zemlok et al. |
| 9,119,657 B2 | 9/2015 | Shelton, IV et al. |
| 9,149,325 B2 | 10/2015 | Worrell et al. |
| 9,332,984 B2 | 5/2016 | Weaner et al. |
| 9,572,577 B2 | 2/2017 | Lloyd et al. |
| 9,795,384 B2 | 10/2017 | Weaner et al. |
| 9,808,246 B2 | 11/2017 | Shelton, IV et al. |
| 9,918,717 B2 | 3/2018 | Czernik |
| 9,943,312 B2 | 4/2018 | Posada et al. |
| 10,238,386 B2 | 3/2019 | Overmyer et al. |
| 10,433,844 B2 | 10/2019 | Shelton, IV et al. |
| 10,456,132 B2 | 10/2019 | Gettinger et al. |
| 10,463,367 B2 | 11/2019 | Kostrzewski et al. |
| 10,639,035 B2 | 5/2020 | Shelton, IV et al. |
| 10,687,813 B2 | 6/2020 | Shelton, IV et al. |
| 10,743,874 B2 | 8/2020 | Shelton, IV et al. |
| 10,743,875 B2 | 8/2020 | Shelton, IV et al. |
| 10,779,825 B2 | 9/2020 | Shelton, IV et al. |
| 10,779,826 B2 | 9/2020 | Shelton, IV et al. |
| 10,828,033 B2 | 11/2020 | Shelton, IV et al. |
| 10,863,984 B2 | 12/2020 | Shelton, IV et al. |
| 10,869,666 B2 | 12/2020 | Shelton, IV et al. |
| 10,966,718 B2 | 4/2021 | Shelton, IV et al. |
| 11,006,955 B2 | 5/2021 | Shelton, IV et al. |
| 11,033,267 B2 | 6/2021 | Shelton, IV et al. |
| 11,071,543 B2 | 7/2021 | Shelton, IV et al. |
| 11,197,670 B2 | 12/2021 | Shelton, IV et al. |
| 11,896,222 B2 | 2/2024 | Shelton, IV et al. |
| 2007/0010838 A1 | 1/2007 | Shelton et al. |
| 2017/0281171 A1* | 10/2017 | Shelton, IV ......... A61B 17/115 |
| 2019/0183502 A1 | 6/2019 | Shelton, IV et al. |

* cited by examiner

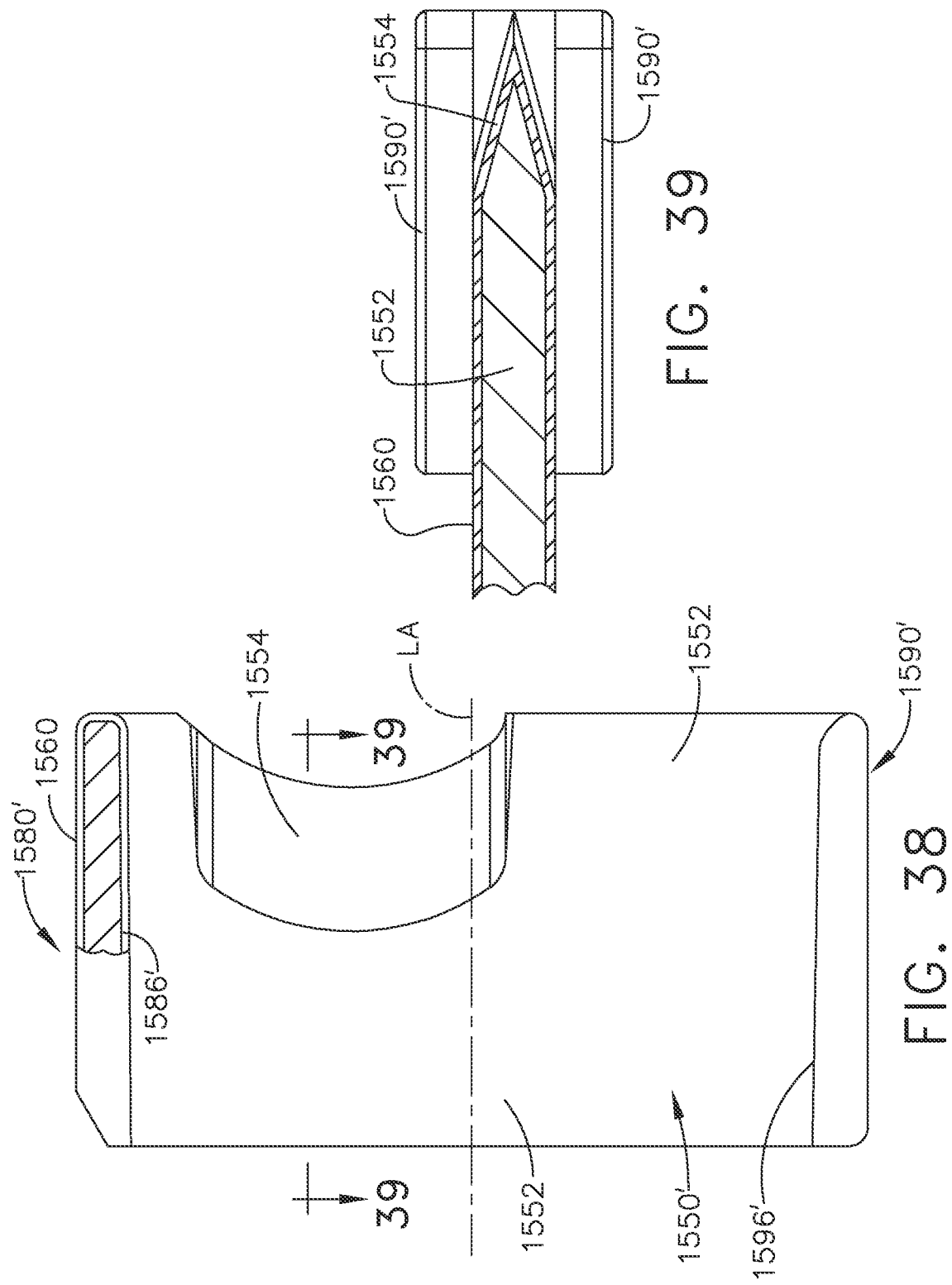

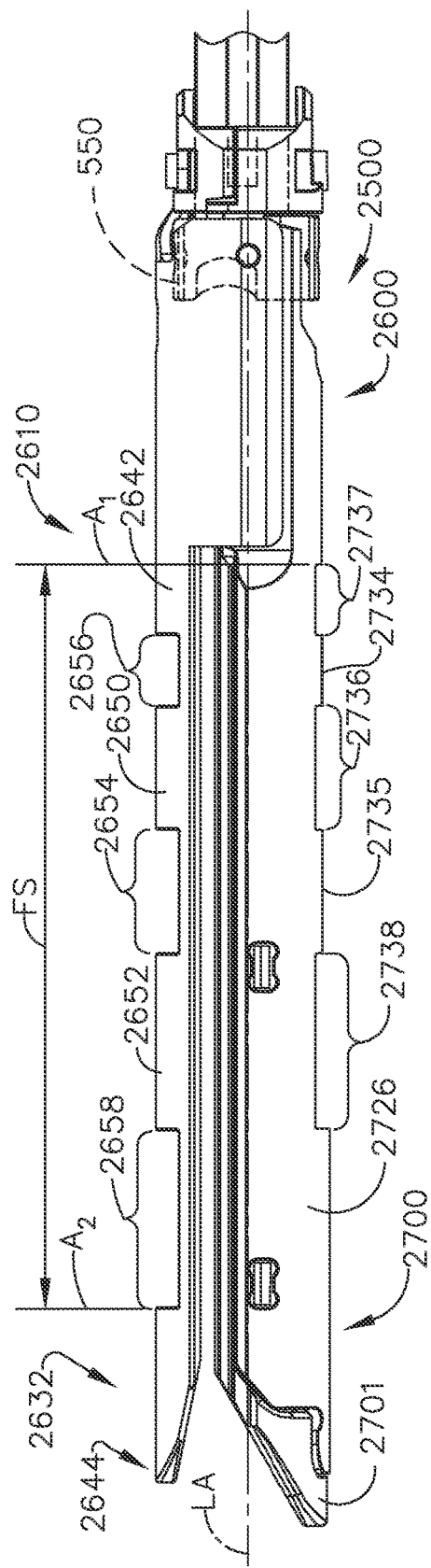
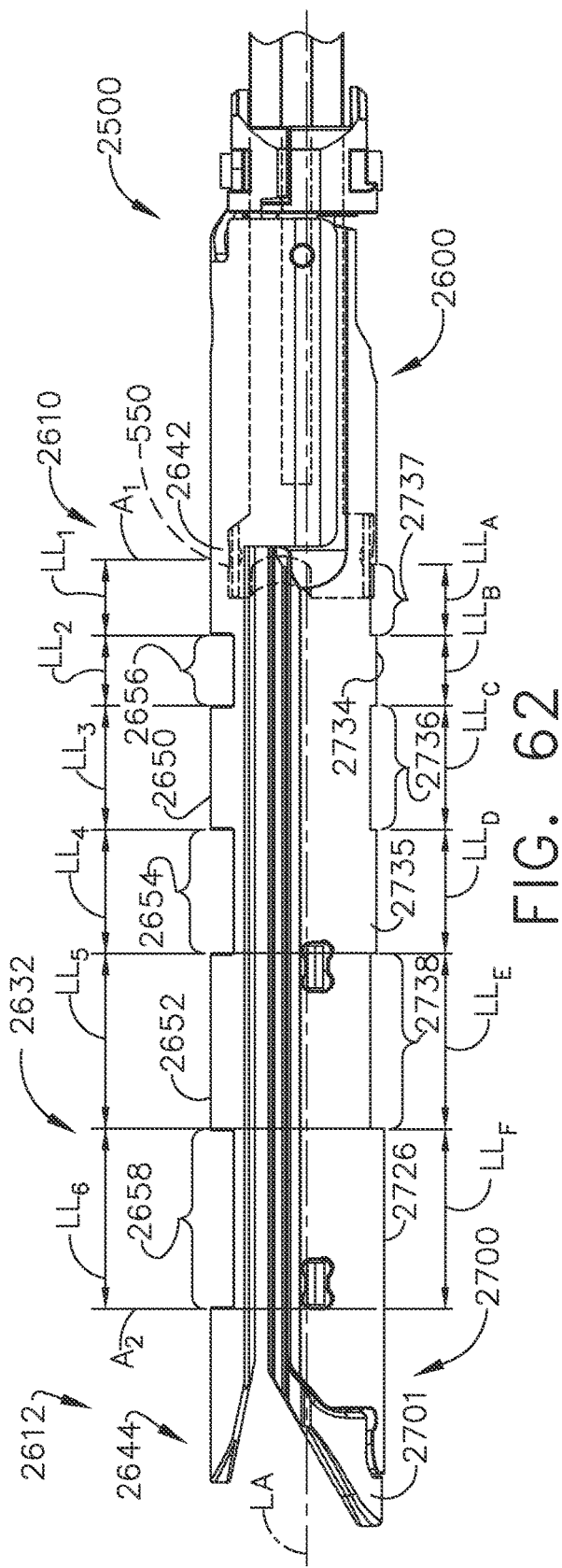

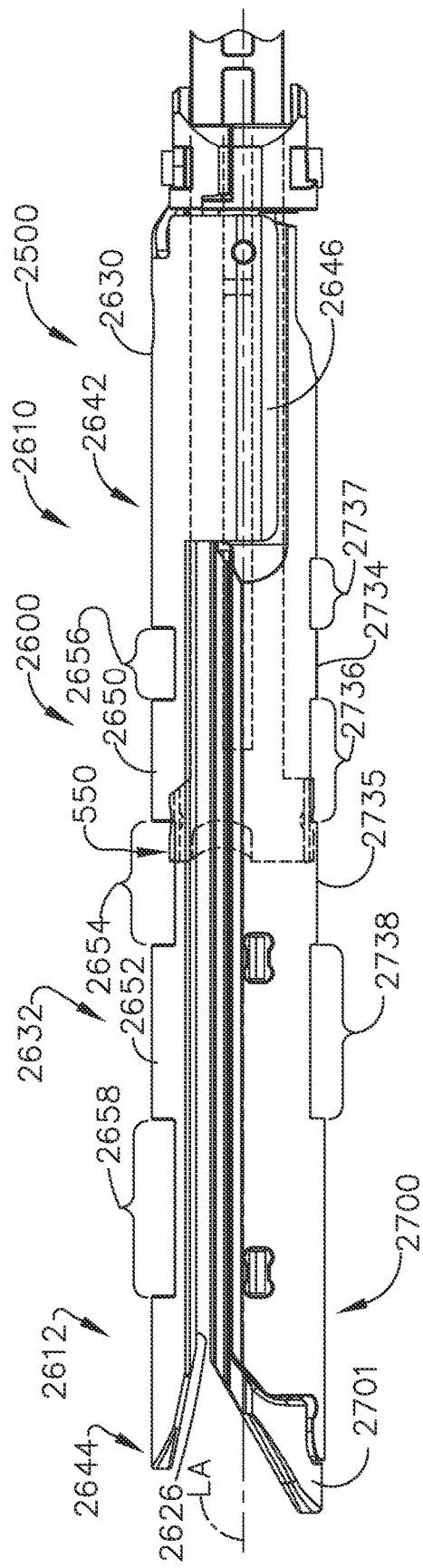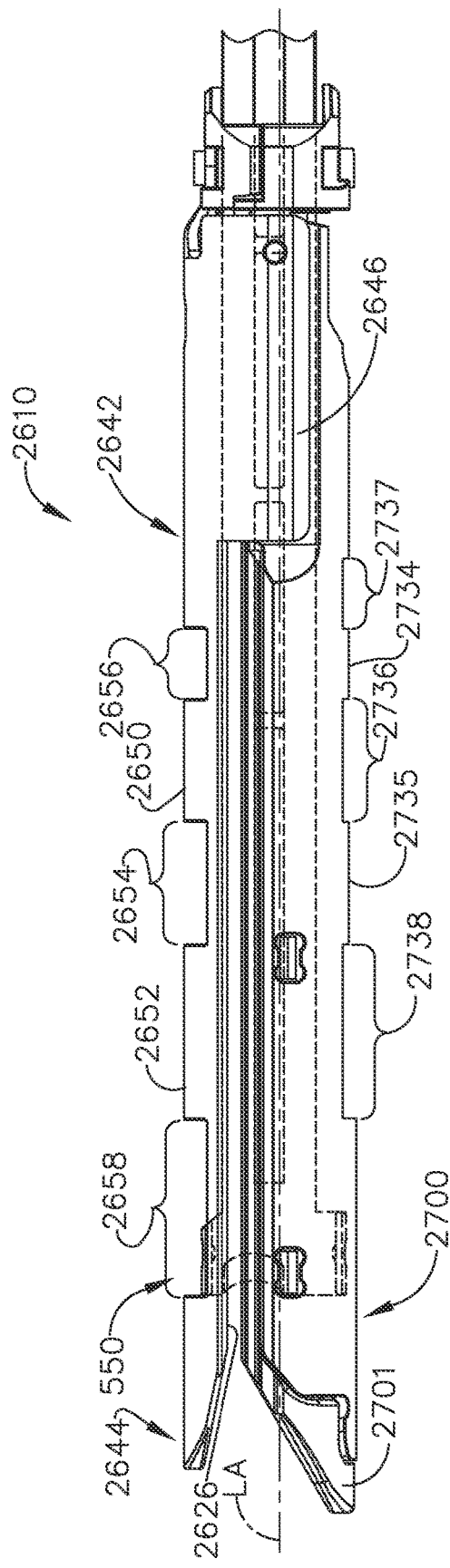

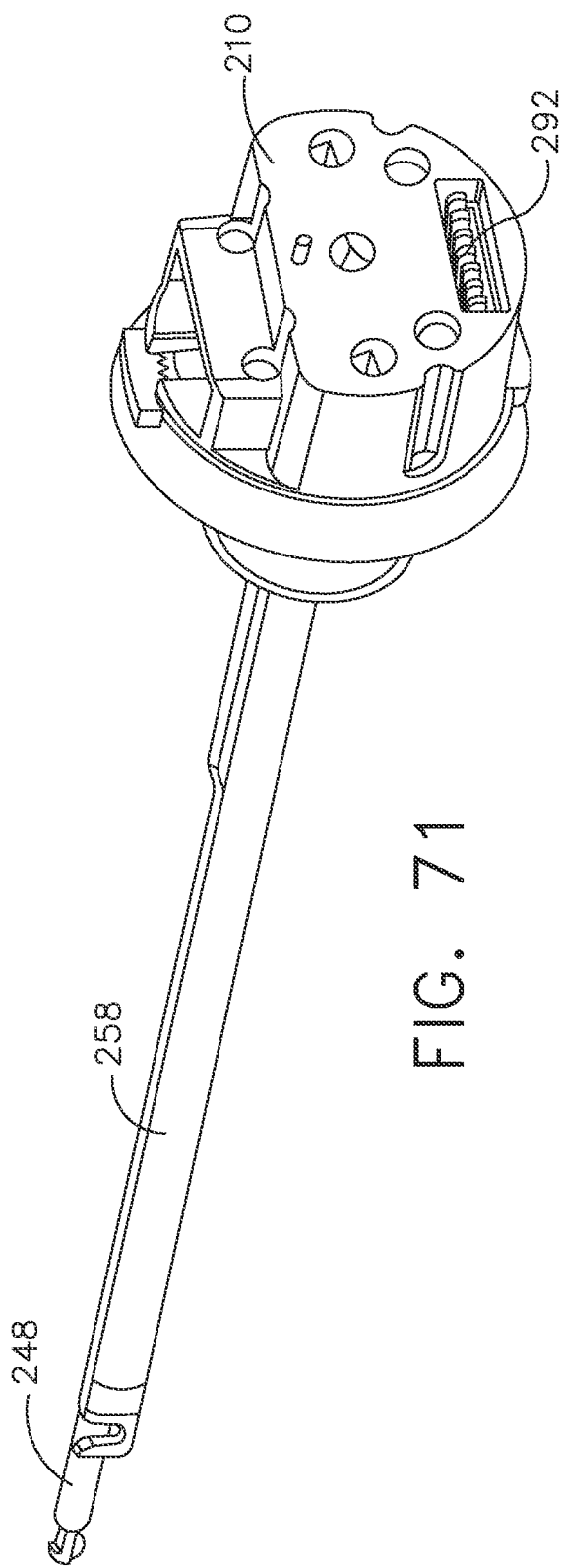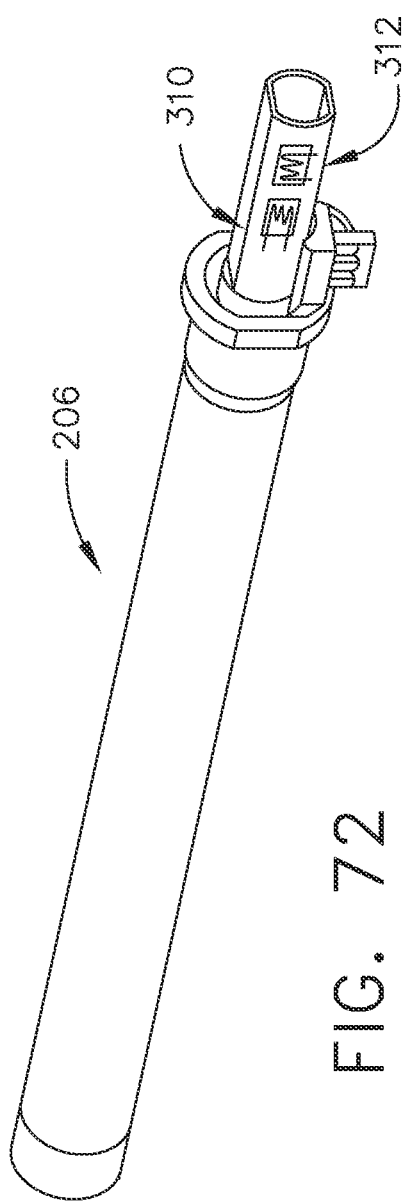
FIG. 71
FIG. 72

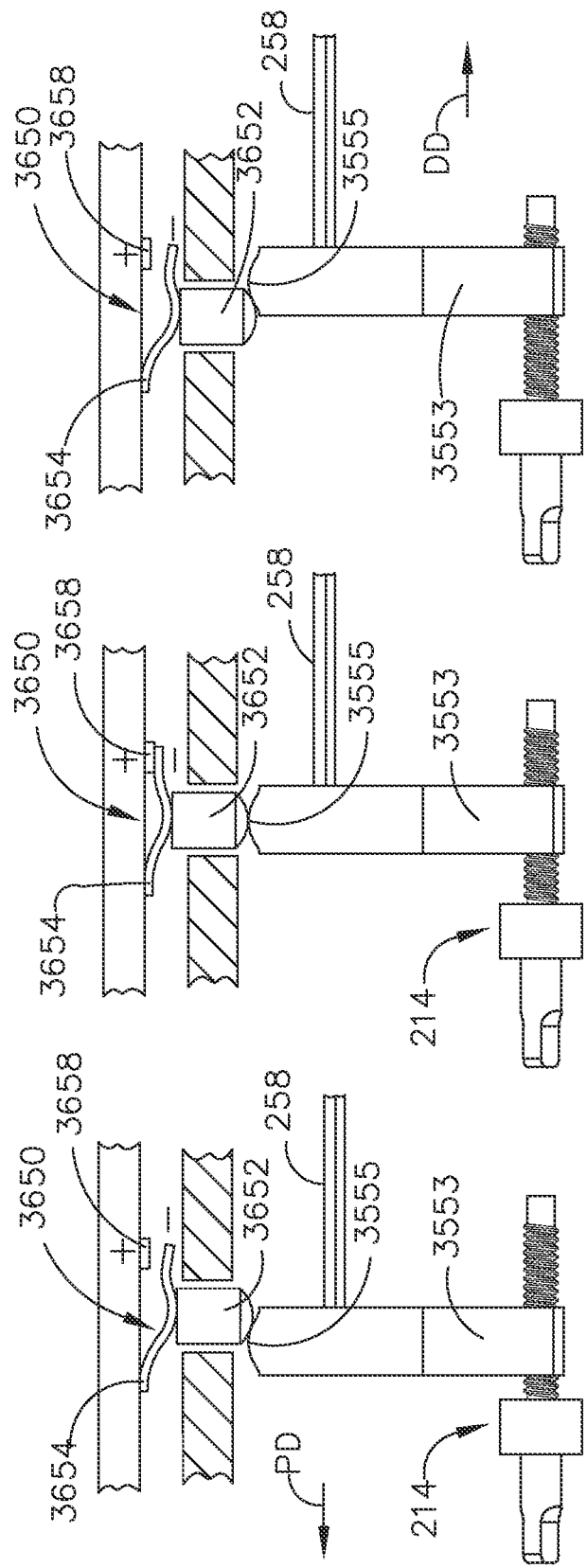

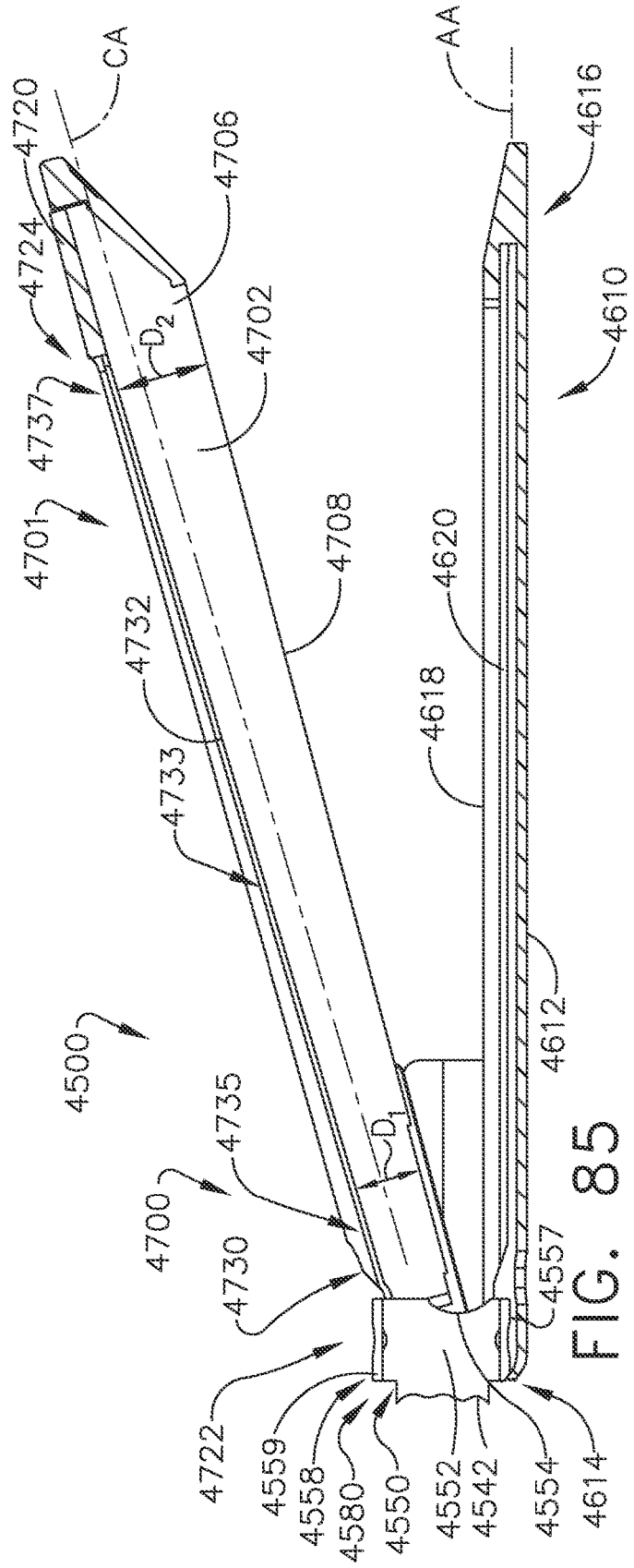

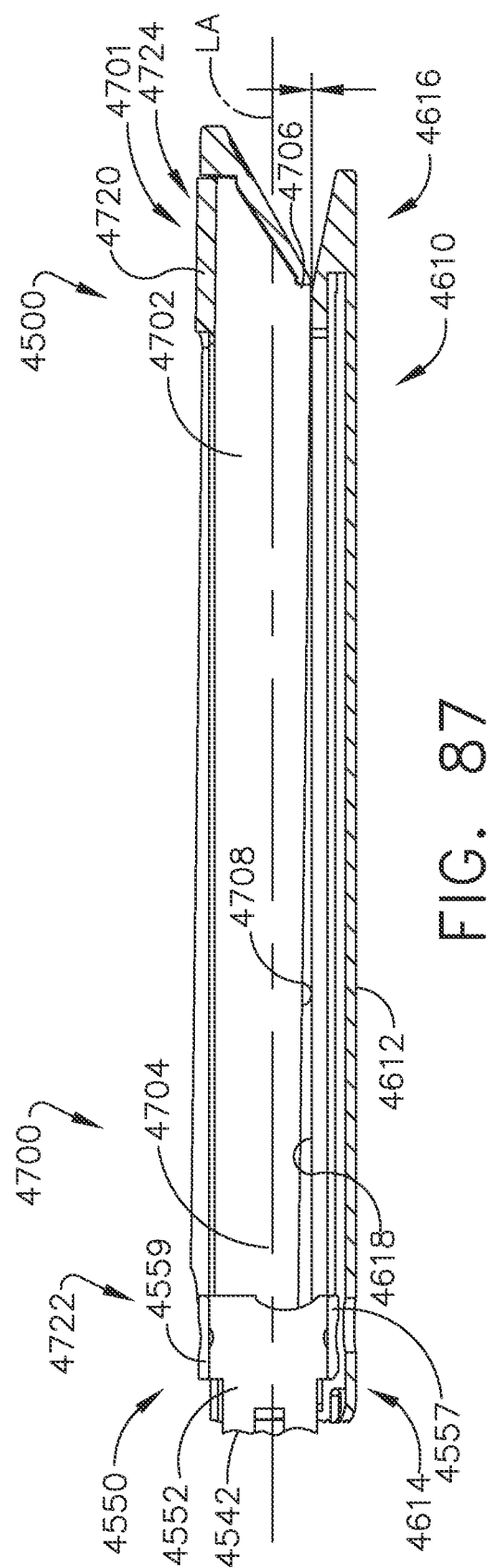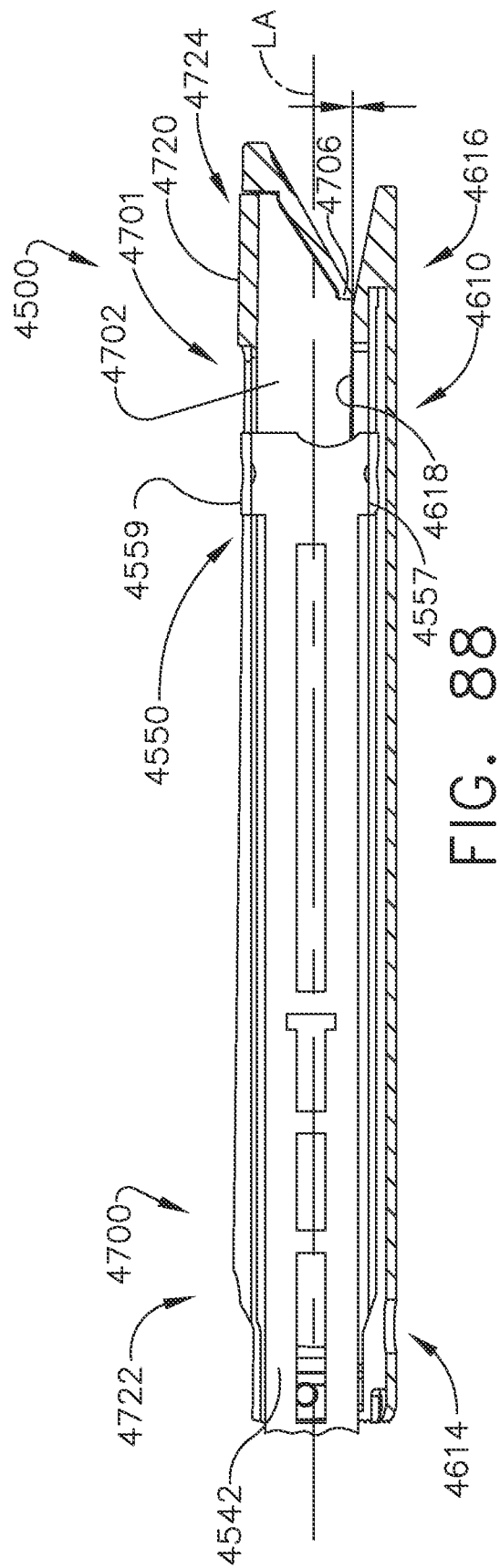

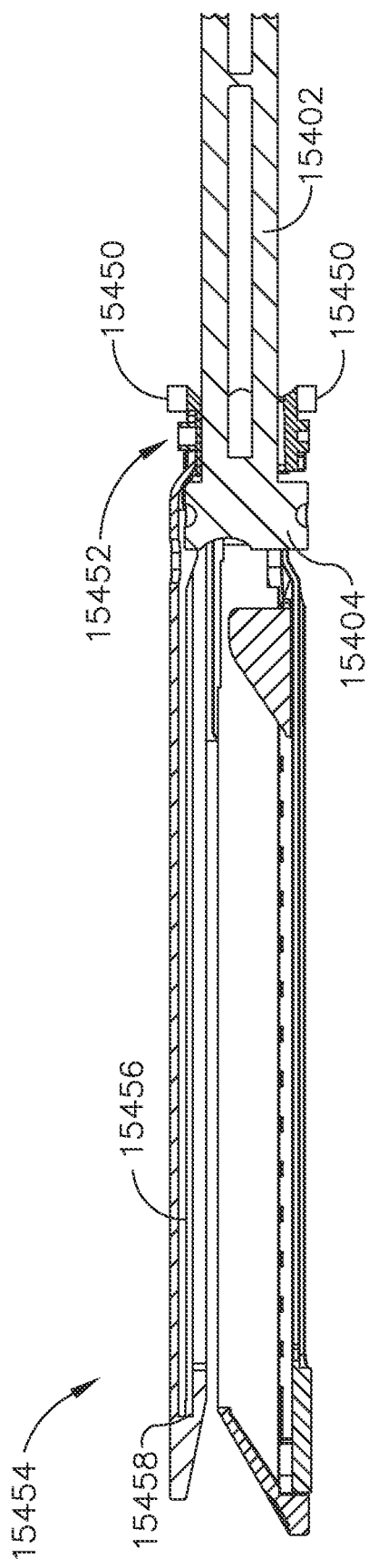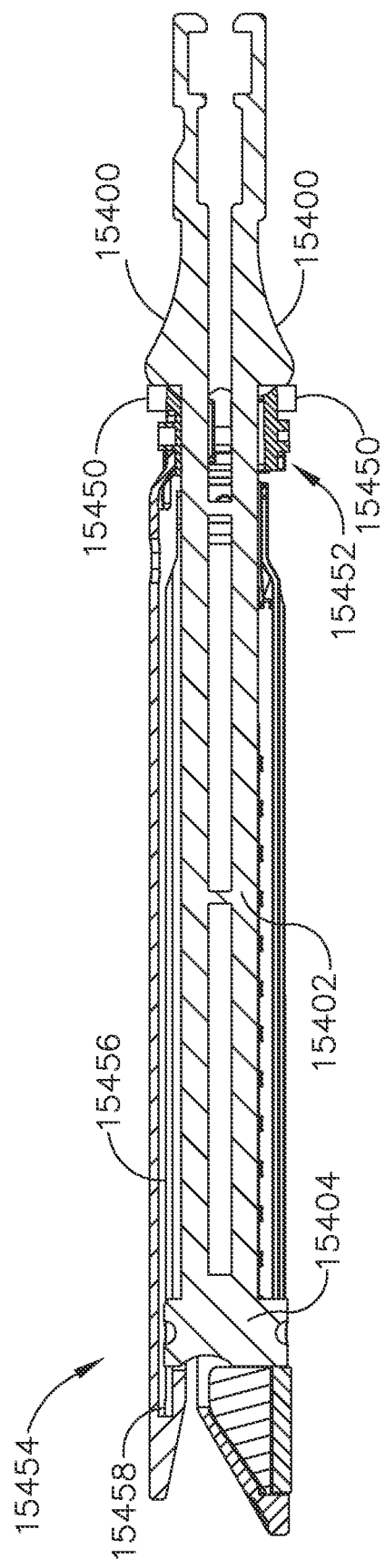

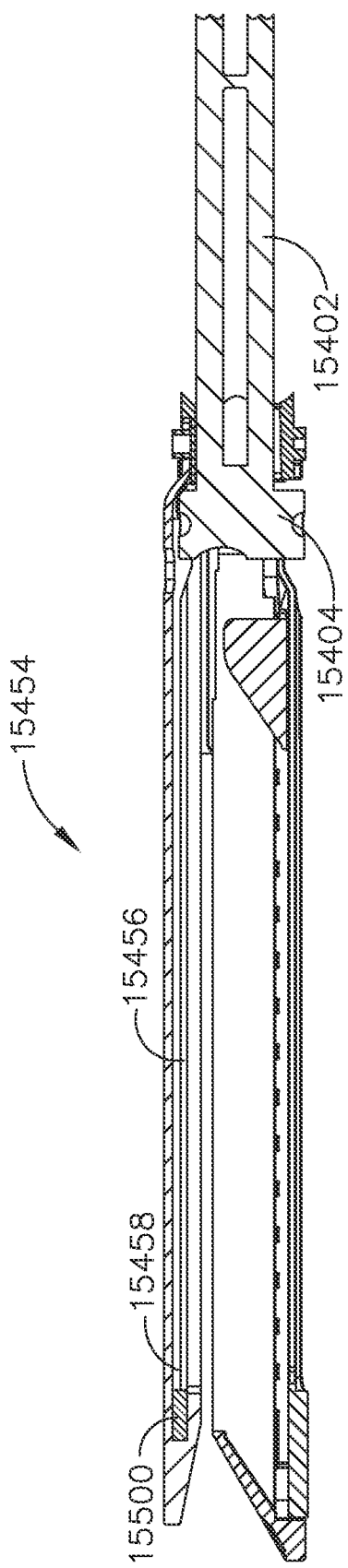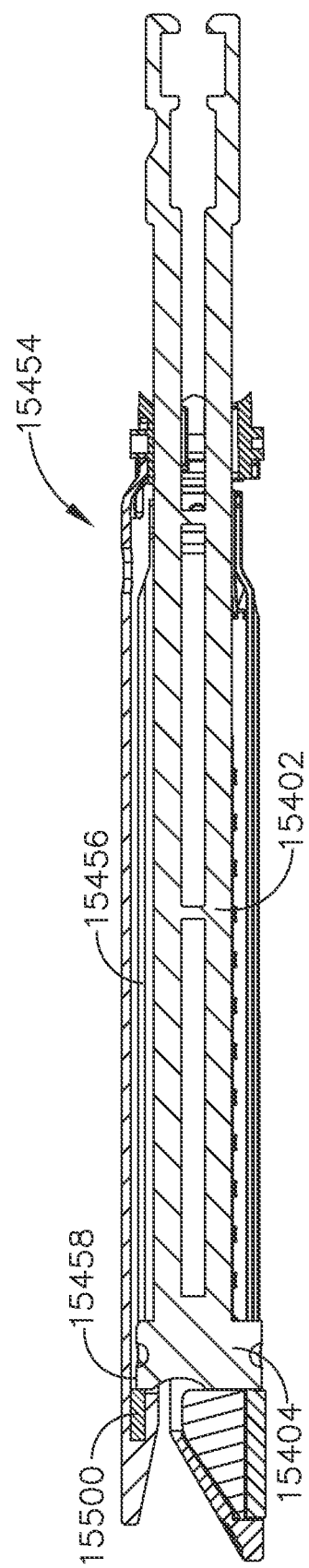

SURGICAL SYSTEMS COMPRISING A CONTROL CIRCUIT

CROSS-REFERENCE TO RELATED APPLICATIONS

This application is a continuation application claiming priority under 35 U.S.C. § 120 to U.S. patent application Ser. No. 17/012,241, entitled METHOD OF OPERATING SURGICAL END EFFECTORS, filed Sep. 4, 2020, which issued on Feb. 13, 2024 as U.S. Pat. No. 11,896,222, which is a continuation application claiming priority under 35 U.S.C. § 120 to U.S. patent application Ser. No. 15/843,704, entitled METHODS OF OPERATING SURGICAL END EFFECTORS, filed Dec. 15, 2017, which issued on Sep. 22, 2020 as U.S. Pat. No. 10,779,826, the disclosures of which are incorporated by reference herein in their entireties.

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 38 is a side elevational view of another dynamic clamping assembly with a portion thereof shown in cross-section;

FIG. 39 is a cross-sectional view of a portion of the dynamic clamping assembly of FIG. 38 taken along line 39-39 in FIG. 38;

FIG. 61 is a side elevational view of the loading unit of FIG. 59 with the jaws in the closed position;

FIG. 62 is another side elevational view of the loading unit of FIG. 61 with the dynamic clamping assembly positioned in a firing position;

FIG. 63 is another side elevational view of the loading unit of FIG. 62 with the dynamic clamping assembly in a partially fired position;

FIG. 64 is another side elevational view of the loading unit of FIG. 63 with the dynamic clamping assembly positioned in the ending position;

FIG. 71 is a perspective view of a portion of an adapter;

FIG. 72 is a perspective view of another portion of an adapter;

FIG. 81 is a partial cross-sectional side view of the articulation system and sensor assembly embodiment of an adapter of FIG. 80 in the unarticulated (neutral) position;

FIG. 82 is another partial cross-sectional side view of the articulation system and sensor assembly embodiment of an adapter of FIGS. 80 and 81 in an articulated position;

FIG. 83 is another partial cross-sectional side view of the articulation system and sensor assembly embodiment of an adapter of FIGS. 80-82 in another articulated position;

FIG. 85 is a partial cross-sectional view of a loading unit tool assembly of another adapter with the jaws thereof in a fully open position;

FIG. 86 is another a partial cross-sectional view of the loading unit tool assembly of FIG. 85 with the jaws thereof in a closed position;

FIG. 87 is another a partial cross-sectional view of the loading unit tool assembly of FIGS. 85 and 86 with a dynamic clamping assembly thereof at the end of a closing stroke and the jaws thereof in a fully closed position;

FIG. 88 is another partial cross-sectional view of the loading unit tool assembly of FIGS. 85-87 with the dynamic clamping assembly thereof approaching the end of a firing stroke;

FIG. 119 is a sectional view of an anvil including a slot stop member;

FIG. 120 illustrates a side elevational view of an anvil including a slot stop member, according to one aspect of the present disclosure.

FIG. 121 is a longitudinal sectional view of an end effector and a drive assembly including a stop member;

FIG. 122 is a longitudinal sectional view of an end effector and a drive assembly including a stop member;

FIG. 123 is a longitudinal sectional view of an end effector including a stop member located distally in the elongated slot; and FIG. 124 is a longitudinal sectional view of an end effector including a stop member located distally in the elongated slot.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
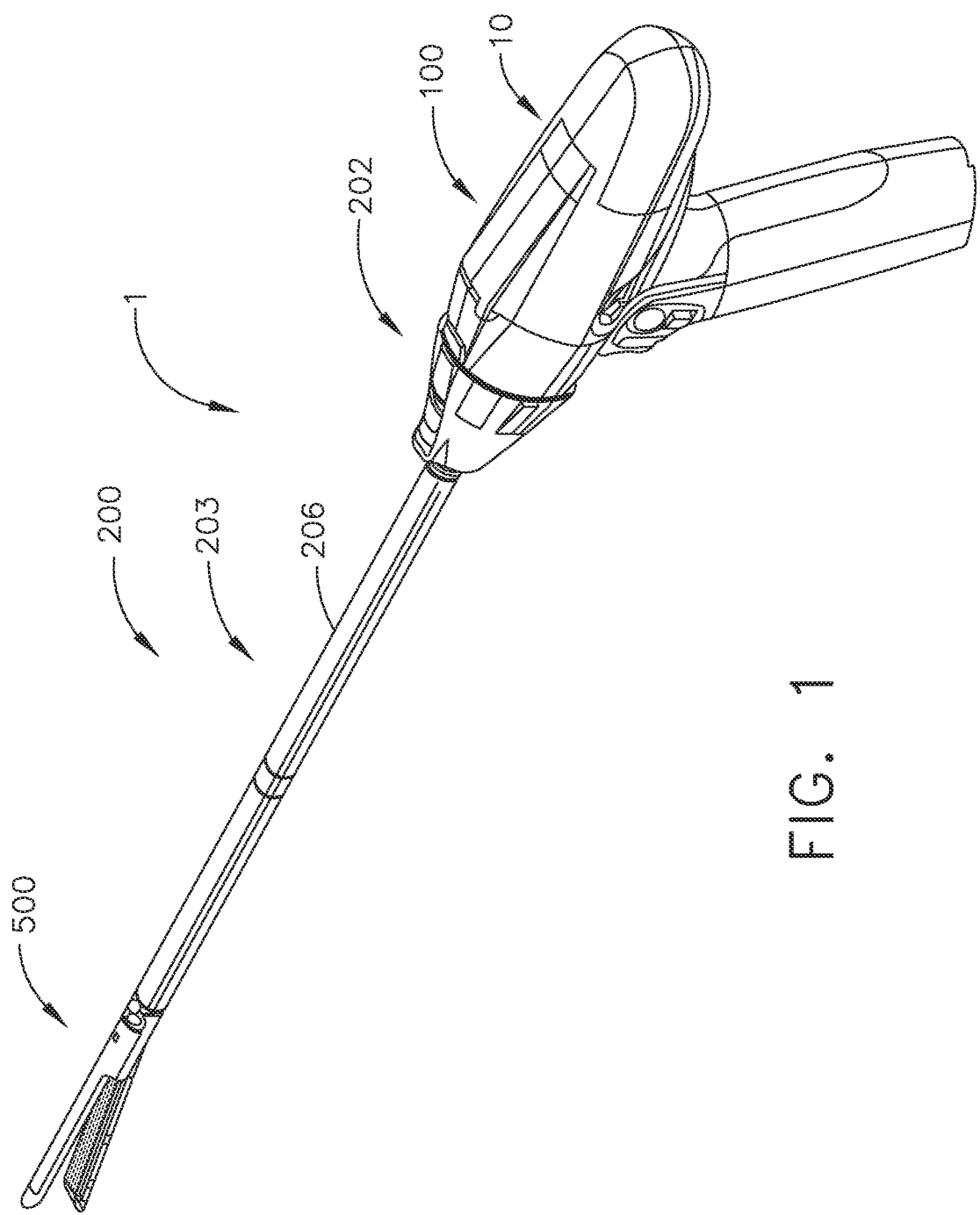
FIG. 1 is a perspective view of an electromechanical surgical system.

Applicant of the present application owns the following U.S. Patent Applications that were filed on Dec. 15, 2017 and which are each herein incorporated by reference in their respective entireties:

U.S. patent application Ser. No. 15/843,485, entitled SEALED ADAPTERS FOR USE WITH ELECTROMECHANICAL SURGICAL INSTRUMENTS, now U.S. Pat. No. 10,743,874;

U.S. patent application Ser. No. 15/843,518, entitled END EFFECTORS WITH POSITIVE JAW OPENING FEATURES FOR USE WITH ADAPTERS FOR ELECTROMECHANICAL SURGICAL INSTRUMENTS, now U.S. Pat. No. 11,006,955;

U.S. patent application Ser. No. 15/843,535, entitled SURGICAL END EFFECTORS WITH CLAMPING ASSEMBLIES CONFIGURED TO INCREASE JAW APERTURE RANGES, now U.S. Pat. No. 11,071,543;

U.S. patent application Ser. No. 15/843,558, entitled SURGICAL END EFFECTORS WITH PIVOTAL JAWS CONFIGURED TO TOUCH AT THEIR RESPECTIVE DISTAL ENDS WHEN FULLY CLOSED, now U.S. Pat. No. 11,197,670;

U.S. patent application Ser. No. 15/843,528, entitled SURGICAL END EFFECTORS WITH JAW STIFFENER ARRANGEMENTS CONFIGURED TO PERMIT MONITORING OF FIRING MEMBER, now U.S. Pat. No. 10,743,875;

U.S. patent application Ser. No. 15/843,567, entitled ADAPTERS WITH END EFFECTOR POSITION SENSING AND CONTROL ARRANGEMENTS FOR USE IN CONNECTION WITH ELECTROMECHANICAL SURGICAL INSTRUMENTS, now U.S. Pat. No. 10,779,825;

U.S. patent application Ser. No. 15/843,556, entitled DYNAMIC CLAMPING ASSEMBLIES WITH IMPROVED WEAR CHARACTERISTICS FOR USE IN CONNECTION WITH ELECTROMECHANICAL SURGICAL INSTRUMENTS, now U.S. Pat. No. 10,966,718;

U.S. patent application Ser. No. 15/843,514, entitled ADAPTERS WITH FIRING STROKE SENSING ARRANGEMENTS FOR USE IN CONNECTION WITH ELECTROMECHANICAL SURGICAL INSTRUMENTS, now U.S. Pat. No. 10,687,813;

U.S. patent application Ser. No. 15/843,501, entitled ADAPTERS WITH CONTROL SYSTEMS FOR CONTROLLING MULTIPLE MOTORS OF AN ELECTROMECHANICAL SURGICAL INSTRUMENT, now U.S. Pat. No. 10,869,666;

U.S. patent application Ser. No. 15/843,508, entitled HANDHELD ELECTROMECHANICAL SURGICAL INSTRUMENTS WITH IMPROVED MOTOR CONTROL ARRANGEMENTS FOR POSITIONING COMPONENTS OF AN ADAPTER COUPLED THERETO, now U.S. Pat. No. 10,828,033;

U.S. patent application Ser. No. 15/843,682, entitled SYSTEMS AND METHODS OF CONTROLLING A CLAMPING MEMBER FIRING RATE OF A SURGICAL INSTRUMENT, now U.S. Pat. No. 11,033,267; and U.S. patent application Ser. No. 15/843,689, entitled SYSTEMS AND METHODS OF CONTROLLING A CLAMPING MEMBER, now U.S. Patent Application Publication No. 2019/0183502.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

FIG. 1 depicts a motor-driven (electromechanical) surgical system 1 that may be used to perform a variety of different surgical procedures. As can be seen in that Figure, one example of the surgical system 1 includes a powered handheld electromechanical surgical instrument 100 that is configured for selective attachment thereto of a plurality of different surgical tool implements (referred to herein as "adapters") that are each configured for actuation and manipulation by the powered handheld electromechanical surgical instrument. As illustrated in FIG. 1, the handheld surgical instrument 100 is configured for selective connection with an adapter 200, and, in turn, adapter 200 is configured for selective connection with end effectors that comprise a single use loading unit ("SULU") or a disposable loading unit ("DLU") or a multiple use loading unit ("MULU"). In another surgical system embodiment, various forms of adapter 200 may also be effectively employed with a tool drive assembly of a robotically controlled or automated surgical system. For example, the surgical tool assemblies disclosed herein may be employed with various robotic systems, instruments, components and methods such as, but not limited to, those disclosed in U.S. Pat. No. 9,072,535, entitled SURGICAL STAPLING INSTRUMENTS WITH ROTATABLE STAPLE DEPLOYMENT ARRANGEMENTS, which is hereby incorporated by reference herein in its entirety.

Figure 2:
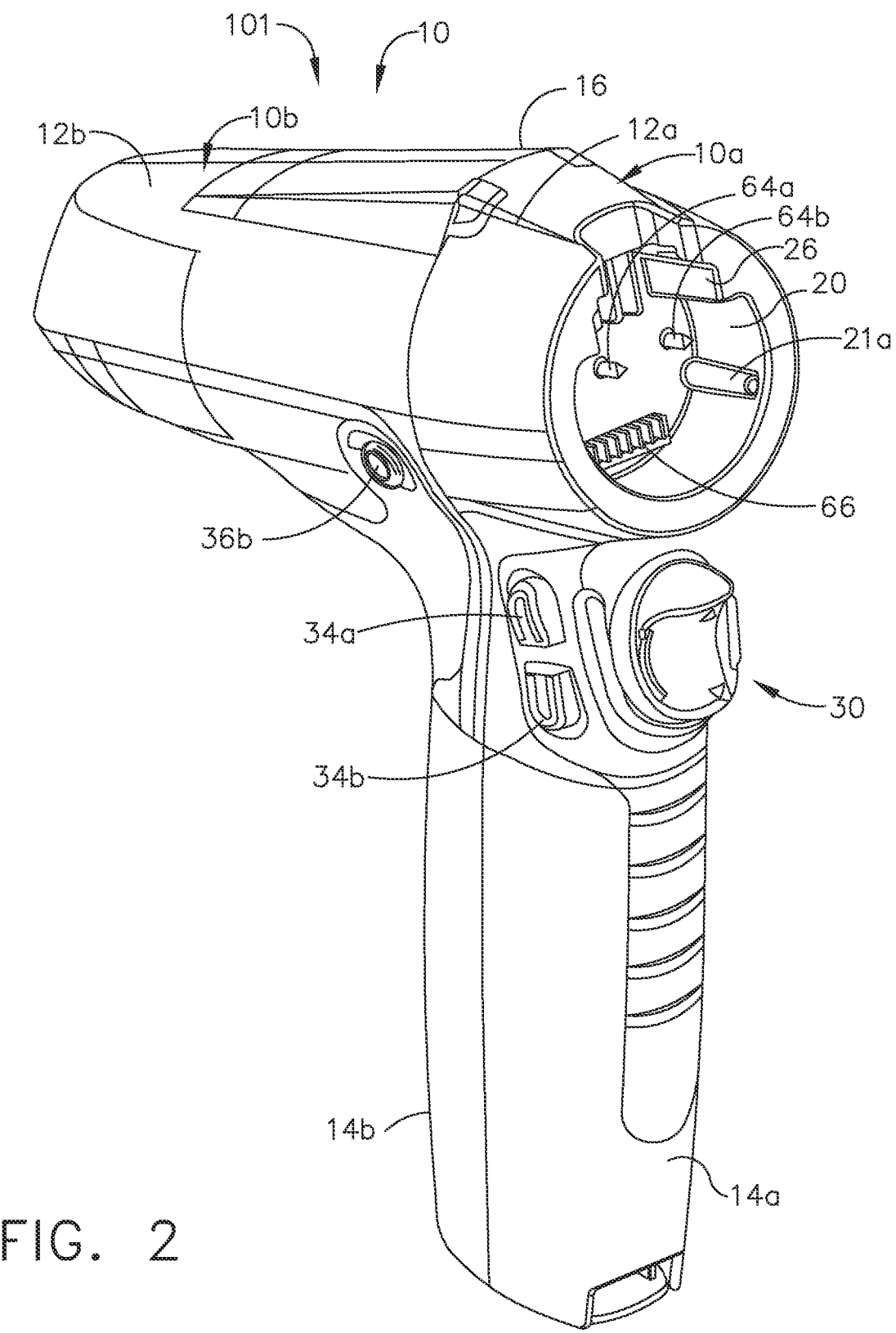
FIG. 2 is a perspective view of a distal end of an electromechanical surgical instrument portion of the surgical system of FIG. 1.

As illustrated in FIGS. 1 and 2, surgical instrument 100 includes a power-pack 101 and an outer shell housing 10 that is configured to selectively receive and substantially encase the power-pack 101. The power pack 101 may also be referred to herein as handle assembly 101. One form of surgical instrument 100, for example, is disclosed in International Publication No. WO 2016/057225 A1, International Application No. PCT/US2015/051837, entitled HANDHELD ELECTROMECHANICAL SURGICAL SYSTEM, the entire disclosure of which is hereby incorporated by reference herein. Various features of surgical instrument 100 will not be disclosed herein beyond what is necessary to understand the various features of the inventions disclosed herein with it being understood that further details may be gleaned from reference to WO 2016/057225 A1 and other references incorporated by reference herein.

Figure 3:
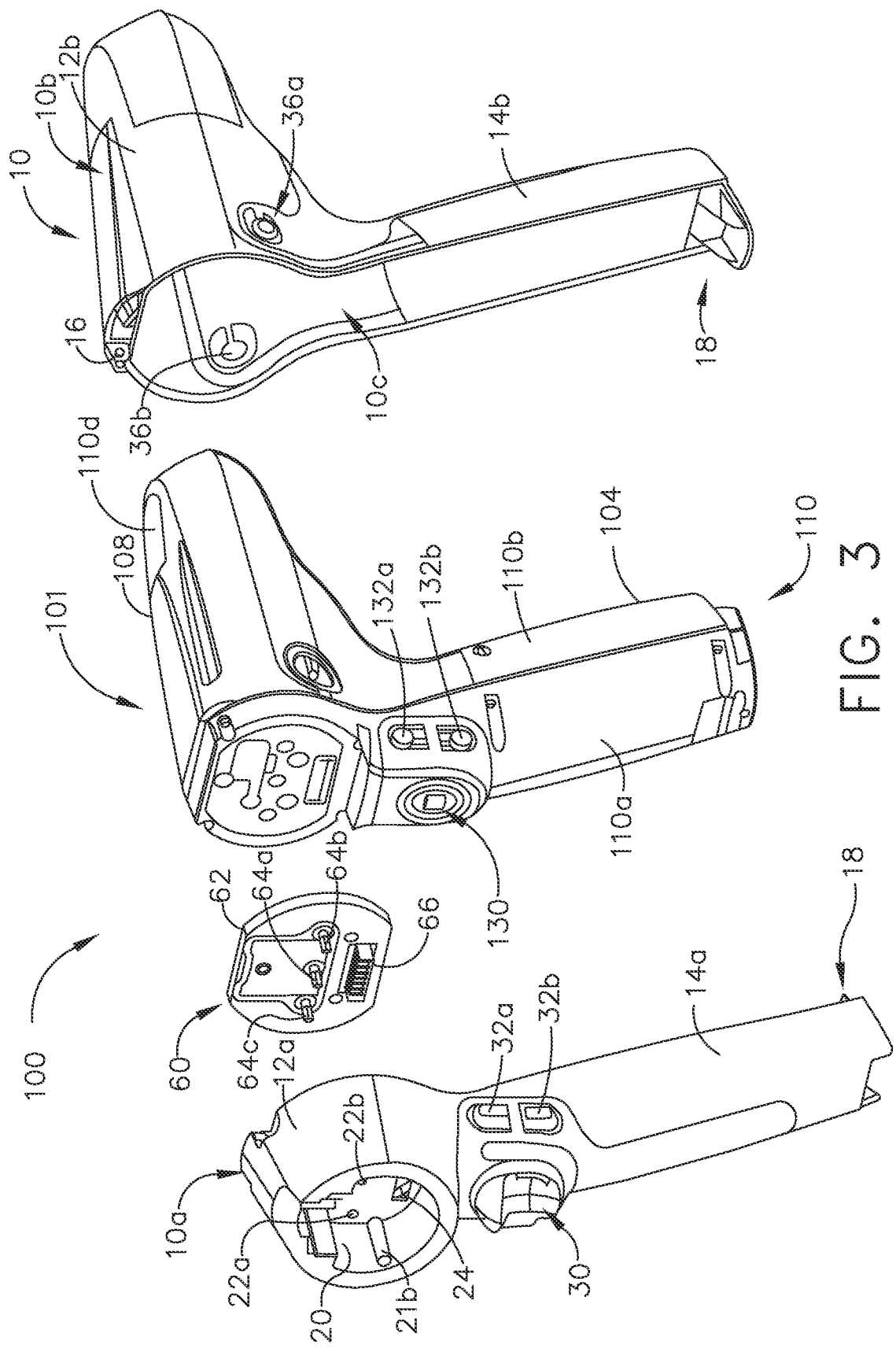
FIG. 3 is an exploded assembly view of an outer shell feature and the electromechanical surgical instrument of FIG. 2.

As illustrated in FIG. 3, outer shell housing 10 includes a distal half-section 10a and a proximal half-section 10b that is pivotably connected to distal half-section 10a by a hinge 16 located along an upper edge of distal half-section 10a and proximal half-section 10b. When joined, distal and proximal half-sections 10a, 10b define a shell cavity 10c therein in which the power-pack 101 is selectively situated. Each of distal and proximal half-sections 10a, 10b includes a respective upper shell portion 12a, 12b, and a respective lower shell portion 14a, 14b. Lower shell portions 14a, 14b define a snap closure feature 18 for selectively securing the lower shell portions 14a, 14b to one another and for maintaining shell housing 10 in a closed condition. Distal half-section 10a of shell housing 10 defines a connecting portion 20 that is configured to accept a corresponding drive coupling assembly 210 of adapter 200 (see FIG. 5). Specifically, distal half-section 10a of shell housing 10 has a recess that receives a portion of drive coupling assembly 210 of adapter 200 when adapter 200 is mated to surgical instrument 100.

Figure 5:
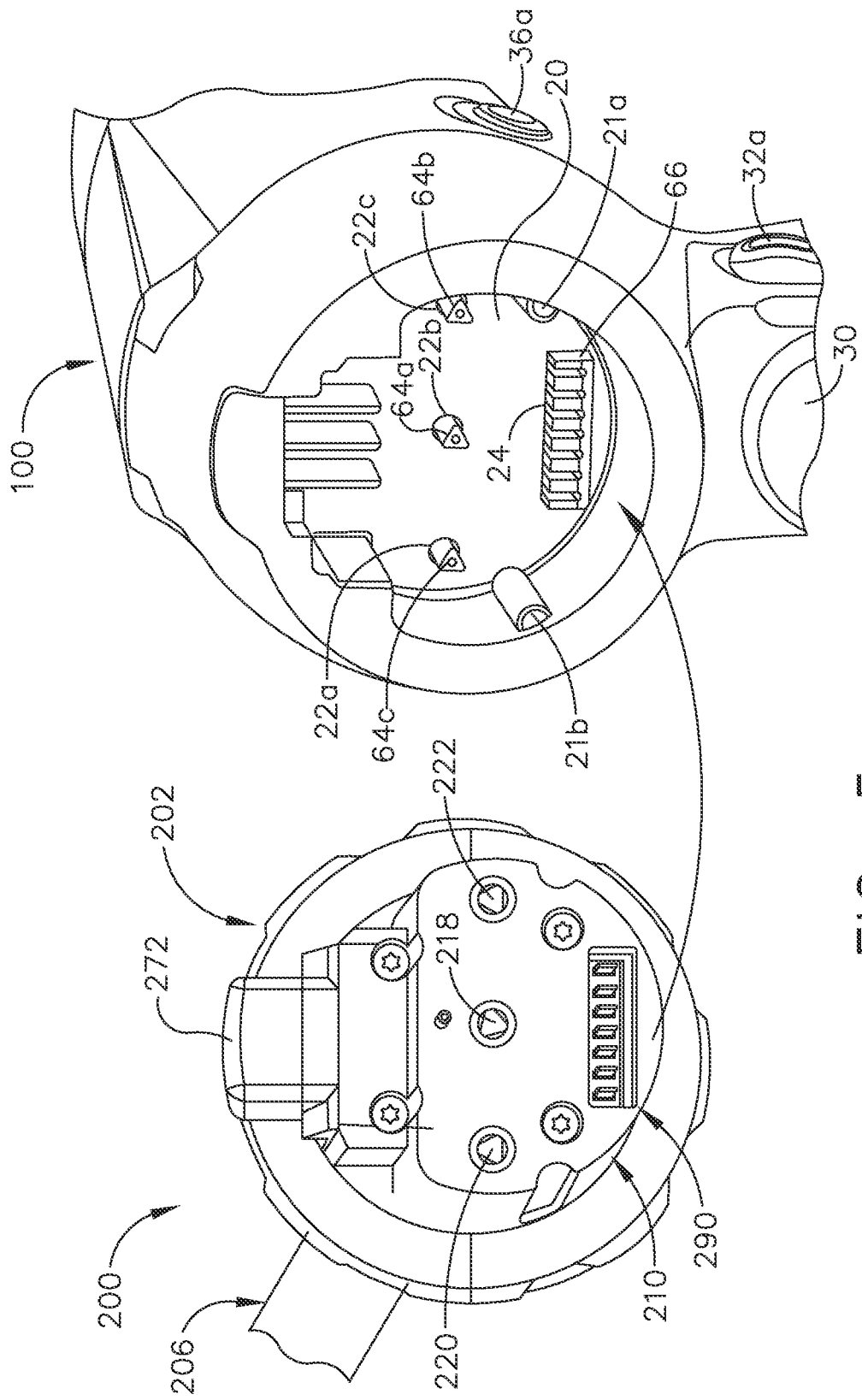
FIG. 5 is a partial exploded assembly view of a portion of an adapter and the electromechanical surgical instrument of the surgical system of FIG. 1.

Connecting portion 20 of distal half-section 10a defines a pair of axially extending guide rails 21a, 21b that project radially inward from inner side surfaces thereof as shown in FIG. 5. Guide rails 21a, 21b assist in rotationally orienting adapter 200 relative to surgical instrument 100 when adapter 200 is mated to surgical instrument 100. Connecting portion 20 of distal half-section 10a defines three apertures 22a, 22b, 22c that are formed in a distally facing surface thereof and which are arranged in a common plane or line with one another. Connecting portion 20 of distal half-section 10a also defines an elongate slot 24 also formed in the distally facing surface thereof. Connecting portion 20 of distal half-section 10a further defines a female connecting feature 26 (see FIG. 2) formed in a surface thereof. Female connecting feature 26 selectively engages with a male connecting feature of adapter 200.

Distal half-section 10a of shell housing 10 supports a distal facing toggle control button 30. The toggle control button 30 is capable of being actuated in a left, right, up and down direction upon application of a corresponding force thereto or a depressive force thereto. Distal half-section 10a of shell housing 10 supports a right-side pair of control buttons 32a, 32b (see FIG. 3); and a left-side pair of control button 34a, 34b (see FIG. 2). The right-side control buttons 32a, 32b and the left-side control buttons 34a, 34b are capable of being actuated upon application of a corresponding force thereto or a depressive force thereto. Proximal half-section of shell housing 10 supports a right-side control button 36a (see FIG. 3) and a left-side control button 36b (see FIG. 2). Right-side control button 36a and left-side control button 36b are capable of being actuated upon application of a corresponding force thereto or a depressive force thereto.

Shell housing 10 includes a sterile barrier plate assembly 60 selectively supported in distal half-section 10a. Specifically, the sterile barrier plate assembly 60 is disposed behind connecting portion 20 of distal half-section 10a and within shell cavity 10c of shell housing 10. The plate assembly 60 includes a plate 62 rotatably supporting three coupling shafts 64a, 64b, 64c (see FIGS. 3 and 5). Each coupling shaft 64a, 64b, 64c extends from opposed sides of plate 62 and has a tri-lobe transverse cross-sectional profile. Each coupling shaft 64a, 64b, 64c extends through the respective apertures 22a, 22b, 22c of connecting portion 20 of distal half-section 10a when the sterile barrier plate assembly 60 is disposed within shell cavity 10c of shell housing 10. The plate assembly 60 further includes an electrical pass-through connector 66 supported on plate 62. Pass-through connector 66 extends from opposed sides of plate 62. Pass-through connector 66 defines a plurality of contact paths each including an electrical conduit for extending an electrical connection across plate 62. When the plate assembly 60 is disposed within shell cavity 10c of shell housing 10, distal ends of coupling shaft 64a, 64b, 64c and a distal end of pass-through connector 66 are disposed or situated within connecting portion 20 of distal half-section 10a of shell housing 10, and are configured to electrically and/or mechanically engage respective corresponding features of adapter 200.

Figure 4:
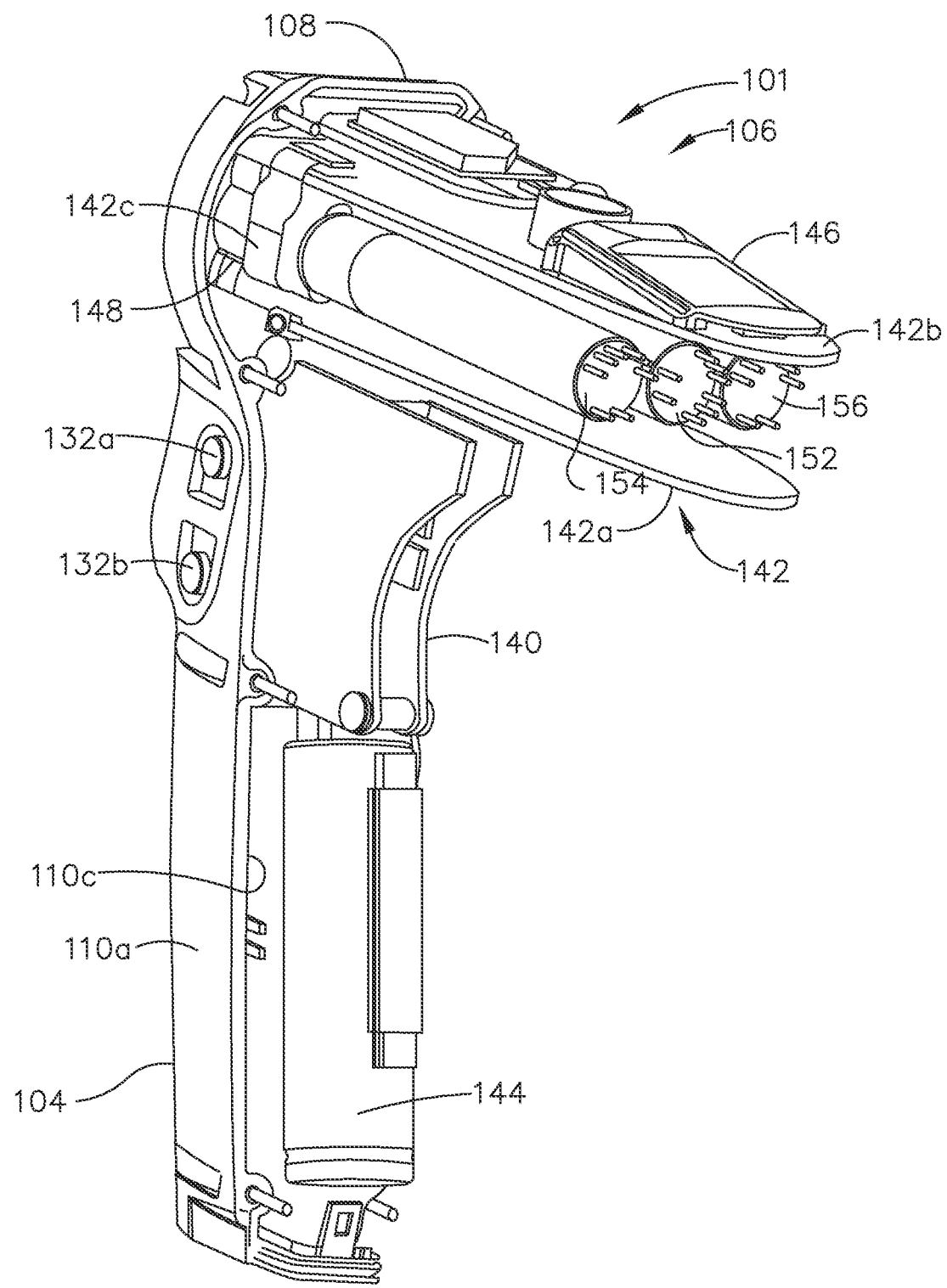
FIG. 4 is a rear perspective view of a portion of the electromechanical surgical instrument of FIG. 2.

Referring to FIGS. 3 and 4, the power-pack or the handle assembly 101 includes an inner handle housing 110 having a lower housing portion 104 and an upper housing portion 108 extending from and/or supported on lower housing portion 104. Lower housing portion 104 and upper housing portion 108 are separated into a distal half section 110a and a proximal half-section 110b connectable to distal half-section 110a by a plurality of fasteners. When joined, distal and proximal half-sections 110a, 110b define the inner handle housing 110 having an inner housing cavity 110c therein in which a power-pack core assembly 106 is situated. Power-pack core assembly 106 is configured to control the various operations of surgical instrument 100.

Distal half-section 110a of inner handle housing 110 supports a distal toggle control interface 130 that is in operative registration with the distal toggle control button 30 of shell housing 10. In use, when the power-pack 101 is disposed within shell housing 10, actuation of the toggle control button 30 exerts a force on toggle control interface 130. Distal half-section 110a of inner handle housing 110 also supports a right-side pair of control interfaces (not shown), and a left-side pair of control interfaces 132a, 132b. In use, when the power-pack 101 is disposed within shell housing 10, actuation of one of the right-side pair of control buttons or the left-side pair of control button of distal half-section 10a of shell housing 10 exerts a force on a respective one of the right-side pair of control interfaces 132a, 132b or the left-side pair of control interfaces 132a, 132b of distal half-section 110a of inner handle housing 110.

With reference to FIGS. 1-5, inner handle housing 110 provides a housing in which power-pack core assembly 106 is situated. Power-pack core assembly 106 includes a battery circuit 140, a controller circuit board 142 and a rechargeable battery 144 configured to supply power to any of the electrical components of surgical instrument 100. Controller circuit board 142 includes a motor controller circuit board 142a, a main controller circuit board 142b, and a first ribbon cable 142c interconnecting motor controller circuit board 142a and main controller circuit board 142b. Power-pack core assembly 106 further includes a display screen 146 supported on main controller circuit board 142b. Display screen 146 is visible through a clear or transparent window 110d (see FIG. 3) provided in proximal half-section 110b of inner handle housing 110. It is contemplated that at least a portion of inner handle housing 110 may be fabricated from a transparent rigid plastic or the like. It is further contemplated that shell housing may either include a window formed therein (in visual registration with display screen 146 and with window 110d of proximal half-section 110b of inner handle housing 110, and/or shell housing 10 may be fabricated from a transparent rigid plastic or the like.

Power-pack core assembly 106 further includes a first motor 152, a second motor 154, and a third motor 156 that are supported by motor bracket 148 and are each electrically connected to controller circuit board 142 and battery 144. Motors 152, 154, 156 are disposed between motor controller circuit board 142a and main controller circuit board 142b. Each motor 152, 154, 156 includes a respective motor shaft 152a, 154a, 156a extending therefrom. Each motor shaft 152a, 154a, 156a has a tri-lobe transverse cross-sectional profile for transmitting rotative forces or torque. Each motor 152, 154, 156 is controlled by a respective motor controller. Rotation of motor shafts 152a, 154a, 156a by respective motors 152, 154, 156 function to drive shafts and/or gear components of adapter 200 in order to perform the various operations of surgical instrument 100. In particular, motors 152, 154, 156 of power-pack core assembly 106 are configured to drive shafts and/or gear components of adapter 200.

As illustrated in FIGS. 1 and 5, surgical instrument 100 is configured for selective connection with adapter 200, and, in turn, adapter 200 is configured for selective connection with end effector 500. Adapter 200 includes an outer knob housing 202 and an outer tube 206 that extends from a distal end of knob housing 202. Knob housing 202 and outer tube 206 are configured and dimensioned to house the components of adapter assembly 200. Outer tube 206 is dimensioned for endoscopic insertion, in particular, that outer tube is passable through a typical trocar port, cannula or the like. Knob housing 202 is dimensioned to not enter the trocar port, cannula of the like. Knob housing 202 is configured and adapted to connect to connecting portion 20 of the outer shell housing 10 of surgical instrument 100.

Figure 6:
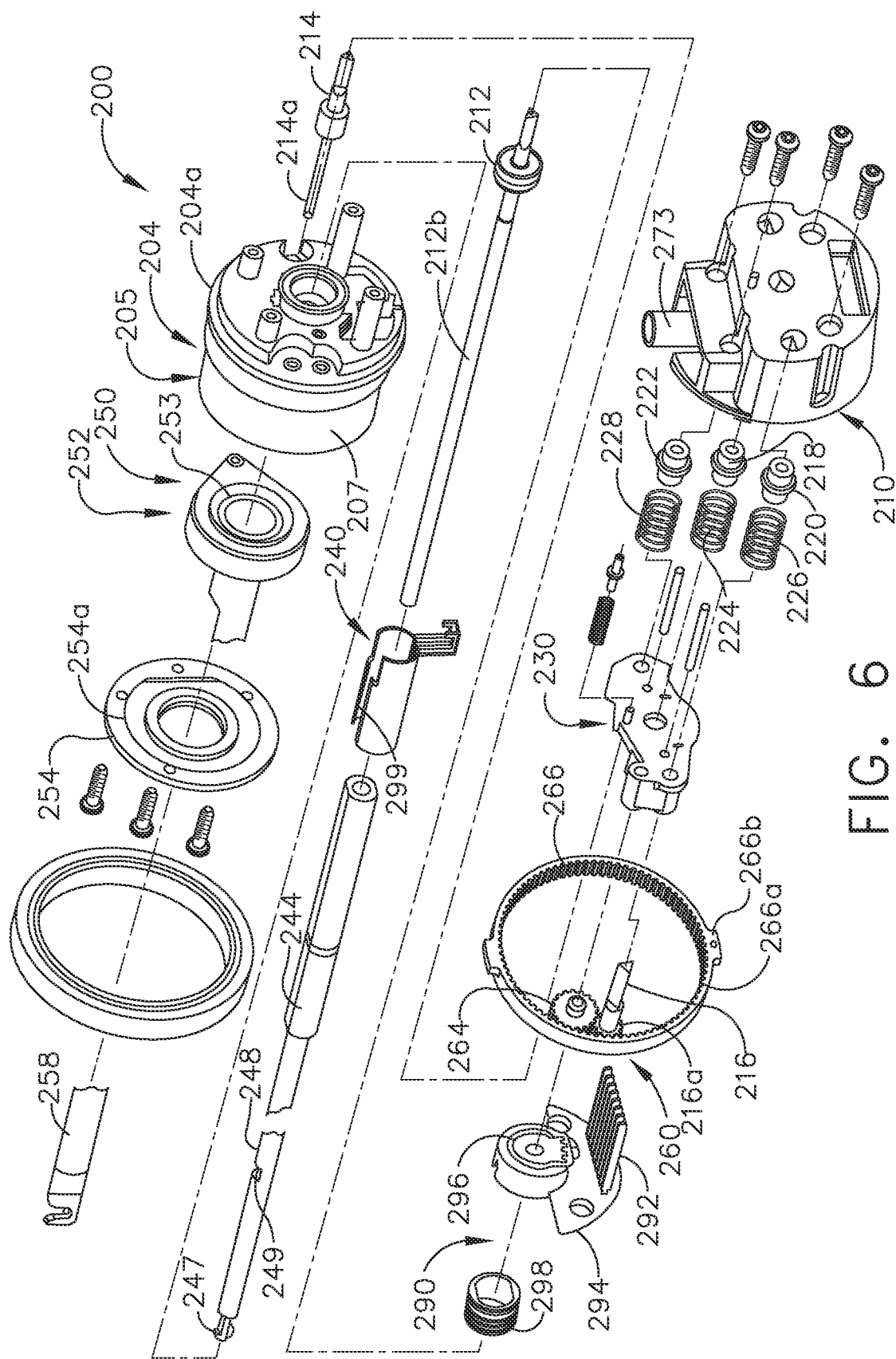
FIG. 6 is an exploded assembly view of a portion of the adapter of FIG. 5.
Figure 9:
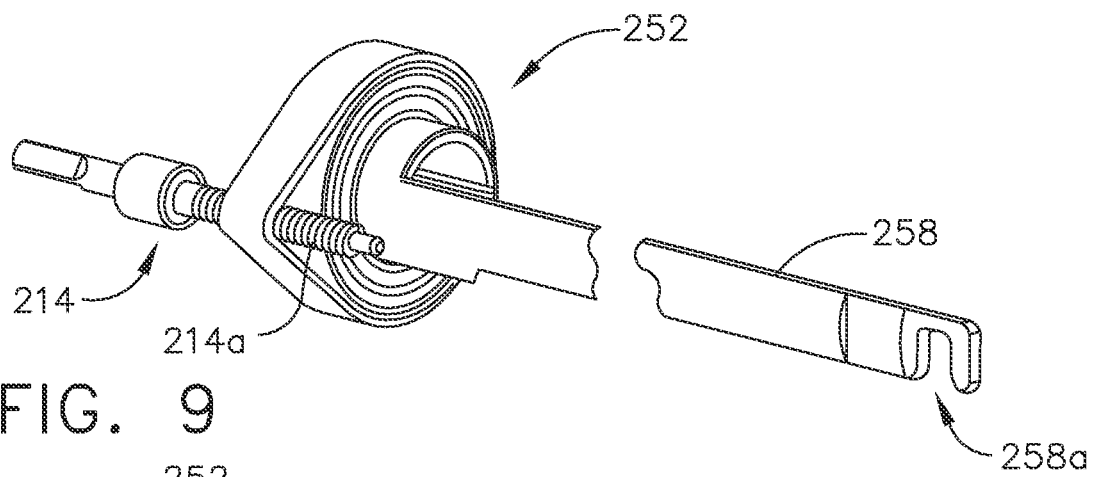
FIG. 9 is another perspective view of the articulation assembly of FIG. 8.
Figure 8:
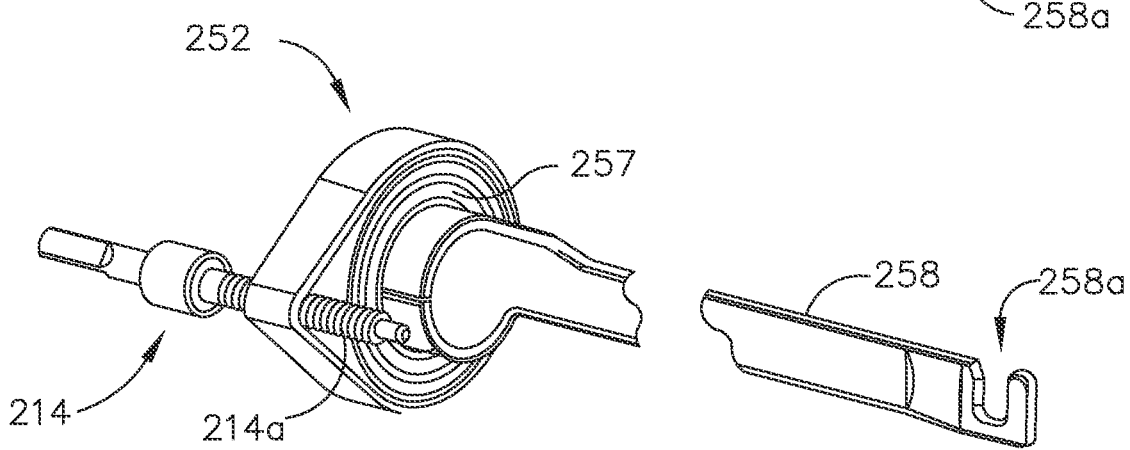
FIG. 8 is a perspective view of the articulation assembly of FIG. 7.
Figure 7:
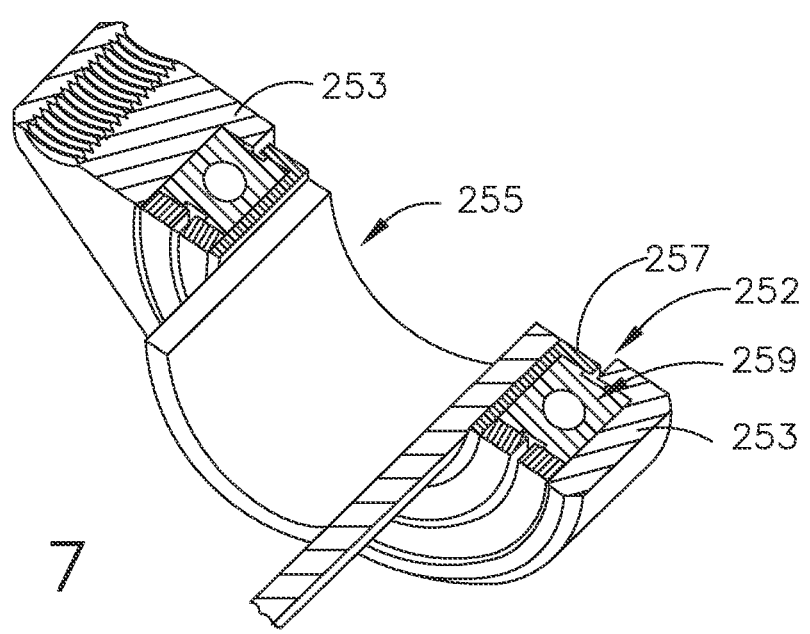
FIG. 7 is a cross-sectional perspective view of a portion of an articulation assembly of an adapter.
Figure 10:
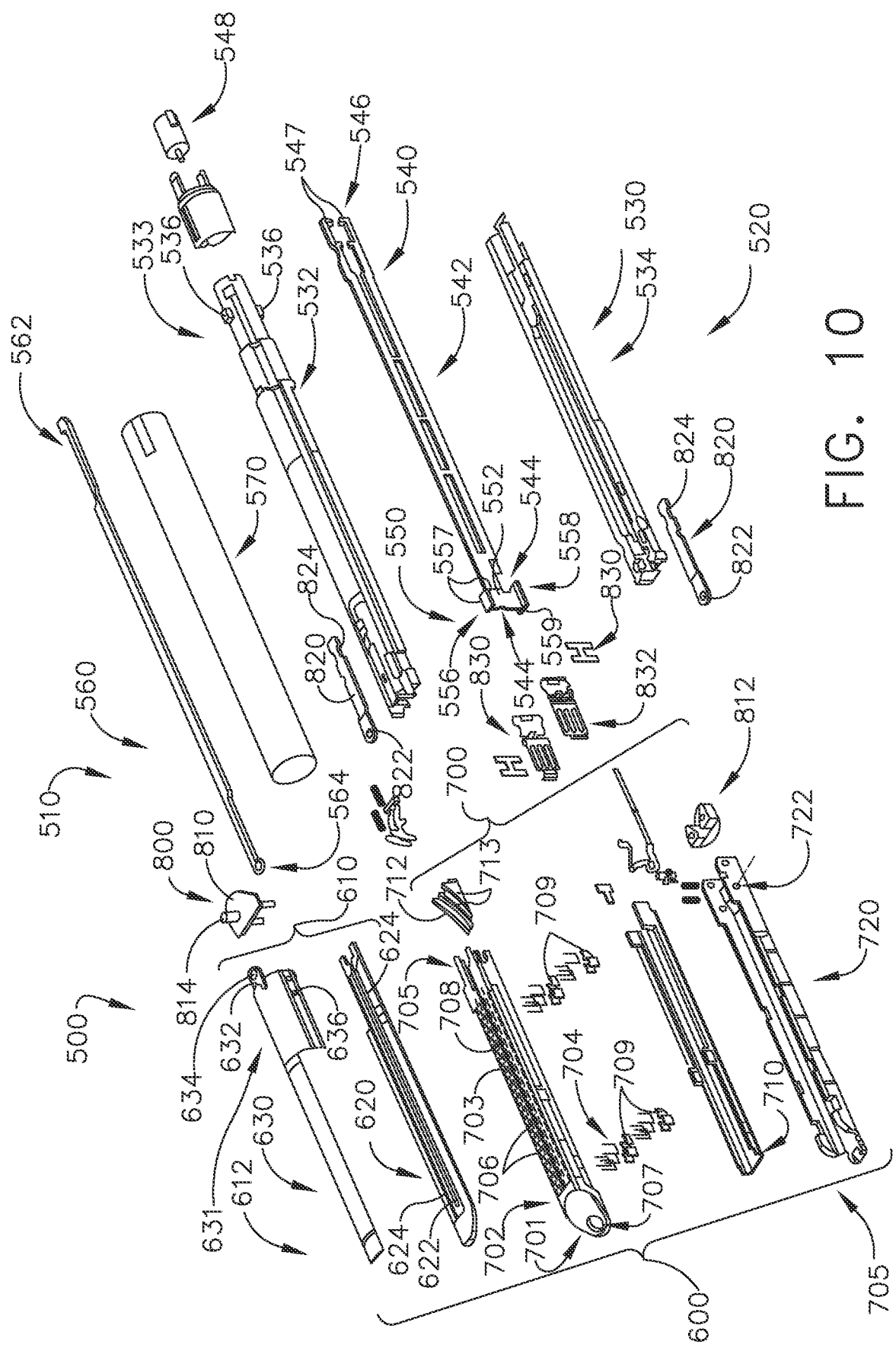
FIG. 10 is an exploded assembly view of a loading unit employed in the electromechanical surgical system of FIG. 1.

Adapter 200 is configured to convert a rotation of either of first or second coupling shafts 64a, 64b of surgical instrument 100 into axial translation useful for operating a drive assembly 540 and an articulation link 560 of end effector 500, as illustrated in FIG. 10 and as will be described in greater detail below. As illustrated in FIG. 6, adapter 200 includes the proximal inner housing assembly 204 that rotatably supports a first rotatable proximal drive shaft 212, a second rotatable proximal drive shaft 214, and a third rotatable proximal drive shaft 216 therein. Each proximal drive shaft 212, 214, 216 functions as a rotation receiving member to receive rotational forces from respective coupling shafts 64a, 64b and 64c of surgical instrument 100. In addition, the drive coupling assembly 210 of adapter 200 is also configured to rotatably support first, second and third connector sleeves 218, 220 and 222, respectively, arranged in a common plane or line with one another. Each connector sleeve 218, 220, 222 is configured to mate with respective first, second and third coupling shafts 64a, 64b, 64c of surgical instrument 100, as described above. Each connector sleeves 218, 222, 220 is further configured to mate with a proximal end of respective first, second, and third proximal drive shafts 212, 214, 216 of adapter 200.

Drive coupling assembly 210 of adapter 200 also includes a first, a second, and a third biasing member 224, 226, and 228 disposed distally of respective first, second, and third connector sleeves 218, 220, 222. Each biasing members 224, 226, and 228 is disposed about respective first, second, and third rotatable proximal drive shaft 212, 214, and 216. Biasing members 224, 226, and 228 act on respective connector sleeves 218, 222, and 220 to help maintain connector sleeves 218, 222, and 220 engaged with the distal end of respective coupling shafts 64a, 64b, and 64c of surgical instrument 100 when adapter 200 is connected to surgical instrument 100.

Also in the illustrated arrangement, adapter 200 includes first, second, and third drive converting assemblies 240, 250, 260, respectively, that are each disposed within inner housing assembly 204 and outer tube 206. Each drive converting assembly 240, 250, 260 is configured and adapted to transmit or convert a rotation of a first, second, and third coupling shafts 64a, 64b, and 64c of surgical instrument 100 into axial translation of an articulation driver or bar 258 of adapter 200, to effectuate articulation of end effector 500; a rotation of a ring gear 266 of adapter 200, to effectuate rotation of adapter 200; or axial translation of a distal drive member 248 of adapter 200 to effectuate closing, opening, and firing of end effector 500.

Still referring to FIG. 6, first force/rotation transmitting/converting assembly 240 includes first rotatable proximal drive shaft 212, which, as described above, is rotatably supported within inner housing assembly 204. First rotatable proximal drive shaft 212 includes a non-circular or shaped proximal end portion configured for connection with first connector sleeve 218 which is connected to respective first coupling shaft 64a of surgical instrument 100. First rotatable proximal drive shaft 212 includes a threaded distal end portion 212b. First force/rotation transmitting/converting assembly 240 further includes a drive coupling nut 244 that threadably engages the threaded distal end portion 212b of first rotatable proximal drive shaft 212, and which is slidably disposed within outer tube 206. Drive coupling nut 244 is slidably keyed within proximal core tube portion of outer tube 206 so as to be prevented from rotation as first rotatable proximal drive shaft 212 is rotated. In this manner, as the first rotatable proximal drive shaft 212 is rotated, drive coupling nut 244 is translated along threaded distal end portion 212b of first rotatable proximal drive shaft 212 and, in turn, through and/or along outer tube 206.

First force/rotation transmitting/converting assembly 240 further includes a distal drive member 248 that is mechanically engaged with drive coupling nut 244, such that axial movement of drive coupling nut 244 results in a corresponding amount of axial movement of distal drive member 248. The distal end portion of distal drive member 248 supports a connection member 247 configured and dimensioned for selective engagement with an engagement member 546 of a drive assembly 540 of end effector 500 (FIG. 10). Drive coupling nut 244 and/or distal drive member 248 function as a force transmitting member to components of end effector 500. In operation, as first rotatable proximal drive shaft 212 is rotated, as a result of the rotation of first coupling shaft 64a of surgical instrument 100, drive coupling nut 244 is translated axially along first rotatable proximal drive shaft 212. As drive coupling nut 244 is translated axially along first rotatable proximal drive shaft 212, distal drive member 248 is translated axially relative to outer tube 206. As distal drive member 248 is translated axially, with connection member 247 connected thereto and engaged with a hollow drive member 548 attached to drive assembly 540 of end effector 500 (FIG. 10), distal drive member 248 causes concomitant axial translation of drive assembly 540 of end effector 500 to effectuate a closure of a tool assembly portion 600 of the end effector 500 and a firing of various components within the tool assembly.

Still referring to FIG. 6, second drive converting assembly 250 of adapter 200 includes second proximal drive shaft 214 that is rotatably supported within inner housing assembly 204. Second rotatable proximal drive shaft 214 includes a non-circular or shaped proximal end portion configured for connection with second coupling shaft 64c of surgical instrument 100. Second rotatable proximal drive shaft 214 further includes a threaded distal end portion 214a configured to threadably engage an articulation bearing housing 253 of an articulation bearing assembly 252. Referring to FIGS. 6-9, the articulation bearing housing 253 supports an articulation bearing 255 that has an inner race 257 that is independently rotatable relative to an outer race 259. Articulation bearing housing 253 has a non-circular outer profile, for example tear-dropped shaped, that is slidably and non-rotatably disposed within a complementary bore (not shown) of inner housing hub 204a. Second drive converting assembly 250 of adapter 200 further includes articulation bar 258 that has a proximal portion that is secured to inner race 257 of articulation bearing 255. A distal portion of articulation bar 258 includes a slot 258a therein, which is configured to accept a hook 562 the articulation link 560 (FIG. 10) of end effector 500. Articulation bar 258 functions as a force transmitting member to components of end effector 500. In the illustrated arrangement and as further discussed in WO 2016/057225 A1, articulation bearing assembly 252 is both rotatable and longitudinally translatable and is configured to permit free, unimpeded rotational movement of end effector 500 when its first and second jaw members 610, 700 are in an approximated position and/or when jaw members 610, 700 are articulated.

In operation, as second proximal drive shaft 214 is rotated, the articulation bearing assembly 252 is axially translated along threaded distal end portion 214a of second proximal drive shaft 214, which in turn, causes articulation bar 258 to be axially translated relative to outer tube 206. As articulation bar 258 is translated axially, articulation bar 258, being coupled to articulation link 560 of end effector 500, causes concomitant axial translation of articulation link 560 of end effector 500 to effectuate an articulation of tool assembly 600. Articulation bar 258 is secured to inner race 257 of articulation bearing 253 and is thus free to rotate about the longitudinal axis relative to outer race 259 of articulation bearing 253.

As illustrated in FIG. 6, adapter 200 includes a third drive converting assembly 260 that is supported in inner housing assembly 204. Third drive converting assembly 260 includes rotation ring gear 266 that is fixedly supported in and connected to outer knob housing 202. Ring gear 266 defines an internal array of gear teeth 266a and includes a pair of diametrically opposed, radially extending protrusions 266b. Protrusions 266b are configured to be disposed within recesses defined in outer knob housing 202, such that rotation of ring gear 266 results in rotation of outer knob housing 202, and vice a versa. Third drive converting assembly 260 further includes third rotatable proximal drive shaft 216 which, as described above, is rotatably supported within inner housing assembly 204. Third rotatable proximal drive shaft 216 includes a non-circular or shaped proximal end portion that is configured for connection with third connector 220. Third rotatable proximal drive shaft 216 includes a spur gear 216 keyed to a distal end thereof. A reversing spur gear 264 inter-engages spur gear 216a of third rotatable proximal drive shaft 216 to gear teeth 266a of ring gear 266. In operation, as third rotatable proximal drive shaft 216 is rotated, due to a rotation of the third coupling shaft 64b of surgical instrument 100, spur gear 216a of third rotatable proximal drive shaft 216 engages reversing gear 264 causing reversing gear 264 to rotate. As reversing gear 264 rotates, ring gear 266 also rotates thereby causing outer knob housing 202 to rotate. Rotation of the outer knob housing 202 causes the outer tube 206 to rotate about longitudinal axis of adapter 200. As outer tube 206 is rotated, end effector 500 that is connected to a distal end portion of adapter 200, is also rotated about a longitudinal axis of adapter 200.

Figure 21:
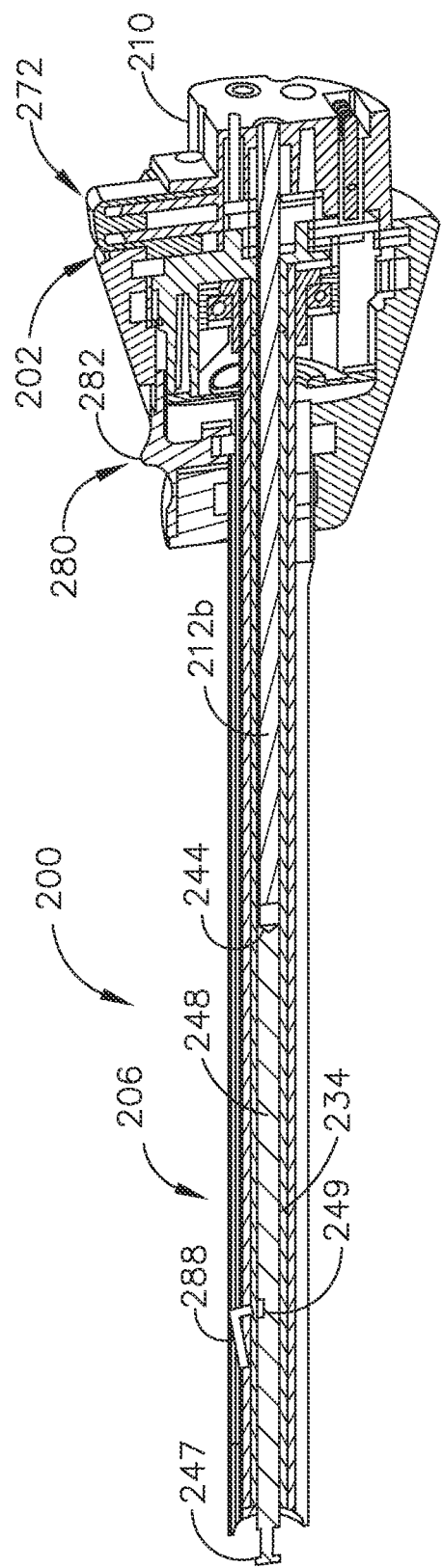
FIG. 21 is a cross-sectional view of another adapter.

Adapter 200 further includes an attachment/detachment button 272 (FIG. 5) that is supported on a stem 273 (FIG. 6) that projects from drive coupling assembly 210 of adapter 200. The attachment/detachment button 272 is biased by a biasing member (not shown) that is disposed within or around stem 273, to an un-actuated condition. Button 272 includes a lip or ledge that is configured to snap behind a corresponding lip or ledge of connecting portion 20 of the surgical instrument 100. As also discussed in WO 2016/057225 A1, the adapter 200 may further include a lock mechanism 280 for fixing the axial position of distal drive member 248. As can be seen in FIG. 21, for example, lock mechanism 280 includes a button 282 that is slidably supported on outer knob housing 202. Lock button 282 is connected to an actuation bar (not shown) that extends longitudinally through outer tube 206. Actuation bar moves upon a movement of lock button 282. In operation, in order to lock the position and/or orientation of distal drive member 248, a user moves lock button 282 from a distal position to a proximal position, thereby causing the lock out (not shown) to move proximally such that a distal face of the lock out moves out of contact with camming member 288, which causes camming member 288 to cam into recess 249 of distal drive member 248. In this manner, distal drive member 248 is prevented from distal and/or proximal movement. When lock button 282 is moved from the proximal position to the distal position, the distal end of actuation bar moves distally into the lock out (not shown), against the bias of a biasing member (not shown), to force camming member 288 out of recess 249, thereby allowing unimpeded axial translation and radial movement of distal drive member 248.

Returning again to FIG. 6, adapter 200 includes an electrical assembly 290 supported on and in outer knob housing 202 and inner housing assembly 204. Electrical assembly 290 includes a plurality of electrical contact blades 292, supported on a circuit board 294, for electrical connection to pass-through connector of plate assembly of shell housing 10 of surgical instrument 100. Electrical assembly 290 serves to allow for calibration and communication information (i.e., life-cycle information, system information, force information) to pass to the circuit board of surgical instrument 100 via an electrical receptacle portion of the power-pack core assembly 106 of surgical instrument 100. Electrical assembly 290 further includes a strain gauge 296 that is electrically connected to circuit board 294. Strain gauge 296 is mounted within the inner housing assembly 204 to restrict rotation of the strain gauge 296 relative thereto. First rotatable proximal drive shaft 212 extends through strain gauge 296 to enable the strain gauge 296 to provide a closed-loop feedback to a firing/clamping load exhibited by first rotatable proximal drive shaft 212. Electrical assembly 290 also includes a slip ring 298 that is non-rotatably and slidably disposed along drive coupling nut 244 of outer tube 206. Slip ring 298 is in electrical connection with circuit board 294 and serves to permit rotation of first rotatable proximal drive shaft 212 and axial translation of drive coupling nut 244 while still maintaining electrical contact of slip ring 298 with at least another electrical component within adapter 200, and while permitting the other electrical components to rotate about first rotatable proximal drive shaft 212 and drive coupling nut 244.

Still referring to FIG. 6, inner housing assembly 204 includes a hub 205 that has a distally oriented annular wall 207 that defines a substantially circular outer profile. Hub 205 includes a substantially tear-drop shaped inner recess or bore that is shaped and dimensioned to slidably receive articulation bearing assembly 252 therewithin. Inner housing assembly 204 further includes a ring plate 254 that is secured to a distal face of distally oriented annular wall 207 of hub 204a. Ring plate 254 defines an aperture 254a therethrough that is sized and formed therein so as to be aligned with second proximal drive shaft 214 and to rotatably receive a distal tip thereof. In this manner, the distal tip of the second proximal drive shaft 214 is supported and prevented from moving radially away from a longitudinal rotational axis of second proximal drive shaft 214 as second proximal drive shaft 214 is rotated to axially translate articulation bearing assembly 252.

Turning next to FIG. 10, in one example, the end effector 500 may be configured for a single use ("disposable loading unit—DLU") and be similar to those DLU's disclosed in U.S. Patent Application Publication No. 2010/0301097, entitled LOADING UNIT HAVING DRIVE ASSEMBLY LOCKING MECHANISM, now U.S. Pat. No. 9,795,384, U.S. Patent Application Publication No. 2012/0217284, entitled LOCKING MECHANISM FOR USE WITH LOADING UNITS, now U.S. Pat. No. 8,292,158, and U.S. Patent Application Publication No. 2015/0374371, entitled ADAPTER ASSEMBLIES FOR INTERCONNECTING SURGICAL LOADING UNITS AND HANDLE ASSEMBLIES, the entire disclosures of each such references being hereby incorporated by reference herein. It is also contemplated that the end effector 500 may be configured for multiple uses (MULU) such as those end effectors disclosed in U.S. Patent Application Publication No. 2017/0095250, entitled MULTI-USE LOADING UNIT, the entire disclosure of which is hereby incorporated by reference herein.

The depicted surgical instrument 100 fires staples, but it may be adapted to fire any other suitable fastener such as clips and two-part fasteners. In the illustrated arrangement, the end effector 500 comprises a loading unit 510. The loading unit 510 comprises a proximal body portion 520 and a tool assembly 600. Tool assembly 600 includes a pair of jaw members including a first jaw member 610 that comprises an anvil assembly 612 and a second jaw member 700 that comprises a cartridge assembly 701. One jaw member is pivotal in relation to the other to enable the clamping of tissue between the jaw members. The cartridge assembly 701 is movable in relation to anvil assembly 612 and is movable between an open or unclamped position and a closed or approximated position. However, the anvil assembly 612, or both the cartridge assembly 701 and the anvil assembly 612, can be movable.

The cartridge assembly 701 has a cartridge body 702 and in some instances a support plate 710 that are attached to a channel 720 by a snap-fit connection, a detent, latch, or by another type of connection. The cartridge assembly 701 includes fasteners or staples 704 that are movably supported in a plurality of laterally spaced staple retention slots 706, which are configured as openings in a tissue contacting surface 708. Each slot 706 is configured to receive a fastener or staple therein. Cartridge body 702 also defines a plurality of cam wedge slots which accommodate staple pushers 709 and which are open on the bottom (i.e., away from tissue-contacting surface) to allow an actuation sled 712 to pass longitudinally therethrough. The cartridge assembly 701 is removable from channel 720 after the staples have been fired from cartridge body 702. Another removable cartridge assembly is capable of being loaded onto channel 720, such that surgical instrument 100 can be actuated again to fire additional fasteners or staples. Further details concerning the cartridge assembly may be found, for example, in U.S. Patent Application Publication No. 2017/0095250 as well as various other references that have been incorporated by reference herein.

Cartridge assembly 701 is pivotal in relation to anvil assembly 612 and is movable between an open or unclamped position and a closed or clamped position for insertion through a cannula of a trocar. Proximal body portion 520 includes at least a drive assembly 540 and an articulation link 560. In one arrangement, drive assembly 540 includes a flexible drive beam 542 that has a distal end 544 and a proximal engagement section 546. A proximal end of the engagement section 546 includes diametrically opposed inwardly extending fingers 547 that engage a hollow drive member 548 to fixedly secure drive member 548 to the proximal end of beam 542. Drive member 548 defines a proximal porthole which receives connection member 247 of drive tube 246 of first drive converting assembly 240 of adapter 200 when the end effector 500 is attached to the distal end of the adapter 200.

End effector 500 further includes a housing assembly 530 that comprises an outer housing 532 and an inner housing 534 that is disposed within outer housing 532. First and second lugs 536 are each disposed on an outer surface of a proximal end 533 of outer housing 532 and are configured to operably engage the distal end of the adapter 200 as discussed in further detail in WO 2016/057225 A1.

With reference to FIG. 10, for example, anvil assembly 612 includes an anvil cover 630 and an anvil plate 620, which includes a plurality of staple forming depressions. Anvil plate 620 is secured to an underside of anvil cover 630. When tool assembly 600 is in the approximated position, staple forming depressions are positioned in juxtaposed alignment with staple receiving slots of the cartridge assembly 701.

The tool assembly 600 includes a mounting assembly 800 that comprises an upper mounting portion 810 and a lower mounting portion 812. A mounting tail 632 protrudes proximally from a proximal end 631 of the anvil cover 630. A centrally-located pivot member 814 extends from each upper and lower mounting portions 810 and 812 through openings 822 that are formed in coupling members 820. In at least one arrangement, the pivot member 814 of the upper mounting portion 810 also extends through an opening 634 in the mounting tail 632 as well. Coupling members 820 each include an interlocking proximal portion 824 that is configured to be received in corresponding grooves formed in distal ends of the outer housing 532 and inner housing 534. Proximal body portion 520 of end effector 500 includes articulation link 560 that has a hooked proximal end 562. The articulation link 560 is dimensioned to be slidably positioned within a slot in the inner housing. A pair of H-block assemblies 830 are positioned adjacent the distal end of the outer housing 532 and adjacent the distal end 544 of axial drive assembly 540 to prevent outward buckling and bulging of the flexible drive beam 542 during articulation and firing of surgical stapling apparatus 10. Each H-block assembly 830 includes a flexible body 832 which includes a proximal end fixedly secured to the distal end of the outer housing 532 and a distal end that is fixedly secured to mounting assembly 800. In one arrangement, a distal end 564 of the articulation link is pivotally pinned to the right H block assembly 830. Axial movement of the articulation link 560 will cause the tool assembly to articulate relative to the body portion 520.

Figure 11:
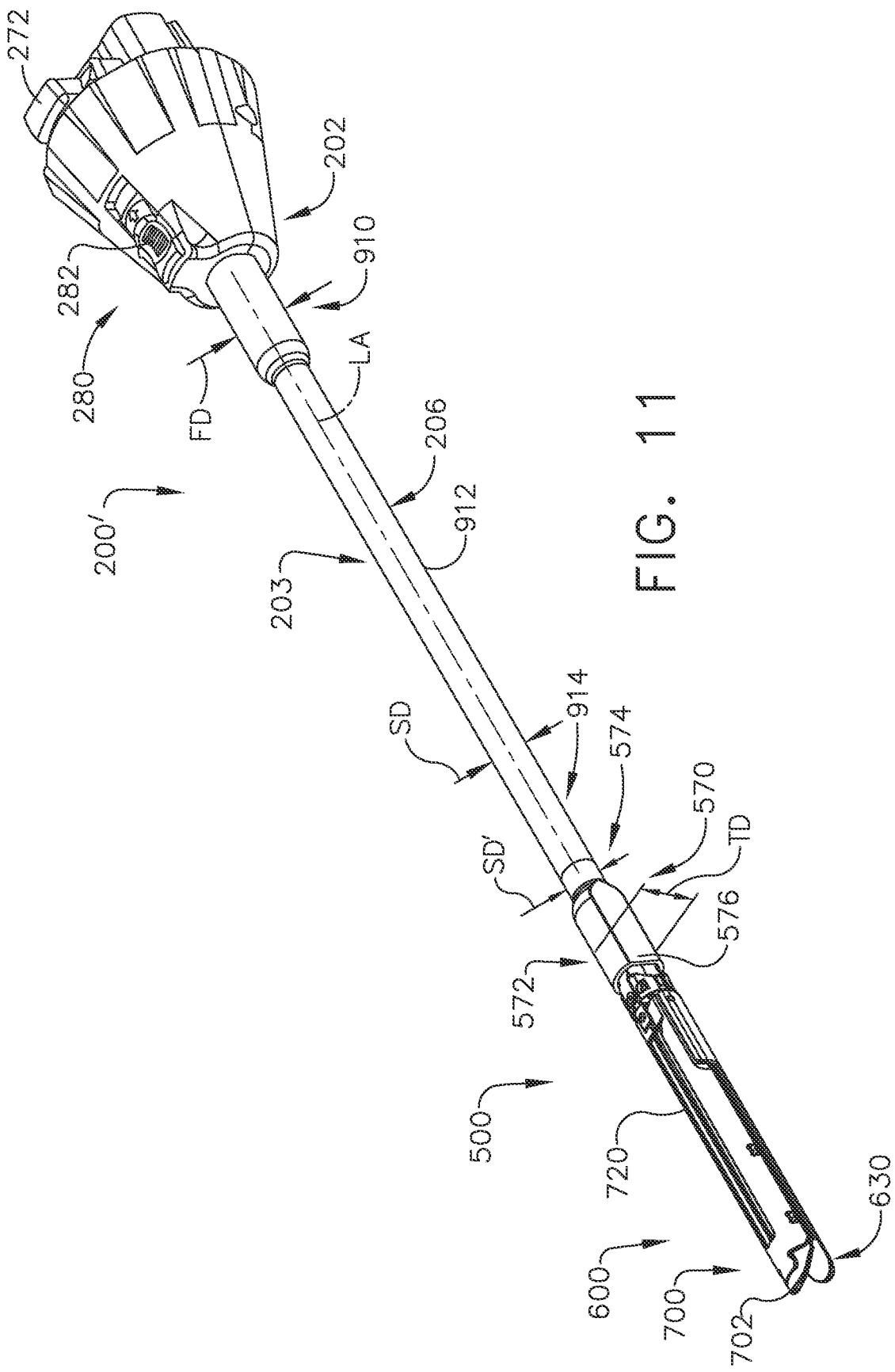
FIG. 11 is a perspective view of an alternative adapter embodiment.
Figure 12:
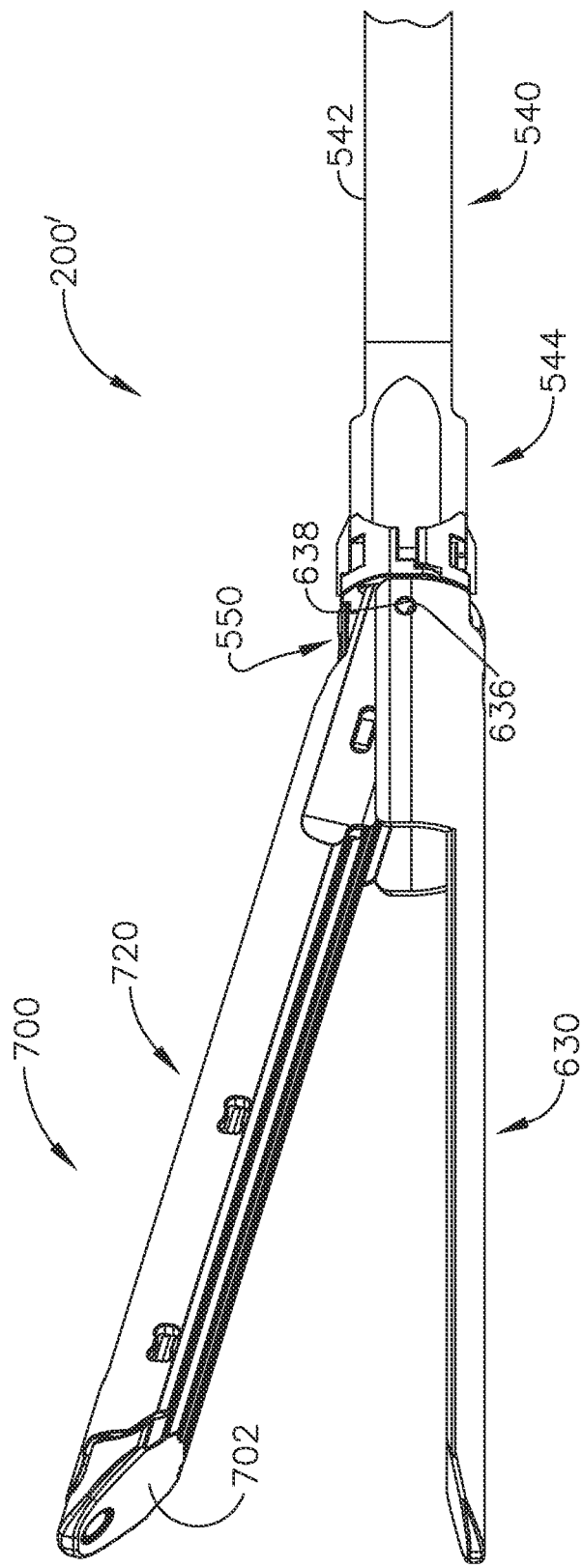
FIG. 12 is a side elevational view of a portion of a loading unit of the adapter of FIG. 11 with the jaws thereof in an open position.

FIGS. 11-15 illustrate an adapter 200' that is substantially identical to adapter 200 described above, except for the differences noted below. As can be seen in FIG. 11, the adapter 200' includes an outer tube 206 that has a proximal end portion 910 that has a first diameter "FD" and is mounted within the outer knob housing 202. The proximal end portion 910 may be coupled to the inner housing assembly 204 or otherwise supported therein in the manners discussed in further detail in WO 2016/057225 A1 for example. The proximal end portion 910 extends proximally from a central tube portion 912 that has a second diameter "SD". In the illustrated embodiment, an end effector 500 is coupled to a distal end 914 of a shaft assembly 203 or outer tube 206. The outer tube 206 defines a longitudinal axis LA that extends between the proximal end portion 910 and the distal end 914 as can be seen in FIG. 11. As can be seen in FIGS. 10 and 11, an outer sleeve 570 of the proximal body portion 520 of the end effector 500 has a distal end portion 572 and a proximal end portion 574. The proximal end portion 574 has a diameter SD' that is approximately equal to the second diameter SD of the central tube portion 912. The distal end portion 572 has a third diameter "TD". In one arrangement, FD and TD are approximately equal and greater than SD. Other arrangements are contemplated wherein FD and TD are not equal, but each are greater than SD. However, it is preferable that for most cases FD and TD are dimensioned for endoscopic insertion through a typical trocar port, cannula or the like. In at least one arrangement (FIG. 11), the outer sleeve 570 is formed with a flat or scalloped side 576 to facilitate improved access within the patient while effectively accommodating the various drive and articulation components of the adapter 200'. In addition, by providing the central tube portion 912 with a reduced diameter may afford the adapter 200' with improved thoracic in-between rib access.

In at least one arrangement, channel 720, which may be machined or made of sheet metal, includes a pair of proximal holes 722 (FIG. 10) that are configured to align with a pair of corresponding holes 636 in the anvil cover 630 to receive corresponding pins or bosses 638 (FIG. 12) to facilitate a pivotal relationship between anvil assembly 612 and cartridge assembly 701. In the illustrated example, a dynamic clamping assembly 550 is attached to or formed at the distal end 544 of the flexible drive beam 542. The dynamic clamping assembly 550 includes a vertical body portion 552 that has a tissue cutting surface 554 formed thereon or attached thereto. See FIG. 10, for example. An anvil engagement feature 556 is formed on one end of the body portion 552 and comprises an anvil engagement tab 557 that protrudes from each lateral side of the body portion 552. Similarly, a channel engagement feature 558 is formed on the other end of the of the body portion 552 and comprises a channel engagement tab 559 that protrudes from each lateral side of the body portion 552. See FIG. 15.

As indicated above, the anvil assembly 612 includes an anvil plate 620. The anvil plate 620 includes an elongate slot 622 that is configured to accommodate the body portion 552 of the dynamic clamping assembly 550 as the dynamic clamping assembly 550 is axially advanced during the firing process. The elongate slot 622 is defined between two anvil plate ledges 624 that extend along each lateral side of the elongate slot 622. See FIG. 10. As the dynamic clamping assembly 550 is distally advanced, the anvil engagement tabs 557 slidably engage the anvil plate ledges 624 to retain the anvil assembly 612 clamped onto the target tissue. Similarly, during the firing operation, the body portion 552 of the dynamic clamping assembly 550 extends through a central slot in the channel 720 and the channel engagement tabs 559 slidably engage channel ledges 725 extending along each side of the central channel slot to retain the cartridge assembly 701 clamped onto the target tissue.

Figure 13:
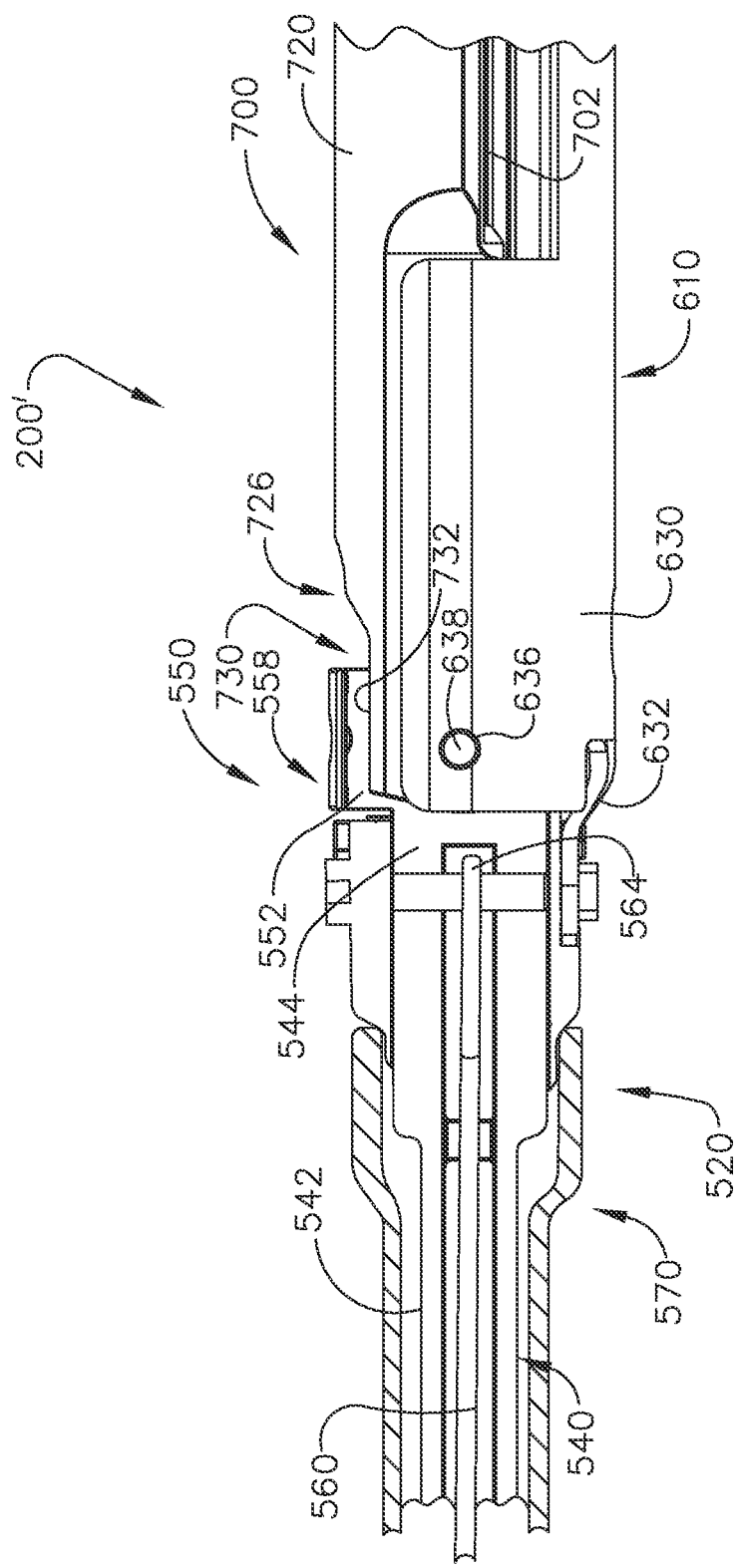
FIG. 13 is another side elevational view of a portion of the loading unit of FIG. 11 with portions thereof shown in cross-section and the jaws thereof in a closed position.
Figure 14:
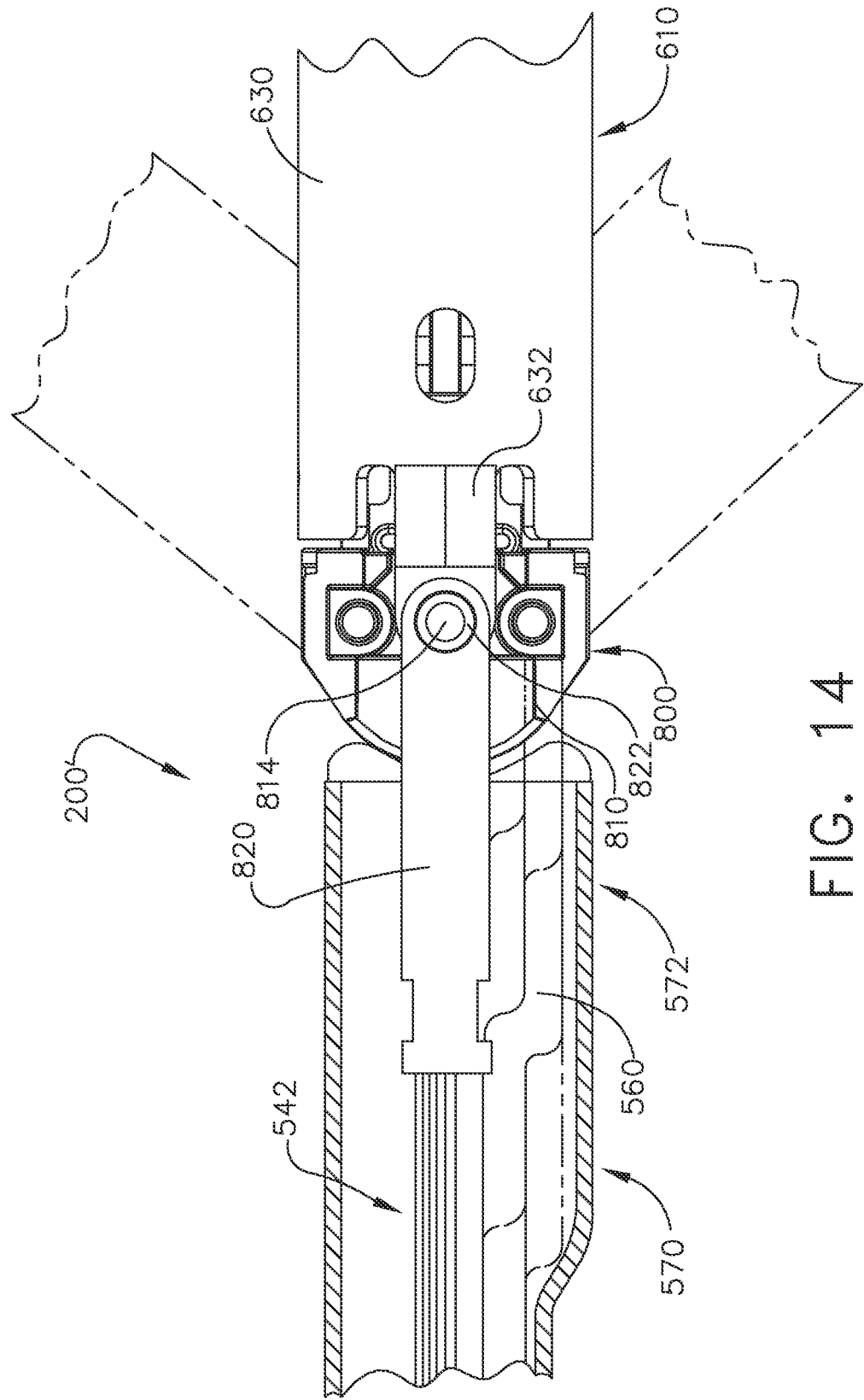
FIG. 14 is a bottom view of a portion of the loading unit of FIG. 13 with portions thereof shown in cross-section.
Figure 15:
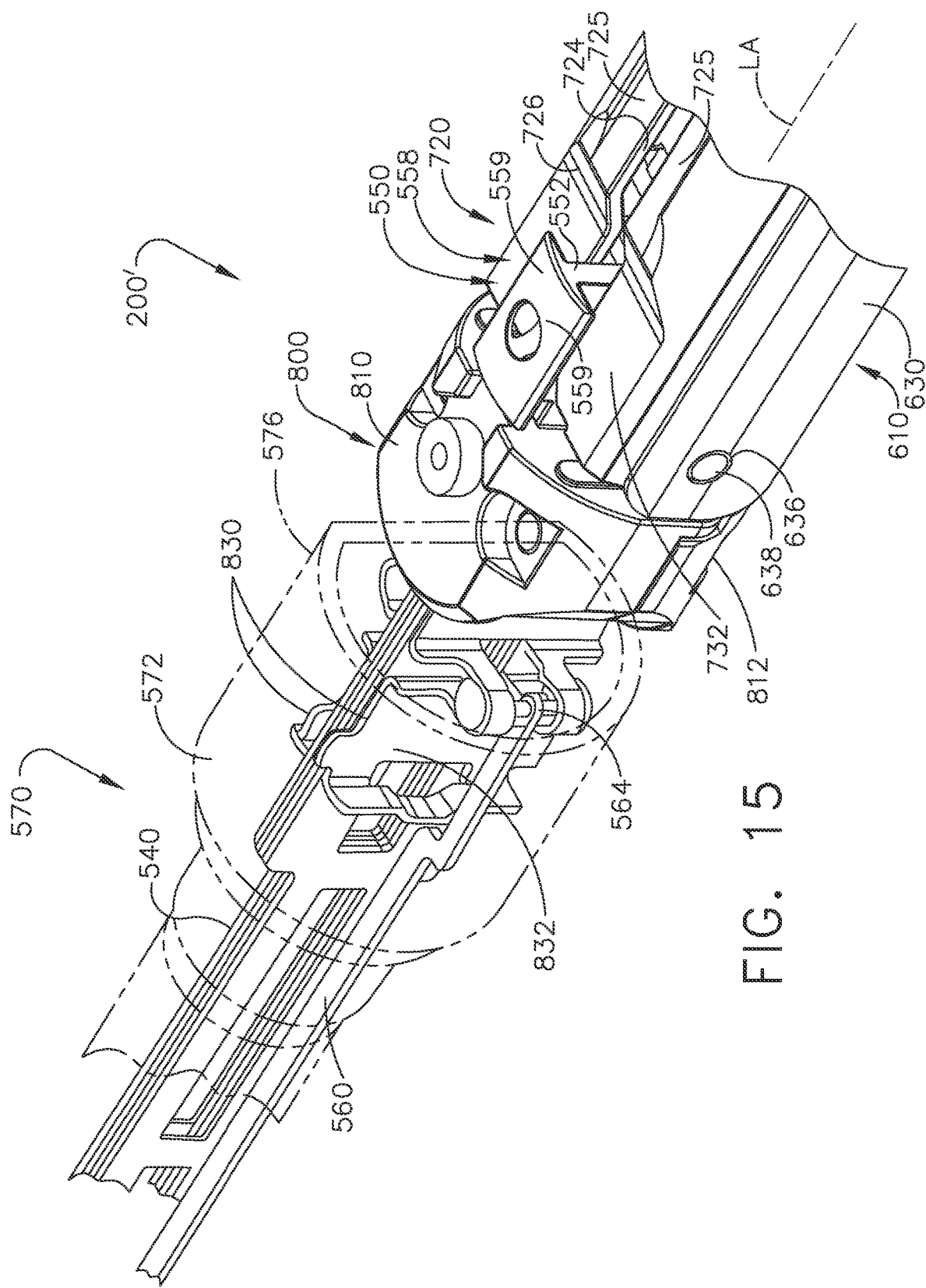
FIG. 15 is a perspective view of a portion of the loading unit of FIG. 14 with a portion of the outer tube shown in phantom lines.

Turning to FIGS. 13 and 15, the channel 720 defines a docking area generally designated as 730 that is configured to accommodate the dynamic clamping assembly 550 when it is in its proximal most position referred to herein as an unfired or starting position. In particular, the docking area 730 is partially defined by planar docking surfaces 732 that provides clearance between the channel engagement tabs 559 on the dynamic clamping assembly 550 to enable the cartridge assembly 701 to pivot to a fully opened position. A ramped or camming surface 726 extends from a distal end of each of the docking surfaces 732. Ramped surface 726 is engaged by the dynamic clamping assembly 550 in order to move the anvil assembly 612 and the cartridge assembly 701 with respect to one another. Similar camming surface could be provided on the anvil assembly 612 in other embodiments. It is envisioned that ramped surfaces 726 may also facilitate the alignment and/or engagement between channel 720 and support plate 620 and/or cartridge body 702. As the drive assembly 540 is distally advanced (fired), the channel engagement tabs 559 on the dynamic clamping assembly 550 engage the corresponding ramped surfaces 726 to apply a closing motion to the cartridge assembly 701 thus closing the cartridge assembly 701 and the anvil assembly 612. Further distal translation of the dynamic clamping assembly 550 causes the actuation sled 712 to move distally through cartridge body 702, which causes cam wedges 713 of actuation sled 712 to sequentially engage staple pushers 709 to move staple pushers 709 vertically within staple retention slots 706 and eject staples 704 into staple forming depressions of anvil plate 620. Subsequent to the ejection of staples 704 from retention slots 706 (and into tissue), the cutting edge 554 of the dynamic clamping assembly 550 severs the stapled tissue as the tissue cutting edge 554 on the vertical body portion 552 of the dynamic clamping assembly 550 travels distally through a central slot 703 of cartridge body 702. After staples 704 have been ejected from cartridge body 702 and a user wishes to use the same instrument 10 to fire additional staples 704 (or another type of fastener or knife), the user can remove the loading unit 510 from the adapter 200' and replace it with another fresh or unspent loading unit. In an alternative arrangement, the user may simply remove the spent cartridge body 702 and replace it with a fresh unspent or unfired cartridge body 702.

During use of conventional adapters, debris and body fluids can migrate into the outer tube of the adapter and detrimentally hamper the operation of the adapter articulation and firing drive systems. In egregious cases, such debris and fluids infiltrate into the inner housing assembly of the adapter which may cause the electrical components supported therein to short out and malfunction. Further, due to limited access to the interior of the outer tube of the adapter, such debris and fluids are difficult to remove therefrom which can prevent or reduce the ability to reuse the adapter.

Figure 16:
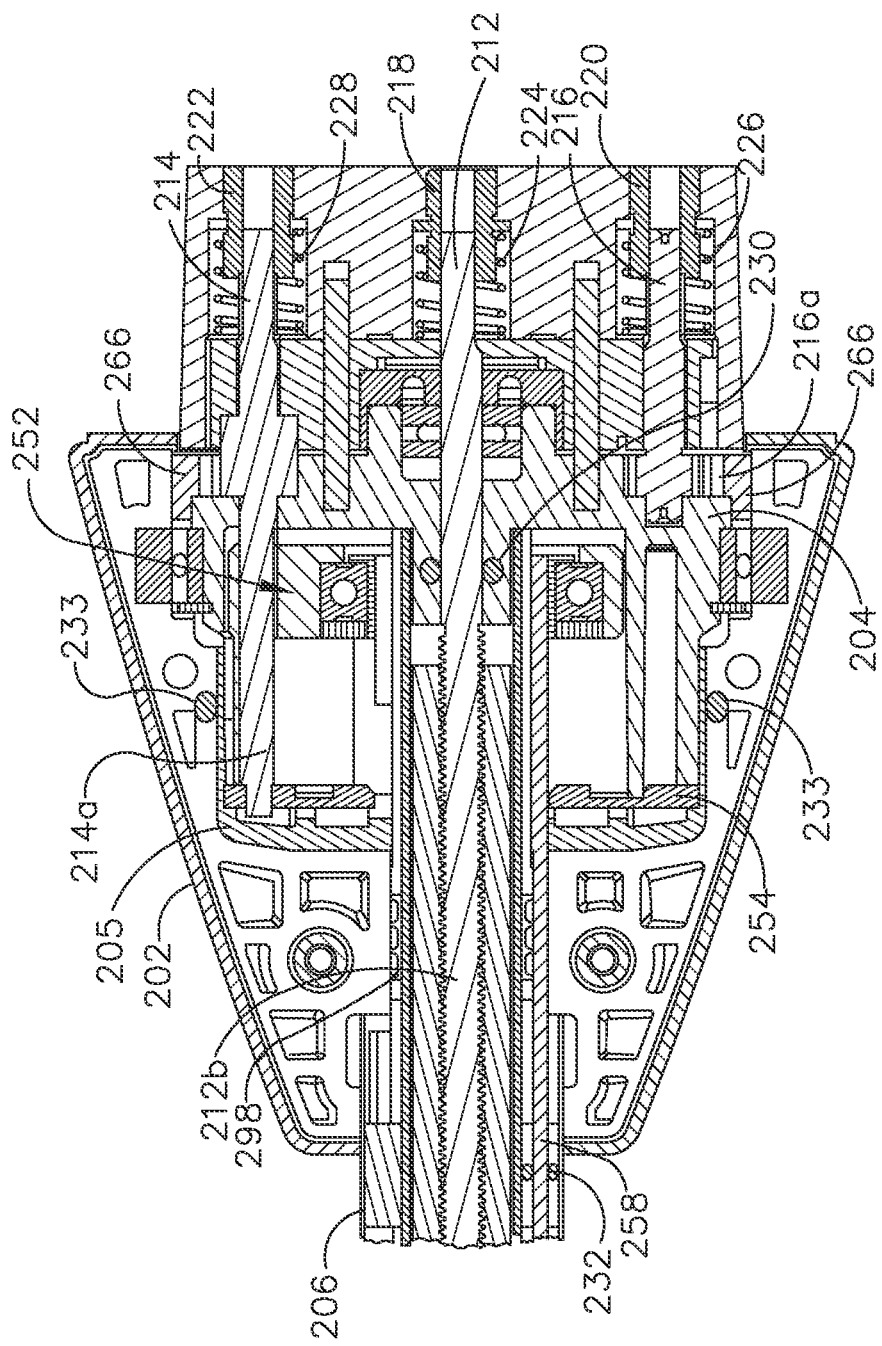
FIG. 16 is a cross-sectional view of a proximal portion of another adapter employing various seal arrangements therein.
Figure 17:
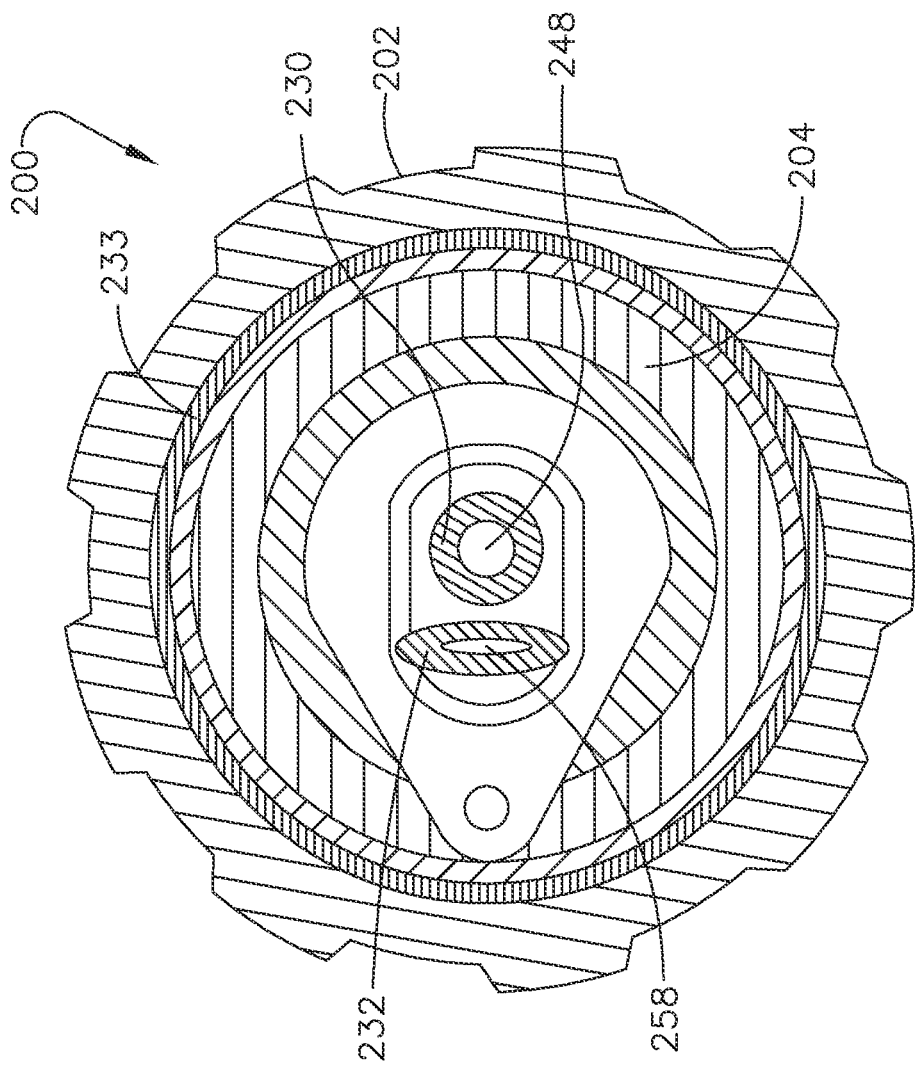
FIG. 17 is an end cross-sectional view of a portion of the adapter of FIG. 16.

Turning to FIGS. 16 and 17, in one arrangement, at least one first seal 230 is provided between the proximal inner housing assembly 204 and the first rotatable proximal drive shaft 212 to prevent fluid/debris infiltration within and proximal to the proximal inner housing assembly 204. In addition, at least one second seal 232 is provided between the articulation bar 258 and the outer tube 206 to prevent fluid/debris from passing therebetween to enter the proximal inner housing assembly 204. At least one third housing seal 233 may be provided around a hub 205 of the proximal inner housing 204 to establish a seal between the hub 205 and the outer knob housing 202. The first, second, and third seals 230, 232, 233 may comprise, for example, flexible O-rings manufactured from rubber or other suitable material.

Figure 20:
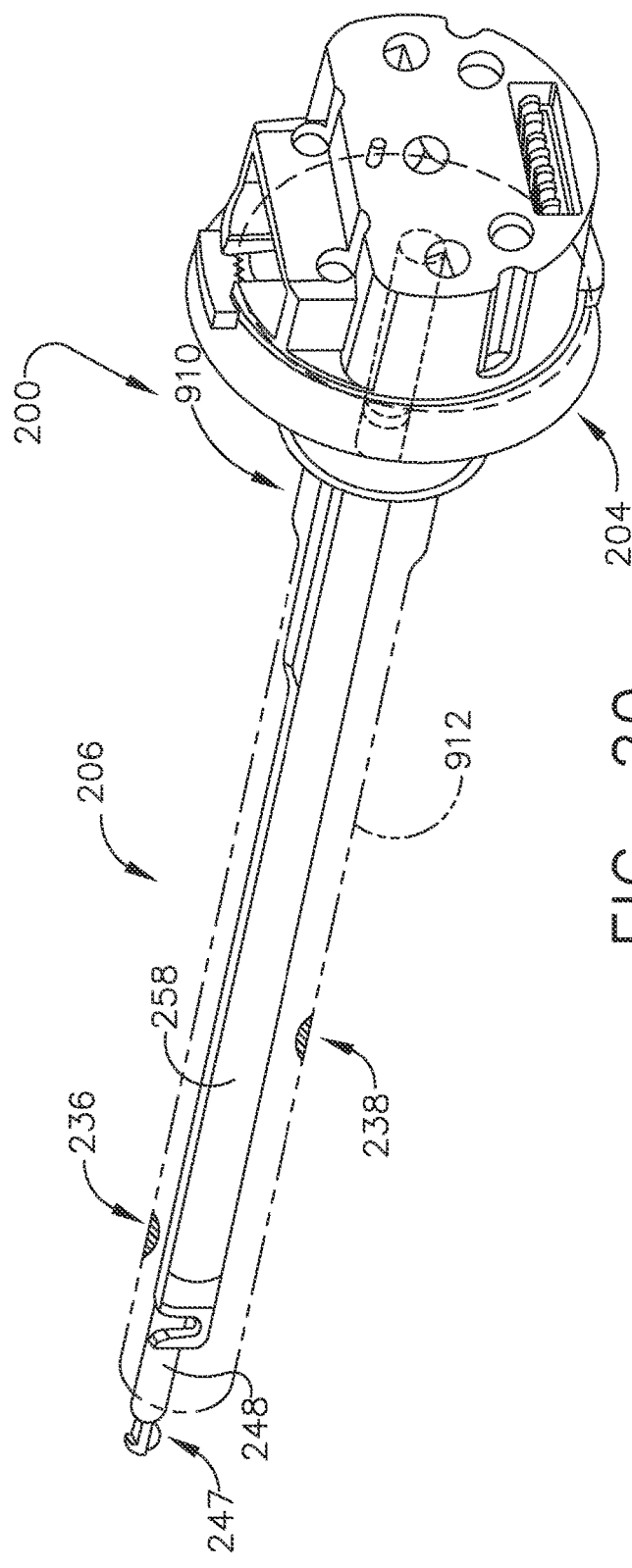
FIG. 20 is a rear perspective view of portions of another adapter.
Figure 18:
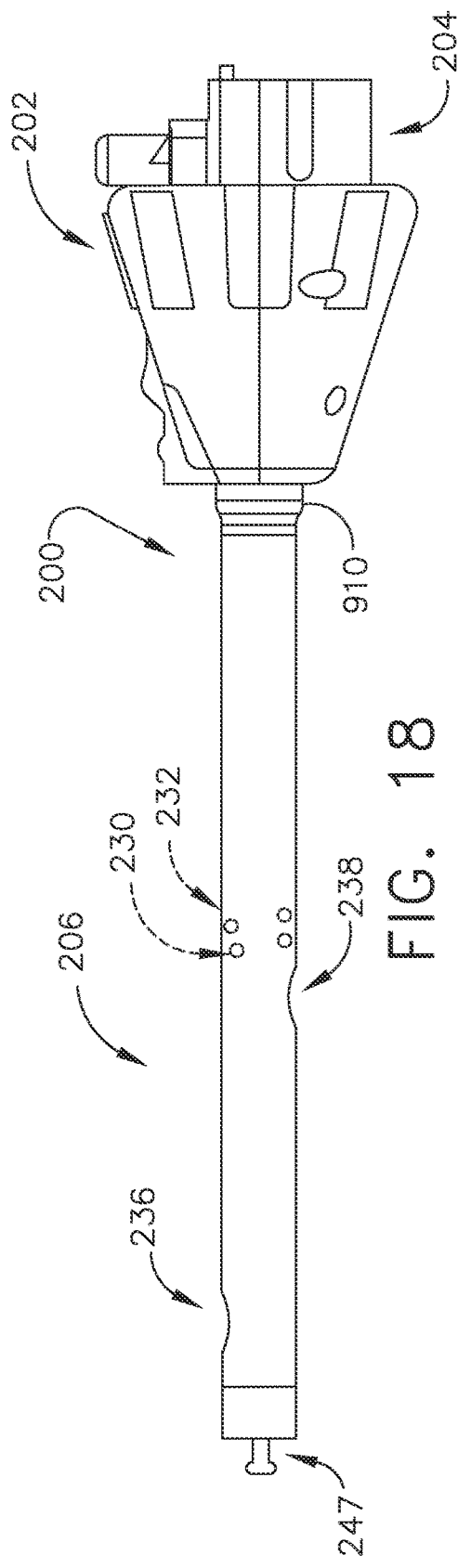
FIG. 18 is a side elevation al view of another adapter.
Figure 19:
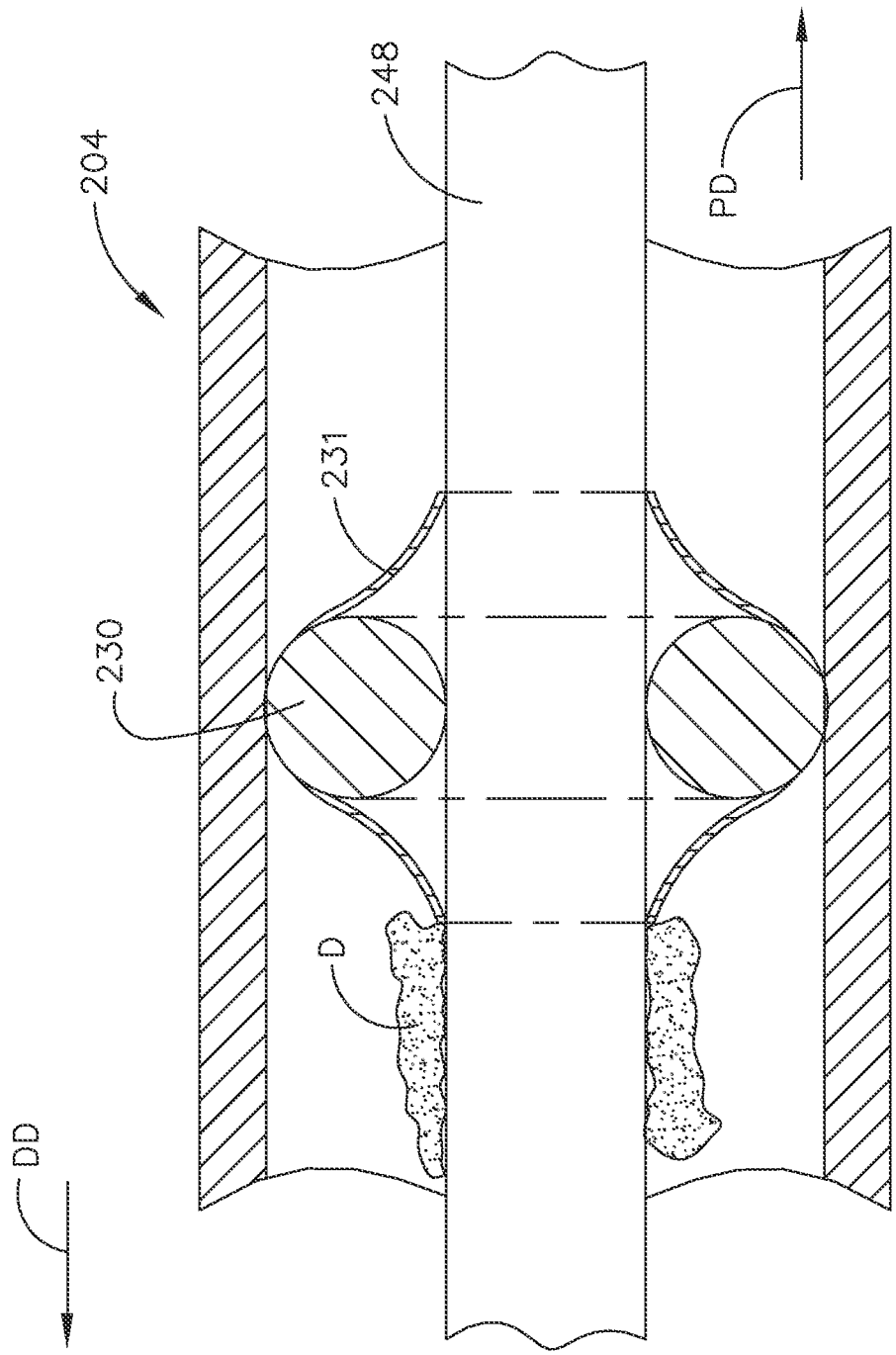
FIG. 19 is a cross-sectional view of a portion of the adapter of FIG. 18.

In other arrangements, it may be desirable for the first and second seals 230, 232 to be located in the adapter 200 distal to the electronic components housed within the outer knob housing 202. For example, to prevent fluids/debris from fouling/shorting the slip ring assembly 298, it is desirable establish seals between the various moving components of the adapter 200 that are operably supported within the outer tube 206 in a location or locations that are each distal to the slip ring assembly 298, for example. The seals 230, 232 may be supported in the wall of the outer tube and/or in mounting member 234 or other separate mounting member/bushing/housing supported within the outer tube 206 and configured to facilitate axial movement of the distal drive member 248 as well as the articulation bar 258 while establishing a fluid-tight seal between the bushing and/or outer tube and the distal drive member 248 and the articulation bar 258. See FIGS. 18 and 20. In the embodiment illustrated in FIG. 19 for example, the first seal 230 may additionally have wiper features 231 that also slidably engage the distal drive member 248 to prevent fluid/debris D from infiltrating in the proximal direction PD into the proximal inner housing assembly 204. In at least one arrangement to enable debris and fluids that have collected in the outer tube 206 distal to the first and second seals 230, 232, at least two flushing ports 236, 238 are provided within the outer tube 206. See e.g., FIGS. 18 and 20. The axially spaced flushing ports 236, 238 are located distal to the first and second seals 230, 232. A flushing solution (e.g., cleaning fluid, saline fluid, air, etc.) may be entered into one or more port(s) to force the errant debris and fluid out of one or more other port(s).

The ability to open the jaws of an endocutter to a large angle enables more tissue to be placed between them. In addition, having the ability to open the jaws to a larger angle also makes it easier for a user to remove the tissue from between the jaws after the stapling process has been completed which helps to simplify the cartridge reloading process when reloadable units are employed. Thus, it is desirable to optimize the speeds and forces required to open the jaws of an end effector such as an endocutter. In the past, a variety of methods have been employed to open the jaws of an endocutter. In one arrangement, a spring was employed to apply a biasing opening force to the jaws. However, such spring opening arrangements may increase the amount of forces needed to close the jaws. They may also have relatively limited motion and can be difficult to install within the end effector.

FIGS. 22-25 illustrate use of an alternative channel 720' of a second jaw 700'. The channel 720' may be identical to channel 720 described above, except for the differences noted below. In the illustrated arrangement, for example, the channel 720' includes a positive channel opening feature 740 that comprises a ramp surface 742 that is located on each side of a central slot 724 in the channel 720'. Each ramp 742 terminates in a planar upper surface 744. As can be further seen in FIG. 22, a channel ledge 725 is formed on each side of the elongate central slot 724 on the top side of the channel 720'. During the firing operation, the body portion 552 of the dynamic clamping assembly 550 extends through the central slot 724 and the channel engagement tabs 559 slidably engage the channel ledges 725 extending along each side of the central slot 724 to retain the cartridge assembly 701 clamped onto the target tissue.

Figure 22:
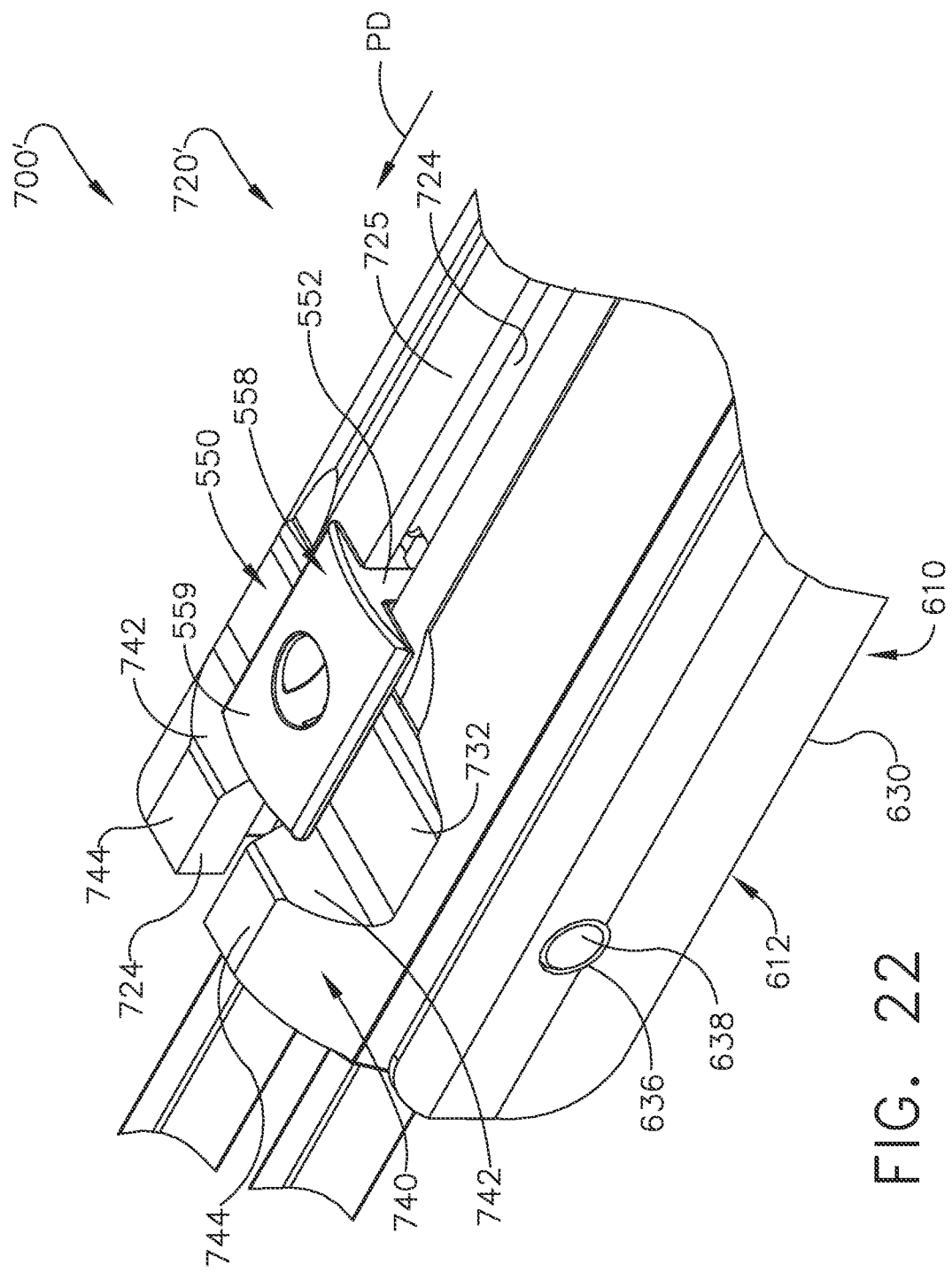
FIG. 22 is a perspective view of a portion of another loading unit of an adapter with the jaws thereof in a closed position.
Figure 23:
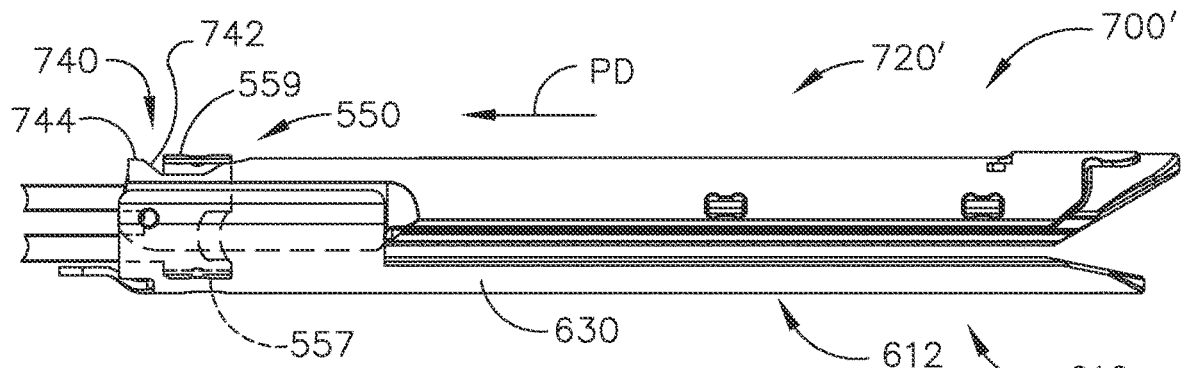
FIG. 23 is a side elevational view of the loading unit of FIG. 22.
Figure 25:
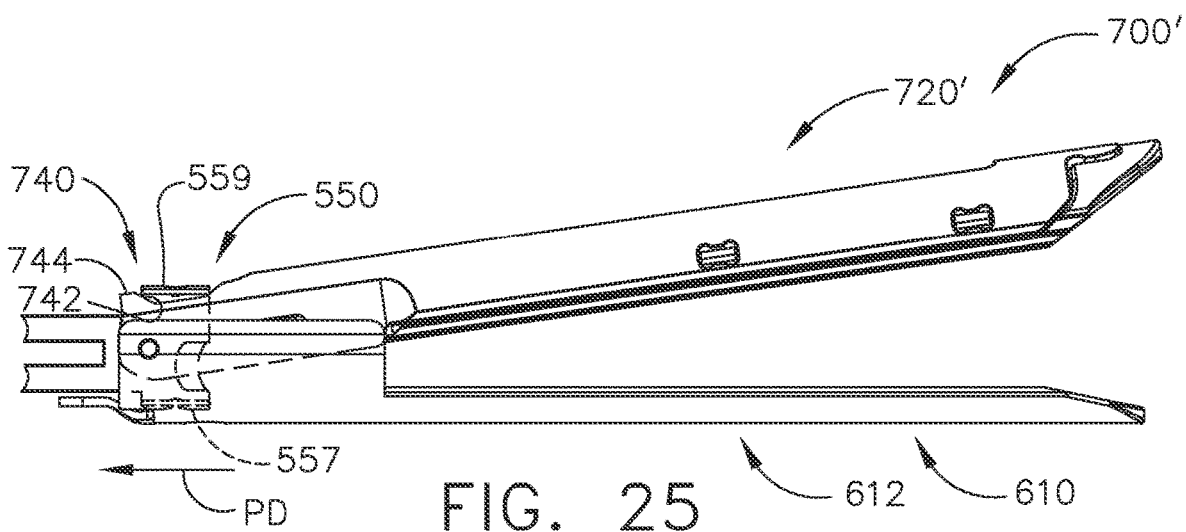
FIG. 25 is a side elevational view of the loading unit of FIG. 24.
Figure 26:
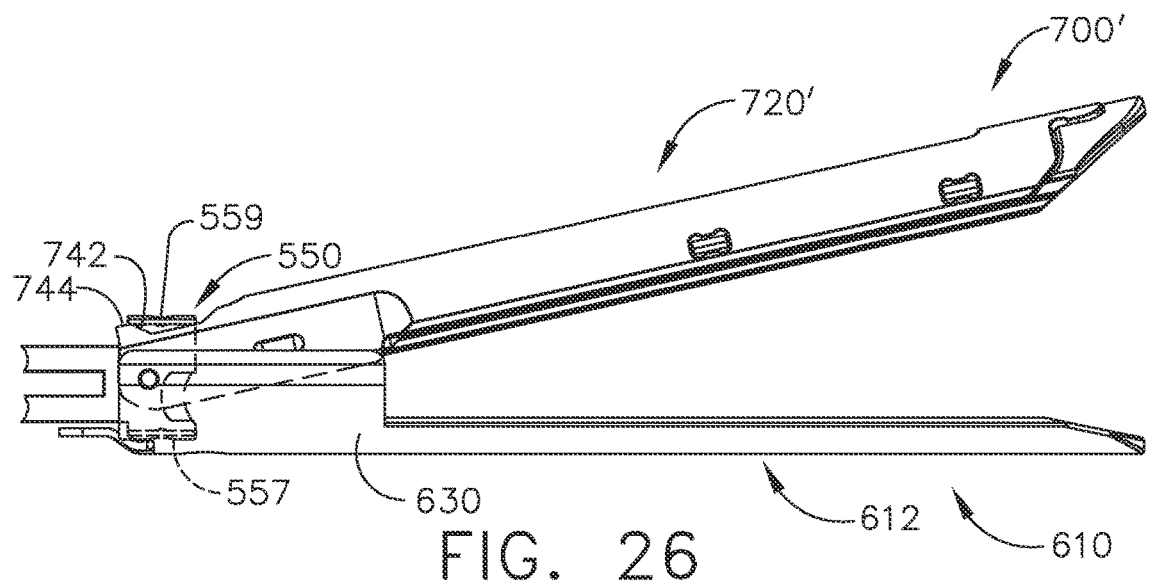
FIG. 26 is another side elevational view of the loading unit of FIGS. 22-25 with the jaws thereof in a fully open position.
Figure 24:
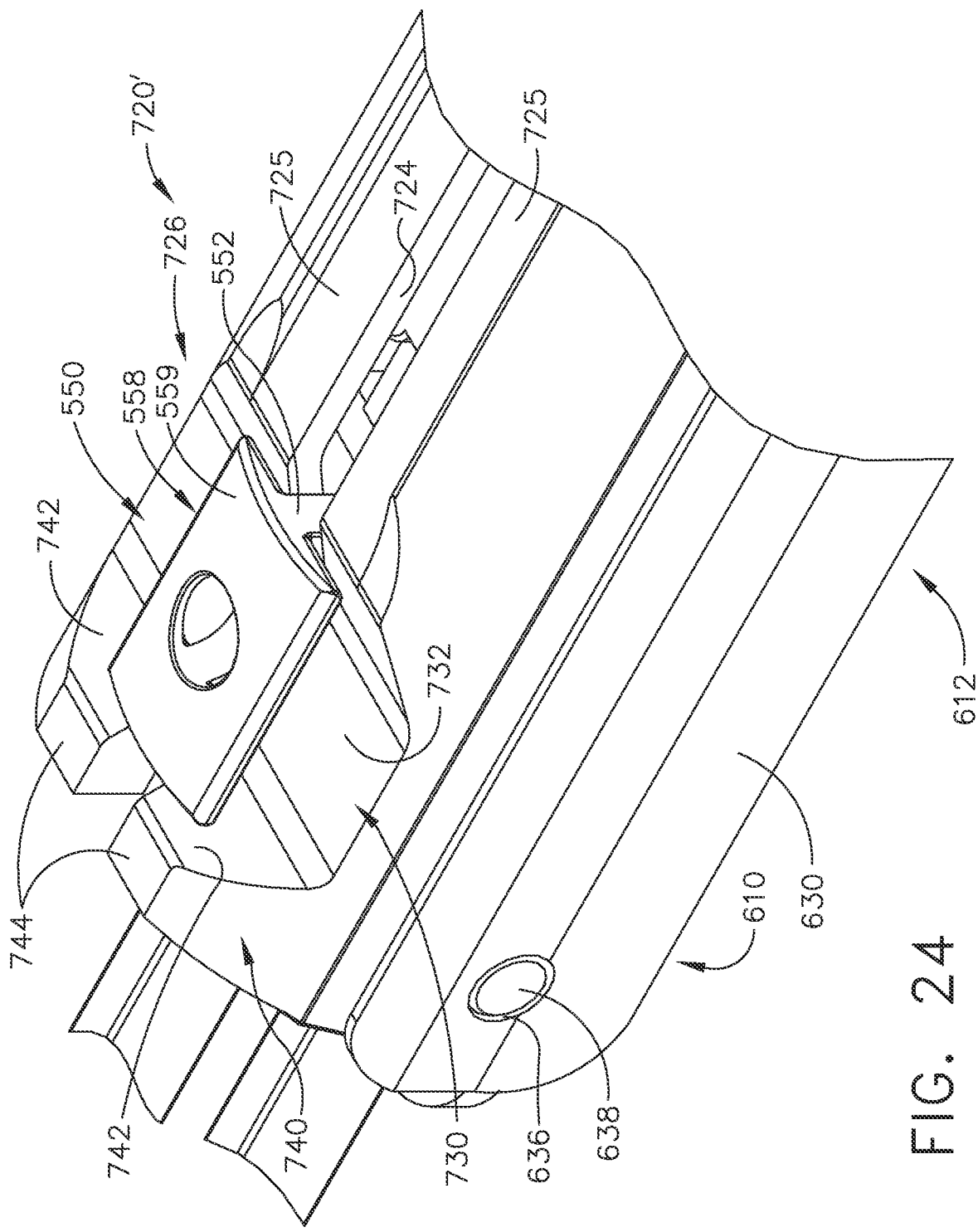
FIG. 24 is a perspective view of the loading unit of FIG. 23 after the dynamic clamping assembly has initially contacted positive channel opening features on a channel of the dynamic loading unit.

FIGS. 22 and 23 illustrate a position of the dynamic clamping assembly 550 as it is retracted in the proximal direction PD. As can be seen in those Figures, the channel engagement tabs 559 have not yet contacted the ramps 742 of the positive channel opening features 740. FIGS. 24 and 25 illustrate initial contact of the channel engagement tabs 559 with the ramp portions 742 of the corresponding positive channel opening features 740. As can be seen in FIG. 25 the channel 720' has started to open (i.e., move away from the anvil assembly 612). FIG. 26 illustrates the position of the dynamic clamping assembly 550 in its starting position wherein the channel 720' is in its fully open position. As can be seen in that Figure, for example, the channel engagement tabs 559 are in engagement with the planar upper surfaces 744 of the ramps 742. Such arrangement may be employed to open the jaws (anvil assembly 612 and cartridge assembly 701) without the use of a spring or springs. However, other variations are contemplated wherein an opening spring is also employed in addition to the positive channel opening features 740.

Figure 27:
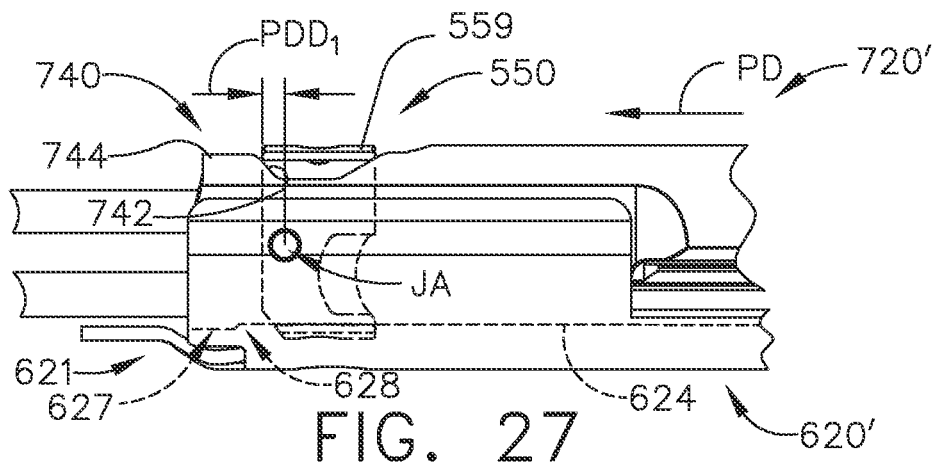
FIG. 27 is a side elevational view of a portion of another loading unit of an adapter with the jaws thereof in a fully closed position.
Figure 28:
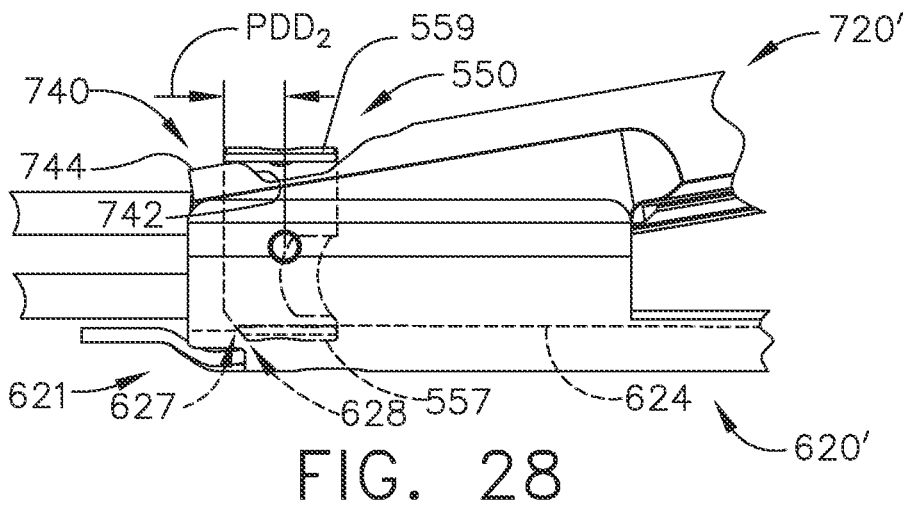
FIG. 28 is another side elevational view of the loading unit of FIG. 27 with the jaws thereof in a partially open position.
Figure 29:
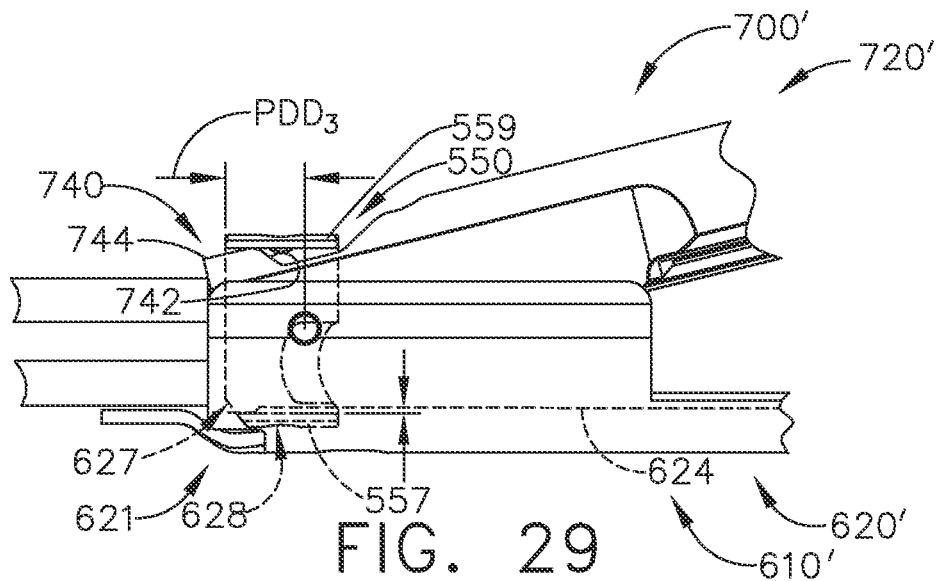
FIG. 29 is another side elevational view of the loading unit of FIGS. 27 and 28 with the jaws thereof in a fully open position.

FIGS. 27-29 illustrate an alternative arrangement where, in addition to the positive channel opening features 740 on the channel 720', positive anvil opening features 627 are provided on a proximal end 621 of the anvil plate 620'. The anvil plate 620' may be identical to anvil plate 620 described above, except for the differences noted below. The positive anvil opening features 627 each comprise an anvil opening ramp 628 provided on each side of the elongate slot 622 (see FIG. 10). As discussed above, the anvil plate has an elongate slot 622 that defines two elongate ledges 624 upon which anvil engagement tabs 557 of the dynamic clamping assembly 550 ride. The positive channel opening features 740 on the channel 720' are longitudinally offset from the positive anvil opening features 627 on the anvil plate 620'. In the illustrated example, the positive channel opening features 740 on the channel 720' are distal to the positive anvil opening features 627 on the anvil plate 620'. FIG. 27 illustrates initial contact of the channel engagement tabs 559 with the ramp surfaces 742 of the positive channel opening features 740. For reference purposes, the distance between the distal edge of each channel engagement tab 559 and the jaw axis JA is labeled as distance $PDD_1$. FIG. 28 illustrates the position of the dynamic clamping assembly 550 after the channel engagement tabs 559 have moved up the ramps 742 onto the planar upper surfaces 744 of the positive channel opening features 740. When in that position, the anvil engagement tabs 557 on the dynamic clamping assembly 550 have contacted the anvil opening ramps 628 of the anvil opening features 627. Thus, comparing the proximal travel distance of the dynamic clamping assembly between FIGS. 27 and 28: $PDD_2 > PDD_1$. FIG. 29 illustrates position of the dynamic clamping assembly 550 after it has moved back to its starting position and the anvil engagement tabs 557 on the dynamic clamping assembly 550 have completely moved past the anvil opening ramps 628 of the anvil opening features 627 and the jaws 700' and 610' are in their fully open positions. Thus, comparing the proximal travel distance of the dynamic clamping assembly between FIGS. 28 and 29: $PDD_3 > PDD_2$. Such positive jaw opening features 740, 627 use either/both longitudinal forces to drive the opening of the jaws or orthogonal forces to drive the opening motions. In the above described example, the positive jaw opening features are longitudinally offset. In other arrangements, however, the anvil engagement tabs 557 contact the ramps 628 at approximately the same time that the tabs 559 contact the ramps 742.

Figure 32:
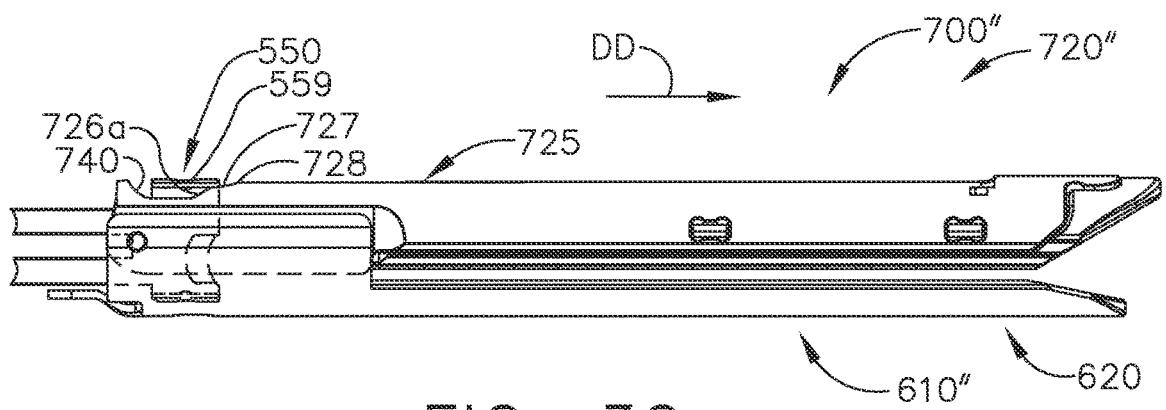
FIG. 32 is another side elevational view of the loading unit of FIGS. 30 and 31, with the jaws thereof in a closed position prior to initiation of a firing stroke.
Figure 31:
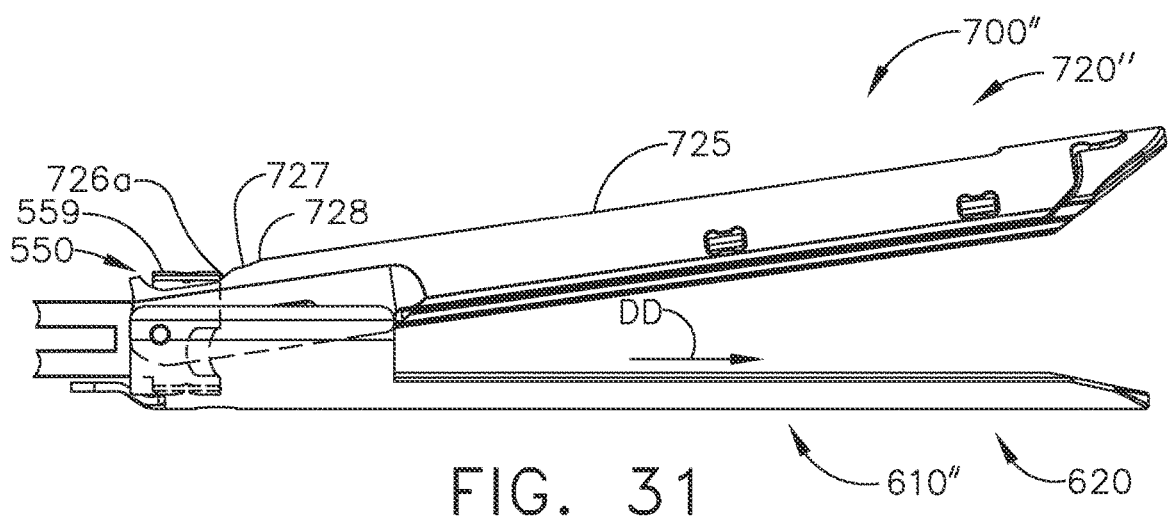
FIG. 31 is another side elevational view of the loading unit of FIG. 30, with the jaws thereof in a partially closed position.
Figure 30:
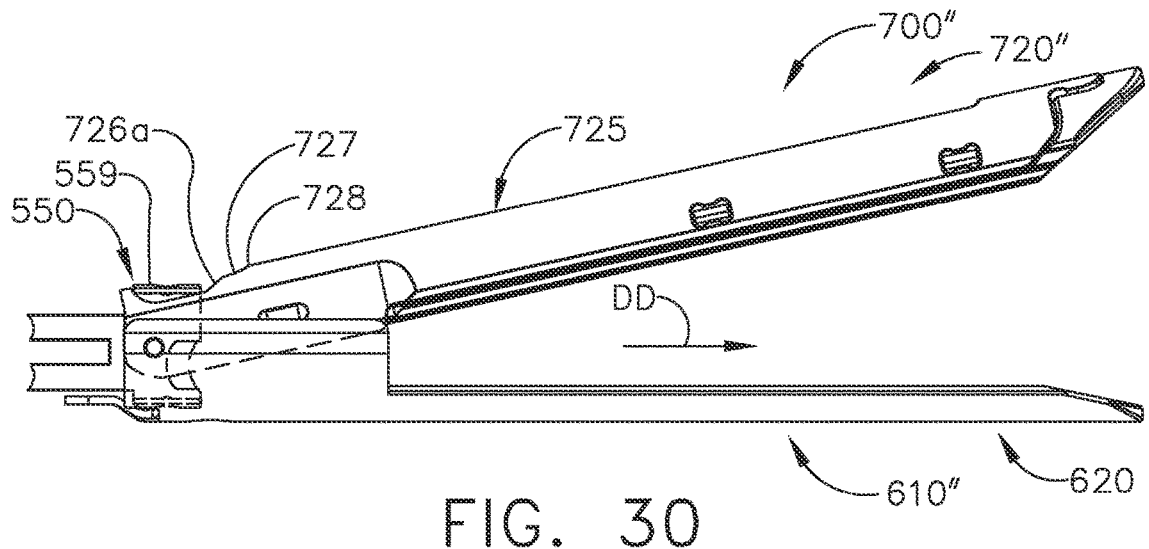
FIG. 30 is a side elevational view of a portion of another loading unit of an adapter with the jaws thereof in a fully open position.

Another feature employed by a channel 720" relates to closure ramps formed on the channel 720". The channel 720" may be identical to channel 720' or 720 described above, except for the differences noted below. As can be seen in FIGS. 30-32, for example, a first closure ramp segment 726a is formed on each side of the elongate slot (not shown) in the channel 720". Each first closure ramp segment 726a transitions into a horizontal plateau ramp segment 727 which in turn transitions into a second closure ramp segment 728. Each second closure ramp segment 728 transitions to a corresponding channel ledge 725. In one arrangement, the slope of each of the first closure ramp segments 726a is the same as the slope of the second closure ramp segments 728. In other arrangements, the slopes are different. FIG. 30 illustrates the position of the channel engagement tabs 559 on the dynamic clamping assembly 550 when the jaws 610", 700" are in their fully open position. FIG. 31 illustrates a position of the dynamic clamping assembly 550 after it has been moved distally so as to bring the channel engagement tabs 559 into sliding engagement with the proximal closure ramp segments 726a so as to begin the jaw closure process. FIG. 32 illustrates another position of the dynamic clamping assembly 550 after it has further moved in the distal direction DD so as to bring the channel engagement tabs 559 into sliding engagement with the plateau ramp segment 727 and prior to starting a firing stroke wherein the channel engagement tabs 559 slidably engage the channel ledges 725 on the channel 720".

Another desirable attribute for surgical end effectors relates to "jaw aperture". "Jaw aperture" may refer to the angle between a staple forming surface on the anvil plate and a tissue contacting surface of the staple cartridge. In existing versions of DLU's, SULU's and MULU's, the upper channel engagement feature or tab on the dynamic clamping unit, when the dynamic clamping unit is in its proximal most or starting position, is generally positioned directly above or distal to a jaw pivot axis about which the cartridge assembly pivots relative to the anvil assembly. Such arrangements commonly limit the jaws from opening relative to each other more than 18-23 mm, for example.

Figure 33:
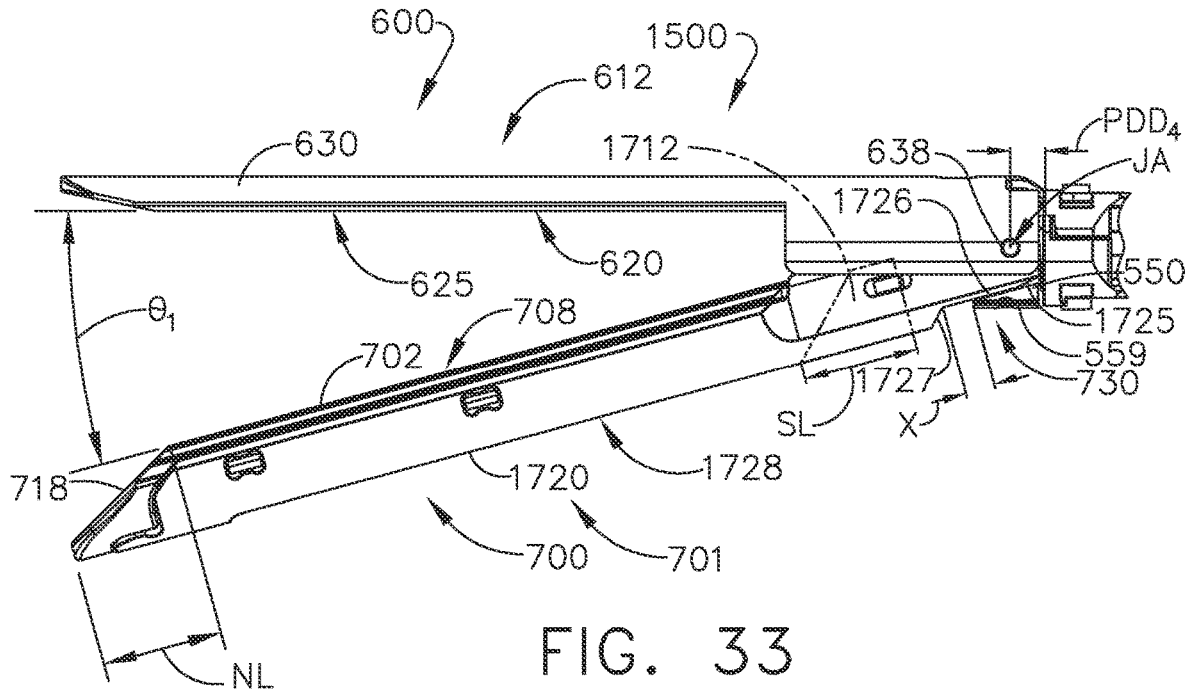
FIG. 33 is a side elevational view of a portion of another loading unit of an adapter with the jaws thereof in a fully open position.

One aspect of the present disclosure involves the formation of a "docking" or "parking" area for the dynamic clamping member when the dynamic clamping member is in its proximal most or starting position. For example, FIG. 33 illustrates an end effector 1500 that includes a parking or docking area 730 for the dynamic clamping assembly 550 when the dynamic clamping assembly 550 is in its proximal most or starting position. In accordance with another aspect, as was described above, the dynamic clamping assembly 550 includes a vertically extending body portion 552 and has an anvil engagement feature 556 that comprises an anvil engagement tab or flange 557 that extends from each lateral side of the body portion 552. In addition, the dynamic clamping assembly 550 includes a channel engagement feature 558 that comprises a channel engagement tab or flange 559 that extends laterally from each lateral side of the body portion 552. As used in this context, the term "flange" connotes a planar feature that extends transversely or perpendicularly from the body portion 552. As such, when viewed from an end, the dynamic clamping assembly 550 resembles an I-beam configuration and may be referred to herein as a dynamic I-beam clamping member. As can be seen in FIG. 33, a portion of the channel engagement flanges 559 extend proximal of the pin 638 that pivotally couples the cartridge assembly 701 to the anvil assembly 612 and which defines a jaw pivot axis JA about which the anvil and channel may move between open and closed positions. In addition, although not viewable in FIG. 33, in at least one arrangement, a portion of each of the anvil engagement flanges 557 also extends proximal to the jaw pivot axis JA when the dynamic I-beam clamping assembly 550 is in the parking or starting position. This distance is labeled as distance "$PDD_4$" in FIG. 33, for example.

A lower end of the body portion 552 of the dynamic I-beam clamping assembly 550 extends through an elongate slot (not shown) in the channel 1720. A first lower surface 1726 is formed on a proximal end 1725 of the channel 1720 on each side of the elongate slot. Each first lower surface 1726 terminates distally in a second closure cam surface or ramp 1727 that corresponds to each channel engagement flange 559 on the dynamic I-beam clamping assembly 550. When the channel engagement flanges 559 engage their corresponding second closure cam surface 1727, the cartridge assembly and the anvil assembly 612 start to close or pivot toward each other by virtue of the interaction of the anvil engagement flanges with corresponding surfaces on the anvil plate and the camming action of the channel engagement tabs with the corresponding second closure cam surfaces 1727 on the channel 1720. Once the dynamic I-beam clamping assembly 550 has moved distally to a point wherein the channel engagement flanges 559 disengage the second closure cam surfaces 1727, the channel engagement flanges 559 engage corresponding third closure surfaces 1728 on the bottom of the channel 1720 to keep the anvil assembly and cartridge assembly closed and resist deflection throughout the firing process (i.e., as the dynamic I-beam clamping assembly is distally advanced through the cartridge assembly 701).

In the illustrated arrangement, when the dynamic I-beam clamping assembly 550 is in the proximal most or starting position, the channel engagement flanges 559 are proximal to the second closure cam surfaces 1727 yet are in contact with the first lower surface 1726 to limit or otherwise restrict the jaws (anvil assembly 612, cartridge assembly 701) to that amount of jaw aperture represented as angle $\Theta_1$ between a staple forming surface 625 on the anvil plate 620 and the tissue contact surface 708 of the cartridge body 702). In the illustrated arrangement, for example, the dynamic I-beam clamping assembly 550 may have to move distally a distance X from the starting position until the channel engagement flanges 559 start to cammingly engage the second closure cam surfaces 1727 to commence the jaw closure process. In that arrangement, the actuation sled 1712 has a length SL and the cartridge body 702 has a nose portion 718 that has a length NL that extends beyond the distal end of the channel 1720.

Figure 34:
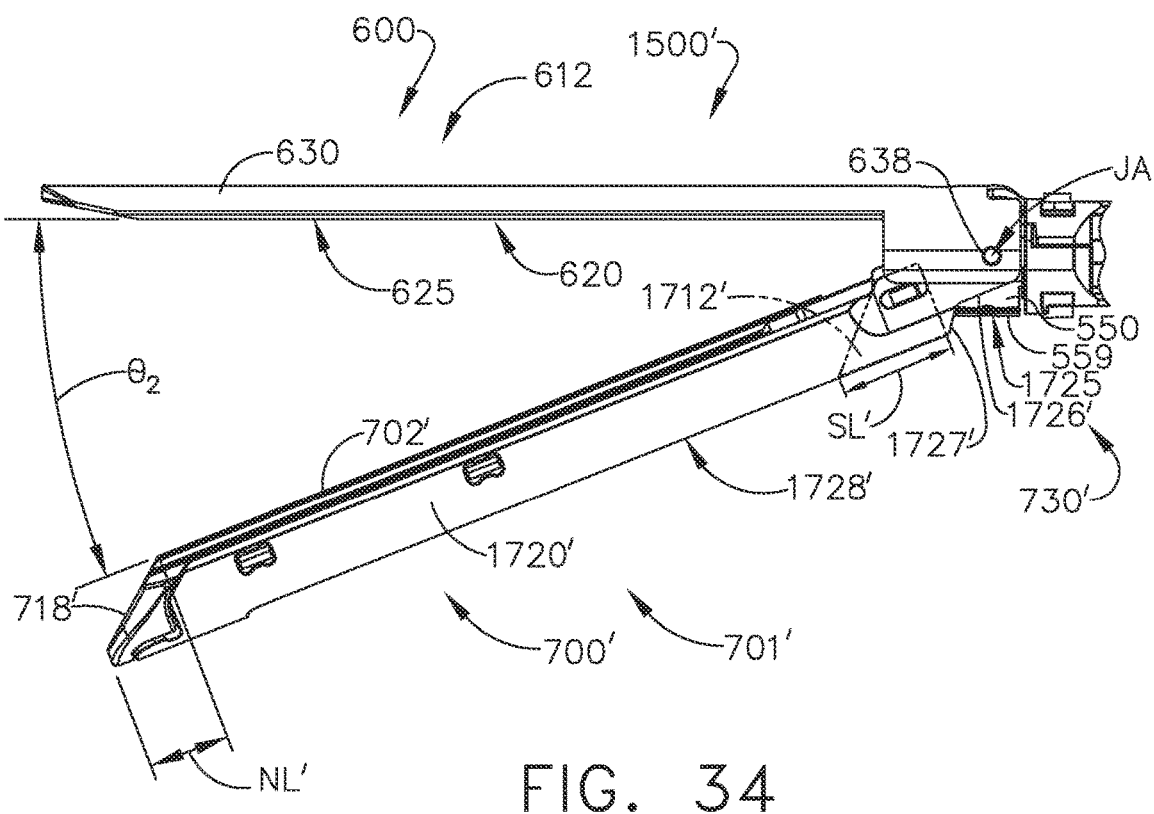
FIG. 34 is a side elevational view of a portion of another loading unit of an adapter with the jaws thereof in a fully open position.

In accordance with another general aspect, FIG. 34 illustrates another end effector 1500' that includes a parking or docking area 730' for the dynamic clamping assembly 550 when the dynamic clamping assembly 550 is in its proximal most or starting position. A first lower surface 1726' is formed on a proximal end 1725 of the channel 1720' on each side of the elongate slot. Each first lower surface 1726' terminates distally in a second closure cam surface or ramp 1727' that corresponds to each channel engagement flange 559 on the dynamic I-beam clamping assembly 550. When the channel engagement flanges 559 cammingly engage their corresponding second closure cam surface 1727', the cartridge assembly 701 and the anvil assembly 612 start to close or pivot toward each other by virtue of the interaction of the anvil engagement flanges 557 with corresponding surfaces on the anvil plate 620 and the camming action of the channel engagement flanges 559 with the corresponding second closure cam surfaces 1727' on the channel 1720'. Once the dynamic I-beam clamping assembly 550 has moved distally to a point wherein the channel engagement flanges 559 disengage the second closure cam surfaces 1727', the channel engagement flanges 559 engage corresponding third closure surfaces 1728' on the bottom of the channel 1720 to keep the anvil assembly and cartridge assembly closed throughout the firing process (i.e., as the dynamic I-beam clamping assembly is distally advanced through the cartridge assembly 701' to its ending position).

In the illustrated arrangement, when the dynamic I-beam clamping assembly 550 is in the proximal most or starting position, the channel engagement tabs 559 are located in abutting engagement with the second closure cam surfaces 1727' and are not spaced therefrom. Thus, when the dynamic I-beam clamping assembly is actuated to move distally, the channel engagement flanges 559 immediately start to cam the cartridge assembly 701' closed. Such arrangement provides a jaw aperture angle $\Theta_2$ that is greater than $\Theta_1$, for example. Thus, unlike the second jaw 700 described above, the dynamic I-beam clamping assembly 550 does not move distally any distance before it begins to cam the second jaw 700' closed. In that arrangement, the actuation sled 1712' has a length SL' and a nose portion 718' that has a length NL' that extends beyond the distal end of the channel 1720'. When compared to the above described arrangement, SL'<SL and NL'<NL, which generally leads to improved maneuverability of the end effector 1500'. In other arrangements, there is at least a portion of the I-beam clamping assembly distal advancement wherein the I-beam clamping assembly is not in contact with both jaws before it enters its closure strike portion wherein it begins to oppose the jaws toward one another.

During the firing process, a considerable amount of friction is generally experienced between the dynamic clamping assembly and the anvil assembly and cartridge assembly. Typically, the dynamic clamping assembly is fabricated from steel and employs steel pins or flanges for contacting the corresponding ledges on the anvil plate and the channel which are also fabricated from steel. As dynamic clamping member is advanced distally, the upper and lower steel pins are brought into slidable frictional contact with the corresponding ledges on the anvil plate and channel to clamp the anvil assembly and cartridge assembly onto the target tissue and drive the actuation sled distally to fire the staples and cut the stapled tissue. Such frictional contact can often result in the erosion of the steel pins and ledges which can significantly reduce the useful life of the end effector. In addition, the increased friction between the pins or flanges of the dynamic clamping assembly and the anvil assembly and cartridge assembly increases the amount of firing force that is required to drive the dynamic clamping assembly from its starting to ending position through the clamped tissue. These large firing forces dictate that the related components within the end effector as well as within the adapter must be sufficiently capable of accommodating such high firing forces. This requires that the various components be manufactured from stronger and often thicker material in an operational environment where operational space is limited (e.g., within the outer tube of the adapter). Thus, higher firing forces lead to more complicated designs and material compositions which lead to increased instrument costs.

Figure 35:
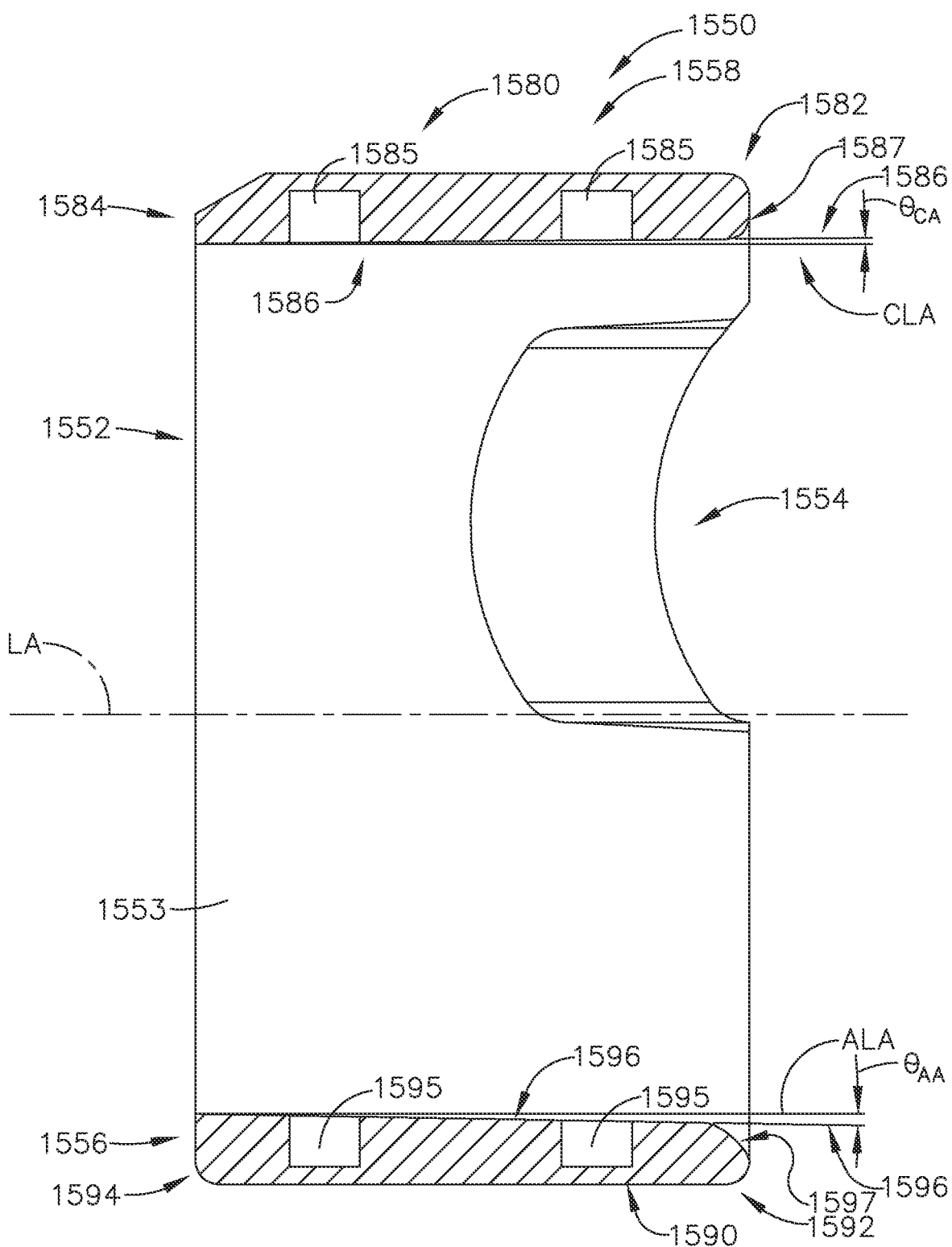
FIG. 35 is a cross-sectional elevational view of a dynamic clamping assembly embodiment.

Another aspect of the present disclosure comprises a dynamic clamping assembly 1550 as illustrated in FIG. 35. In the illustrated example, the dynamic clamping assembly 1550 comprises a vertically extending body portion 1552 that has a tissue cutting portion 1554 formed therein. The body portion 1552 is sized to be slidably received within the elongate slot 622 of the anvil plate 620 (FIG. 10) as well as within the central slot 724 of the channel 720 (FIG. 15). The cartridge assembly 701 generally includes a proximal end 705 and a distal end and 707 and defines a longitudinal axis LA therebetween. See FIGS. 10 and 15. The dynamic clamping assembly 1550 further includes at least one channel engagement feature 1558. In the illustrated arrangement, a channel engagement feature 1558 extends from each lateral side 1553 of the body portion 1552. In one example, each channel engagement feature 1558 comprises a channel engagement flange 1580 that has a distal end 1582, a proximal end 1584, and a channel ledge engagement surface 1586 extending therebetween. The channel ledge engagement surface 1586 is configured to slidably ride on or engage a corresponding one of the channel ledges 725 formed on each side of the central slot 724 in the channel 720. In the illustrated arrangement, a distal end 1587 of the channel ledge engagement surface 1586 is radiused to reduce friction between the channel ledge engagement surface 1586 and the channel ledges 725. In accordance with another aspect, in at least one arrangement, the channel ledge engagement surface 1586 angles from the proximal end 1584 to the distal end 1584 away from the longitudinal axis LA. For example, in FIG. 35, axis CLA is parallel to the longitudinal axis LA and may also be parallel to the upper surface 729 of each channel ledge 725 when the cartridge assembly 701 is in the closed position. In at least one arrangement, for example, the channel ledge engagement surface 1586 angles away from axis CLA a channel angle $\Theta_{CA}$. Stated another way, the channel ledge engagement surface 1586 is not parallel with the upper surface 729 of a corresponding one of the channel ledges 725 when the cartridge assembly 701 is in the closed position. In one arrangement, $\Theta_{CA}$ may be approximately 0.5°, for example. Other angles, however, are contemplated. Such arrangement may lower point loads on the distal end 1582 of the flange 1580. In an alternative arrangement (not shown), the anvil engagement surface on each of the anvil engagement flanges may have two distinct linear segments wherein one segment is arranged at an angle of the positive anvil opening ramps 628 (FIGS. 27-29) and the other linear segment may match the angle of each of the anvil plate ledges 624. In still other alternative arrangements (not shown) the length of each of the channel engagement flanges may be longer than the length of the anvil engagement flanges which may allow the loads to be distributed over a larger area of the channel ledge which may lower the potential local contact loads and lower galling. Similar favorable results may be obtained wherein each of the anvil engagement flanges are longer than the channel engagement flanges.

Still referring to FIG. 35, the dynamic clamping assembly 1550 further includes at least one anvil engagement feature 1556. In the illustrated arrangement, an anvil engagement feature 1556 extends from each lateral side 1553 of the body portion 1552. In one example, each anvil engagement feature 1556 comprises a flange 1590 that has a distal end 1592, a proximal end 1594 and an anvil ledge engagement surface 1596 extending therebetween. The anvil ledge engagement surface 1596 is configured to slidably ride on or engage a corresponding one of the anvil plate ledges 624 formed on each side of the elongate slot 622 in the anvil plate 620. In the illustrated arrangement, a distal end 1597 of the anvil ledge engagement surface 1596 is radiused to reduce friction between the anvil ledge engagement surface 1596 and the anvil plate ledges 624. In accordance with another aspect, in at least one arrangement, the anvil ledge engagement surface 1596 angles from the proximal end 1594 to the distal end 1592 away from the longitudinal axis LA. For example, in FIG. 35, axis ALA is parallel to the longitudinal axis LA and may also be parallel to the lower surface 626 of each anvil plate ledge 624 when the anvil assembly 612 is in the closed position. In at least one arrangement, for example, the anvil ledge engagement surface 1596 angles away from axis ALA an anvil angle $\Theta_{AA}$. Stated another way, the anvil ledge engagement surface 1596 is not parallel with the lower surface of a corresponding one of the anvil plate ledges 624 when the anvil plate 620 is in the closed position. In one arrangement, $\Theta_{AA}$ may be approximately 1°, for example. Other angles, however, are contemplated. Such arrangement may lower the point loads on the distal end 1592 of the flange 1590. Other arrangements are contemplated wherein only the channel ledge engagement surfaces or the anvil ledge engagement surfaces are angled. For example, in another arrangement, the channel ledge engagement surface of each channel engagement flange may be approximately parallel to the longitudinal axis LA and the anvil ledge engagement surface on each of the anvil ledge engagement flanges are angles as described herein. In another arrangement, the channel ledge engagement surface of each channel ledge engagement flange is angled as described above, but the anvil ledge engagement surface of each anvil engagement flange is not angled relative to the longitudinal axis LA, but rather is approximately parallel thereto.

Figure 36:
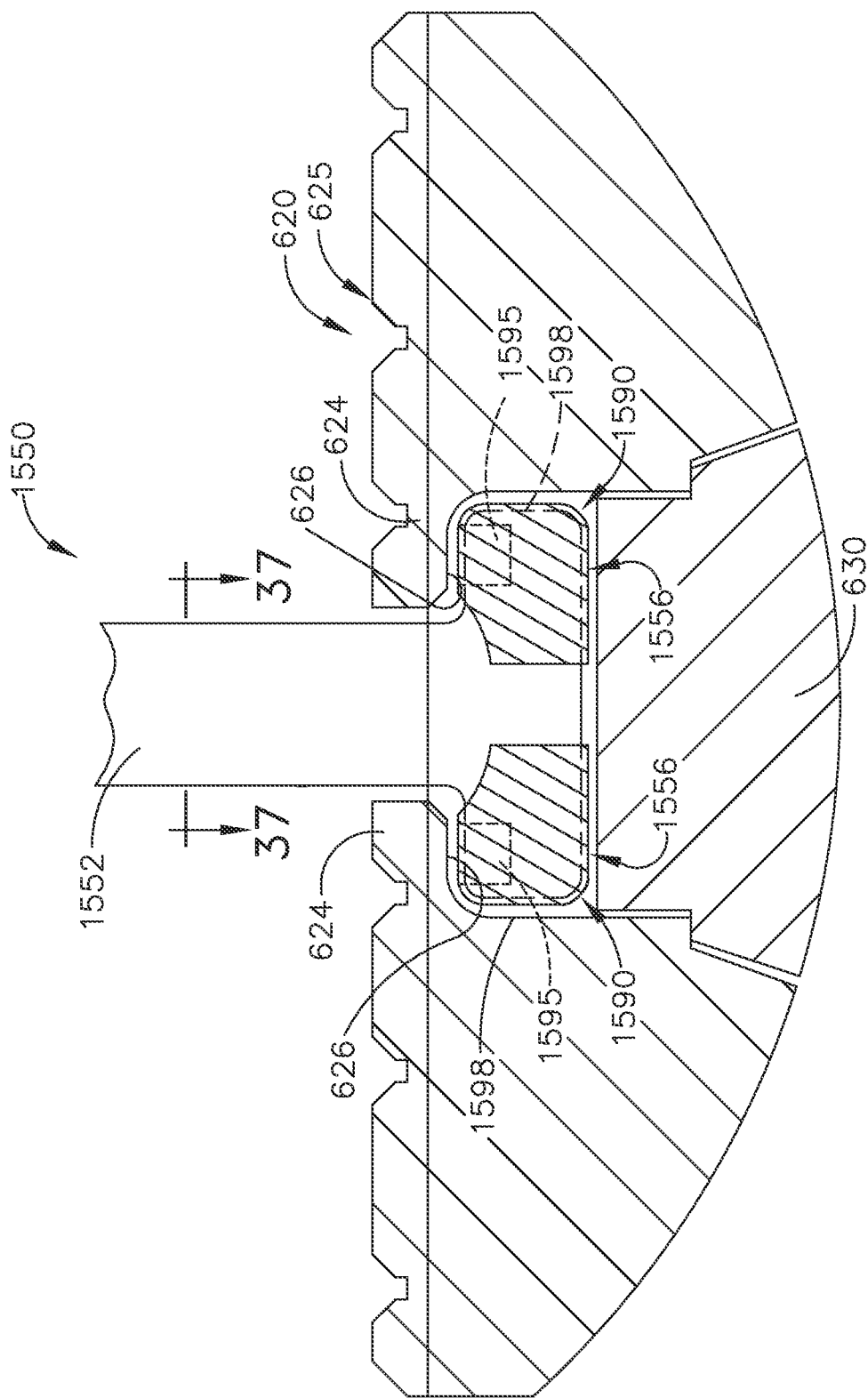
FIG. 36 is an end elevational view of a portion of the dynamic clamping assembly of FIG. 35 interacting with an anvil assembly of a loading unit of an adapter shown in cross-section.

Turning to FIG. 36, in accordance with yet another aspect of the present disclosure, each of the anvil engagement flanges 1590 is coated with a ceramic material 1598. One form of ceramic coating that may be employed comprises ceramic coatings that may comprise, for example, diamond-like carbon (DLC), titanium nitride (TiN), zirconium nitride (ZrN), titanium-niobium-nitride (TiNbN), calcium phosphates ($Ca_3(PO_4)_2$), and a hydroxyapatite ($Ca_{10}(PO_4)_6°(OH)_2$). Although not strictly regarded as a coating (but as a native oxide layer), another popular metallic-ceramic composite is an in-situ grown monoclimic zirconia onto a zirconium niobium alloy (i.e., oxidized zirconia, OxZr). A similar coating may be applied to each of the channel engagement flanges 1580. In addition, a similar ceramic coating may be applied to the lower surface 626 of each of the anvil plate ledges 624 as well as to the upper surface 729 of each channel ledge 725. In the alternative, the entire anvil plate ledges 624 and the entire channel ledges 725 may be coated with the ceramic coating. Such coating may be applied using 3D printing technology and form a surface with significantly higher hardness than the material to which it is applied and can also be highly polished to result in significantly lower frictional drag between those components during firing. Other methods of applying coatings that may be effectively employed include but are not limited to indirect resin composite-aerosol deposition as well as plasma and vapor deposition.

In accordance with another general aspect of the present disclosure, one form of the dynamic clamping member 1550 includes at least one channel flange insert 1585 that is embedded into the corresponding channel engagement flange 1580. In the illustrated example, two channel flange inserts 1585 are embedded into each channel flange 1580. Still referring to FIG. 36, the dynamic clamping member 1550 further includes at least one anvil flange insert 1595 that is embedded into the corresponding anvil engagement flange 1590. In the illustrated example, two anvil flange inserts 1595 are embedded into each anvil flange 1590. As shown, each channel flange insert 1585 and each anvil flange insert 1595 has a rectangular cross-sectional shape. However, other numbers, sizes and shapes of channel flange and anvil flange inserts are contemplated. In at least one example, each anvil flange insert 1595 extends from the outer coating or cover 1598.

In accordance with another general aspect, for those arrangements wherein each channel ledge 725 and each anvil plate ledge 624 is fabricated from metal (or other material) having, for example, a hardness measured on the Rockwell C scale of approximately HRC 39-45, each of the channel flange inserts 1585 and each of the anvil flange inserts 1595 may be fabricated from a material having a hardness value that is greater than the hardness value of the channel ledges 725 and the anvil plate ledges 624. For example, the channel flange inserts 1585 and the anvil flange inserts 1595 may be fabricated from ceramic materials that include, but are not limited to for example, alumina ($Al_2O_3$), zirconia ($ZrO_2$), zirconia-toughened alumina (ZTA), alumina matrix composites (AMC), alumina-toughened zirconia (ATZ), silicon nitride ($Si_3N_4$), and hydroxyapatite (Hap) that has a hardness value of approximately HRC 55-70. In these instances, the material comprising the channel flange inserts and the anvil flange inserts has a crystalline structure that differs from the crystalline structure(s) of the material(s) from which the anvil plate ledges and channel ledges are fabricated.

Figure 37:
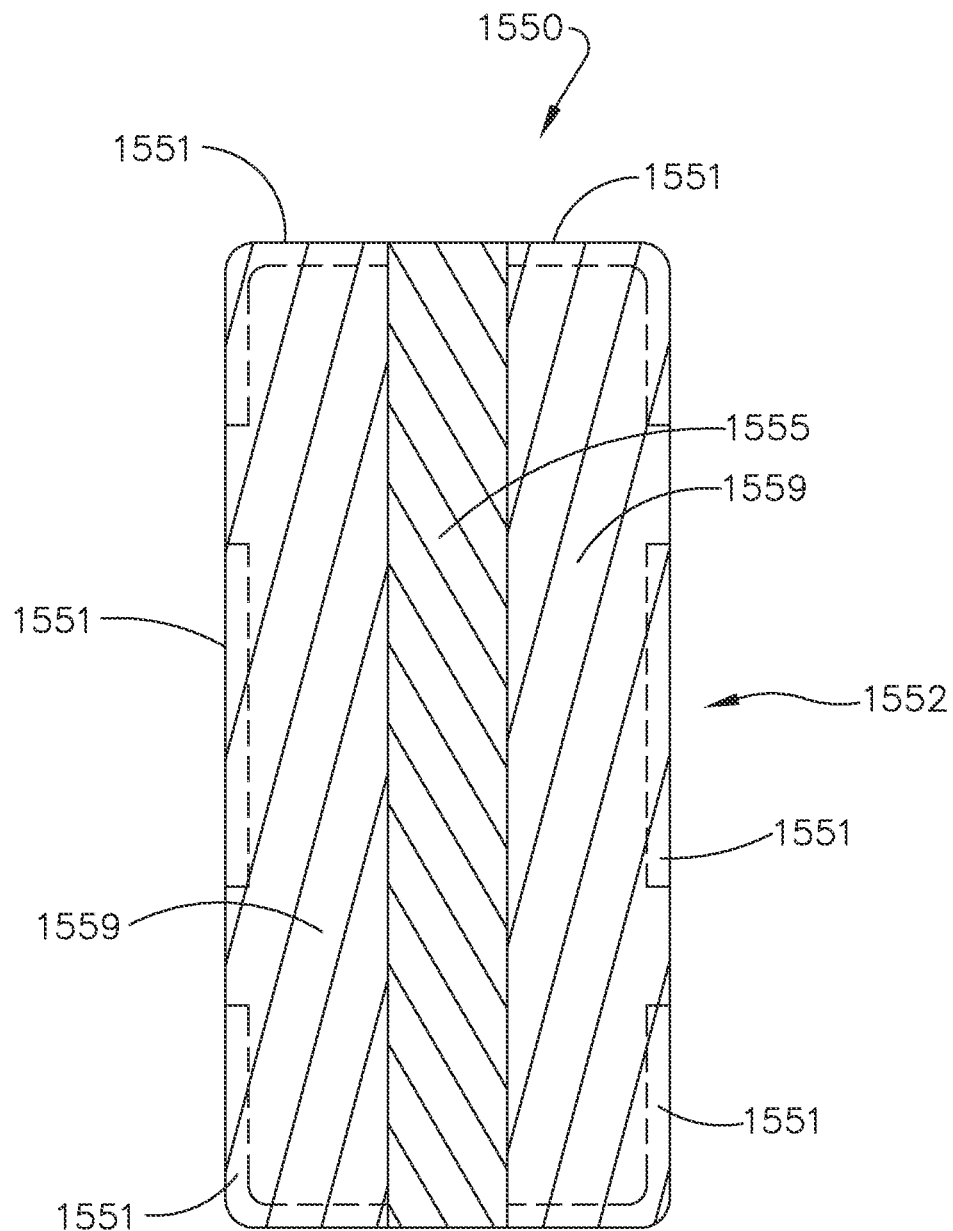
FIG. 37 is a cross-sectional view of a body portion of the dynamic clamping assembly of FIG. 36 taken along line 37-37 in FIG. 36.
Figure 40:
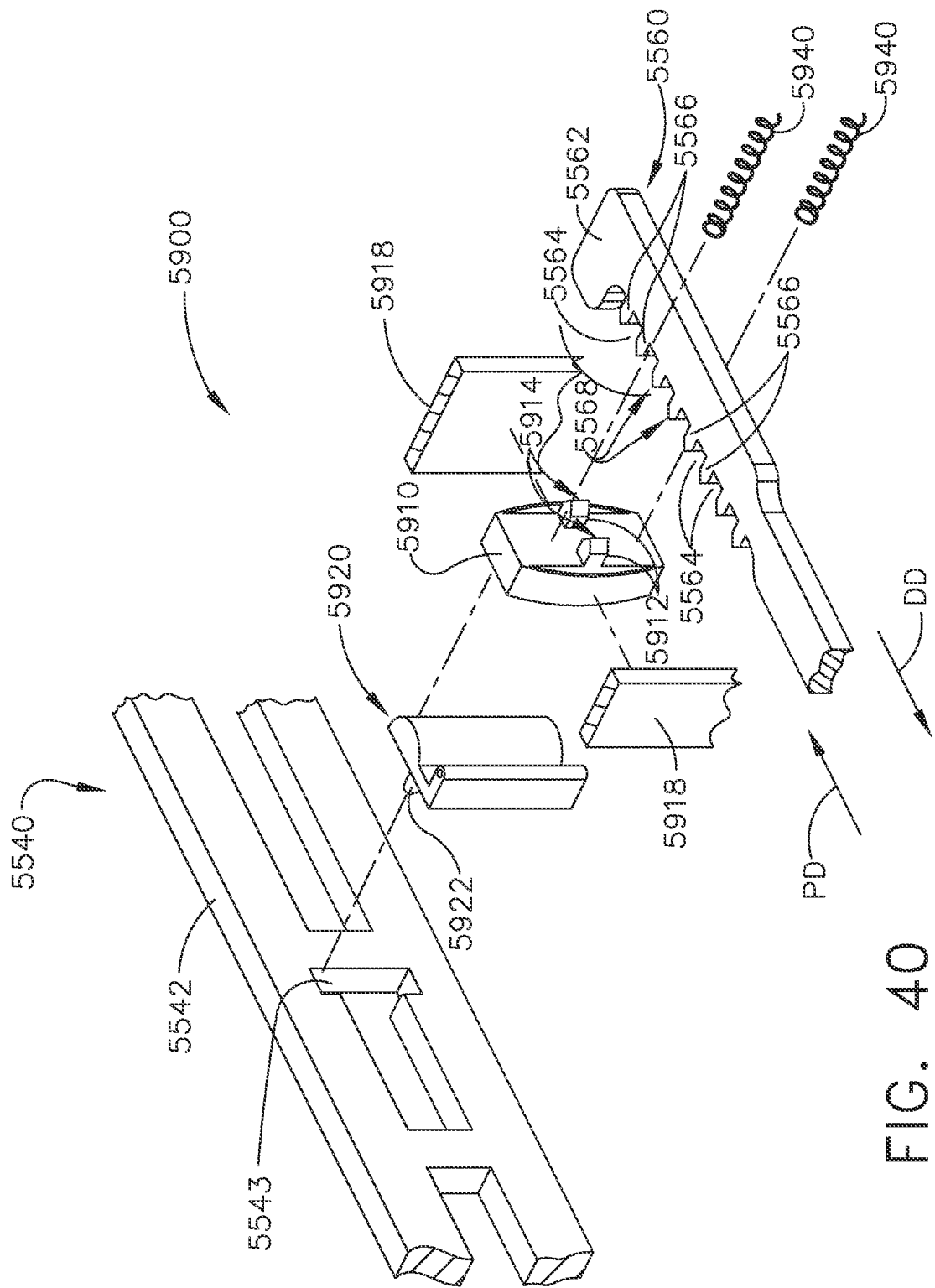
FIG. 40 is an exploded perspective assembly view of portions of an articulation locking system embodiment of an adapter.
Figure 41:
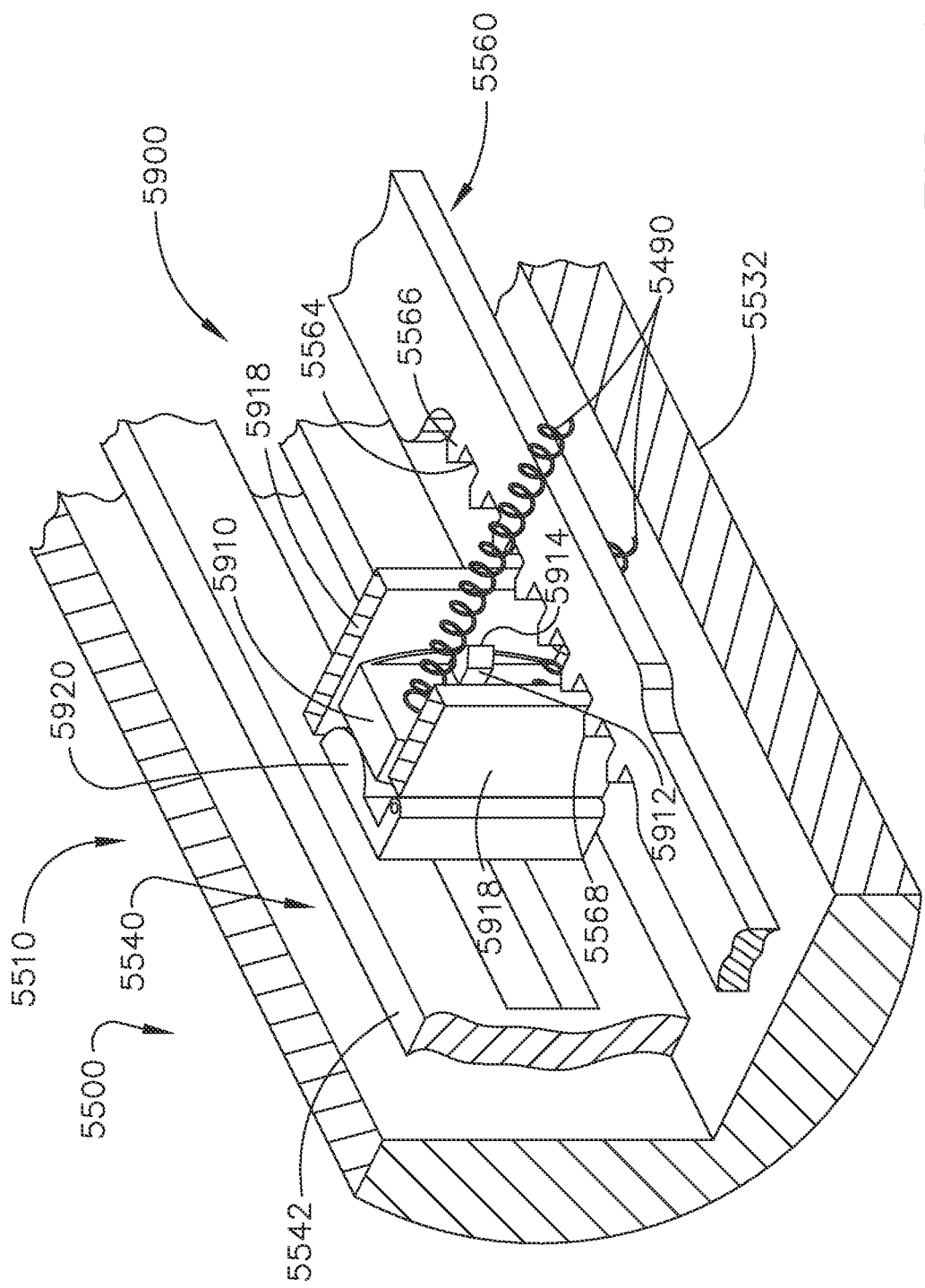
FIG. 41 is a partial cross-sectional perspective view of a portion of an adapter and the articulation locking system of FIG. 40.

FIG. 37 is a cross-sectional view of the central body portion 1552 of the dynamic clamping assembly 1550 taken along line 37-37 in FIG. 36. In the illustrated example, the central body portion 1552 comprises a central region 1555 that may be fabricated from 420 or 440 SS—high Rockwell C 400 series stainless steel. A ceramic side region 1559 is attached to each lateral side of the central region. Each ceramic side region may have a hardness that is greater than the hardness of the central region. Hardened inserts 1551 are also attached to the surfaces of the ceramic side regions. The hardened inserts may be fabricated from 420 or 440 SS—high Rockwell C 400 series stainless steel.

FIGS. 38 and 39 illustrate another dynamic clamping assembly 1550' that is similar to the dynamic clamping assembly 1550 except for the differences discussed below. As can be seen in FIG. 38, a channel ledge engagement surface 1586' of a channel engagement flange 1580' and an anvil ledge engagement surface 1596' of an anvil engagement flange 1590' are each approximately parallel to the longitudinal axis LA. Each of the channel engagement flanges 1580' as well as a body portion 1552 of the dynamic clamping assembly 1550' are coated with a material 1560 that may comprise a coating material sold under the trademark MEDCOAT/2000™ by the Electrolizing Corporation of Ohio. In the alternative, a Nitride coating may be employed. These coatings may be applied after the tissue cutting portion 1554 has been formed and sharpened. Applying the coating of material 1560 to the tissue cutting portion 1554 may enhance and improve its sharpness.

Figure 42:
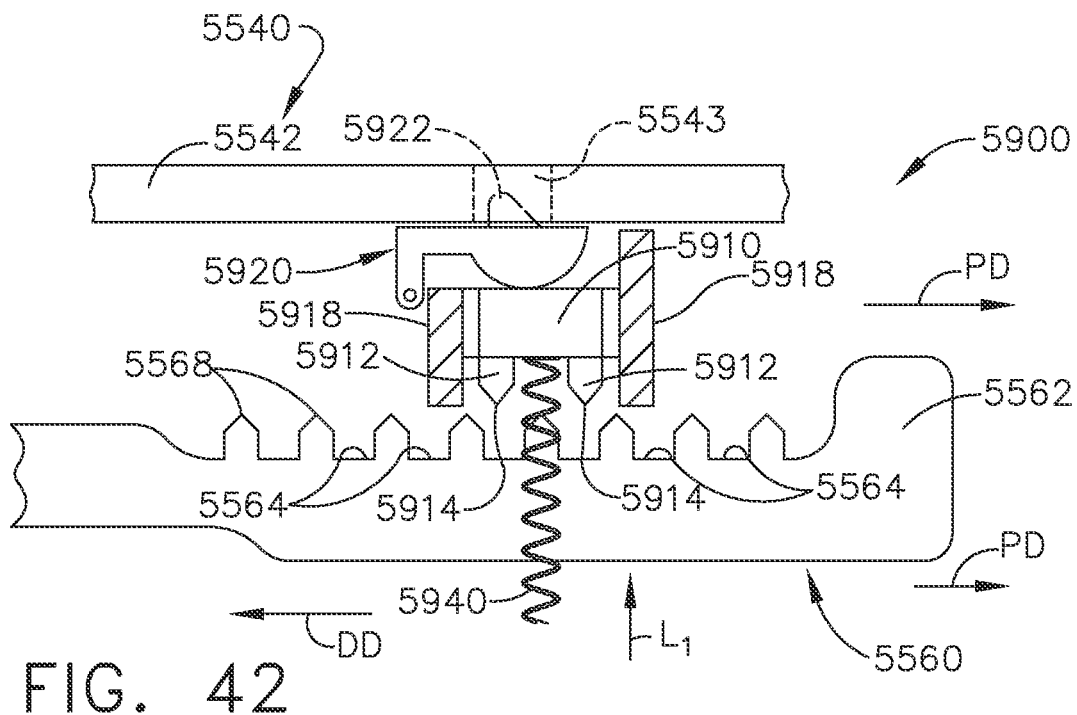
FIG. 42 is a partial top cross-sectional view of the articulation locking system of FIGS. 40 and 41 in an unlocked position.
Figure 43:
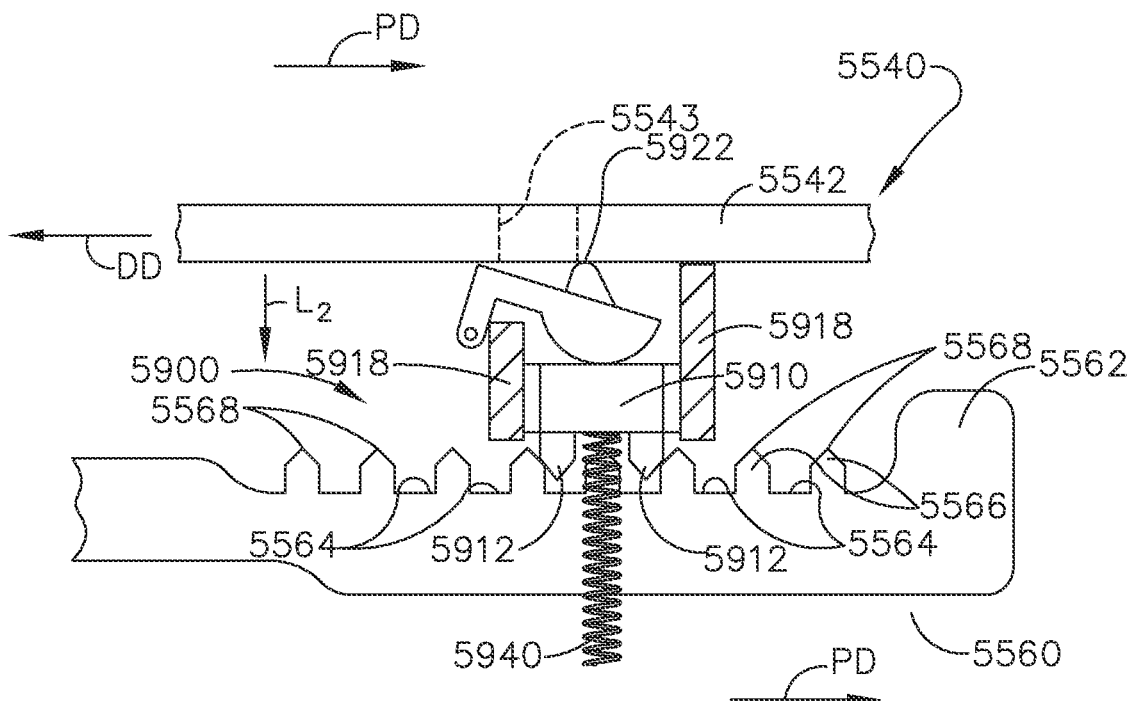
FIG. 43 is another partial top cross-sectional view of the articulation locking system of FIGS. 40-42 in a locked position.

FIGS. 40-43 depict an articulation locking system 5900 for locking an articulation link 5560 of a surgical end effector 5500 in the form of a loading unit 5510 (DLU or MLU). The loading unit 5510 is identical to the loading unit 510 except for the differences noted below. As can be seen in FIGS. 40-43, the illustrated articulation locking system 5900 comprises a laterally displaceable lock member 5910 that includes lock teeth 5912 that are configured to lockingly engage lock grooves 5564 formed in a proximal end 5562 of the articulation link 5560. The locking system 5900 further comprises a locking cam 5920 that is pivotally coupled to an outer housing 5532. Outer housing 5532 is similar to outer housing 532 described above. The lock member 5910 is constrained to move laterally (directions $L_1$ and $L_2$) between two mounting features 5918 mounted or formed within the outer housing 5532 as can be seen in FIGS. 42 and 43. The locking cam 5920 includes a cam actuator 5922 that is configured to operably interface with a flexible drive beam 5542 of a drive assembly 5540. As can be most particularly seen in FIG. 40, a cam opening 5543 is provided in the flexible drive beam 5542 for receiving the cam actuator 5922 when the drive assembly 5540 is in the unactuated or unfired position. When in a starting or unfired position, the locking cam 5920 is biased into an unactuated position by a pair of biasing members 5940 that bear upon the lock member 5910 to laterally displace the lock member 5910 in the lateral direction $L_1$. When in that position, the lock teeth 5912 of the lock member 5910 are out of engagement with the lock grooves 5564 formed in the proximal end 5562 of the articulation link 5560 such that the articulation link 5560 may be axially moved in the proximal direction PD and distal direction DD by the articulation bar 258 of an adapter to which the end effector 5500 is operably attached. Thus, when in the unlocked position illustrated in FIG. 42, the articulation link 5560 may be axially moved to articulate the end effector into a desired articulated position. Once the clinician has articulated the end effector into the desired orientation, the drive assembly 5540 is actuated to distally advance the flexible firing beam 5542. As the firing beam 5542 is advanced distally, the cam actuator 5922 causes the locking cam 5920 to pivot and bias the lock member 5910 in the lateral direction $L_2$ so as to bring the locking teeth 5912 thereof into locking engagement with the lock grooves 5564. As can be seen in FIGS. 40-43, the lock grooves 5564 are defined between lock teeth 5566. The lock teeth 5566 each have pointed ends 5568 that are configured to cooperate with pointed ends 5914 on lock teeth 5912 to provide axial lead in assistance into the locked position.

Figure 44:
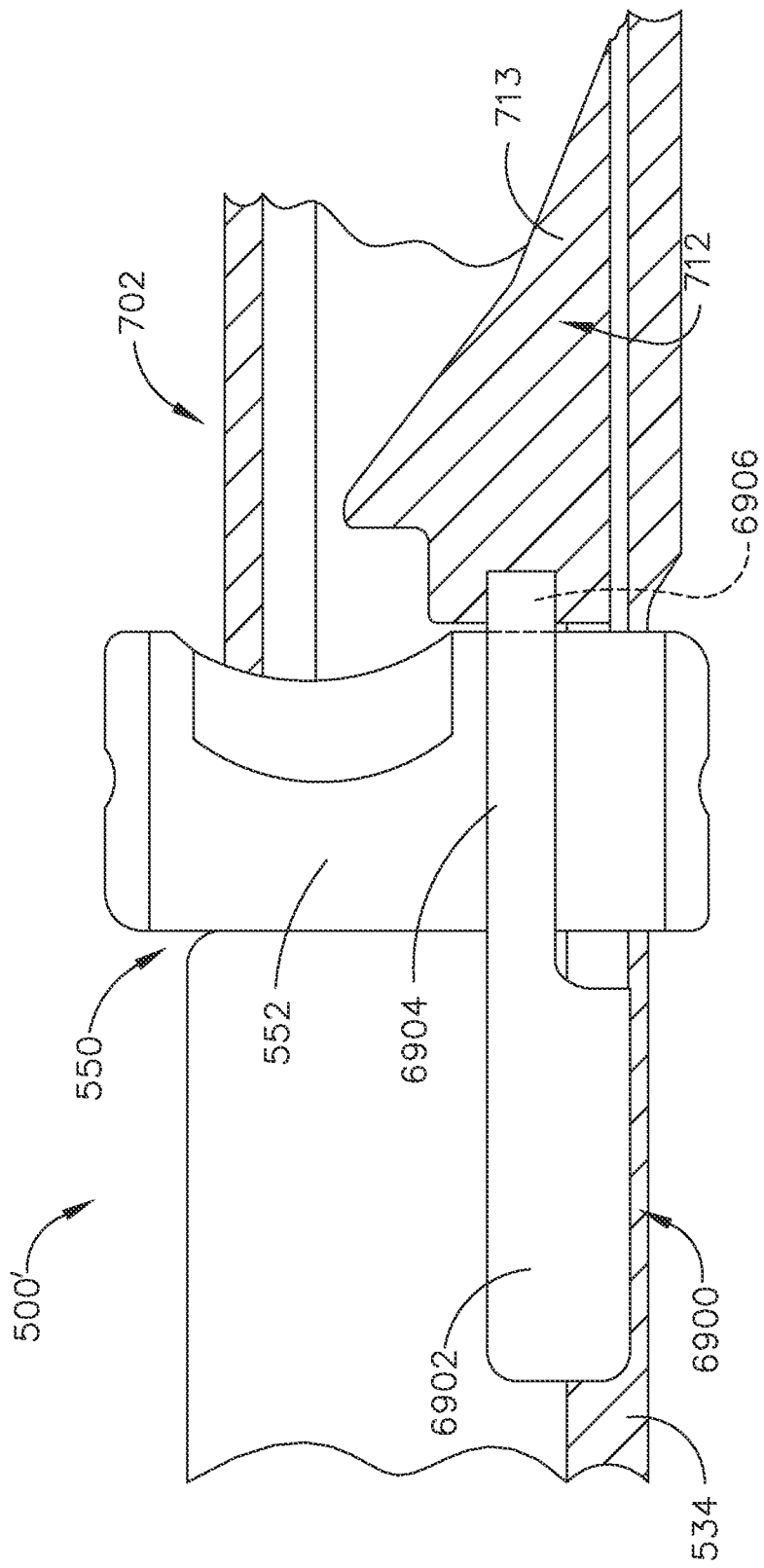
FIG. 44 is a partial cross-sectional view of a portion of a drive assembly locking system of an adapter in an unlocked position.
Figure 45:
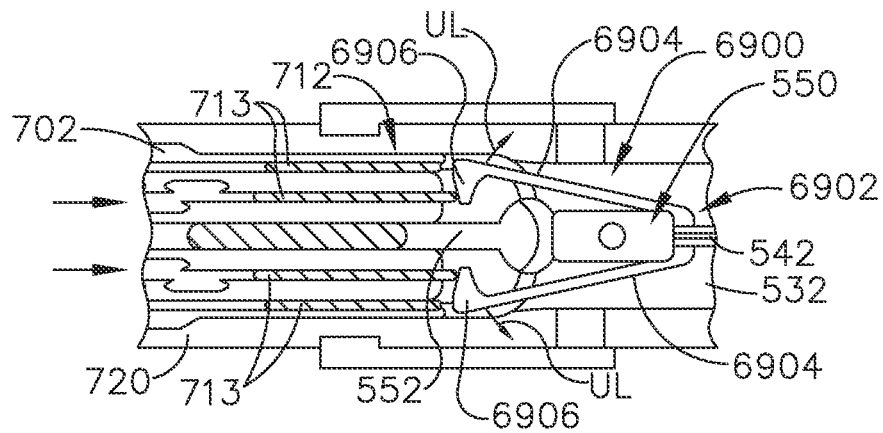
FIG. 45 is a partial cross-sectional view of the drive assembly locking system of FIG. 44 with an unfired cartridge loaded in an end effector and the drive assembly locking system in an unlocked position.
Figure 46:
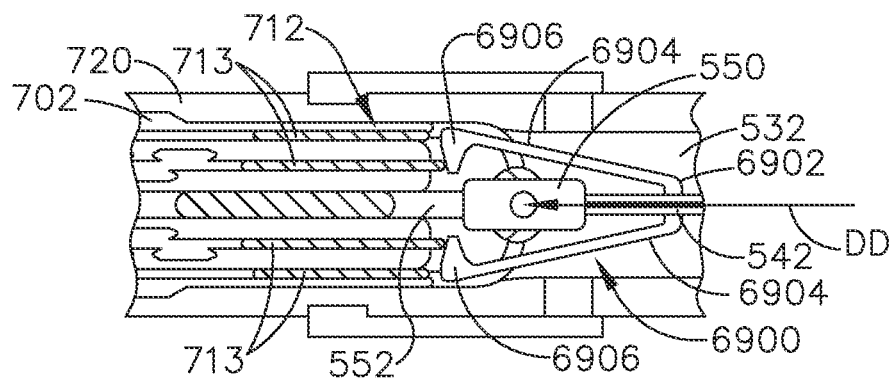
FIG. 46 is another partial cross-sectional view of the drive assembly locking system of FIGS. 44 and 45 with an unfired cartridge loaded in the end effector and the drive assembly locking system in an unlocked position and a dynamic clamping assembly thereof starting to move through a closing stroke.
Figure 47:
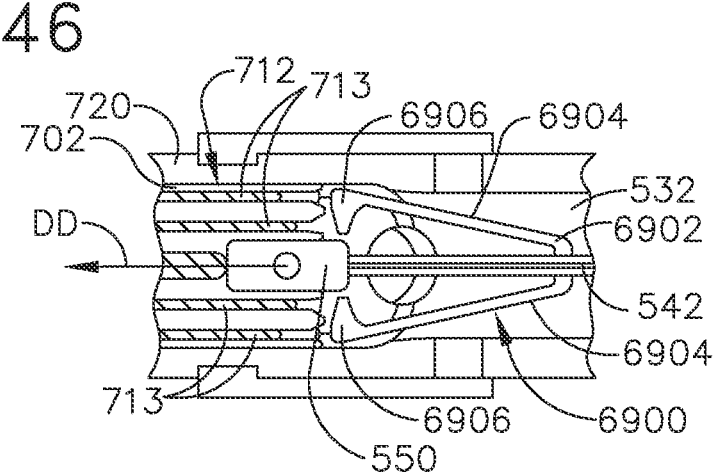
FIG. 47 is another partial cross-sectional view of the drive assembly locking system of FIGS. 44-46 with an unfired cartridge loaded in the end effector and the drive assembly locking system in a firing position ready to start moving through a firing stroke.

FIGS. 44-54 illustrate a drive assembly locking system 6900 for preventing the axial advancement of a dynamic clamping assembly 550 of a surgical end effector 500' unless an unfired cartridge 702 has been properly loaded into the channel 720 of the end effector 500', for example. As used in this context, the term "unfired cartridge" means that the cartridge 702 has not been fired and contains all of its staples 704 with the actuation sled 712 in its starting and unfired or ready to fire position therein. As can be seen in FIG. 44, in one example, the drive assembly locking system 6900 comprises lock member 6902 that is supported by an inner housing 534 of the end effector 500' and is configured to retainingly engage a body portion 552 of a dynamic clamping assembly 550. As can be seen in FIGS. 45-47, the lock member 6902 comprises two lateral lock arms 6904 that each has a latch feature 6906 thereon. The lateral lock arms 6904 are normally biased inward such that the latch features 6906 thereon retainingly engage the body portion 552 of the dynamic clamping assembly 550 when the dynamic clamping assembly 550 is located in its starting/unfired position. Thus, when the latch features 6906 are in retaining engagement with the dynamic clamping assembly 550, the dynamic clamping assembly 550 is prevented from being driven distally (fired).

FIGS. 44 and 45 illustrate a portion of the end effector 500' wherein an unfired cartridge 702 has been properly loaded into the end effector 500'. The unfired cartridge 702 supports an actuator sled 712 in an unactuated position therein wherein portions of cam wedges 713 of the actuator sled 712 engage the latch features 6906 and bias each of the lateral lock arms 6904 out of locking engagement (arrows UL in FIG. 45) with the body portion 552 of the dynamic clamping assembly 550. When in that unlocked position (FIGS. 45 and 46), the dynamic clamping assembly 550 can be driven distally to fire the staples in the cartridge 702 (FIG. 47) and cut the tissue clamped therein. Once the dynamic clamping assembly 550 has been distally driven to its ending position within the cartridge 702, it is then retracted in the proximal direction PD back to its starting position. The actuation sled 712 remains at the distal end of the cartridge 702.

Figure 48:
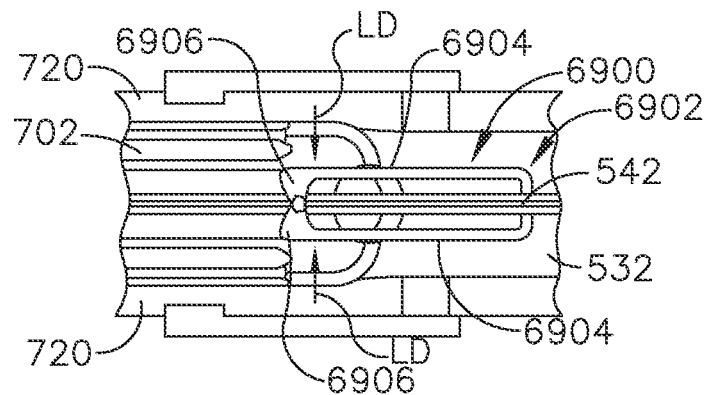
FIG. 48 is another partial cross-sectional view of the drive assembly locking system of FIGS. 44-47 after the dynamic clamping assembly has been distally advanced through the firing stroke.
Figure 49:
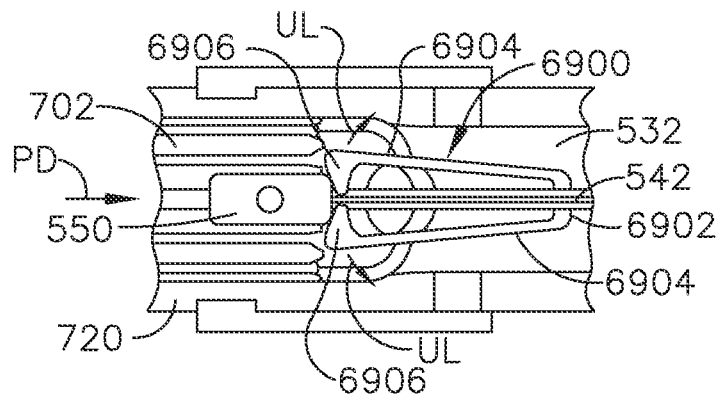
FIG. 49 is another partial cross-sectional view of the drive assembly locking system of FIGS. 44-48 as the dynamic clamping assembly is being retracted but before resuming a starting position.
Figure 50:
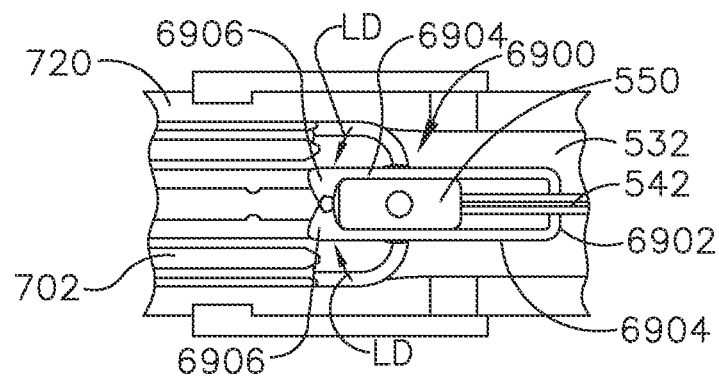
FIG. 50 is another partial cross-sectional view of the drive assembly locking system of FIGS. 44-48 after the dynamic clamping assembly has been retracted back to the starting position and the drive assembly locking system is in the locked position.
Figure 51:
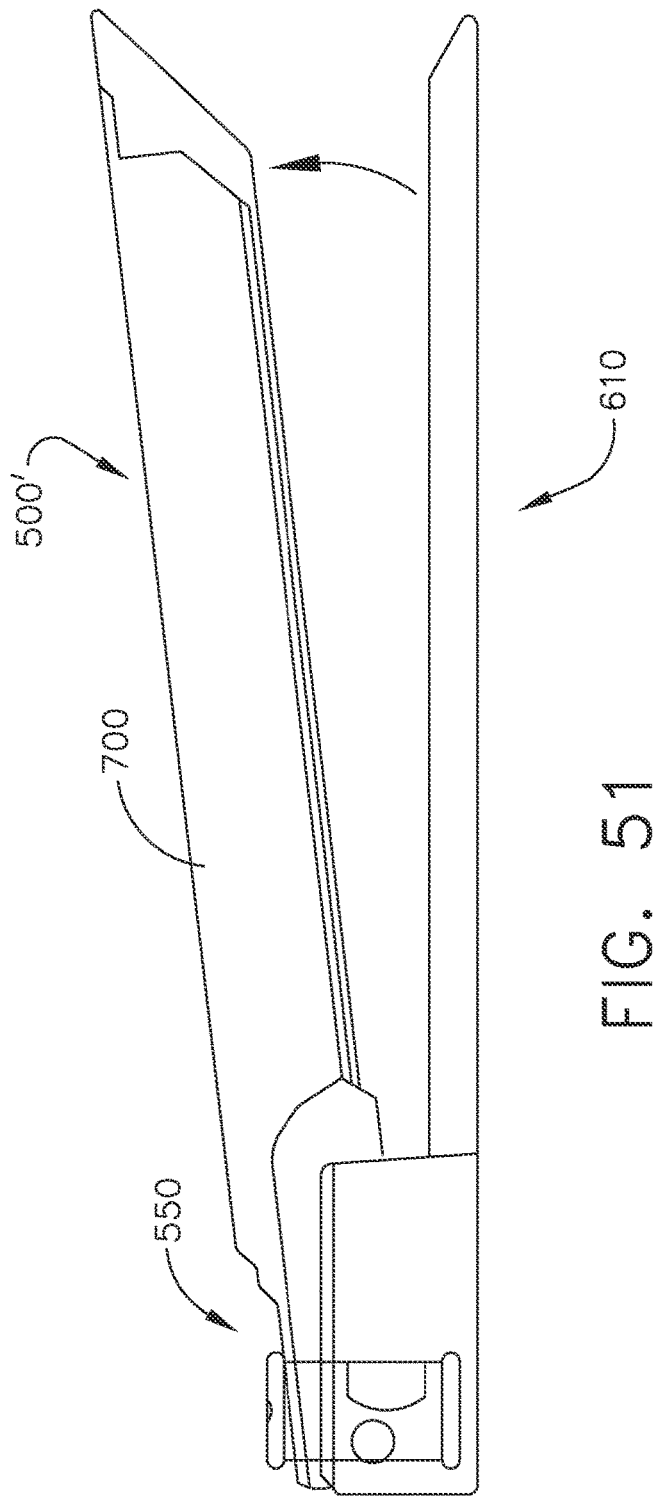
FIG. 51 is a side view of the end effector of FIGS. 44-50 with the dynamic clamping assembly shown in a starting position and the jaws thereof in a fully open position.
Figure 52:
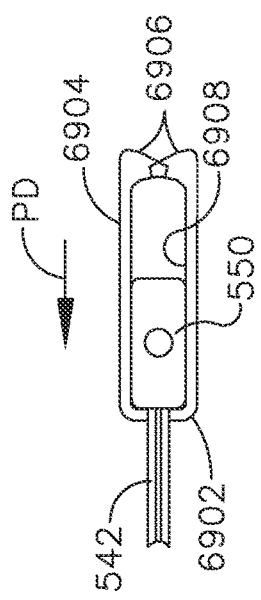
FIG. 52 shows the position of a drive lock member of the drive assembly locking system of FIGS. 44-50 in a locked position around the dynamic clamping assembly when in the starting position.
Figure 53:
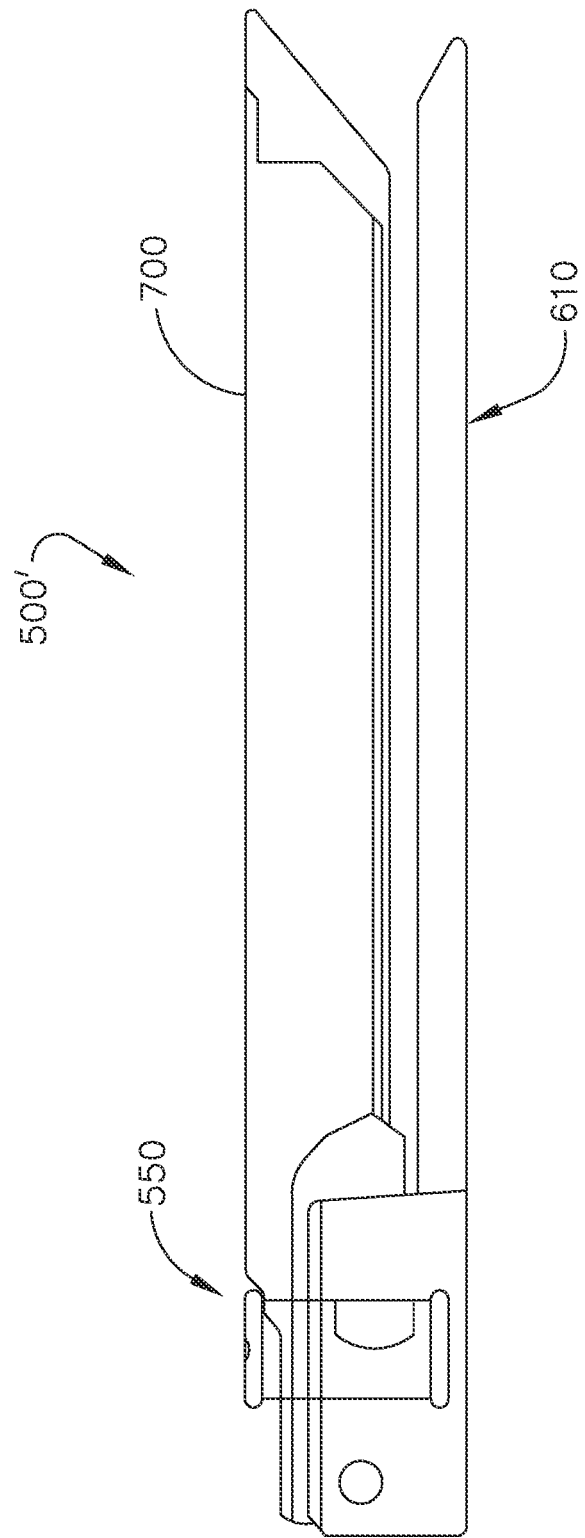
FIG. 53 is a side view of the end effector of FIG. 51 after the dynamic clamping assembly has completed a closure stroke and is in a firing position.
Figure 54:
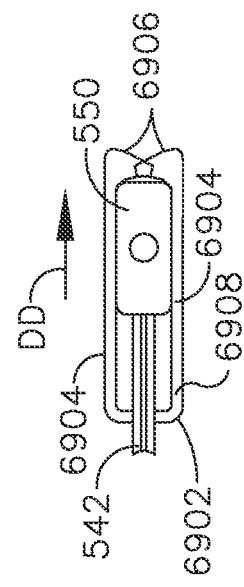
FIG. 54 shows the position of a drive lock member of the drive assembly locking system of FIGS. 44-50 in a locked position around the dynamic clamping assembly in the firing position.

FIG. 48 illustrates the lock member 6902 after the dynamic clamping member has been driven distally out of its starting position. As can be seen in that Figure, the lock arms 6902 are biased inwardly (arrows LD). During the retraction process, the dynamic clamping assembly 550 will contact the latch features 6906 as it is retracted in the proximal direction PD as shown in FIG. 49. As the dynamic clamping assembly 550 contacts the latch features 6906, the lock arms 6904 are biased laterally outward (arrows UL) until the dynamic clamping assembly 550 is fully retracted into the starting position at which point the lock arms 6904 move back to the locked configuration wherein the latch features 6906 once again retainingly engage the dynamic clamping assembly 550. See FIG. 50. Thus, the dynamic clamping assembly 550 is once again prevented from being driven distally until a new unfired cartridge is loaded into the channel. Should the clinician attempt to refire the dynamic clamping member 550 before the now spent cartridge is replaced, they will be unable to do so. Further, should the clinician unwittingly load a partially fired cartridge into the end effector 500', the lock member 6902 will prevent the dynamic clamping assembly 550 from being fired, because the actuation sled in the partially fired cartridge will not be in the starting position to unlock the lock member 6902. FIG. 51 illustrates the end effector 500' with the jaws 610, 700 in the fully open position. FIG. 52 illustrates the dynamic clamping assembly 550 in a position corresponding to the fully open position. FIG. 53 illustrates the end effector 500' with the jaws 610, 700 in the fully closed position. FIG. 54 illustrates the position of the dynamic clamping assembly 550 after it has moved the jaws 610, 700 to the fully closed position but prior to firing. Because the jaws 610, 700 are moved from the fully open to fully closed position by the dynamic clamping assembly 550, the lock member 6902 is configured to permit such axial movement of the dynamic clamping assembly 550 while still being in the locked position. As can be seen in FIGS. 52 and 54, for example, when the lock arms 6904 are in the normally locked position, an axial pocket 6908 is defined therebetween to permit the axial movement of the dynamic clamping assembly 550 that is required to open and close the jaws 610, 700 without permitting the dynamic clamping assembly 550 from being distally moved beyond the fully closed position unless an unfired cartridge is loaded into the channel of the end effector.

Figure 55:
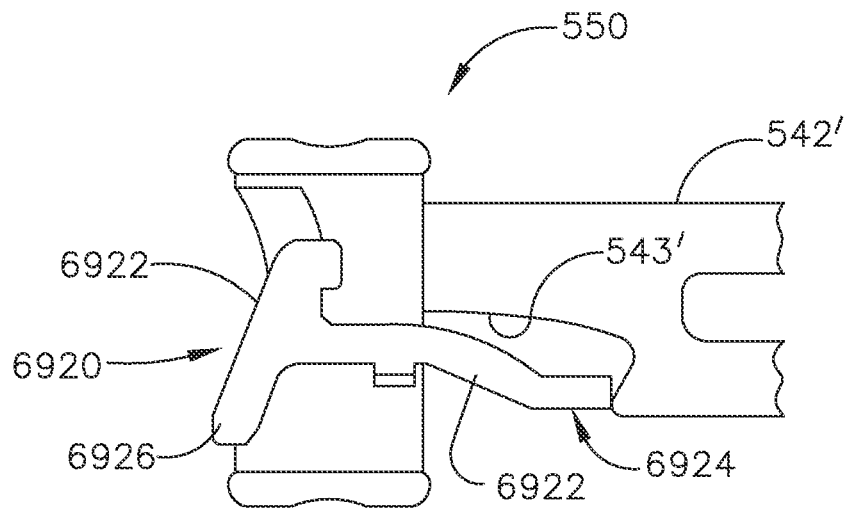
FIG. 55 is a side view of a dynamic clamping assembly and a pivoting lock member of another drive assembly locking system in a locked position prior to installing an unspent cartridge into an end effector of an adapter.
Figure 56:
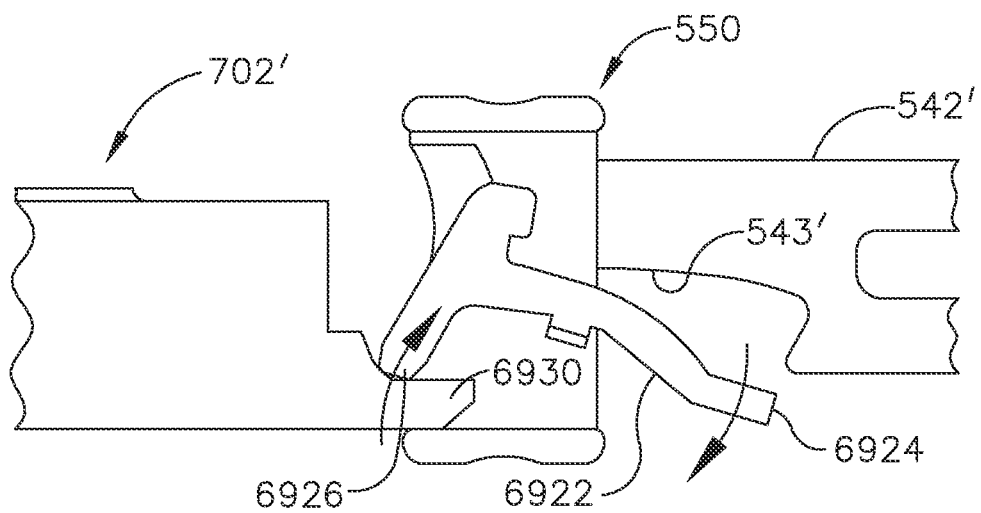
FIG. 56 is another side view of the drive assembly locking system of FIG. 55 with an unspent cartridge supported in position to move the pivoting lock member into an unlocked position.
Figure 57:
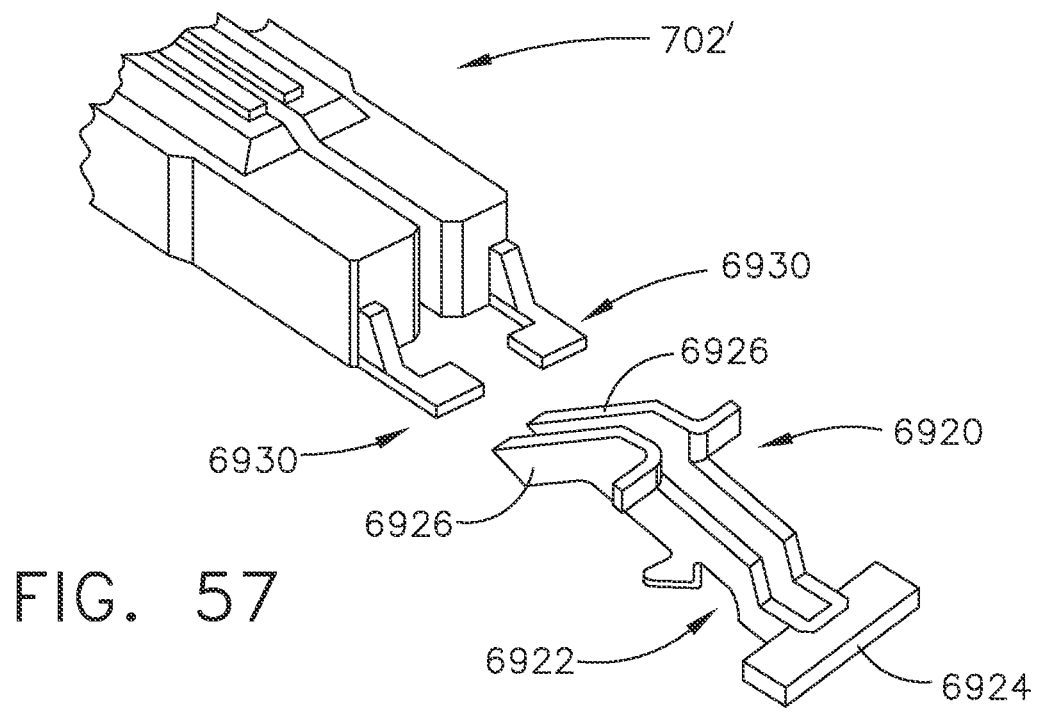
FIG. 57 is an exploded view of the pivoting lock member and cartridge shown in FIG. 56.
Figure 59:
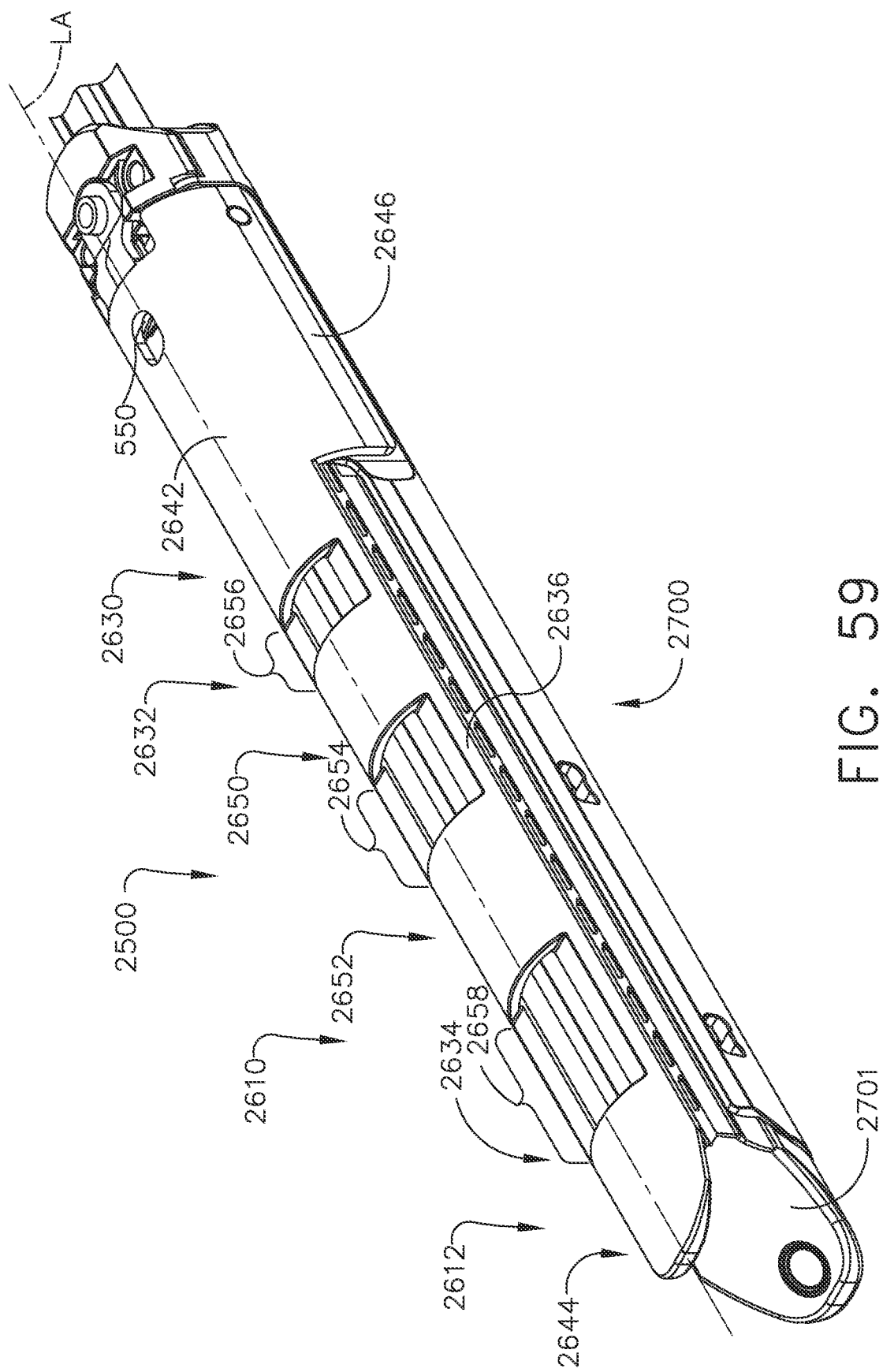
FIG. 59 is a top perspective view of another loading unit of an adapter with the jaws thereof in a closed position and a dynamic clamping assembly positioned in a firing position.

FIGS. 55-57 illustrate another drive assembly locking system 6920 for preventing the axial advancement of the dynamic clamping assembly 550 of an end effector of an adapter of the type disclosed herein unless a cartridge 702' has been properly loaded into the channel of the end effector. In this example, the cartridge 702' is formed with a pair of proximally extending unlocking features 6930 that are configured to unlocking engage a pivoting lock member 6922. The pivoting lock member 6922 is configured to pivot between a locked position wherein a lockout feature 6924 is received within a lock cavity 543' that is formed in a flexible drive beam 542' (FIG. 55) of the end effector. When the lockout feature 6924 is received within the lock cavity 543', the drive beam 542' (and the dynamic clamping assembly 550 coupled thereto) cannot be advanced distally to fire staples that are stored in the cartridge 702'. The lock member 6922 also includes a distally extending unlocking arm 6926 that corresponds to each unlocking feature 6930 on the cartridge 702'. When the cartridge 702' is properly loaded into the end effector, the unlocking features 6930 engage the corresponding unlocking arms 6926 to pivot the lock member 6922 to the unlocked position wherein the lockout feature 6924 is pivoted out of the lock cavity 543 to thereby permit the drive beam 542' to be distally advanced to fire the dynamic clamping assembly 550. In an alternative arrangement, the proximally extending unlocking features 6930 are not formed on the cartridge 702, but instead are formed on the actuation sled (not shown) that is supported in the cartridge. When the actuation sled is in the unactuated position (corresponding to an unfired or fresh cartridge) the unlocking features thereon will engage the unlocking arms 6926 on the lock member 6922 to pivot the lock member into the unlocked position.

Figure 58:
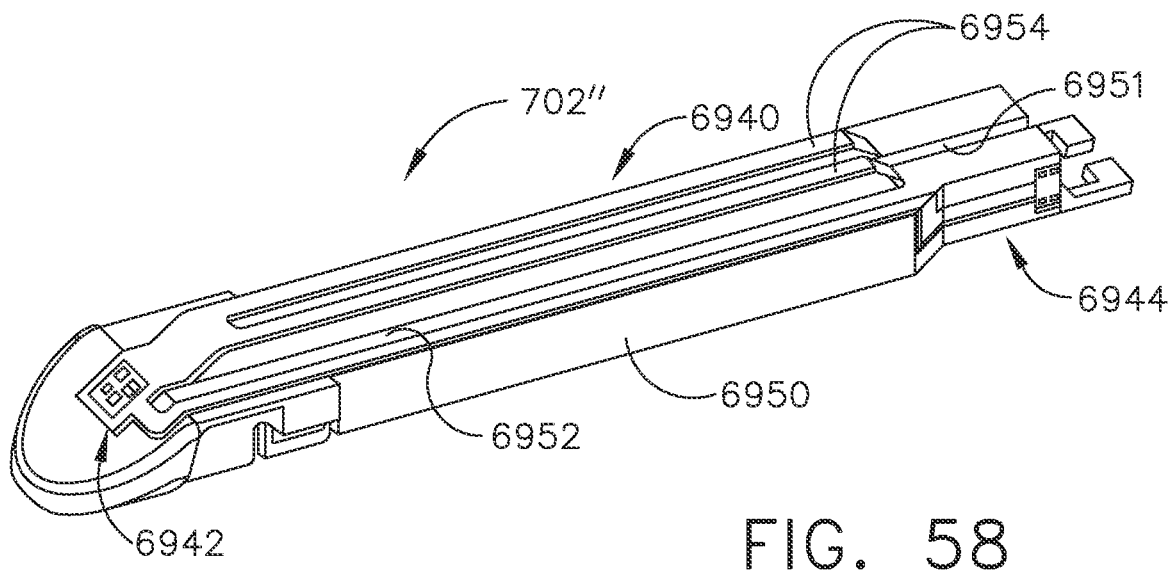
FIG. 58 is a perspective view of another cartridge embodiment.

FIG. 58 illustrates another cartridge 702" arrangement that employs a flexible circuit member 6940 that is attached to a deck surface 6952 of the cartridge body 6950. In the illustrated arrangement, a raised deck portion 6954 extends on each side of an elongate slot 6951 in the cartridge body 6950 to detect the position of a dynamic clamping member of the end effector. The flexible circuit 6940 may include a circuit microchip 6942 that communicates with the circuit board 294 in the adapter in which it is mounted. The flexible circuit member 6940 includes contacts 6944 that electrically contact corresponding contacts (not shown) in a channel of the end effector which are ultimately connected to a circuit board 294 (FIG. 6) of an adapter or other control board arrangement therein. The flexible circuit member 6940 may facilitate better control of the advancement of the dynamic clamping assembly by monitoring its location and using that information to control a firing motor in the surgical instrument. For example, such arrangement may be employed to change the speed or power capability at the beginning or end of the firing stroke. This information may also be used to change the maximum acceptable torque limits at the very beginning of the firing stroke and at the end of the firing stroke. In other arrangements, a deformable member may be provided within the MULU opening for the distal end of the firing rod which could allow for a shock absorbing stop at the end of the stroke but also as a leading force indicator on the current of the motor as the rod gets near the ends of its metallic slot travel. Placement of a portion of the MULU or DLU which has a high moment of inertia but also a higher elastic strain capability would allow this part of the ground force return system to absorb any high force spikes that occur due to the motor's inability to dynamically brake fast enough in case of a series of metallic components inadvertently colliding. This elongatable and preferably elastic component may be in series with the ground and DLU bayonet attachment. Such arrangement may comprise plastic bendable features that exist at the attachment point of the metal articulation pivot I-plates. Such arrangement may also comprise a separate part in cooperation with these attachments and the bayonet connection which has a stretchable aspect with maximum stretch limiting secondary features that allow for limited stretch length but tolerate impact deflections.

During a surgical procedure, it is desirable for a clinician to be able to monitor the progress or location of a dynamic clamping member of the adapter being employed. FIGS. 59-64 illustrate another end effector 2500 that includes means for ascertaining a position of a dynamic clamping assembly 550 of the end effector 2500 to both close and serially fire staples from a staple cartridge while continuing to further close the jaws of the end effector 2500. In one form, the end effector 2500 includes a tool assembly 2600 that may be identical to the tool assembly 600 described above, except for the differences discussed herein. The tool assembly 2600 includes a first jaw 2610 that comprises an anvil assembly 2612 and a second jaw 2700 that that comprises a cartridge assembly 2701. In one form, the anvil assembly 2612 comprises an anvil plate 2620 that includes a staple forming undersurface 2626 which is configured in confronting relationship with the cartridge assembly 2701. An anvil cover 2630 is attached to the anvil plate 2620.

Figure 60:
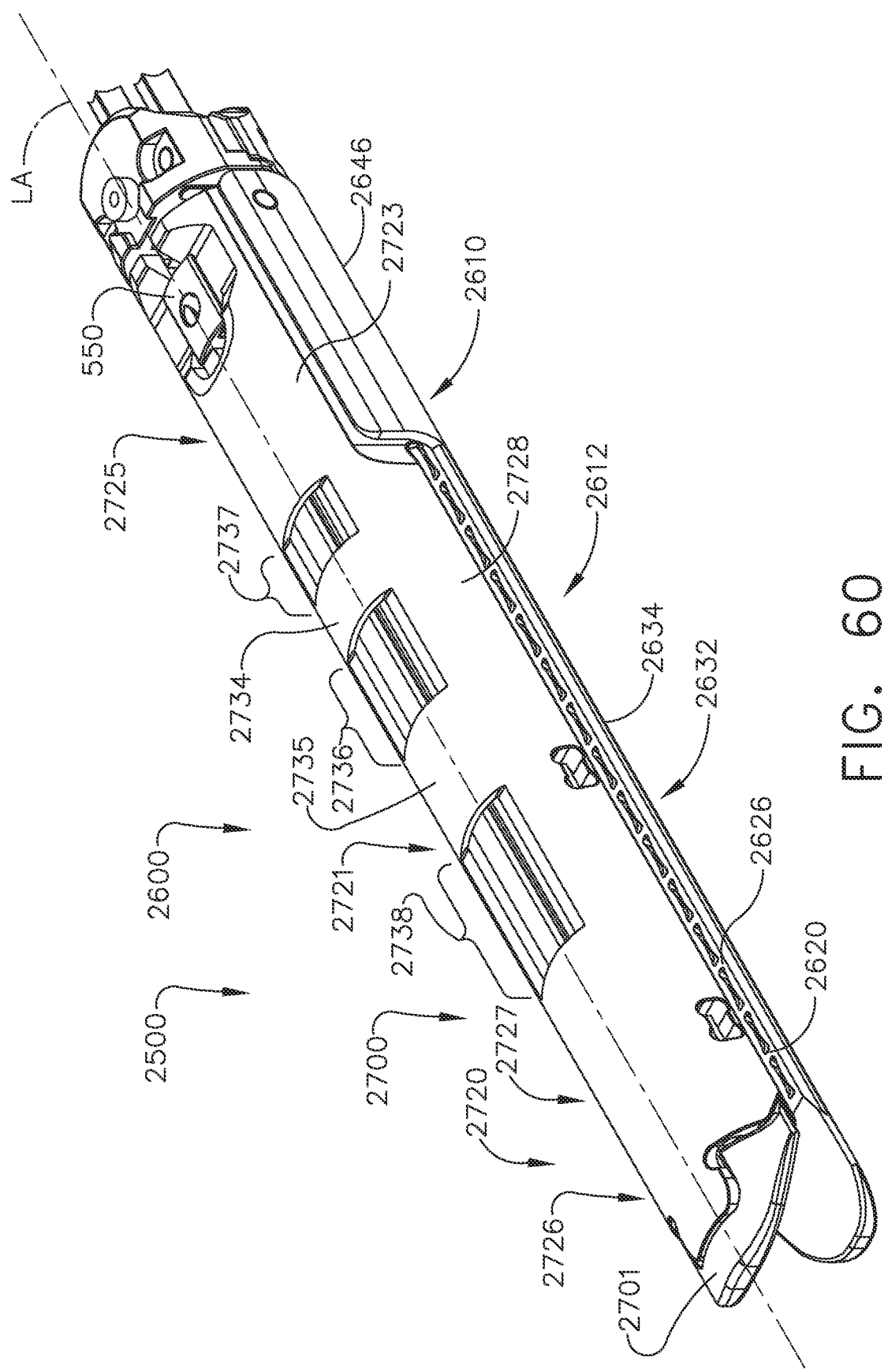
FIG. 60 is a bottom perspective view of the loading unit of FIG. 59.

In the illustrated example, the anvil cover 2630 comprises a body portion 2632 that extends from a proximal end 2642 to a distal end 2644. As shown, the anvil cover 2630 may also include a pair of downwardly extending tissue stops 2646 that serve to prevent target tissue from extending proximally past the proximal-most staples that are stored in the cartridge assembly 2701. FIGS. 60 and 61 illustrate the tool assembly 2600 wherein the dynamic clamping assembly 550 is in a starting position. Stated another way, in FIGS. 60 and 61, the dynamic clamping assembly 550 is in its proximal-most position. As can be most particularly seen in FIG. 59, for example, the anvil cover body portion 2632 comprises a first lateral side portion 2634 and a second lateral side portion 2636 that is laterally spaced from the first lateral side portion 2634. A plurality of first jaw stiffener features 2650, 2652 extend between the first and second lateral side portions 2634 and 2636. The stiffener features 2650 and 2652 are longitudinally offset from each other to define a first jaw opening 2654 therebetween. Additionally, the first jaw stiffener feature 2650 is longitudinally separated from the proximal end portion 2642 by a proximal first jaw opening 2656 and the second jaw stiffener feature 2652 is longitudinally separated from the distal end portion 2644 by a distal first jaw opening 2658 as shown.

Turning next to FIG. 60, the second jaw 2700 comprises a channel 2720 that is configured to operably support the cartridge assembly 2701 therein. The channel 2720 comprises a channel body portion 2721 that includes a proximal end portion 2723 and a distal end portion 2726. The channel 2720 further comprises a primary lateral side portion 2727 and a secondary lateral side portion 2728 that is laterally spaced from the primary lateral side portion 2727. A plurality of second jaw stiffener features 2734, 2735 extend between the primary and secondary lateral side portions 2727 and 2728. The second jaw stiffener features 2734 and 2735 are longitudinally offset from each other to define a second jaw opening 2736 therebetween. Additionally, the second jaw stiffener feature 2734 is longitudinally separated from a proximal end portion 2725 by a proximal second jaw opening 2737 and the second jaw stiffener feature 2735 is longitudinally separated from the distal end portion 2726 by a distal second jaw opening 2738 as shown.

The first jaw stiffeners 2650, 2652 and the second jaw stiffeners 2734, 2735 serve to stiffen the first and second jaws 2610, 2700, respectively while clamping target tissue therebetween. Additionally, the longitudinally displaced openings 2654, 2656, 2658, 2736, 2737, 2738 enable the clinician to view the progress and location of the dynamic clamping assembly during firing (e.g., the portion of the distal advancement of the dynamic clamping assembly 550 wherein the staples are fired from the cartridge assembly 701). For example, as shown in FIG. 62, reference axis $A_1$ corresponds to the locations of the proximal-most staples or fasteners in the cartridge assembly 2701. Reference axis $A_2$ corresponds to the locations of the distal-most staples or fasteners in the cartridge assembly 2701. In the illustrated example, the proximal second jaw opening 2737 extends distally from the proximal-most fastener locations (represented by reference axis $A_1$) to the second jaw stiffener feature 2734 and the distal first jaw opening 2658 extends proximally from the distal most fastener locations (represented by axis $A_2$) to the first jaw stiffener feature 2652.

Still referring to FIG. 62, the proximal end portion 2642 of the first jaw 2610 is in vertical registration (e.g., directly above) with the proximal second jaw opening 2737 in the second jaw 2700 when the jaws 2610, 2700 are in their fully closed positions as shown. In at least one example, the longitudinal length $LL_1$ of the proximal end portion 2642 and the longitudinal length $LL_A$ of the proximal second jaw opening 2737 are approximately equal. Likewise, the first proximal jaw opening 2656 is in vertical registration with the second jaw stiffener feature 2734 when the jaws are in the fully closed positions. The longitudinal length $LL_2$ of the proximal first jaw opening 2656 is approximately equal to the longitudinal length $LL_B$ of the second jaw stiffener feature 2734. The first jaw stiffener feature 2650 is in vertical registration with the second jaw opening 2736. The longitudinal length $LL_3$ of the first jaw stiffener feature 2650 is approximately equal to the longitudinal length $LL_C$ of the second jaw opening 2736. The second jaw stiffener feature 2735 is in vertical registration with the first jaw opening 2654. The longitudinal length $LL_D$ of the second jaw stiffener feature 2735 is approximately equal to the longitudinal length $LL_4$ of the first jaw opening 2654. The first jaw stiffener feature 2652 is in vertical registration with the second jaw opening 2738. The longitudinal length $LL_5$ of the first jaw stiffener feature 2652 is approximately equal to the longitudinal length $LL_E$ of the second jaw opening 2738. The distal-most first jaw opening 2658 is in vertical registration with the distal end portion 2726 of the second jaw 2700 that extends from the distal-most fastener location $A_2$ to the second jaw opening 2738. The longitudinal length of the distal first jaw opening $LL_6$ is approximately equal to the longitudinal length $LL_F$ of the distal end portion 2726.

In the illustrated example, the first jaw stiffener features 2650, 2652, as well as the proximal end portion 2642 and distal end portion 2644 of the first jaw 2610, extend transversely to the longitudinal axis between the first and second lateral side portions 2634 and 2636 and have an arcuate cross-sectional shape. The first jaw stiffener features 2650, 2652, as well as the proximal end portion 2642 and distal end portion 2644 of the first jaw 2610, may also be referred to as "stiffener bridges". Likewise the second jaw stiffener features 2734, 2735 as well as the proximal end portion 2725 and distal end portion 2726 of the second jaw 2700 extend transversely to the longitudinal axis LA between the primary and secondary lateral side portions 2727 and 2728 and have an arcuate cross-sectional shape. The second jaw stiffener features 2734, 2735, as well as the proximal end portion 2725 and distal end portion 2726 of the second jaw 2700 may also be referred to as "stiffener bridges".

FIG. 62 illustrates a position of the dynamic clamping assembly 550 in a firing or ready to fire position. As can be seen in that Figure, a portion of the dynamic clamping assembly 550 may be viewed by the clinician through the proximal second jaw opening 2737. In FIG. 63, the dynamic clamping assembly 550 has been distally advanced and, when in that position, the clinician may view the position of the dynamic clamping assembly 550 through the first jaw opening 2654 as well as the second jaw opening 2736. FIG. 64 illustrates the position of the dynamic clamping assembly 550 in its final or ending position wherein the distal-most staples have been fired. As can be seen in that Figure, the position of the dynamic clamping assembly 550 is viewable through the first jaw opening 2658. Thus, by longitudinally staggering the positions of the first and second jaw stiffener features as well as the first and second jaw openings in the above-described manner, such arrangement serves to maintain a stiffness of the end effector 2500 and more particularly the tool assembly 2600 of the end effector 2500 and even more particularly the first and second jaws 2610, 2700 thereof when the first and second jaws are in their fully closed or clamped positions and the dynamic clamping assembly 550 is distally advanced to cut the clamped tissue and fire the staples supported in the cartridge assembly. In addition, such arrangement enables the clinician to observe a position of the dynamic clamping assembly 550 at any position during a firing stroke of the dynamic clamping assembly 550. As used in this context, the "firing stroke" means the range of movement of the dynamic clamping assembly 550 from a firing position FP or ready to fire position prior to firing any staples to an ending firing position wherein all of the staples have been fired thereby. Alternative arrangements are contemplated wherein additional stiffening features and jaw openings are employed in the above-described manner in the first and second jaws. Still other arrangements are contemplated wherein only one of the first and second jaws include the spaced stiffener features that permit the user to monitor the movement of the dynamic clamping assembly (firing member).

Figure 65:
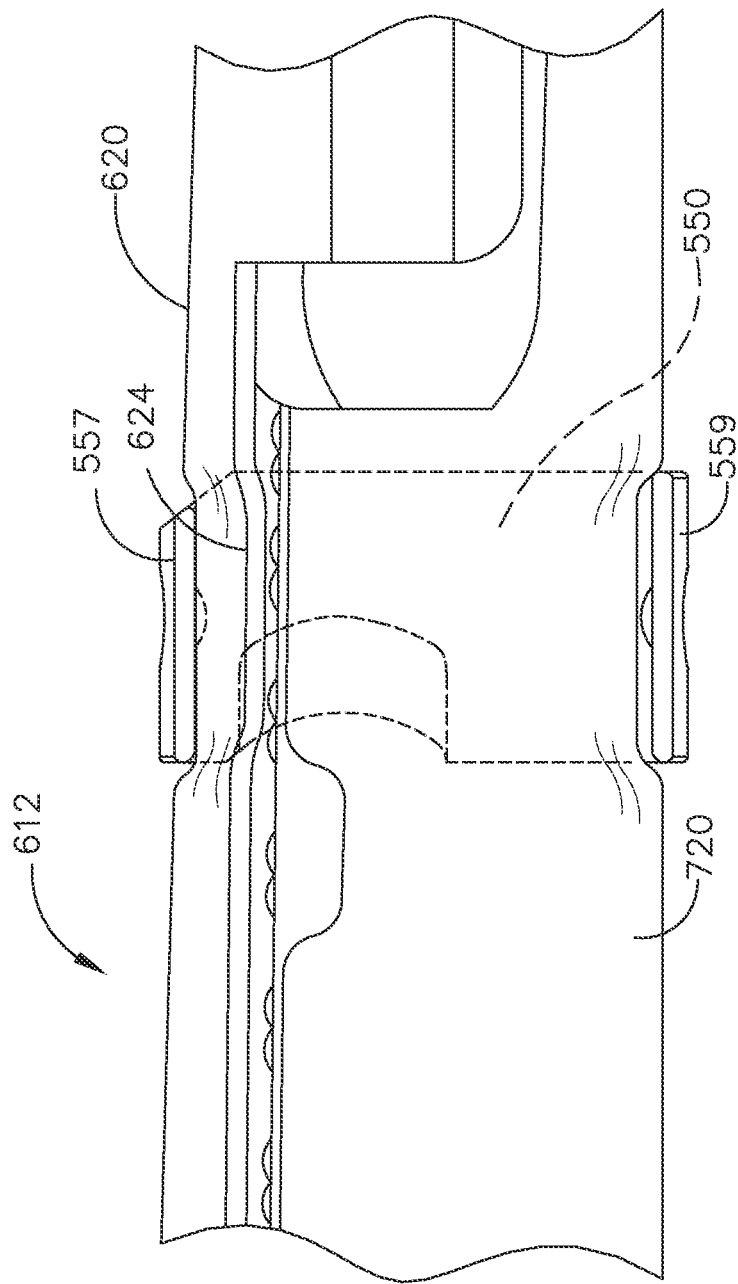
FIG. 65 is a partial side elevational view of another loading unit illustrating a dynamic clamping assembly thereof in a partially fired configuration.

FIG. 65 illustrates a conventional dynamic clamping assembly 550 applying clamping forces to an anvil assembly 612 which may lead to the undesirable deflection of the ledges 624 on the anvil plate 620 by the anvil engagement features 557 as well as the deflection of channel ledges formed in the channel 720 by the channel engagement features 559. Unlike end effectors which employ a secondary jaw closure system, such arrangement that employs the dynamic clamping assembly to apply all closure forces to the first and second jaws. Such design relies, for example, on very high local rolling forces to cause tissue compression and establish a proper tissue gap between the jaws. Separate and independent closure and firing systems, to the contrary, rely on projection of force as distal as possible.

Figure 66:
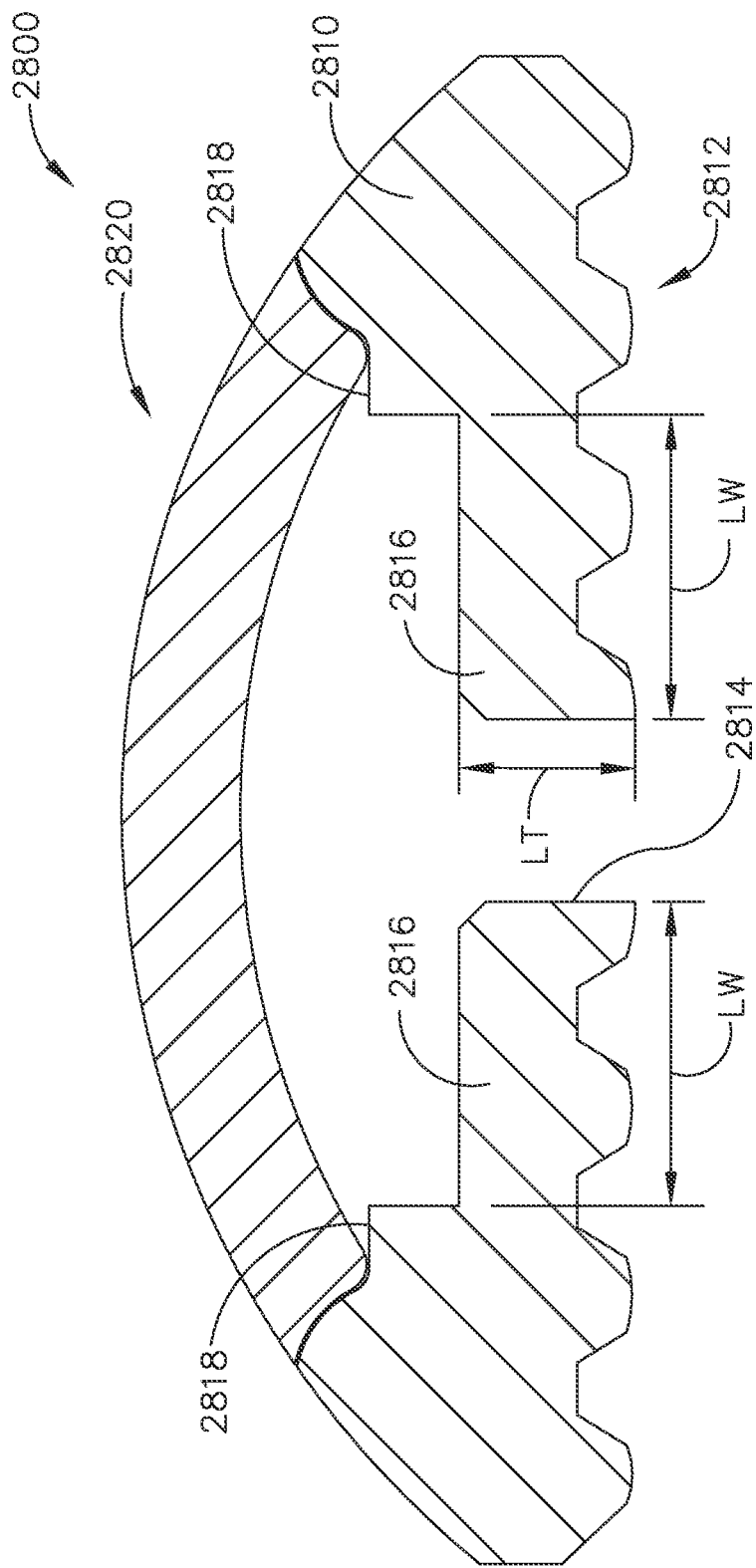
FIG. 66 is a cross-sectional end view of a portion of an anvil assembly of a loading unit.

FIG. 66 illustrates a portion of an anvil assembly 2800 that comprises an anvil plate 2810 that includes a staple forming undersurface 2812 thereon. The anvil plate 2810 includes an elongate slot 2814 that is configured to accommodate the body portion of a dynamic clamping assembly 550 as the dynamic clamping assembly is axially advanced during the firing process. The elongate slot 2814 is defined between two anvil plate ledges 2816 that extend along each lateral side of the slot 2814. As a dynamic clamping member is distally advanced, anvil engagement tabs or pins on the dynamic clamping assembly 550 slidably engage the anvil plate ledges 2816 to retain the anvil assembly 2800 clamped onto the target tissue. An anvil cover plate or an anvil cap 2820 is received on cap ledges 2818 on the anvil plate 2810 and may be welded or otherwise attached thereto. Each of the anvil plate ledges 2816 extends inwardly in a cantilever configuration and has a ledge width LW. As the dynamic clamping assembly 550 clampingly engages the anvil assembly 2800, the anvil engagement features or tabs 556 of the dynamic clamping assembly 550 engage the ledges 2816 to apply the closing motions thereto. In this arrangement, however, the ledges 2816 are more robust and have a ledge thickness LT that is greater than the ledge thickness of the ledges on an anvil plate 620, for example.

Figure 67:
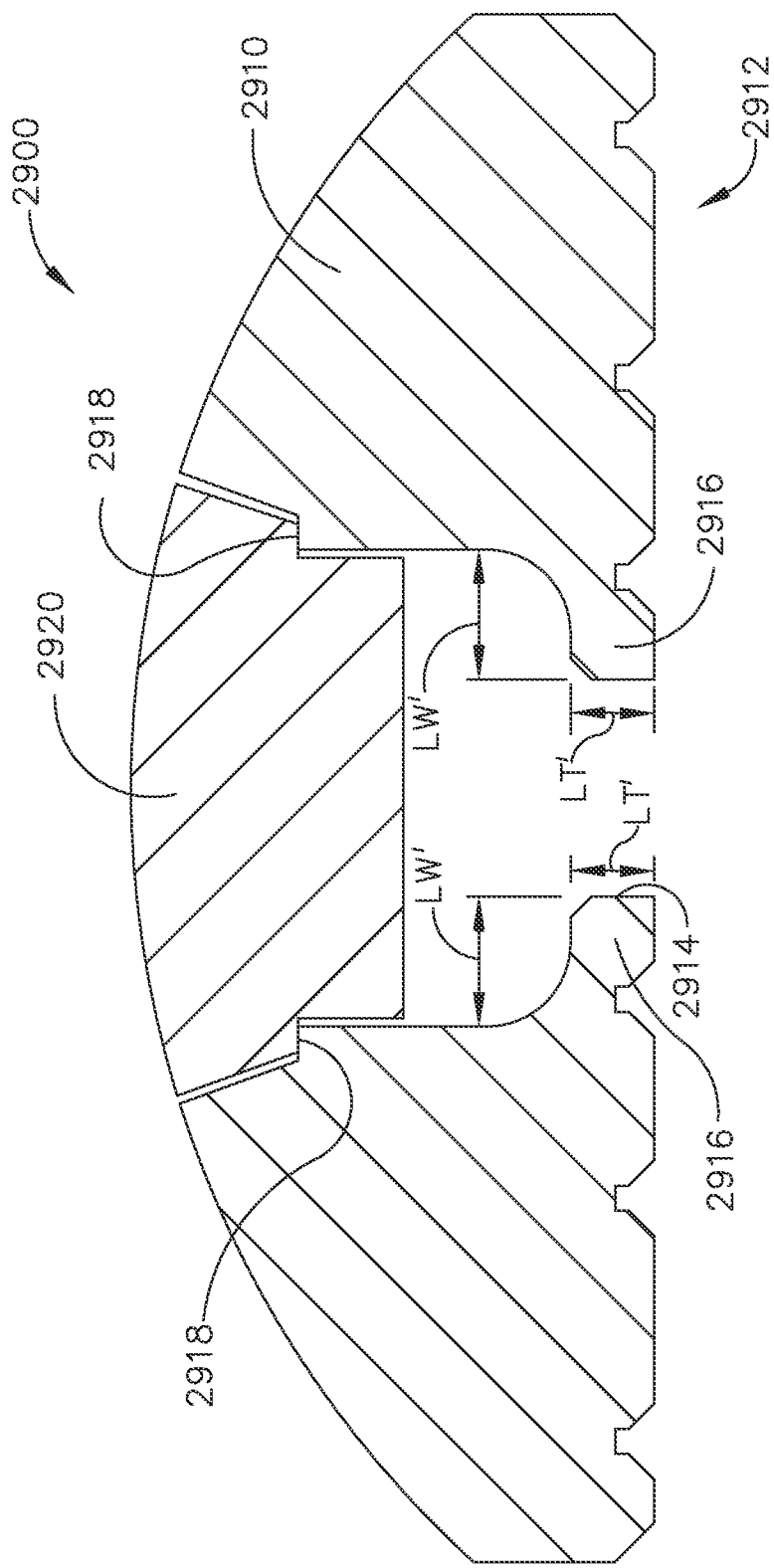
FIG. 67 is a cross-sectional end view of a portion of another anvil assembly of a loading unit.

FIG. 67 illustrates another anvil assembly 2900 that comprises an anvil plate 2910 that includes a staple forming undersurface 2912 thereon. The anvil plate 2910 includes an elongate slot 2914 that is configured to accommodate the body portion of a dynamic clamping assembly 550 as the dynamic clamping assembly is axially advanced during the firing process. The elongate slot 2914 is defined between two anvil plate ledges 2916 that extend along each lateral side of the slot 2914. An anvil cover plate or an anvil cap 2920 is received on ledges 2918 on the anvil plate 2910 and may be welded or otherwise attached thereto. Each of the anvil plate ledges 2916 extend inwardly in a cantilever configuration. Although each ledge 2916 has a ledge thickness LT' that is less than the ledge thickness LT (FIG. 66), each ledge 2916 has a ledge width LW' that is less than the ledge width LW of ledges 2816. Such shorter ledges 2916 will experience less deflection that the ledges on the anvil plate 620, for example. Such arrangement represents an improvement over past anvil plate arrangements because the ledges 2916 are shorter which may limit the amount of deflection experienced during the high load advancement of the dynamic clamping assembly.

Figure 69:
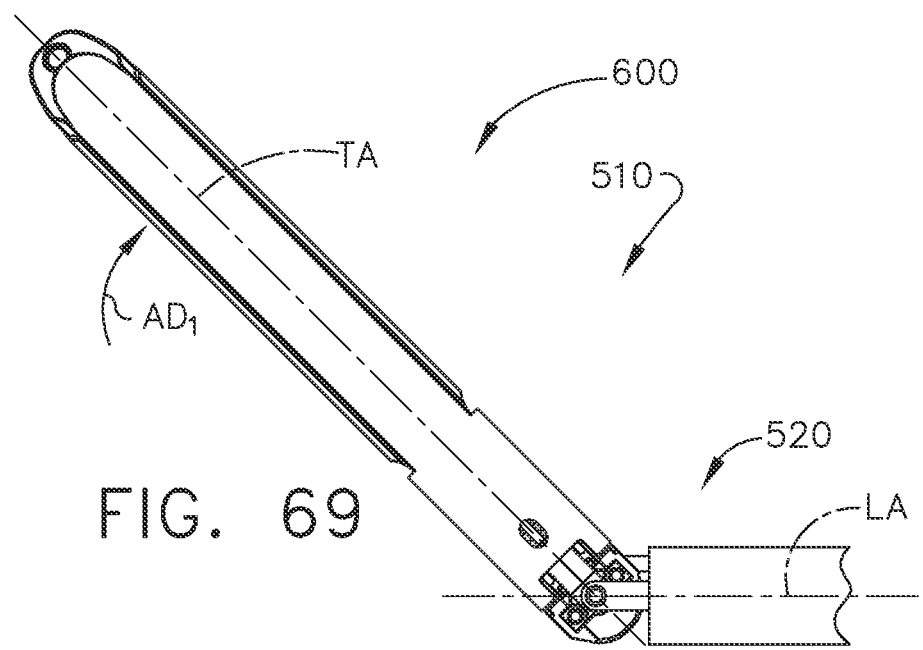
FIG. 69 is another top view of the loading unit of FIG. 68 with the tool assembly in a first articulated position.
Figure 68:
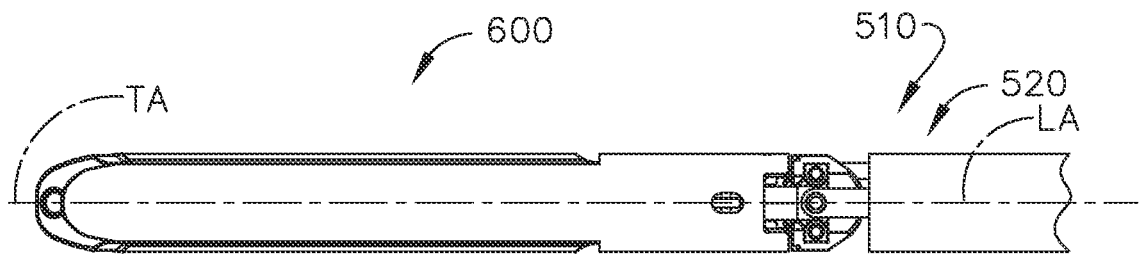
FIG. 68 is a top view of a loading unit of an adapter with the tool assembly thereof in an unarticulated position.
Figure 70:
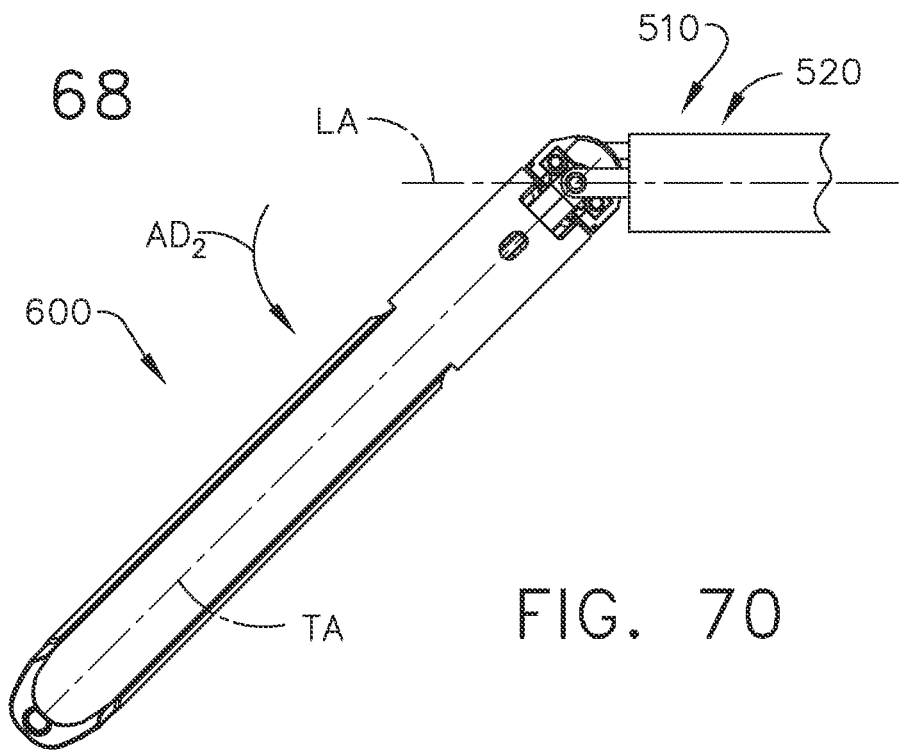
FIG. 70 is another top view of the loading unit of FIGS. 68 and 69 with the tool assembly in a second articulated position.

As discussed above, in one example, the surgical end effector 500 comprises a loading unit 510 that is configured to be operably coupled to a distal end of a shaft assembly of an adapter. As can be seen in FIGS. 68-70, in one arrangement the loading unit 510 comprises a proximal body portion 520 and a tool assembly 600 that is configured to be articulated relative to the proximal body portion 520. When the proximal body portion 520 is coupled to the shaft assembly, the proximal body portion 520 is axially aligned with a longitudinal axis LA that is defined by the shaft assembly of the adapter. When the tool assembly 600 is in an unarticulated position (FIG. 68), an axis TA of the tool assembly 600 is aligned with the longitudinal axis LA of the adapter shaft assembly, for example. The tool assembly 600 may also be articulated to a first side (FIG. 69) wherein the tool axis TA is transverse to the longitudinal axis LA as well as to a second side (FIG. 70) wherein the tool axis TA is transverse to the longitudinal axis LA. During some articulation motions, an articulation bar 258 of the adapter may encounter significant resistive forces. Sensing the resisting forces on the articulation frame or articulation bar 258 which is interconnected to an articulation link 560 of the DLU or MLU via a strain gauge or other deflection oriented circuit would enable the control circuit for the articulation motor to back drive the articulation motor when the force exceeds a predetermined threshold. Such action would remove some or all of the resistance provided to the articulation frame via the drive member of the adapter and thereby prevent internal drive damage and/or minimize collateral tissue damage. FIG. 72 illustrates use of multi-axis strain gauges 310, 312 on the outer tube assembly 206. The multi-axis strain gauges 310, 312 are connected to the circuit board 294 located within the inner housing assembly 204 (shown in FIG. 6). The strain gauges may, in the alternative, be mounted on the articulation bar 258. In at least one arrangement, for example, the strain goes negative as the force on the articulation bar 258 increases. Such arrangement may be particularly useful when the user intended to straighten the tool assembly (FIG. 68) to pull it back through a trocar, but failed to get the tool assembly 600 fully straightened. In such case, the end effector may become jammed within the trocar cannula and/or result in high loading of the articulation frame or articulation bar 258 and drive shaft 214. This condition might be completely mitigated if the articulation system could sense this condition via load on the articulation bar 258 or drive screw 214 and longitudinally adjust the position of the articulation bar 258 by energizing the articulation motor of the surgical instrument 100 to which the adapter is attached until the bending forces are below the predetermined threshold.

Articulation of the end effector 500 or, more particularly, the articulation of the tool assembly 600 of the end effector 500 is controlled by rotating the second proximal drive shaft 214 that is in threaded engagement with the articulation bearing assembly 252 as was discussed above. See FIGS. 6-9. The second drive converting assembly 250 of adapter 200 further includes articulation bar 258 that has a proximal portion that is secured to inner race 257 of articulation bearing 255. See FIG. 7. A distal portion of articulation bar 258 includes a slot 258a therein, which is configured to accept a hook 562 of the articulation link 560 (FIG. 10) of end effector 500. Articulation bar 258 functions as a force transmitting member to components of end effector 500. In the illustrated arrangement and as further discussed in WO 2016/057225 A1, articulation bearing assembly 252 is both rotatable and longitudinally translatable and is configured to permit free, unimpeded rotational movement of the tool assembly 600 of the end effector 500 when its jaw members 610, 700 are in an approximated position and/or when jaw members 610, 700 are articulated.

In operation, as second proximal drive shaft 214 is rotated due to a rotation of second connector sleeve 222, as a result of the rotation of the second coupling shaft 64c of surgical instrument 100, articulation bearing assembly 252 is translated axially along threaded distal end portion 214a of second proximal drive shaft 214. This axial translation of the articulation bearing assembly 252 causes the articulation bar 258 to be axially translated relative to outer tube 206. As articulation bar 258 is translated axially, it causes concomitant axial translation of articulation link 560 of end effector 500 to effectuate an articulation of tool assembly 600. Articulation bar 258 is secured to inner race 257 of articulation bearing 253 and is thus free to rotate about the longitudinal axis relative to outer race 259 of articulation bearing 253.

Figure 73:
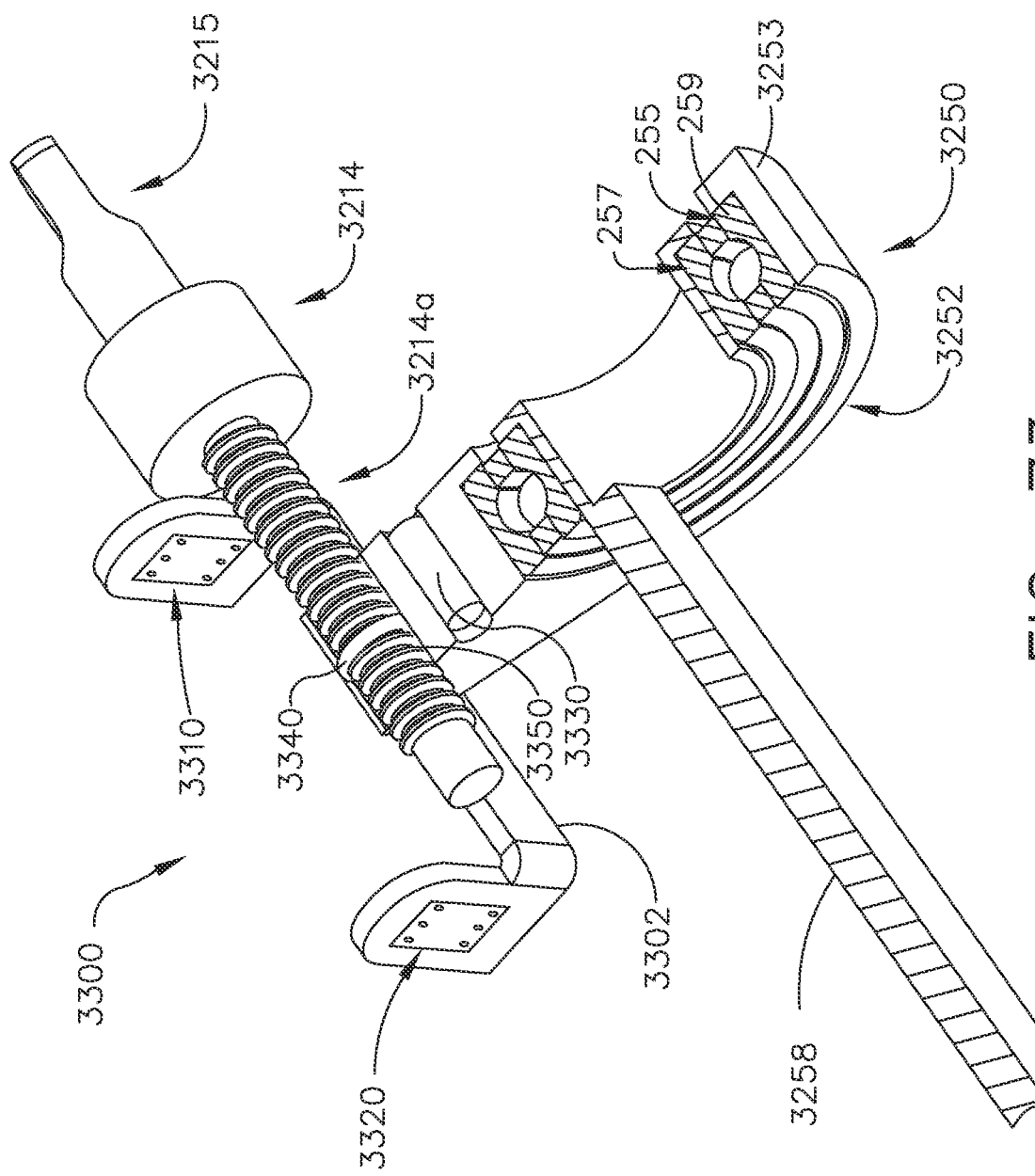
FIG. 73 is a partial cross-sectional perspective view of an articulation system and sensor assembly embodiment of an adapter in an unarticulated (neutral) position.
Figure 74:
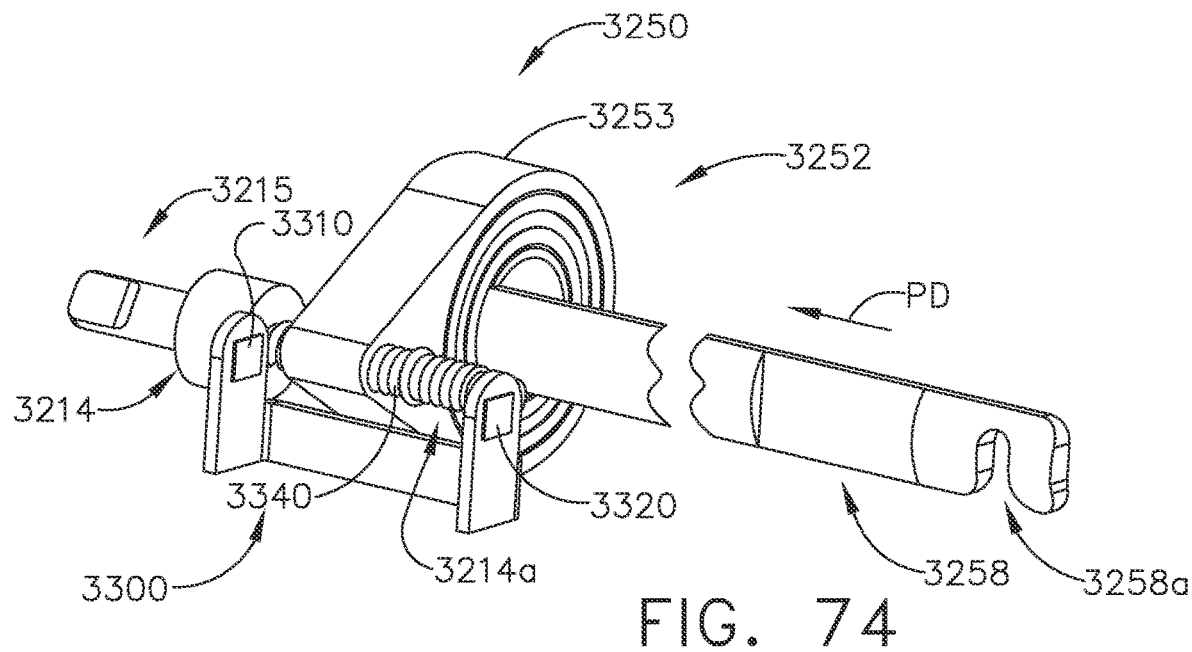
FIG. 74 is another perspective view of the articulation system and sensor assembly of FIG. 73 in a first articulated position.
Figure 75:
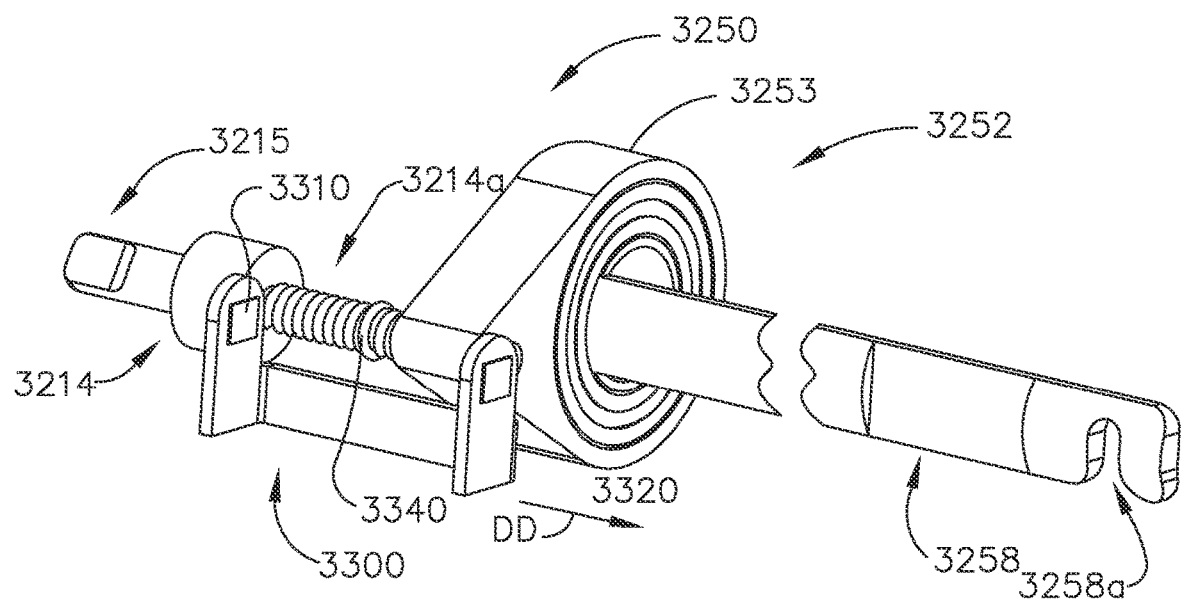
FIG. 75 is another perspective view of the articulation system and sensor assembly of FIGS. 73 and 74 in a second articulated position.

It may be desirable to control the articulation of the end effector and to monitor the articulated position thereof during a surgical procedure. FIGS. 73-75 illustrate an improved articulation control system or second drive converting assembly 3250. The second drive converting assembly 3250 in many aspects is identical to the second drive converting assembly 250 described above, except for the specific differences discussed below. As can be seen in FIG. 73, the second drive converting assembly 3250 includes second proximal drive shaft 3214 that is rotatably supported within inner housing assembly 204 (shown in FIG. 6). Second rotatable proximal drive shaft 3214 includes a non-circular or shaped proximal end portion 3215 that is configured for connection with second coupling shaft 64c of surgical instrument 100. Second rotatable proximal drive shaft 3214 further includes a threaded distal end portion 3214a that is configured to threadably engage an articulation bearing housing 3253 of an articulation bearing assembly 3252. Housing 3253 supports an articulation bearing 255 that has an inner race 257 that is independently rotatable relative to an outer race 259. Articulation bearing housing 3253 has a non-circular outer profile, for example teardropped shaped, that is slidably and non-rotatably disposed within a complementary bore (not shown) of inner housing hub 204a (FIG. 6). Second drive converting assembly 3250 further includes articulation bar 3258 that has a proximal portion that is secured to inner race 257 of articulation bearing 255. A distal portion of articulation bar 3258 includes a slot 3258a therein, which is configured to accept a hook 562 of the articulation link 560 (FIG. 10) of end effector 500. Articulation bar 3258 functions as a force transmitting member to components of end effector 500.

In the illustrated arrangement, the articulation bearing housing 3253 is in threaded engagement with the threaded distal end portion 3214a of the second rotatable proximal drive shaft 3214. The bearing housing 3253 may also be referred to herein as an articulation driver arrangement. In at least one example, the bearing housing or articulation driver arrangement 3252 is configured to move axially in two directions from a central or neutral position (FIG. 73) to a proximal axial position (FIG. 74) and to a distal axial position (FIG. 75). When the bearing housing 3253 is in the central or neutral position, the tool assembly 600 is axially aligned with the proximal body portion 520 such that the tool assembly axis TA is aligned with the longitudinal axis LA (FIG. 68). Stated another way, the tool assembly or surgical end effector is unarticulated. The tool assembly 600 is oriented in the unarticulated position initially to facilitate insertion of the end effector through a trocar cannula. When the second rotatable proximal drive shaft 3214 is rotated in a first rotary direction, the bearing housing 3252 is driven in a proximal axial direction from the neutral position. As the bearing housing 3252 moves in the proximal direction PD, the tool assembly 600 articulates in a first articulation direction $AD_1$ until the bearing housing 3252 reaches the proximal axial position (FIG. 74) at which point the tool assembly 600 is fully articulated in the articulation direction $AD_1$ shown in FIG. 69, for example. When the second rotatable proximal drive shaft 3214 is rotated in a second rotary direction (opposite the first rotary direction), the bearing housing 3253 is driven in a distal direction DD from the neutral position. As the bearing housing 3253 moves in the distal direction DD, the tool assembly 600 articulates in a second articulation direction $AD_2$ until the bearing housing 3253 reaches the distal axial position (FIG. 75) at which point the tool assembly 600 is fully articulated in the articulation direction $AD_2$ shown in FIG. 70, for example.

As discussed above, to insert the surgical end effector into the patient through a cannula of a trocar, the tool assembly may need to be in the unarticulated position and it may need to be returned to the unarticulated position to enable the surgical end effector to be removed from the patient through the trocar cannula after the procedure is completed. Thus, the articulation control system may need to be able to precisely control the axial position of the bearing housing to ensure that the tool assembly is precisely aligned with the proximal housing to avoid possible jamming of the end effector with the trocar cannula. In one example, an articulation sensor assembly, generally indicated as 3300 is employed to communicate with a motor controller circuit board 142a (FIG. 4), or other controller arrangement of the electromechanical surgical instrument 100 to which the adapter is operably coupled. In the illustrated example, the articulation sensor assembly 3300 comprises a proximal sensor 3310 and a distal sensor 3320 that are mounted to a sensor bracket 3302. In addition, the bearing housing 3253 includes a sensor magnet 3330 as can be seen in FIG. 73. The proximal and distal sensors 3310, 3320 may comprise conventional Hall sensors and be wired to the adapter circuit board 294 (FIG. 6) for ultimate electrical communication with the motor controller circuit board 142a in the electromechanical surgical instrument 100 (FIG. 4). The sensors 3310, 3320 serve to detect the position of the sensor magnet 3330 so as to monitor when the bearing housing 3253 nears the neutral position and reaches the neutral position and convey that information back to the motor controller circuit board. Such arrangement enables a motor controller algorithm to vary the speed of the articulation motor as it approaches the neutral position to allow the user to stop near the neutral position without the system intentionally pausing at that predetermined position.

In addition to the above described articulation sensor assembly, an O-ring 3340 or similar feature is located on the threaded portion 3214a of the second rotatable proximal drive shaft 3214 in place of or over some of the threads of the threaded portion 3214a. In such an arrangement, a spike in the articulation motor current (e.g., motor 156—FIG. 4) will occur when the O-ring 3340 encounters a threaded portion 3350 of the bearing housing 3253. This current spike will occur when the O-ring 3340 encounters the threads 3350 to increase rotary resistance or friction when entering from a proximal direction or a distal direction of travel and is used to determine the distance that the bearing housing 3253 is from the neutral position. Once a spike in motor current is detected, an algorithm controlling the articulation motor 156 sets the drive screw rotary position to zero and the articulation motor 156 then rotates the drive screw 3214 in the proper rotary direction to drive the bearing housing 3253 axially to reach the neutral position. In alternative arrangements of the O-ring, select threads of the threaded portion 3214a may be removed or omitted or intentionally damaged or altered to alter the rotational resistance/friction and thus alter the amount of motor current drawn by the articulation motor to facilitate control of the articulation motor in the above-described manner.

Figure 76:
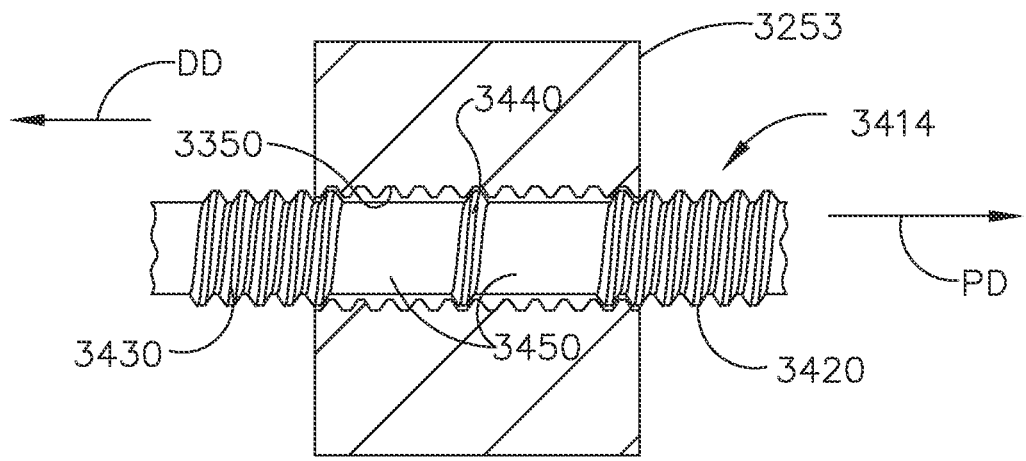
FIG. 76 is a partial cross-sectional view a portion of an alternative proximal drive shaft and bearing housing of an alternative articulation system in an unarticulated (neutral) position.
Figure 77:
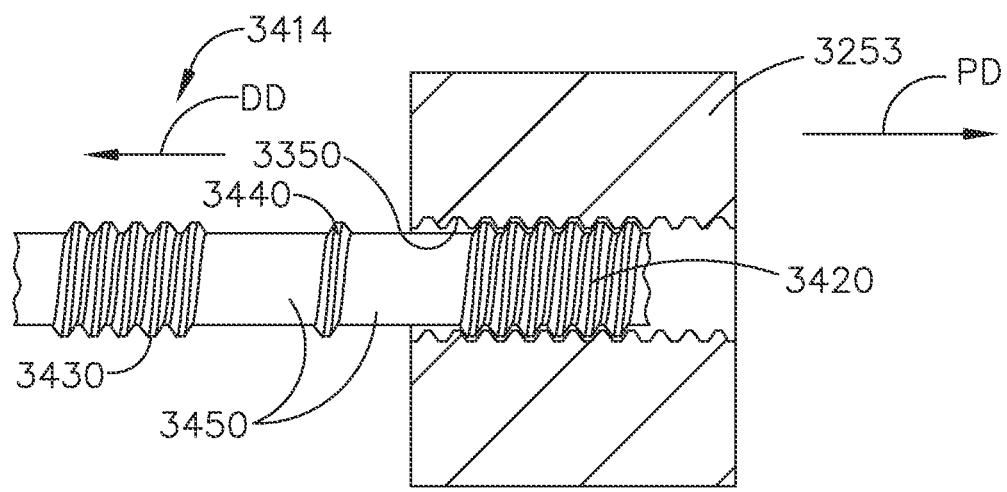
FIG. 77 is another partial cross-sectional view the portion of an alternative proximal drive shaft and bearing housing of the alternative articulation system of FIG. 76 in an articulated position.

FIGS. 76 and 77 depict an alternative proximal drive shaft 3414 that may be employed to axially advance the bearing housing 3253 and detect the position of the bearing housing 3253 as the drive shaft 3414 is rotated in the first and second rotary directions. As can be seen in FIGS. 76 and 77, the proximal drive shaft 3414 is formed with a proximal set of threads 3420, a distal set of threads 3430 and a center thread 3440. The center thread 3440 is centrally located between the proximal set of threads 3420 and the distal set of threads 3430 and is separated therefrom by unthreaded portions 3450. Threads 3420, 3430, 3440 are configured to threadably engage internal threads 3350 formed in the bearing housing 3253. FIG. 76 illustrates the bearing housing 3253 in the neutral position. As can be seen in FIG. 76, the least mount of threads (including the threads of the proximal thread segment 3420, the distal thread segment 3430 and the center thread 3430) are in threaded contact with the threads 3350 of the bearing housing 3253 and will thus result in the lowest amount of current drawn by the articulation motor. FIG. 77 illustrates the bearing housing 3253 being moved in the proximal direction with all of the threads of the proximal thread segment 3420 in threaded engagement with the threads in the bearing housing 3253 which will cause the articulation motor 156 to experience a higher amount of current. Such higher current will also be experienced when the bearing housing 3253 is driven in the distal direction DD. By monitoring when the current is at its lowest magnitude or is approaching the lowest magnitude, an algorithm controlling the articulation motor 156 may be used to slow down and stop the articulation motor 156 in the various manners described herein.

Figure 78:
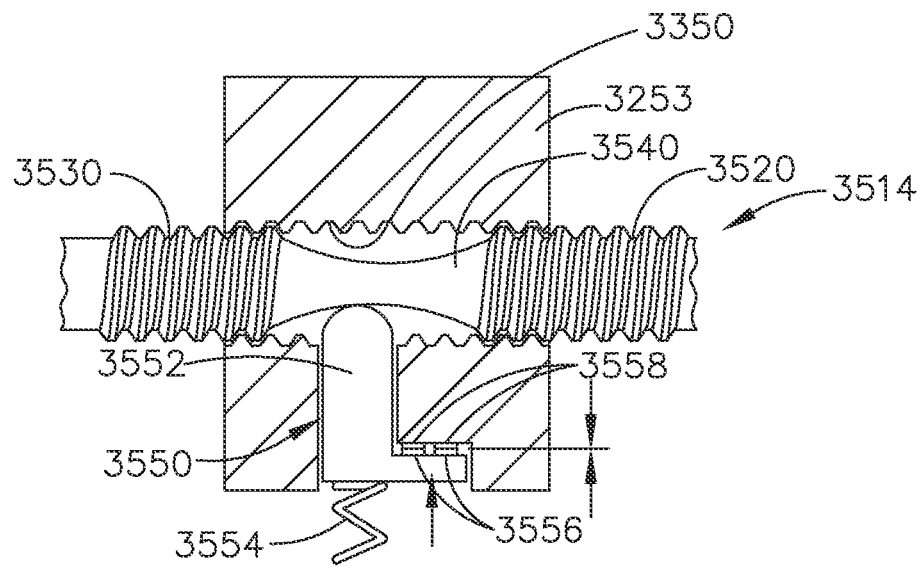
FIG. 78 is a partial cross-sectional view a portion of an alternative proximal drive shaft and bearing housing of an alternative articulation system in an unarticulated (neutral) position.
Figure 79:
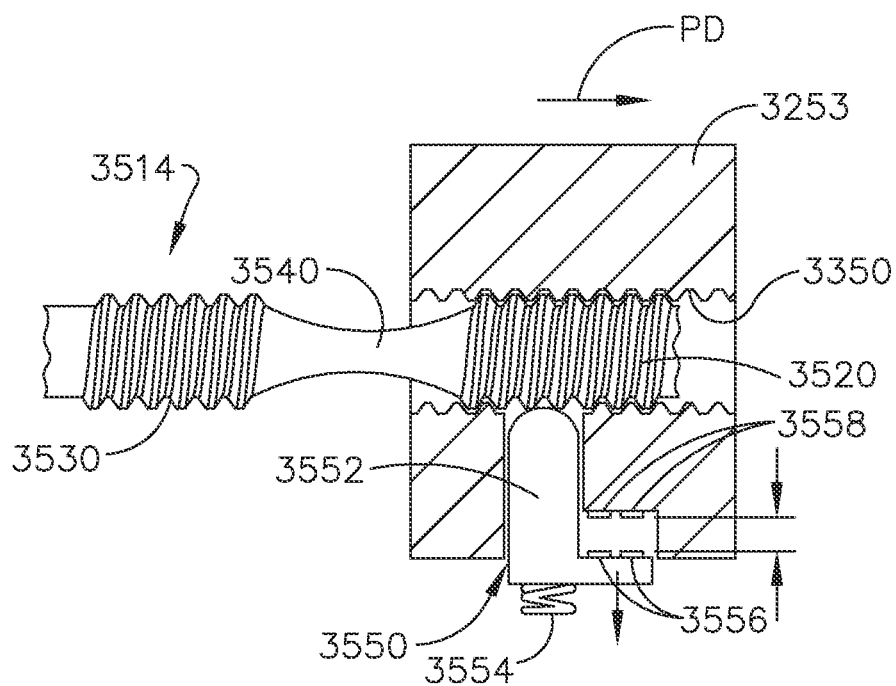
FIG. 79 is another partial cross-sectional view the portion of an alternative proximal drive shaft and bearing housing of the alternative articulation system of FIG. 78 in an articulated position.
Figure 80:
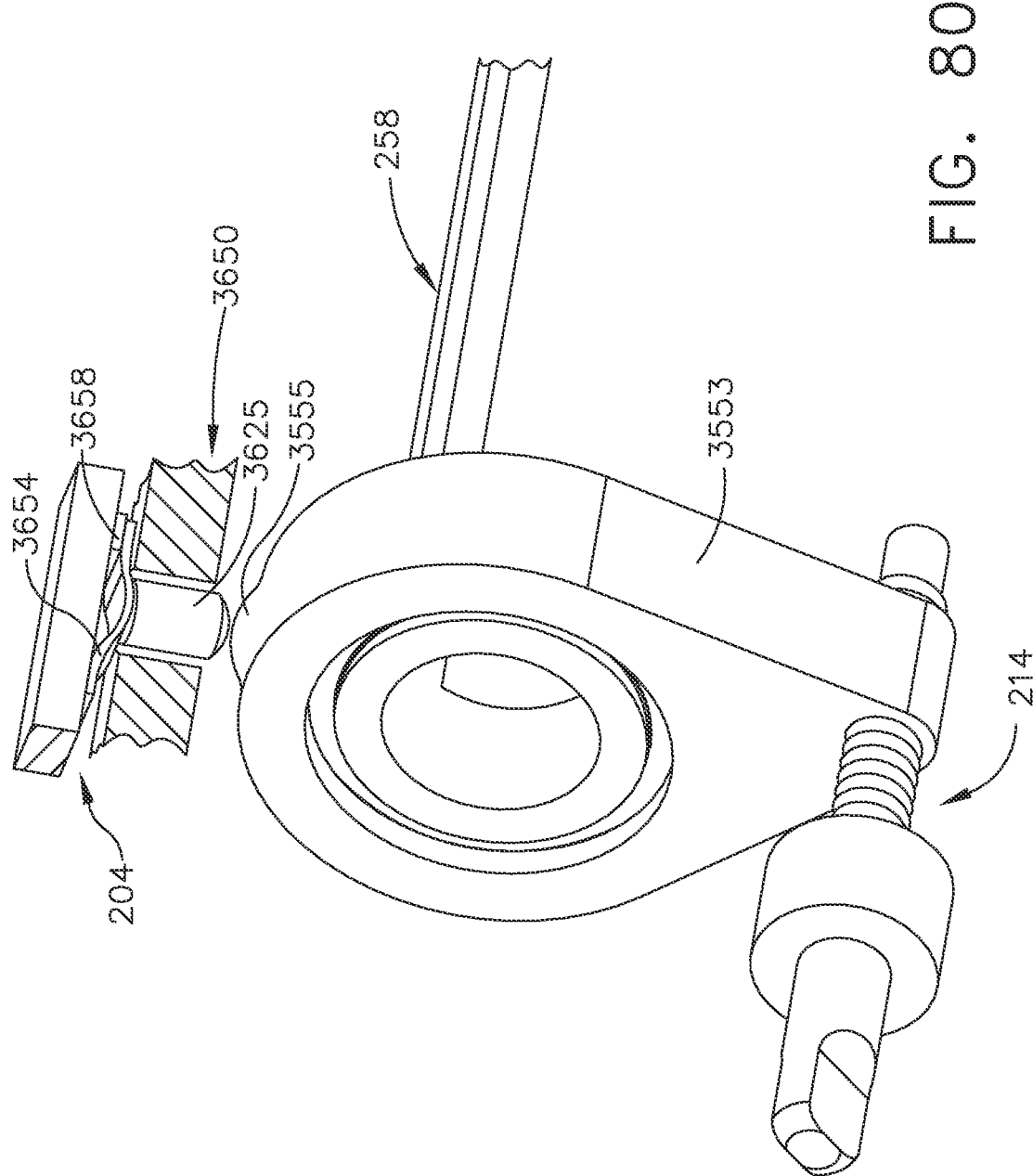
FIG. 80 is a partial cross-sectional perspective view of another articulation system and sensor assembly embodiment of an adapter in an unarticulated (neutral) position.

FIGS. 78 and 79 depict an alternative proximal drive shaft 3514 and switch arrangement 3550 that may be employed to detect when the bearing housing 3253 approaches and reaches the neutral position as the drive shaft 3514 is rotated in the first and second rotary directions. As can be seen in FIGS. 78 and 79, the proximal drive shaft 3514 is formed with a proximal set of threads 3520 and a distal set of threads 3530 that are separated by an unthreaded central portion 3540 that has a diameter that decreases or tapers from each end so that it is smallest in its center. Threads 3520, 3530 are configured to threadably engage internal threads 3350 formed in the bearing housing 3253. In this arrangement, the switch arrangement 3550 comprises a radially movable switch plunger 3552 that is supported in the bearing housing 3253 and is biased into contact the drive shaft 3514 by a biasing member such as a spring 3554. The switch plunger 3552 includes contacts 3556 that are configured to operably interface with contacts 3558 in the bearing housing 3253. FIG. 78 illustrates the bearing housing 3253 in the neutral position. As can be seen in FIG. 78, the switch plunger 3552 is in contact with approximately the center of the unthreaded central portion 3540 of the drive shaft 3514 such that the contacts 3556 are in contact with the contacts 3558. Contacts 3556/3558 communicate with the motor control circuit in the surgical instrument 100 through the circuit board 294 to indicate that the bearing housing 3253 is in the neutral position. FIG. 79 illustrates the bearing housing 3253 being moved in the proximal direction PD with all of the threads of the proximal thread segment 3520 in threaded engagement with the threads in the bearing housing 3253 and the switch plunger 3552 in contact with the proximal thread segment 3520 which moves the contacts 3556 away from contacts 3558 as shown. This condition will also occur when the bearing housing 3253 is moved in the distal direction. Such arrangements may be employed to control the articulation motor in the above-described manners.

FIGS. 80-83 depict an alternative switch arrangement 3650 for detecting when the bearing housing 3553 is in the neutral position. In this arrangement for example, the switch arrangement 3650 is supported in the inner housing 204 and includes a radially movable switch plunger 3652. As can be seen in FIGS. 80-83, the bearing housing 3553 is formed with an activator detent 3555 that is configured to interact with the switch plunger 3652. The switch plunger 3652 interacts with a leaf spring 3654 that is configured to engage a contact 3658 in the inner housing 204. FIG. 81 illustrates the bearing housing 3553 in a neutral position. When in that position, the switch plunger 3652 has biased the leaf spring 3654 into contact with the contact 3658 to complete a circuit to inform the motor controller circuit through the circuit board 294 that the bearing housing 3553 is in the neutral position. FIG. 82 illustrates the bearing housing 3553 in a position that is proximal to the neutral position such that the detent 3555 on the bearing housing 3553 is proximal to the center of the switch plunger 3652 to enable the spring 3654 to move out of contact with the contact 3658. FIG. 83 illustrates the bearing housing 3553 in a position distal to the neutral position such that the detent 3555 on the bearing housing 3553 is distal to the center of the switch plunger 3652 to enable the leaf spring 3654 to move out of contact with the contact 3658. Such arrangements may be employed to control the articulation motor 158 in the above-described manners.

As described above, in at least some examples, the adapter 200 employs a proximal rotary drive shaft 216 that is ultimately rotated by a corresponding motor in the surgical instrument 100 to rotate the shaft assembly about the longitudinal axis LA. During a procedure, it is desirable for the clinician to know the exact rotary position of the shaft assembly for adjustment purposes and resetting purposes. One arrangement, for example, could employ an optical detector arrangement for detecting incremental etched or printed markings on the outer shaft tube 206, for example. Such markings may be provided completely around a proximal end portion of the outer tube 206 that allow for detection and indication of multiple 360 increments. Longitudinal marks may correlate with a ring advancing feature that moves one increment distal for each full 360° rotation.

Figure 84:
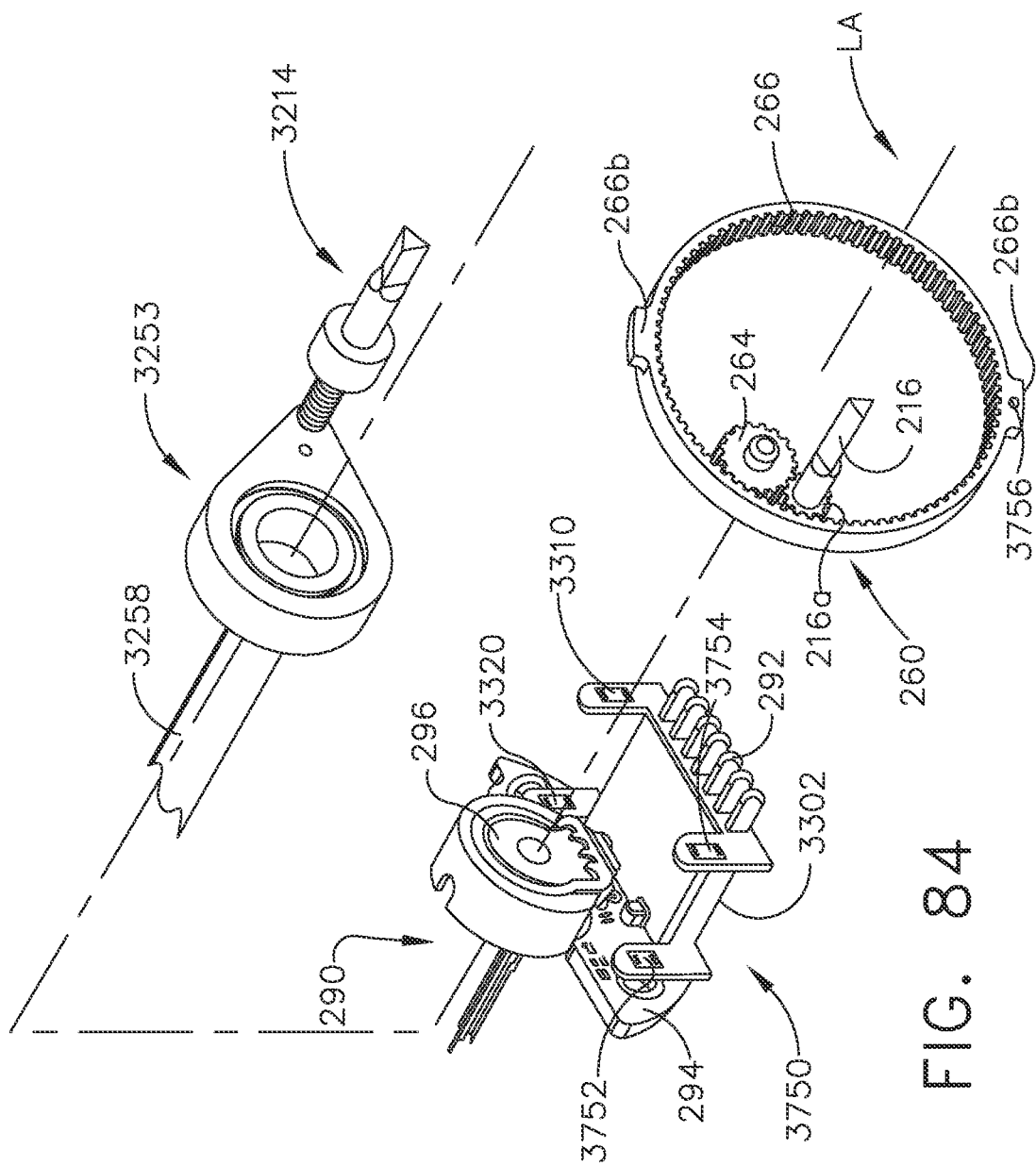
FIG. 84 is a perspective view of portions of an articulation system and sensor system and a shaft rotation system and sensor arrangement of another adapter.

FIG. 84 illustrates another rotational detection system 3750 that may be employed to detect and control the rotation of the shaft assembly about the longitudinal axis LA. As can be seen in that Figure, the rotational detection system 3750 includes a pair of rotational sensors 3752, 3754 that are configured to sense the position of a sensor magnet 3756 in one of the opposed, radially extending protrusions 266b. The sensors 3752, 3754 are below the centerline of the adapter. In another arrangement, one rotational sensor is employed and a sensor magnet is mounted in each of the protrusions 266b. The magnets are oriented so their polarities are different. Due to the different polarities, a single sensor is able to detect the positions of both magnets ensuring unique tracking of each magnet and proper determination of position. This information is transmitted to the motor controller circuit in the surgical instrument 100 through circuit board 294 and contacts 292. A control algorithm may be employed to control the second motor 154 such that the rotation of the shaft assembly may be limited to rotate through a certain range or stop at a certain point or to bring the rotations induced within the last use back to a zero position. In other examples, multiple 360° rotation overall limiting features which allow the shaft to turn a predetermined number of 360° rotations before instructing the user to counter rotate. In other arrangements, the system may automatically cause the motor to counter rotate the shaft assembly after the first closure cycle after the cartridge is reloaded or the DLU is replaced.

FIGS. 85-88 illustrate an end effector 4500 that may be used in connection with the various adapter arrangements described herein. In on arrangement, the end effector 4500 comprises a first jaw 4610 in the form of an anvil assembly 4612. The anvil assembly 4612 comprises a proximal end portion 4614 and a distal end portion 4616 that define a first longitudinal jaw axis or an anvil axis AA. The anvil assembly 4612 further comprises a first jaw surface or anvil surface 4618 that may include staple forming pockets (not shown) therein. In at least one arrangement, the anvil surface 4618 is approximately parallel to the anvil axis AA.

Still referring to FIGS. 85-88, the end effector 4500 further comprise a second jaw 4700 that comprises a cartridge assembly 4701. In at least one example, the cartridge assembly 4701 comprises a channel 4720 that is configured to operably support a staple cartridge 4702 therein. The channel 4720 comprises a proximal channel end portion 4722 and a distal channel end portion 4724 that defines a second longitudinal jaw axis or longitudinal channel axis CA. The proximal end portion 4722 is pivotally pinned or otherwise pivotally coupled to the proximal end portion 4614 of the anvil assembly 4612. The staple cartridge 4702 comprises a cartridge proximal end portion 4704 and a cartridge distal end portion 4706 and includes a cartridge deck surface 4708 that faces the anvil surface 4618. The cartridge assembly 4701 and anvil assembly 4612 are selectively pivotable between a fully open position shown in FIG. 85 to a closed position (FIG. 86) to a fully closed position (FIG. 87) by a dynamic clamping assembly 4550.

FIGS. 85-88 illustrate one form of a dynamic clamping assembly 4550 that comprises a vertical body portion 4552 that has a tissue cutting surface 4554 formed thereon or attached thereto. An anvil engagement feature 4556 is formed on one end of the body portion 4552 and comprises an anvil engagement tab 4557 that protrudes from each lateral side of the body portion 4552. Similarly, a channel engagement feature 4558 is formed on the other end of the of the body portion 4552 and comprises a channel engagement tab 4559 that protrudes from each lateral side of the body portion 4552. As can be seen in FIG. 88, the body portion 4552 is attached to or formed at a distal end of a flexible drive beam 4542 that is operated in the various manners described above.

FIG. 85 illustrates the jaws 4610, 4700 in a fully open position. When in that position, the dynamic clamping assembly 4550 is in a parking area 4580 defined adjacent the proximal end portion 4704 of the cartridge assembly 4701 as well as the proximal channel end portion 4722 and the proximal end portion 4614 of the anvil assembly 4612. When in a starting position in the parking area 4580, the channel engagement features 4758 may not engage the channel and the anvil engagement features may not engage the anvil assembly 4612. The anvil assembly 4612 is formed with a pair of longitudinally extending anvil ledges 4620 that are spaced from each other by an elongate anvil slot (not shown) that is configured to receive a portion of the body portion 4552 of the dynamic clamping assembly 4550 to extend therethrough. The anvil ledges 4620 are configured to be slidably engaged by the anvil engagement tabs 4557 on the dynamic clamping assembly 4550 as the dynamic clamping assembly 4550 is driven in the distal direction DD through the end effector 4500. Likewise, the proximal channel end portion 4722 comprises a cam surface or ramp arrangement 4730 that is configured to be initially engaged by the channel engagement tabs 4559 on the dynamic clamping assembly 4550 as the dynamic clamping assembly 4550 is initially moved distally from the starting position. The channel 4720 is formed with a pair of longitudinally extending channel ledges 4732 that are configured to be slidably engaged by the channel engagement tabs 4559 as the dynamic clamping assembly is driven from the starting position to ending position.

In one arrangement, the cam surface arrangement 4730 is configured such that upon initial engagement of the channel engagement tabs 4559 therewith, the cartridge assembly 4701 and anvil assembly 4612 are pivoted to a fully closed position wherein the cartridge distal end portion 4706 actually contacts the distal end portion 4616 of the anvil assembly 4612. Such arrangement may be useful when manipulating the target tissue and/or adjacent tissue prior to clamping the target tissue between the jaws. The clinician can move the dynamic clamping assembly to the initial closure position wherein the cam surface arrangement 4730 is initially engaged by the channel engagement tabs 4559 to bring the distal end portions 4706 and 4616 together to grasp and manipulate tissue.

Once the target tissue has been located between the anvil surface 4618 and the cartridge deck surface 4708, the dynamic clamping assembly is moved distally through the surgical end effector 4500. As the dynamic clamping assembly 4550 moves distally, the clamped tissue applies an opening force or forces to the anvil 4612 and cartridge assembly 4701 which must be overcome by the dynamic clamping assembly 4550 as it moves distally. These forces increase the amounts of frictional forces that are generated between the anvil engagement tabs 4557 and the anvil ledges 4620 and the channel engagement tabs 4559 and the channel ledges 4732. In one arrangement, as can be seen in FIG. 85, the channel ledges 4732 each include an upper ledge surface 4733 that is engaged by a corresponding one of the channel engagement tabs 4559. The channel ledges 4732 are oriented at an angle such that a proximal end 4735 of each of the channel ledges 4732 is spaced from the cartridge deck surface 4708 a first distance $D_1$ and a distal end 4737 of each of the channel ledges 4732 is spaced from the cartridge deck surface 4708 a second distance $D_2$ wherein $D_2 > D_1$. FIG. 86 illustrates the jaws 4600, 4700 in a closed position wherein the distal end 4706 of the cartridge 4702 is still spaced from the distal end 4616 of the anvil assembly 4612 (the cartridge deck surface 4708 and the anvil surface 4618 are spaced from each other, but approximately parallel to each other). When in that position, the upper ledge surface 4733 is angled (approximately 0.5°-2.0°, for example) relative to a longitudinal axis LA. FIGS. 87 and 88 illustrate the jaws 4610, 4700 in a fully closed position (the distal end 4706 of the cartridge 4702 is in contact with the distal end 4616 of the anvil assembly 4612). When in that configuration, the upper ledge surface 4733 is approximately parallel to the longitudinal axis LA. Such arrangement can reduce the amount of frictional resistance experienced by the dynamic clamping assembly 4550 as the dynamic clamping assembly 4550 is driven distally (direction DD) through a firing stroke wherein the dynamic clamping assembly 4550 not only retains the jaws 4600, 4700 clamped onto the target tissue, but cuts the target tissue and fires the staples operably supported in the staple cartridge 4702 through the cut tissue.

Figure 89:
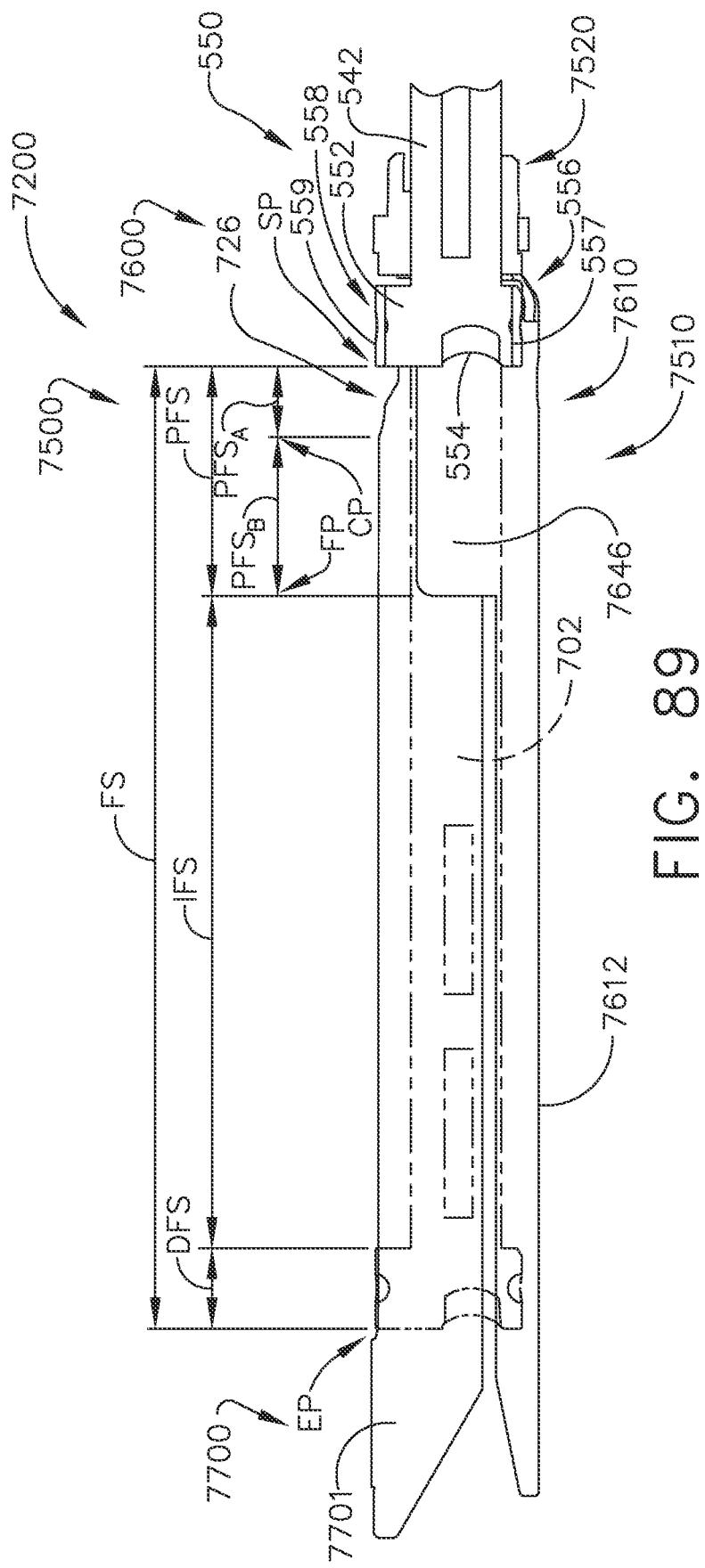
FIG. 89 is a side elevational view of a tool assembly of an adapter with the dynamic clamping assembly in a starting position and the jaws otherwise shown in a closed position for clarity.
Figure 90:
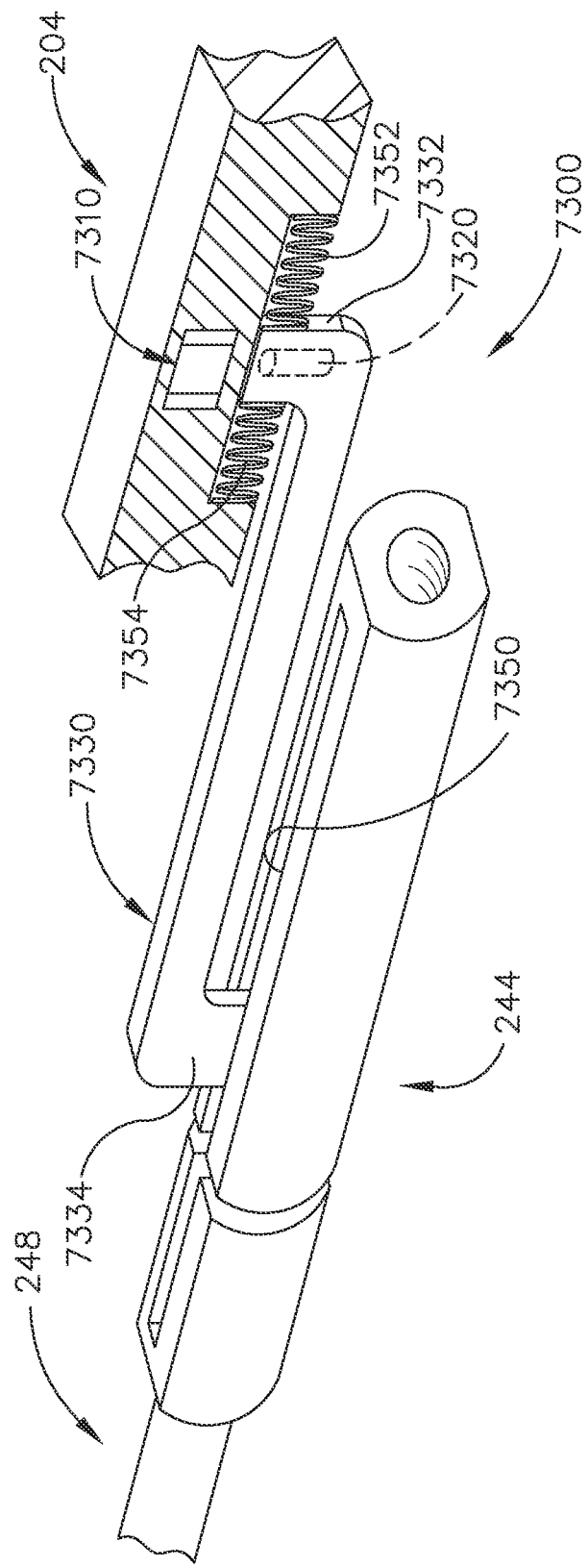
FIG. 90 is a partial perspective and cross-sectional view of a firing system sensor assembly or system of an adapter.

FIG. 89 illustrates a surgical end effector 7500 that comprises a portion of an adapter 7200 that is configured to be used in connection with an electromechanical surgical instrument 100, for example. In the illustrated arrangement, the surgical end effector 7500 comprises a loading unit 7510. The loading unit 7510 comprises a proximal body portion 7520 and a tool assembly 7600. Tool assembly 7600 includes a pair of jaw members including a first jaw 7610 that comprises an anvil assembly 7612 and a second jaw 7700 that comprises a cartridge assembly 7701. One jaw member is pivotal in relation to the other to enable the clamping of tissue between the jaw members. The cartridge assembly 7701 is movable in relation to anvil assembly 7612 and is movable between an open or unclamped position and a closed or approximated position. However, the anvil assembly 7612, or both the cartridge assembly 7701 and the anvil assembly 7612, can be movable.

The cartridge assembly 7701 is identical to cartridge assembly 701 described in detail above. The loading unit 7510 includes a dynamic clamping assembly 550 that is attached to or formed at the distal end of the flexible drive beam 542. The dynamic clamping assembly 550 includes a vertical body portion 552 that has a tissue cutting surface 554 formed thereon or attached thereto. An anvil engagement feature 556 is formed on one end of the body portion 552 and comprises an anvil engagement tab 557 that protrudes from each lateral side of the body portion 552. Similarly, a channel engagement feature 558 is formed on the other end of the of the body portion 552 and comprises a channel engagement tab 559 that protrudes from each lateral side of the body portion 552. As indicated above, the flexible drive beam 542 interfaces with a hollow drive member 548 (FIG. 10) that is configured to be attached to an axially movable firing member or distal drive member 248 (FIG. 6) of the adapter 7200 to which it is attached. As was also described above, the distal drive member 248 is configured to be axially advanced in the distal and proximal directions when the proximal drive shaft 212 is rotated. In particular, a threaded portion 212b is configured to threadably engage a drive coupling nut 244 that is attached to the distal drive member 248. The drive coupling nut 244 is slidably received in a mounting bushing 299 that enables the drive coupling nut 244 to move axially, but prevents the drive coupling nut 244 from rotating. Proximal drive shaft 212 is configured to receive rotary motions from a source of rotary motions (motor 152, for example) in the electromechanical surgical instrument 100 (see FIG. 4). Actuation of motor 152 will result in the rotation of the proximal drive shaft 212 and the axial displacement of the distal drive member 248 when the adapter 7200 is coupled to the electromechanical surgical instrument 100. As was also discussed above, the motor 152 is part of a power-pack core assembly 106 and is electrically connected to controller circuit board 142 and battery 144. See FIG. 4.

Turning again to FIG. 89, the dynamic clamping assembly 550 is configured to axially move through the first and second jaws through a firing stroke FS that extends from a starting position SP of the dynamic clamping assembly 550 to an ending position EP of the dynamic clamping assembly 550. When the dynamic clamping assembly 550 is located in the starting position (shown in solid lines in FIG. 89), the jaws 7610, 7700 would be in their fully open position. However, to illustrate the firing stroke portions, FIG. 89 illustrates the jaws 7610 and 7700 in a closed position. When the dynamic clamping assembly 550 is axially advanced in a distal direction DD from the starting position through a proximal portion $PFS_A$ of the firing stroke FS, the distal clamping assembly 550 will move the jaws 7610, 7700 from the fully open position to a closed position CP. As the distal clamping assembly 550 continues to move distally from the closed position CP through a portion $PFS_B$ of the firing stroke FS, the dynamic clamping assembly 550 retains the jaws 7610, 7700 in the closed position, but it has not yet encountered tissue that has been clamped between the jaws 7610, 7700. As can be seen in FIG. 89, for example, the first jaw 7610 includes upwardly extending tissue stops 7646 that prevent tissue that is clamped between the jaws 7610, 7700 from extending proximally beyond that point. Such point, designated as the firing point FP in FIG. 89, coincides with the locations of the proximal most fasteners that are stored in the staple cartridge 702 that is mounted in the cartridge assembly 7701. Such arrangement ensures that, when the cutting surface 554 on the dynamic clamping assembly first encounters the clamped tissue, the tissue severed thereby will be stapled or fastened. As the dynamic clamping assembly 550 is driven distally from the firing point FP through an intermediate portion IFS of the firing stroke FS, the dynamic clamping assembly fires or causes a majority of the fasteners stored in the cartridge body 702 to be ejected therefrom into forming engagement with the first jaw 7610. Further distal advancement of the dynamic clamping assembly through a distal portion DFS of the firing stroke FS will result in the final cutting of the clamped tissue and ejection of the remaining fasteners associated with that portion of the firing stroke.

As the dynamic clamping assembly 550 is distally advanced through the firing stroke FS, it may be useful to control the output of rotary motions from the motor 152. For example, more power may be required to advance the dynamic clamping assembly 550 through the intermediate firing stroke portion IFS than is needed to advance the dynamic clamping assembly 550 through a proximal portion of the firing stroke PFS and a distal portion of the firing stroke DFS because of the additional resistance encountered when cutting the clamped tissue and firing the fasteners therethrough. In addition, as the dynamic clamping assembly 550 passes through the intermediate firing stroke IFS, the amount of power required after it passes through the midpoint of the intermediate firing stroke portion may start to diminish because of the diminishing tissue resistance due to the migration of the fluids from that remaining portion of the clamped tissue, for example.

In the illustrated example, the end effector 7500 is configured for use in connection with adapter 7200. Adapter 7200 is identical to adapter 200 except for the differences noted herein. In one arrangement, the adapter 7200 employs a means for determining when the dynamic clamping assembly 550 is axially located within the intermediate portion of the firing stroke and communicating a signal indicative of that position back to a control circuit for the motor 152 to control the output of the motor 152. In one form, the means for determining comprises a firing system sensor assembly generally designated as 7300. In the illustrated example shown in FIGS. 90-93, the sensor assembly 7300 comprises a fixed sensor 7310 that is mounted within inner housing assembly 204 or outer tube 206. The fixed sensor 7310 may comprise a Hall effect sensor that is wired to or otherwise communicates with the electrical assembly 290 (FIG. 6) which serves to allow for communication of corresponding signals to a motor controller circuit of surgical instrument 100 that controls the motor 152, for example.

Still referring to FIGS. 90-93 the sensor assembly 7300 further comprises a sensor actuator 7320 that is mounted on a sensor coupler arm 7330 that movably interfaces with the drive coupling nut 244. In one form, the sensor coupler arm 7330 includes a proximal support tab 7332 upon which the sensor actuator 7320 is supported. In one arrangement, the sensor actuator 7320 comprises a magnet that is configured to be detected by the Hall effect sensor 7310. The sensor coupler arm 7330 further includes a distal mounting tab 7334 that is configured to be slidably received within an axial slot 7350 provided in the drive coupling nut 244. The proximal support tab 7332 is biased into axial sensing alignment so that the sensor actuator 7320 may be sensed by the fixed sensor 7310. In the illustrated arrangement, for example, the proximal support tab 7332 is biased into axial sensing alignment by a proximal spring 7352 and a distal spring 7354 that are mounted within the inner housing assembly 204 or outer tube 206.

Figure 91:
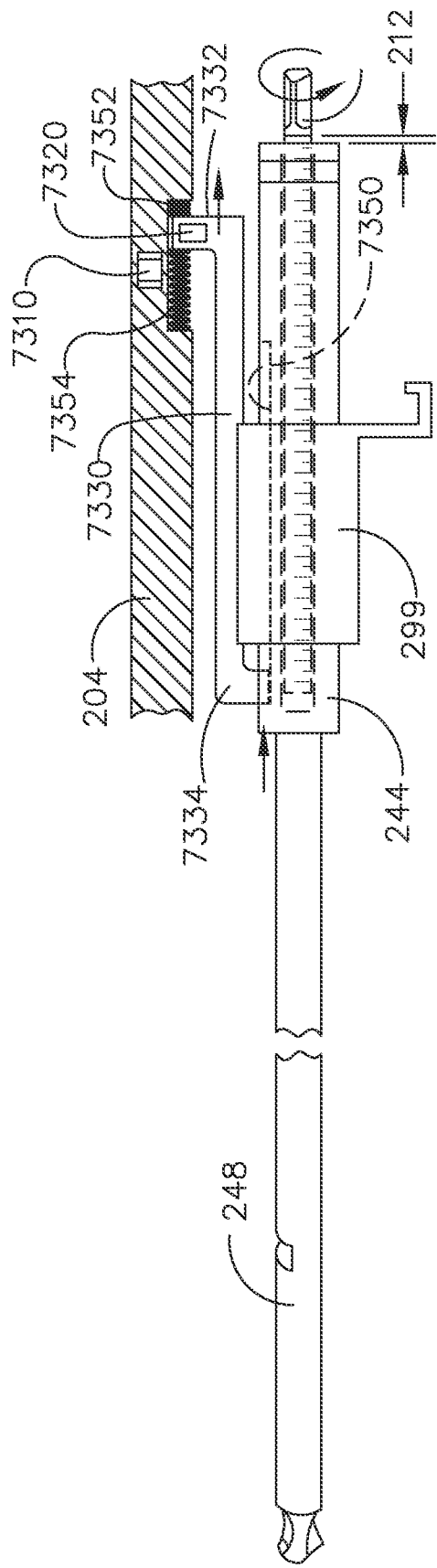
FIG. 91 is a partial side cross-sectional view of the firing system sensor assembly of FIG. 90 in a starting position.
Figure 92:
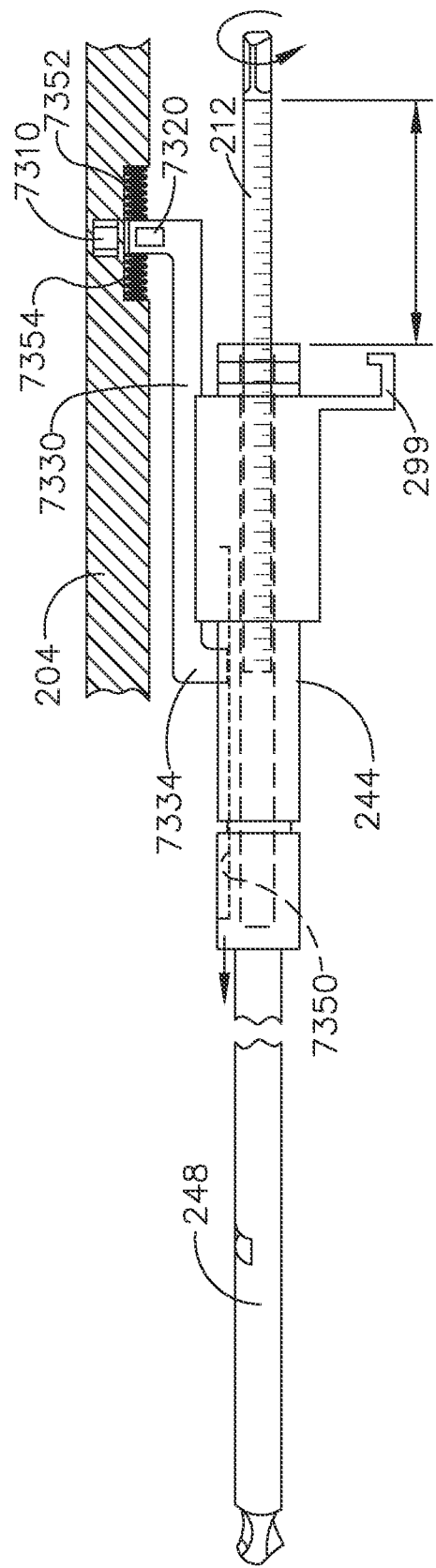
FIG. 92 is another partial side cross-sectional view of the firing system sensor assembly of FIGS. 90 and 91 after the firing system has completed a closure stroke and prior to starting a firing stroke.
Figure 93:
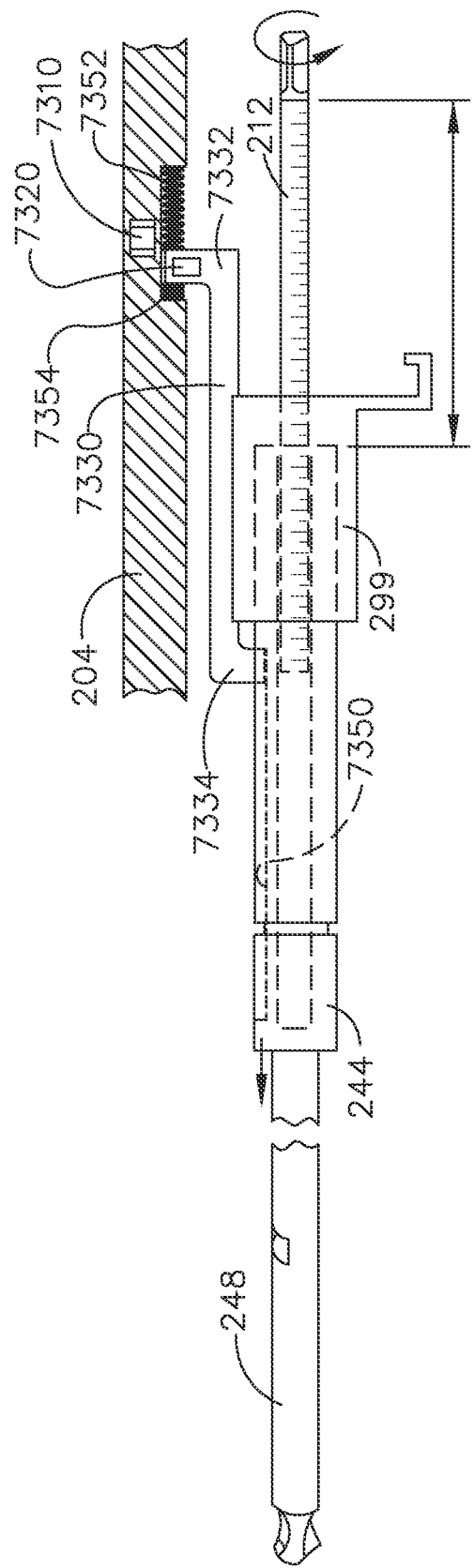
FIG. 93 is another partial side cross-sectional view of the firing system sensor assembly of FIGS. 90-92 after the firing system has completed the firing stroke.
Figure 94:
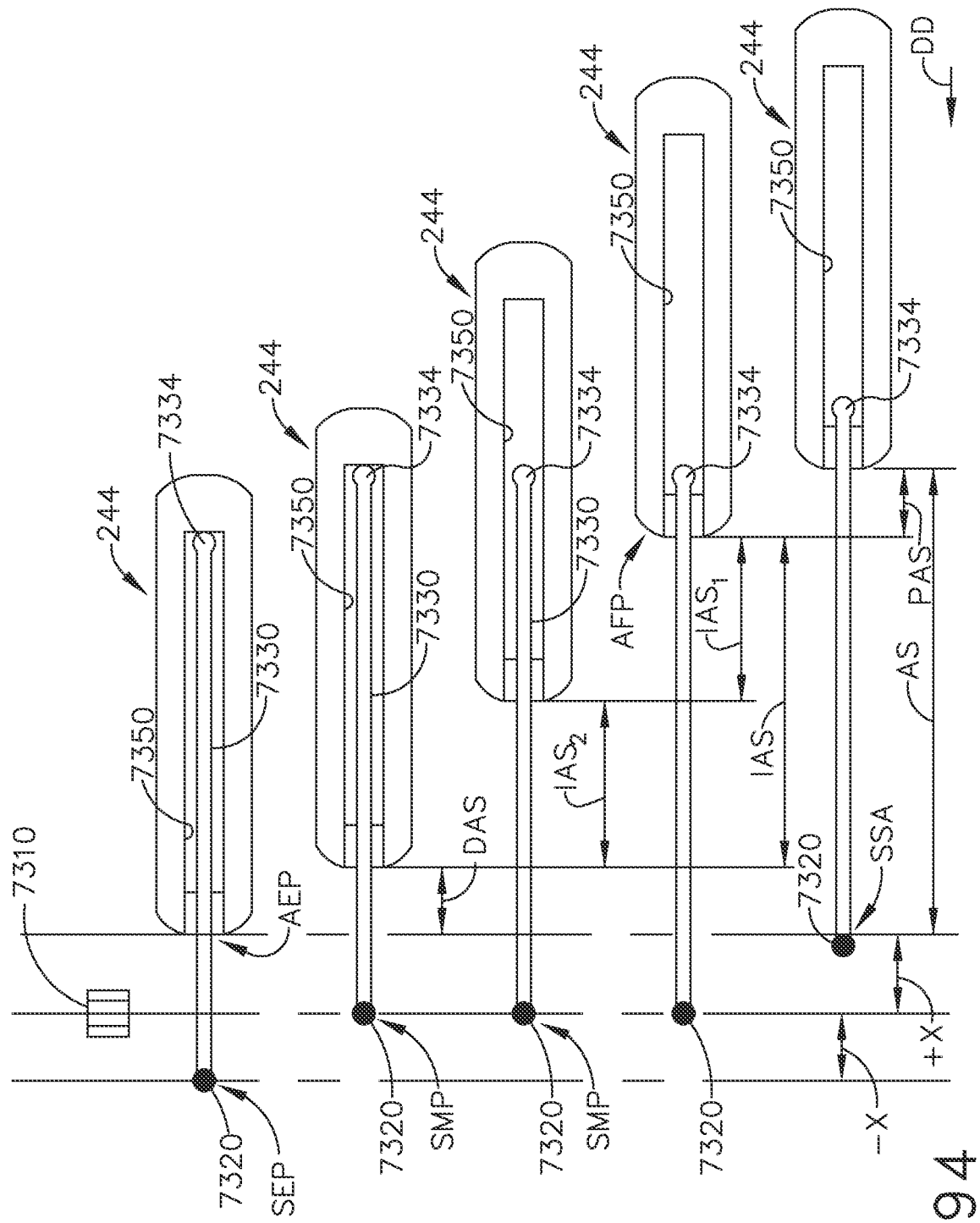
FIG. 94 is a diagrammatical depiction of portions of the firing system sensor assembly of FIGS. 90-93 as the firing system is moved from a starting position to an ending position.
Figure 95:
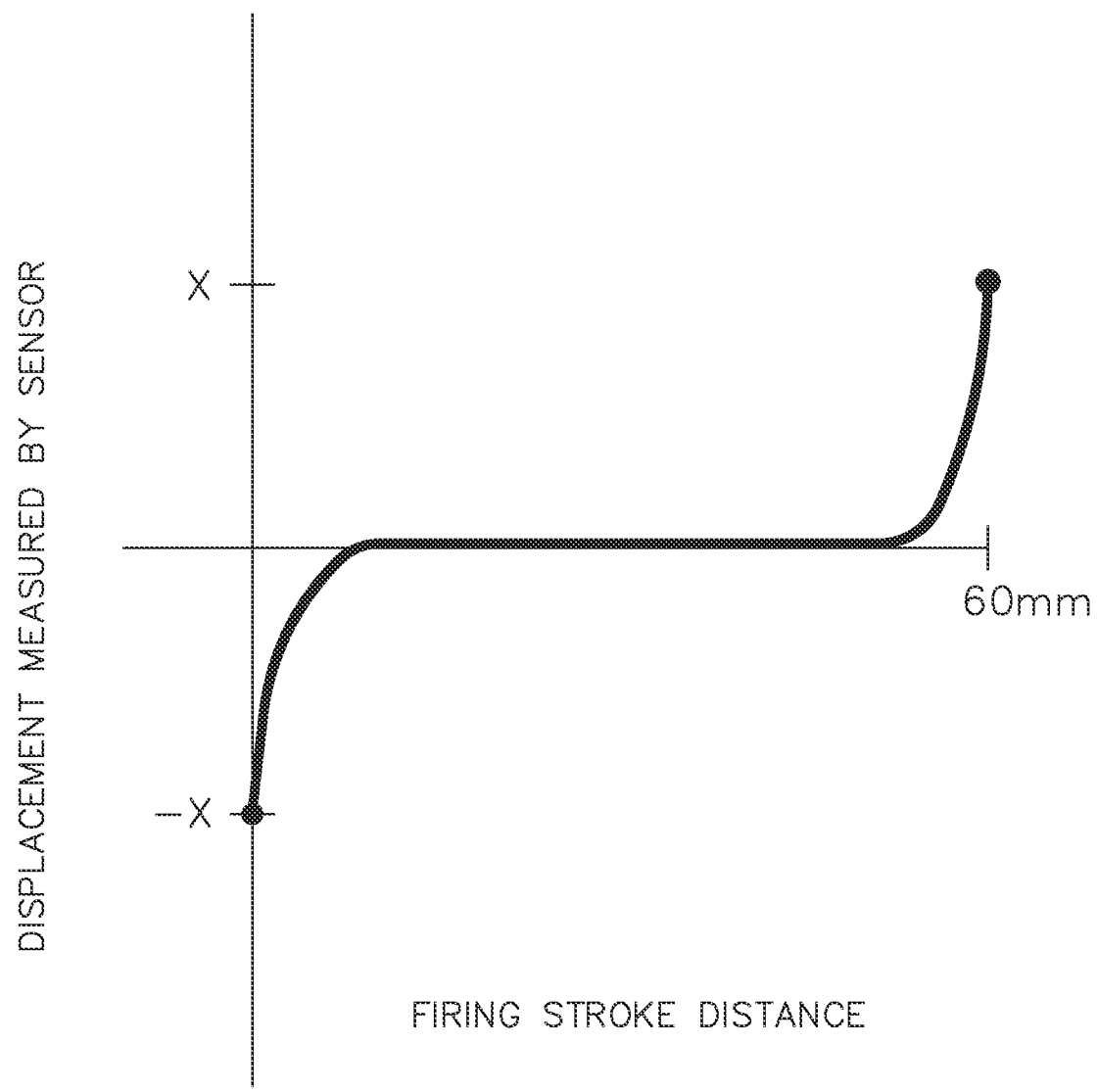
FIG. 95 is a graphical depiction of a displacement measured by the firing system sensor assembly of FIGS. 90-93 based upon the firing stroke distance of a dynamic clamping assembly.

FIGS. 91-94 illustrate an actuation stroke of the drive coupling nut 244 that corresponds to the firing stroke FS of the dynamic clamping assembly 550. FIG. 91 illustrates the position of the drive coupling nut 244 when the dynamic clamping assembly 550 is in the starting position. As can be seen in that Figure, the drive coupling nut 244 has driven the sensor coupler arm 7330 proximally so that the sensor actuator 7320 is proximal to the fixed sensor 7310 and out of sensing alignment therewith. This starting position of the sensor actuator 7320 is designated as SSA in FIG. 94. As the rotary drive shaft 212 is initially rotated, the drive coupling nut 244 is axially driven in the distal direction DD through a proximal portion PAS of the actuation stroke AS. The proximal portion PAS of the actuation stroke AS corresponds to the proximal portion PFS of the firing stroke FS of the dynamic clamping assembly 550. The drive coupling nut 244 is driven to an actuation firing point AFP (FIG. 94) that corresponds with the firing point FP (FIG. 89) of the dynamic clamping assembly 550. As the drive coupling nut 244 approaches the actuation firing point AFP, the springs 7352 and 7354 serve to move the sensor actuator 7320 into sensing alignment with the fixed sensor 7310. As the drive coupling nut 244 is driven distally from the actuation firing point AFP through an intermediate portion IAS of the actuation stroke AS, the springs 7352, 7354 serve to bring the sensor actuator 7320 into sensing alignment with the fixed sensor 7310. After the drive coupling nut 244 moves distally through a first portion of the intermediate actuation stroke $IAS_1$ the springs 7352, 7354 serve to bias the sensor actuator 7320 into a sensor midpoint SMP that corresponds to the midpoint of the intermediate portion of the firing stroke FS of the dynamic clamping assembly 550. As the drive coupling nut 244 moves through the intermediate portion IAS of the actuation stroke, the springs 7352, 7354 bias the sensor actuator 7320 into sensing alignment with the fixed sensor 7310. Then signals indicative of the position of the dynamic clamping assembly may be transmitted by the fixed sensor 7310 to the motor control circuit as the drive nut 244 moves through the entire intermediate actuation stroke portion IAS. FIG. 92 illustrates a position of the drive nut 244 when in the intermediate portion of the actuation stroke. The fixed sensor 7310 and/or the springs 7352, 7354 may be calibrated so that the fixed sensor 7310 sends signals indicative of the specific position of the sensor actuator 7320 as it passes through the first portion of the intermediate actuation stroke $IAS_1$ to the sensor midpoint SMP, so that the motor 152 may be appropriately controlled. For example, it may be desirable to start to decrease the power or current to the motor 152 as the sensor actuator 7320 approaches the sensor midpoint SMP and then throughout a second portion of the intermediate actuation stroke $IAS_2$ until the drive nut 244 reaches the end of the intermediate actuation stroke IAS at which point it begins a distal portion DAS of the actuation stroke which corresponds to the distal portion of the firing stroke DFS (FIG. 89). When the drive nut 244 reaches the actuator end point AEP which corresponds to the end point EP of the dynamic clamping assembly 550, the proximal tab 7344 of the sensor coupler arm 7330 is at the end of the slot 7350 in the drive nut 244 and the sensor actuator 7320 is pulled out of sensing alignment with the fixed senor 7310 as shown in FIG. 93. When in that position, power to the motor 152 has been completely stopped. The motor may then be operated to rotate the drive shaft 212 in an opposite direction to retract the dynamic clamping assembly 550 back to the starting position wherein the jaws are moved to their fully open position. FIG. is a graph that plots the displacement of the dynamic clamping assembly as measured by the sensor assembly 7300 verse the firing stroke distance of the dynamic clamping assembly for one example. +X is the distance traveled by the dynamic clamping assembly between the firing point FP and the midpoint of the intermediate portion of the firing stroke. This corresponds to the distance that the sensor actuator 7320 travels between the starting position SSA of the sensor actuator 7320 and the sensor midpoint SMP as shown in FIG. 94. −X is the distance traveled by the dynamic clamping assembly 550 between the midpoint of the intermediate portion of the firing stroke and the end position EP. This corresponds to the distance that the sensor actuator 7320 travels between the sensor midpoint SMP and a sensor end point SEP as shown in FIG. 94.

During use of an adapter 200 and electromechanical surgical instrument 100, the surgical end effector 500 is generally positioned in an unarticulated position (the longitudinal axis defined by the proximal housing portion is axially aligned with the longitudinal axis LA of the shaft assembly of the adapter) to permit the surgical end effector 500 to be inserted through a trocar cannula into the patient.

Once the surgical end effector 500 has been inserted into the patient, the clinician may activate the source of rotary actuation motions (motor 156) to apply an amount of rotary articulation motions to the rotary articulation drive shaft 214 in the adapter 200 to axially displace the articulation driver or bar 258 an amount necessary to articulate the surgical end effector 500 into a desired articulated position. Once the surgical end effector 500 has been articulated in the desired articulated position, the motor 156 is deactivated so that the end effector 500 remains articulated during the firing stroke.

After the surgical end effector 500 has been articulated into the desired articulated position and the source of rotary articulation motions has been deactivated in the electromechanical surgical instrument 100, the clinician activates the source of rotary firing motions (motor 152) to apply an initial amount of rotary firing motions to the rotary firing drive shaft 214 in the adapter 200 to axially displace the distal drive member 248 to ultimately cause the dynamic clamping assembly 550 in the surgical end effector 500 to move from the starting position to a firing position. As the dynamic clamping assembly 550 moves from the starting position to the firing position, the dynamic clamping assembly applies a closing motion to the anvil assembly 612 and cartridge assembly 701 of the end effector 500 to move the anvil 612 and cartridge assembly 701 from a fully open position to a closed position. At that point, the clinician may cease actuation of the motor 152 or motor 152 may continue to be actuated to drive the dynamic clamping assembly 550 through its firing stroke wherein it cuts the clamped tissue and causes the fasteners stored in the cartridge assembly 701 to be ejected into forming engagement with the anvil 612. As the flexible firing beam 542 applies the axial firing motions from the distal drive member 248 to the dynamic clamping assembly 550, the flexible firing beam 542 must flex around the articulation joint to accommodate the articulated position of tool assembly 600 relative to the proximal body portion 520. Such flexing of the firing beam 542 applies resistive forces to the tool assembly 600 that seek to undesirably straighten or align the tool assembly 600 with the proximal body portion 520 and essentially move the tool assembly 600 out of the desired articulated position. In at least one form, the adapter 8200 depicted in FIG. 96 may address such problem.

Figure 96:
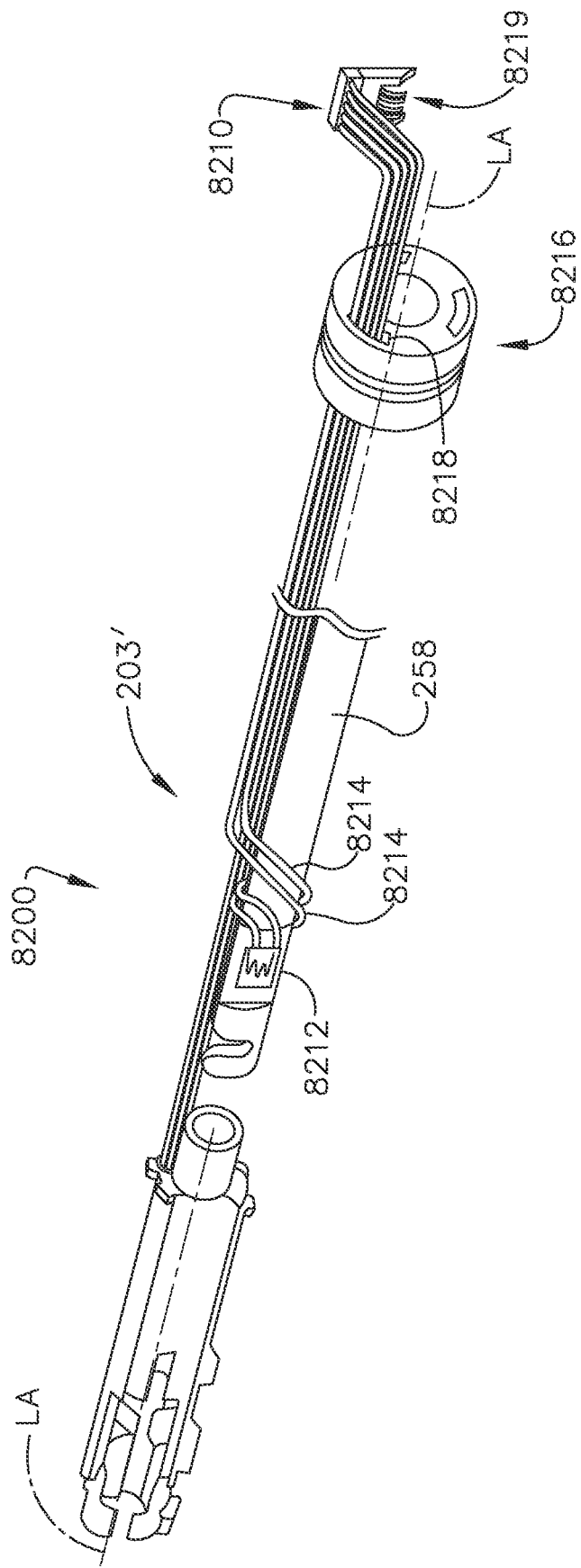
FIG. 96 is a perspective view of portions of an adapter that includes an arrangement for measuring an amount of strain experienced by an articulation driver of the adapter.

FIG. 96 illustrates a portion of adapter 8200 which is otherwise identical to adapter 200 described above. As can be seen in that Figure, adapter 8200 includes a control system 8210 that operably interfaces with the articulation driver 258 and is configured to communicate electrical signals back to a motor control circuit for the motor 156 that applies the rotary articulation motions in the electromechanical surgical instrument. In the illustrated arrangement, for example, the control system 8210 includes a strain gauge 8212 that is or attached to the articulation driver 258. Leads 8214 for the strain gauge extend through an opening 8218 in an internal bushing 8216 that may be mounted in the inner housing 204 to be coupled to a connector 8219 that may interface with a slip ring arrangement (not shown) that is in electrical contact with the electrical assembly 290, for example. In such arrangement, the leads 8214 are long enough to permit the shaft assembly 203' to rotate about the longitudinal axis LA. In an alternative arrangement, the leads 8214 are attached to a connector that is supported within the inner housing 204 and configured to electrical interface with the slip ring 298 of the electrical assembly 290 (FIG. 6). In such arrangement, the slip ring 298 is in electrical communication with a circuit board 294. The circuit board 294 includes a plurality of electrical contact blades 292 for electrical connection to pass-through connector 66 of plate assembly 60 of shell housing of the surgical instrument 100. Such arrangement facilitates passage of signals from the strain gauge 8212 to the motor controller circuit board 142a in the surgical instrument 100.

Figure 97:
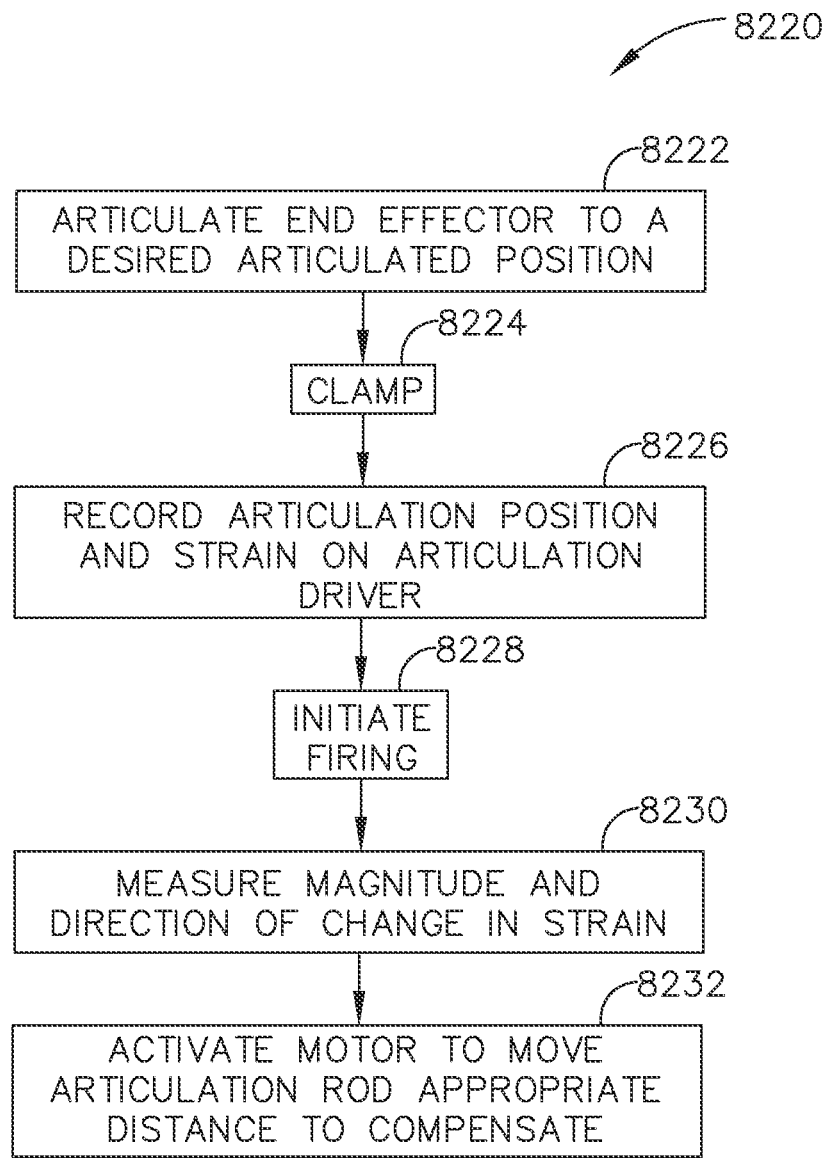
FIG. 97 is a flow chart depicting a method of controlling motors of an electromechanical surgical device attached to an adapter of FIG. 96.

FIG. 97 illustrates the actions of one method 8220 for controlling various features of the adapter 8200 when operably coupled to the surgical instrument 100 or other motor powered system after the surgical end effector 500 of the adapter 8200 has been entered into the patient. When a trocar is employed, the surgical end effector 500 is in an unarticulated position with the jaws 610, 700 closed to enable the surgical end effector 500 to pass through the cannula of the trocar. Once the surgical end effector 500 has entered the patient, the anvil 612 and cartridge assembly 701 of the surgical end effector 500 are opened to the fully open position. This may be accomplished by reversing the motor 152 (through manual controls or automatic controls) to move the dynamic clamping assembly 550 back to its starting position. Thereafter, the end effector 500 is then articulated to a desired articulated position (action 8222). This is accomplished by actuating the source of rotary articulation motions (motor 156) in the surgical instrument 100 or other motor powered system (through manual controls or automatic controls). In the example of FIG. 97, the clamping action 8224 encompasses first opening the jaws (if the end effector was articulated to the desired articulated position with the jaws closed) and then clamping the jaws onto a target tissue. This is accomplished by reversing the motor 152 or other motor driven system (through manual controls or automatic controls) to move the dynamic clamping assembly 550 back to its starting position (if the jaws were closed) and then actuating the motor 152 (through manual controls or automatic controls) to move the dynamic clamping assembly 550 from its starting position to its firing position (action 8224).

Still referring to FIG. 97, once the target tissue has been clamped between the jaws (anvil assembly 612 and cartridge assembly 701) the axial position of the articulation driver 258 may be recorded as well as the amount of strain experienced by the articulation driver 258 is recorded by the motor controller circuit (action 8226). Other means may also be employed to determine and record the articulated position of the surgical end effector. In an alternative arrangement, the amount of strain experienced by the articulation driver may be recorded prior to clamping. Thereafter, the firing stroke is initiated (action 8228). This may be accomplished by actuating the motor 152 or other motor driven system (through manual controls or automatic controls) to move the dynamic clamping assembly 550 from its firing position to its ending position within the end effector 500. As the dynamic clamping assembly 550 moves from the firing position to ending position, the dynamic clamping assembly 550 cuts the clamped tissue and ejects the fasteners stored in the cartridge assembly into forming engagement with the anvil. During this firing stroke (action 8228), the magnitude and direction of a change in the amount of strain experienced by the articulation driver 258 is measured and sent to the motor control circuit (action 8230). The motor control circuit compares this strain information to the previously recorded strain information and if necessary, the motor 156 or other motor driven system is reactivated (through manual controls or automatic controls) to move the articulation driver 258 in an appropriate axial direction to bring the recorded strain approximately back to the previously recorded strain information or at least reduce the amount of strain being experienced by the articulation driver 258 as the dynamic clamping assembly 550 is being driven from the firing position to ending position (action 8232) to maintain the surgical end effector in the desired articulated position.

As was discussed above, the electromechanical surgical instrument 100 includes the power-pack or the handle assembly 101 and an outer shell housing 10 that is configured to selectively receive and substantially encase the handle assembly 101. A sterile barrier plate 60 is interposed between the handle assembly 101 and the outer shell housing to facilitate operable coupling of rotatable motor drive shafts of the motors through the sterile barrier to the corresponding drive shafts of an adapter coupled thereto. Rotation of the motor drive shafts then function to drive shafts and/or gear components of adapter 200 in order to perform the various operations of the surgical instrument 100. During operation, it may be desirable to control the motors to adjust the rate of shaft rotation and/or the direction of shaft rotation based upon the location of the various components of the adapter 200 that is coupled thereto. For example, it may be desirable to control the rate of rotation (and direction) of motor 152 and rotatable drive shaft 152a depending upon the position of the dynamic clamping assembly 550 within the end effector. For example, when the dynamic clamping assembly 550 is nearing the end of its firing stroke, it may be useful to slow its distal advancement down so as to avoid slamming the dynamic clamping assembly and/or related components into the cartridge body at the end of the firing stroke. Further, there may be times during the firing stroke when it may be useful to slow down the dynamic clamping assembly 550 advancement or to speed it up. Similar conditions may also occur which relate to the operation of motors 154 and 156.

Figure 98:
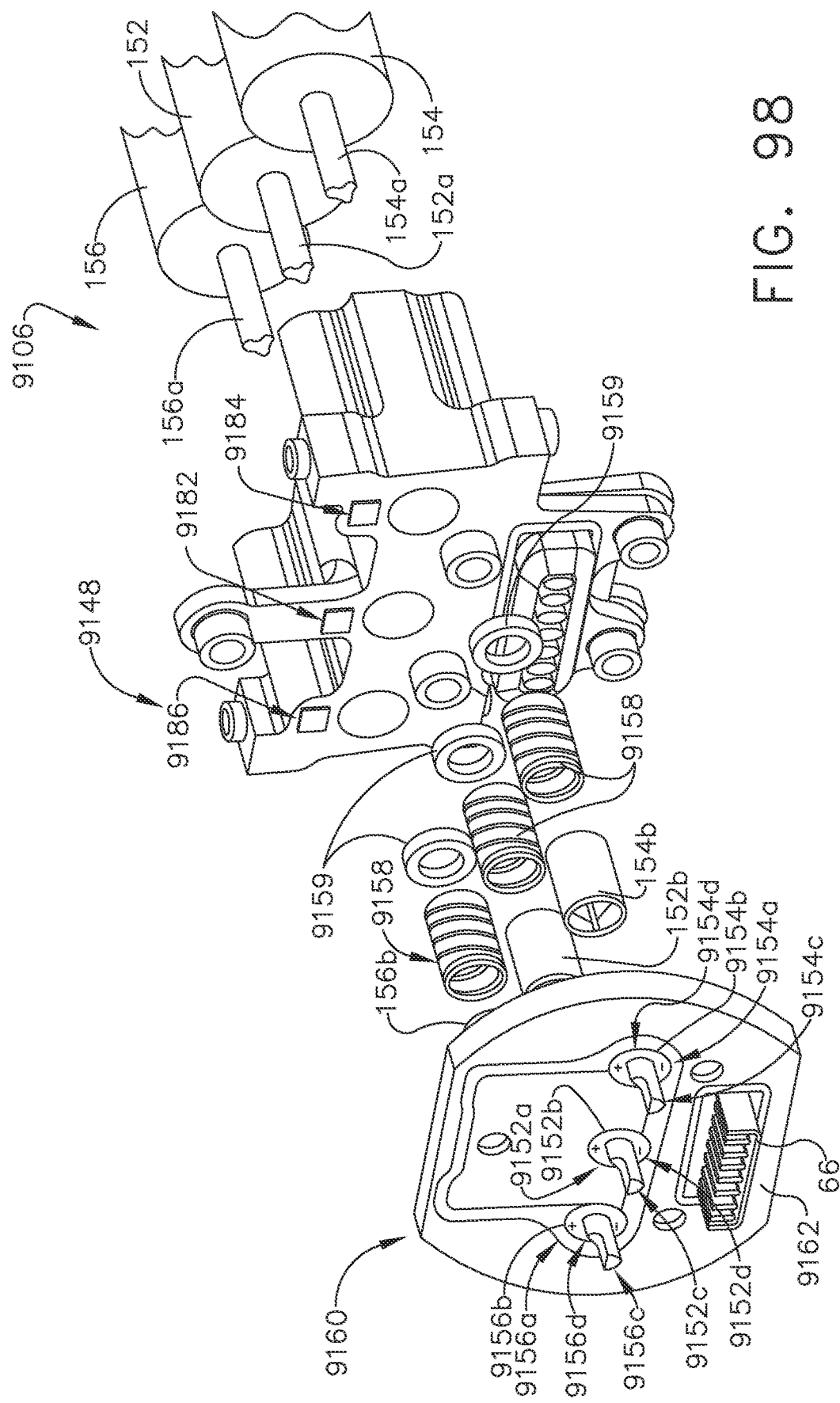
FIG. 98 is an exploded assembly perspective view of a motor control system of an electromechanical surgical device for controlling the motors thereof.

FIG. 98 illustrates a portion of a power pack core assembly 9106 and motor control system 9180 that may be employed to control the operation of motors 152, 154, 156 and which is entirely located within the sterile barrier or outer shell housing 10. Power pack core assembly 9106 is substantially identical to power pack core assembly 106 described above, except for the differences discussed below. As can be seen in FIG. 98, each motor 152, 154, 156 is supported on a motor bracket 9148 that is similar to motor bracket 148 described above. The motor bracket 9148 rotatably supports three rotatable drive connector sleeves 152b, 154b, 156b that are keyed to respective motor shafts 152a, 154a, 156a of motors 152, 154, 156. Drive connector sleeves 152b, 154b, 156b non-rotatably receive proximal ends of respective rotatable coupling shaft assemblies 9152a, 9154a, 9156a of a plate assembly 9160.

Plate assembly 9160 is identical to plate assembly 60 except for the differences discussed below. For example, rotatable coupling shaft assembly 9152a comprises a coupler bushing 9152b that is rotatably supported in a plate 9162 of plate assembly 9160. A coupler shaft 9152c is non-rotatably coupled to said coupler bushing 9152b. A proximal end of coupler shaft 9152c extends proximally from the plate 9162 to be drivingly engaged with the drive connector sleeve 152b. A distal end of coupler shaft 9152c is configured to extend through a corresponding aperture 22b (FIG. 3) in connecting portion 20 of distal half-section 10a when sterile barrier plate assembly 9160 is disposed within shell cavity 10c of shell housing 10. Rotatable coupling shaft assembly 9154a comprises a coupler bushing 9154b that is rotatably supported in plate 9162. A coupler shaft 9154c is non-rotatably coupled to said coupler bushing 9154b. A proximal end of coupler shaft 9154c extends proximally from the plate 9162 to be drivingly engaged with the drive connector sleeve 154b. A distal end of coupler shaft 9154c is configured to extend through a corresponding aperture 22c (see FIG. 5) in connecting portion 20 of distal half-section 10a when sterile barrier plate assembly 9160 is disposed within shell cavity 10c of shell housing 10. Rotatable coupling shaft assembly 9156a comprises a coupler bushing 9156b that is rotatably supported in plate 9162. A coupler shaft 9156c is non-rotatably coupled to said coupler bushing 9156b. A proximal end of coupler shaft 9156c extends proximally from the plate 9162 to be drivingly engaged with the drive connector sleeve 156b. A distal end of coupler shaft 9156c is configured to extend through a corresponding aperture 22a (FIG. 3) in connecting portion 20 of distal half-section 10a when sterile barrier plate assembly 9160 is disposed within shell cavity 10c of shell housing 10.

Still referring to FIG. 98, Drive connector sleeves 152b, 154b, 156b are each spring biased away from respective motors 152, 154, 156 by corresponding springs 9158 and washers 9159. Drive connector sleeve 152b serves to drivingly couple rotatable motor drive shaft 152a to the coupler shaft 9152c. Drive connector sleeve 154b serves to drivingly couple rotatable motor drive shaft 154a to the coupler shaft 9154c. Drive connector sleeve 156b serves to drivingly couple rotatable motor drive shaft 156a to the coupler shaft 9156c.

The motor control system 9180 includes a controller circuit board 142a and battery 144 (FIG. 4) that are coupled to each motor 152, 154, 156. Each motor 152, 154, 156 is controlled by a respective motor controller. The motor controllers are disposed on motor controller circuit board 142a. In on example, the motor controllers comprise A3930/31K motor drivers from Allegro Microsystems, Inc. The A3930/31K motor drivers are designed to control a 3-phase brushless DC (BLDC) motor with N-channel external power MOSFETs, such as the motors 152, 154, 156. Each of the motor controllers is coupled to a main controller disposed on the main controller circuit board 142b. The main controller is also coupled to memory, which is also disposed on the main controller circuit board 142b. In one example, the main controller comprises an ARM Cortex M4 processor from Freescale Semiconductor, Inc. which includes 1024 kilobytes of internal flash memory. The main controller communicates with the motor controllers through an FPGA, which provides control logic signals. The control logic of the motor controllers then outputs corresponding energization signals to their respective motors 152, 154, 156 using fixed frequency pulse width modulation (PWM).

In the illustrated arrangement, the motor control system 9180 further comprises stationary sensors 9182, 9184, 9186 that are wired to or otherwise communicate with the main controller circuit board 142b and/or the motor controllers. For example, stationary sensor 9182 is associated with motor 152 and is wired to or otherwise communicates with the main controller circuit board 142b and/or the motor controller for motor 152. Stationary sensor 9184 is associated with motor 154 and is wired to or otherwise communicates with the main controller circuit board 142b and/or the motor controller for motor 154. Stationary sensor 9186 is associated with motor 156 and is wired to or otherwise communicates with the main controller circuit board 142b and/or the motor controller for motor 156. In one example, sensors 9182, 9184, 9186 comprise Hall effect sensors that are arranged to detect sensor actuators associated with coupler shafts 9152c, 9154c, 9156c. For example, the coupler bushing 9152b may be magnetized or support a magnet 9152d therein. Coupler bushing 9154b may be magnetized or support a magnet 9154*d* therein. Coupler bushing 9156*b* may be magnetized or support a magnet 9156*d* therein.

Actuation of motor 152 will result in the rotation of the drive coupler shaft 9152*c* and the accompanying magnet 9152*d*. Sensor 9182 is configured to detect the rotary travel of magnet 9152*d* and convey signals indicative of such position to the motor controller or processor controlling motor 152. These signals may be used by the controller/processor to maintain, increase or reduce the rate of rotation of the rotatable motor drive shaft 152*a* depending upon the signals. The processor may also change the direction of rotation of the rotatable drive shaft 152*a*. Actuation of motor 154 will result in the rotation of the drive coupler shaft 9154*c* and the accompanying magnet 9154*d*. Sensor 9184 is configured to detect the rotary travel of magnet 9154*d* and convey signals indicative of such position to the motor controller or processor controlling motor 154. These signals may be used by the controller/processor to maintain, increase or reduce the rate of rotation of the rotatable motor drive shaft 154*a* depending upon the signals. The processor may also change the direction of rotation of the rotatable drive shaft 154*a*. Actuation of motor 156 will result in the rotation of the drive coupler shaft 9156*c* and the accompanying magnet 9156*d*. Sensor 9186 is configured to detect the rotary travel of magnet 9156*d* and convey signals indicative of such position to the motor controller or processor controlling motor 156. These signals may be used by the controller/processor to maintain, increase or reduce the rate of rotation of the rotatable motor drive shaft 156*a* depending upon the signals. The processor may also change the direction of rotation of the rotatable drive shaft 156*a*.

Figure 99:
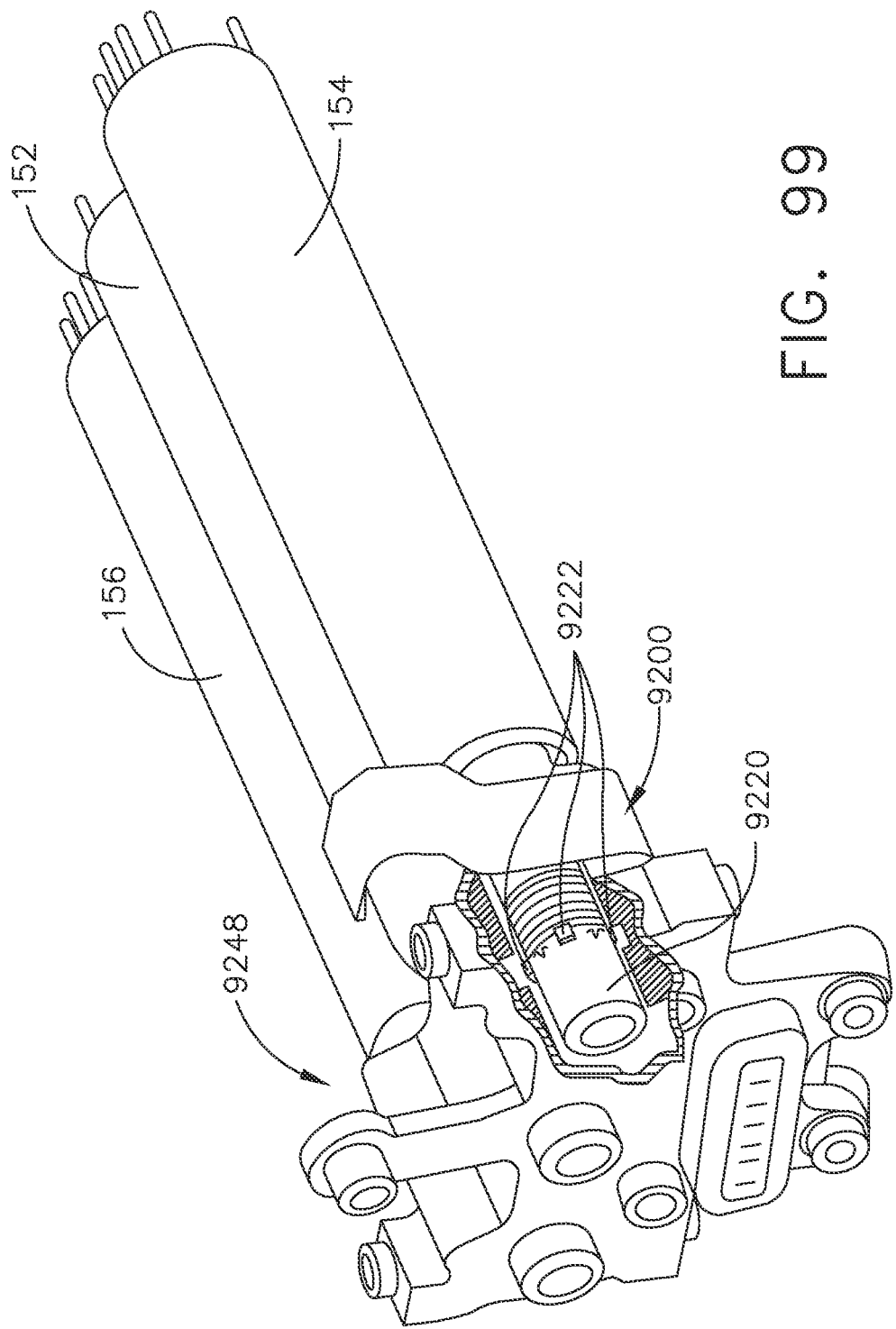
FIG. 99 is a perspective view of another motor control system of an electromechanical surgical device for controlling the motors thereof.
Figure 100:
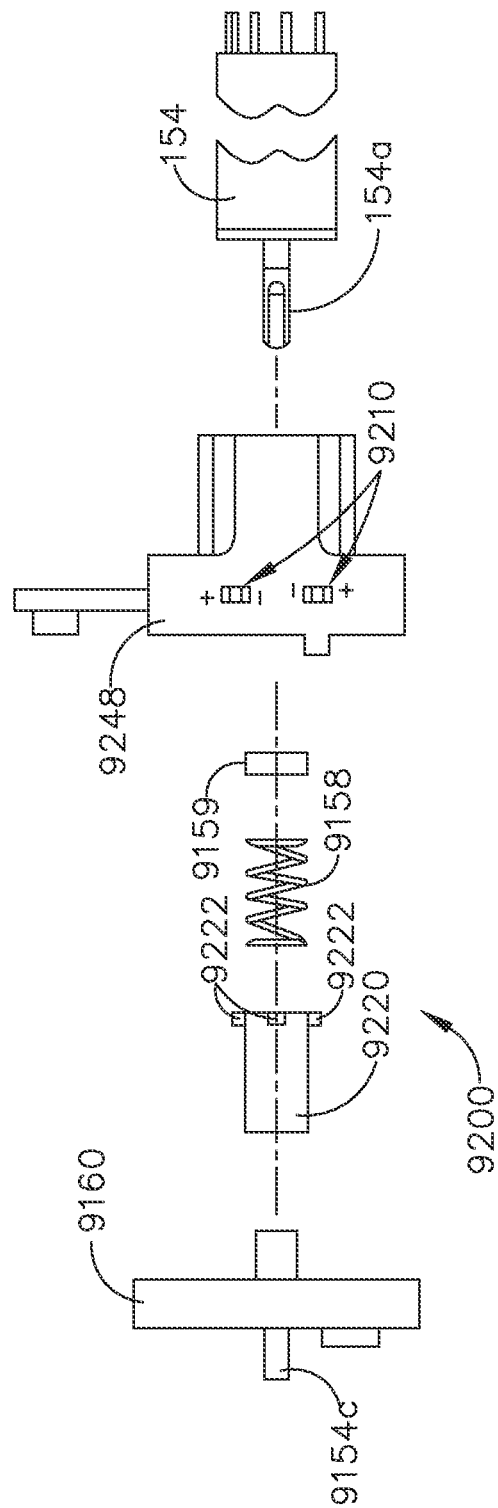
FIG. 100 is an exploded side view of the motor control system of FIG. 99.
Figure 101:
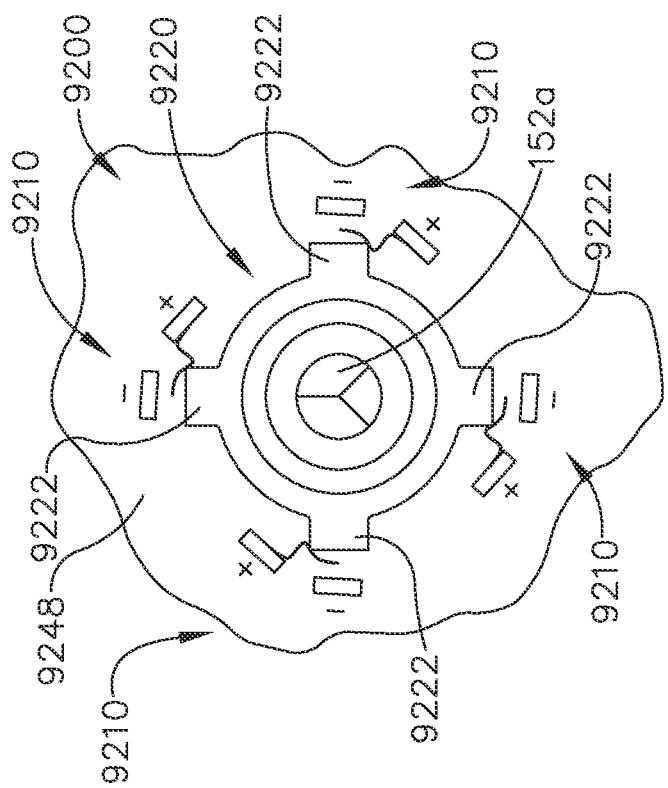
FIG. 101 is a partial end view of a portion of the motor control system associated with one of the motors of an electromechanical surgical instrument.

FIGS. 99-101 illustrate an alternative motor control system 9200 for controlling the operation of motors 152, 154, 156. In this example, at least one switch 9210 is associated with each of the rotatable motor drive shafts 152*a*, 154*a*, 156*a* and is mounted in the motor bracket 9248 which supports the motors 152, 154, 156. In the illustrated example, four switches 9210 are circumferentially spaced around each of the rotatable drive shafts 152*a*, 154*a*, 156*a*. FIG. 101 illustrates such switch arrangement for rotatable motor drive shaft 152*a*. Each switch 9210 is wired to or otherwise communicates with the main controller circuit board 142*b* and/or the motor controller for the corresponding motor 152, 154, 156. In one arrangement, each drive connector sleeve has at least one switch actuator thereon. FIGS. 99-101 illustrate drive connector sleeve 9220 which has four circumferentially spaced switch actuator nubs 9222 formed thereon for operable interaction with the corresponding switches 9210. The drive connector sleeves 9220 serve to operably couple the rotatable motor drive shafts 152*a*, 154*a*, 156*a* to their corresponding coupler shafts 9152*c*, 9154*c*, 9156*c*. As the rotatable motor drive shafts 152*a*, 154*a*, 156*a* rotate, the drive connector sleeve 9220 that is non-rotatably connected thereto also rotates causing the corresponding switch actuators 9222 to rotate into and out of actuatable contact with the corresponding switches 9210 to convey signals indicative of the rotary position of the corresponding drive shaft 152*a*, 154*a*, 156*a* to the motor controller or processor controlling that particular motor. These signals may be used by the controller/processor to maintain, increase or reduce the rate of rotation of the rotatable motor drive shaft depending upon the signals. The processor may also change the direction of rotation of the rotatable drive shaft.

The surgical instrument 100 can include sensor assemblies for detecting various states and/or parameters associated with the operation of the surgical instrument 100. A control circuit or processor can monitor these sensed states and/or parameters and then control the operation of the surgical instrument 100 accordingly. For example, the surgical instrument 100 can monitor the current drawn by the motor driving the first force/rotation transmitting/converting assembly 240 (FIG. 6) in order to control the speed at which the clamping member 550 (FIG. 10) is translated. As another example, the surgical instrument 100 can monitor the gap or distance between the jaw members or the anvil plate 620 (FIG. 10) and the cartridge body 702 (FIG. 10) when the end effector 500 is clamped in order to control the speed at which the clamping member 550 is driven thereafter. These and other sensor assemblies with corresponding logic executed by a control circuit or processor in conjunction with the sensor assemblies are described herein below.

Figure 102:
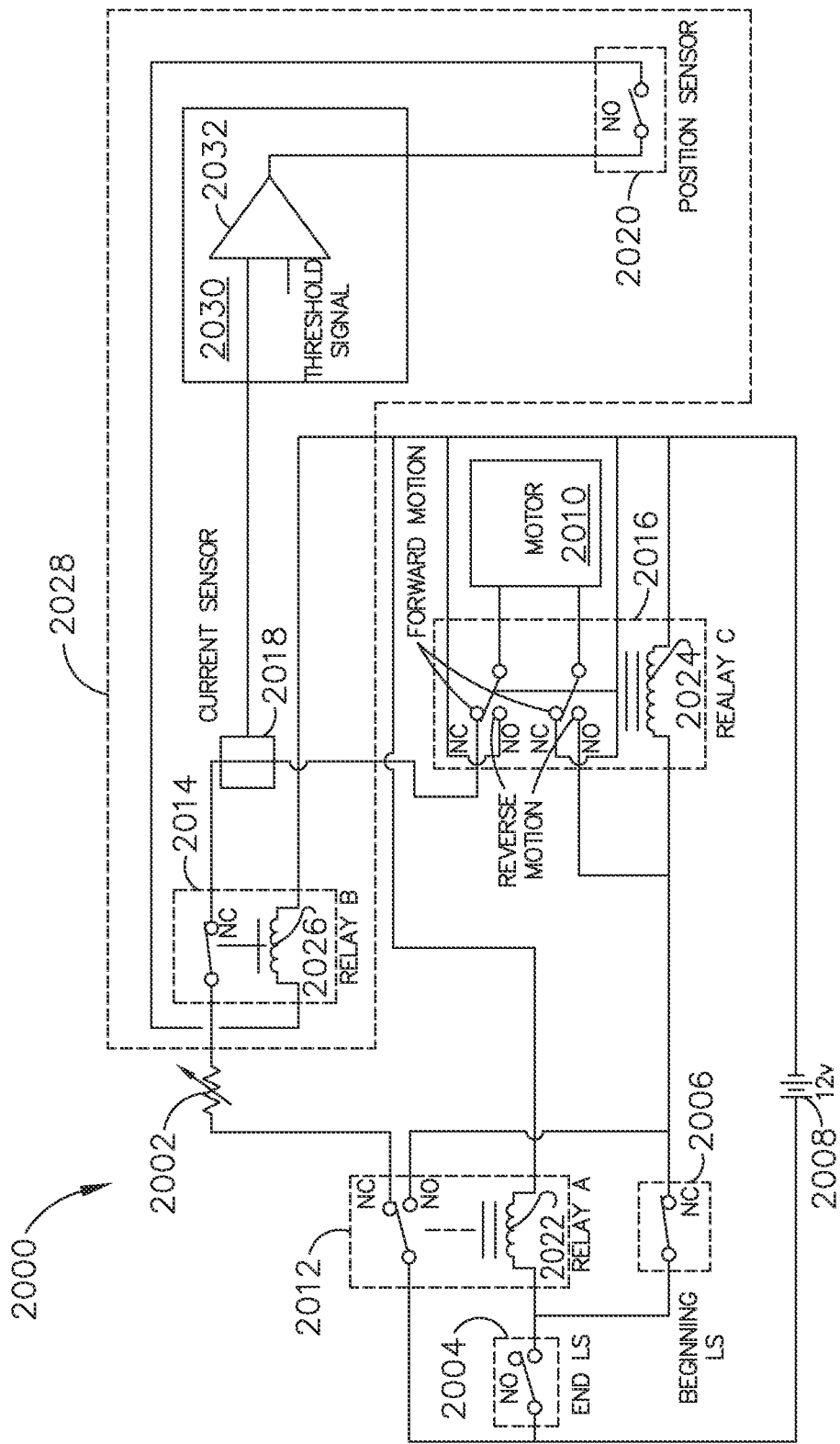
FIG. 102 is a schematic diagram of a circuit for controlling a motor of a surgical instrument.
Figure 103:
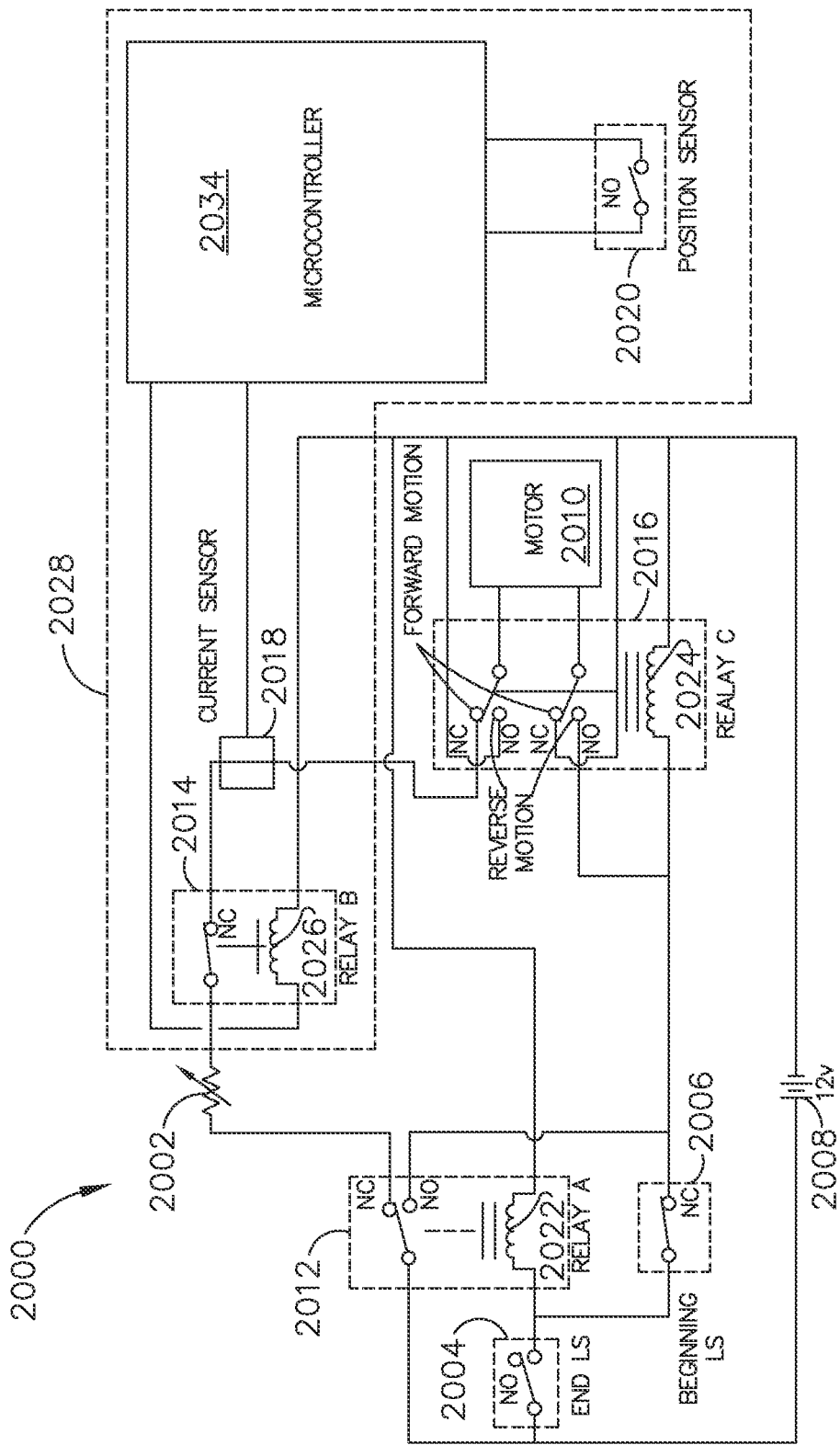
FIG. 103 is a schematic diagram of a circuit for controlling a motor of a surgical instrument.

FIGS. 102 and 103 illustrate schematic diagrams of a circuit 2000 for controlling a motor 2010 of a surgical instrument 100, according to various aspects of the present disclosure. In the depicted aspects, the circuit 2000 includes a switch 2002, a first limit switch 2004 (e.g., a normally open switch), a second limit switch 2006 (e.g., a normally closed switch), a power source 2008, and a motor 2010 (e.g., a motor that is configured to drive the first force/rotation transmitting/converting assembly 240). The circuit 2000 can further include a first relay 2012 (e.g., a single-pole double-throw relay), a second relay 2014 (e.g., a single-pole single-throw relay), a third relay 2016 (e.g., a double-pole double-throw relay), a current sensor 2018, and a current detection module 2030. In one aspect, the circuit 2000 can include a motor control circuit 2028 that is configured to sense the electrical current through the motor 2010 and then control the current accordingly. In the aspect depicted in FIG. 102, the second relay 2014, the current sensor 2018, the position sensor 2020, and the current detection module 2030 collectively form the motor control circuit 2028. In the aspect depicted in FIG. 103, the second relay 2014, the current sensor 2018, the position sensor 2020, and the controller 2034 collectively form the motor control circuit 2028. As described below, the motor control circuit 2028 controls the current to the motor 2010 by interrupting the current based upon the sensed current, thus deactivating the motor 2010 when certain conditions occur.

The switch 2002 is activated when an operator of the surgical instrument 100 initiates the firing of the clamping member 550 to clamp the end effector 500 and cut and/or staple tissue. The first limit switch 2004 is configured to remain open when the cutting/stapling operation of the end effector 500 is not yet complete. When the first limit switch 2004 is open, the coil 2022 of first relay 2012 is de-energized, thus forming a conductive path between the power source 2008 and the second relay 2014 via a normally-closed contact of the first relay 2012. The coil 2026 of the second relay 2014 is controlled by the current detection module 2030 and the position sensor 2020 as described below. When the coil 2026 of the second relay 2014 and the coil 2022 of the first relay 2012 are de-energized, a conductive path between the power source 2008 and a normally-closed contact of the third relay 2016 is formed. The third relay 2016 controls the rotational direction of the motor 2010 based on the states of switches 2004, 2006. When first limit switch 2004 is open and the second limit switch 2006 is closed (indicating that the clamping member 550 has not yet fully deployed distally), the coil 2024 of the third relay 2016 is de-energized. Accordingly, when coils 2022, 2024, 2026 are collectively de-energized, current from the power source 2008 flows through the motor 2010 via the normally-closed contacts of the third relay 2016 and causes the forward rotation of the motor 2010, which in turn causes the clamping member 550 to be driven distally by the motor 2010 to clamp the end effector 500 and cut and/or staple tissue.

When the clamping member 550 has been fully advanced distally, the first limit switch 2004 is configured to close. When the first limit switch 2004 is closed, the coil 2022 of the first relay 2012 is energized and the coil 2024 of third relay 2016 is energized via a normally open contact of the first relay 2012. Accordingly, current now flows to the motor 2010 via normally-open contacts of relays 2012, 2016, thus causing reverse rotation of the motor 2010 which in turn causes the clamping member 550 to retract from its distal position and the first limit switch 2004 to open. The second limit switch 2006 is configured to open when the clamping member 550 is fully retracted. The coil 2022 of the first relay 2012 remains energized until the second limit switch 2006 is opened, indicating the complete retraction of the clamping member 550.

The magnitude of current through the motor 2010 during its forward rotation is indicative of forces exerted upon the clamping member 550 as it is driven distally by the motor 2010. If a staple cartridge 702 is not loaded into the end effector 500, an incorrect staple cartridge 702 is loaded into the end effector 500, or if the clamping member 550 experiences unexpectedly high resistance from the tissue as it cuts and/or staples the tissue, the resistive force exerted against the clamping member 550 causes an increase in motor torque, which thereby causes the motor current to increase. If the motor current exceeds a threshold, the motor control circuit 2028 can cut off the electrical current to the motor 2010, which deactivates the motor and causes the advancement of the clamping member 550 to pause. Accordingly, by sensing the current through the motor 2010, the motor control circuit 2028 can differentiate between when the clamping member 550 is being advanced within or outside normal operational thresholds.

The current sensor 2018 may be coupled to a path of the circuit 2000 that conducts current to the motor 2010 during its forward rotation. The current sensor 2018 may be any current sensing device (e.g., a shunt resistor, a Hall effect current transducer, etc.) suitable for generating a signal (e.g., a voltage signal) representative of sensed motor current. The generated signal may be input to the current detection module 2030 for processing therein. According to the aspect depicted in FIG. 102, the current detection module 2030 may be configured for comparing the signal generated by the current sensor 2018 to a threshold signal (e.g., a threshold voltage signal) via a comparator circuit 2032 for receiving the threshold and current sensor 2018 signals and generating a discrete output based on a comparison of the received signals. In some aspects, a value of the threshold signal may be empirically determined a priori by measuring the peak signal generated by the current sensor 2018 when the clamping member 550 is initially deployed (e.g., over an initial period or length of its distal movement) during a cutting and stapling operation. In other aspects, the value of the threshold signal can be a pre-determined value that can, in one example, be retrieved from a memory.

In some aspects, it may be desirable to limit the comparison of the sensed motor current to the threshold value to a particular position or range(s) of positions along the firing stroke of the clamping member 550. In these aspects, the motor control circuit 2028 further includes a position sensor 2020 that is configured to generate a signal indicative of the position of the clamping member 550 (or alternatively, a component of the second or third force/rotation transmitting/ converting assemblies 250, 260 for aspects wherein the motor 2010 represented in FIGS. 102 and 103 drives the second or third force/rotation transmitting/converting assemblies 250, 260). The position sensor 2020 can include, for example, the position sensing assembly depicted in FIG. 104 and described in fuller detail below. The position sensor 2020 is connected in series with the comparator circuit 2032 (or the microcontroller 2034 of the aspect depicted in FIG. 103) to limit the comparison based on the position of the clamping member 550. Accordingly, if the signal generated by the current sensor 2018 exceeds the threshold signal (indicating that unexpectedly high resistance is being encountered by the clamping member 550) and the clamping member 550 is within a particular zone as determined by the position sensor 2020, the coil 2026 of the second relay 2014 will be energized. This causes normally-closed switch of the second relay 2014 to open, thereby interrupting current flow to the motor 2010 and pausing the advancement of the clamping member 550. In this way, if the threshold signal is exceeded when the position of the clamping member 550 is not at a position that activates the position sensor 2020, then the motor control circuit 2038 will not deactivate the motor 2010, regardless of the result of the comparison. In other aspects, the motor control circuit 2038 is configured to monitor the motor current along the entirety of the firing stroke of the clamping member 550. In these aspects, the motor control circuit 2038 lacks the position sensor 2020 (or the position sensor 2020 is deactivated) and the output of the comparator circuit 2032 (or the microcontroller 2034) is fed directly to the second relay 2014. Accordingly, if the signal generated by the current sensor 2018 exceeds the threshold signal at any point along the firing stroke of the clamping member 550, then current flow to the motor 2010 is interrupted, in the manner described above.

According to the aspect depicted in FIG. 103, the motor control circuit 2028 can include a processor-based microcontroller 2034 in lieu of the current detection module 2030 described above. Although not shown for purposes of clarity, the microcontroller 2034 may include components well known in the microcontroller art, such as a processor, a random access memory (RAM) unit, an erasable programmable read-only memory (EPROM) unit, an interrupt controller unit, timer units, analog-to-digital conversion (ADC) and digital-to-analog conversion (DAC) units, and a number of general input/output (I/O) ports for receiving and transmitting digital and analog signals. In on example, the microcontroller 2034 includes motor controllers comprising A3930/31K motor drivers from Allegro Microsystems, Inc. The A3930/31K motor drivers are designed to control a 3-phase brushless DC (BLDC) motor with N-channel external power MOSFETs, such as the motors 152, 154, 156 (FIG. 4). Each of the motor controllers is coupled to a main controller disposed on the main controller circuit board 142b (FIG. 4). The main controller is also coupled to memory, which is also disposed on the main controller circuit board 142b (FIG. 4). In one example, the main controller comprises an ARM Cortex M4 processor from Freescale Semiconductor, Inc. which includes 1024 kilobytes of internal flash memory. The main controller communicates with the motor controllers through an FPGA, which provides control logic signals. The control logic of the motor controllers then outputs corresponding energization signals to their respective motors 152, 154, 156 using fixed frequency pulse width modulation (PWM).

The current sensor 2018 and the position sensor 2020 may be connected to analog and digital inputs, respectively, of the microcontroller 2034, and the coil 2026 of the second relay 2014 may be connected to a digital output of the microcontroller 2034. It will be appreciated that in aspects in which the output of the position sensor 2020 is an analog signal, the position sensor 2020 may be connected to an analog input instead. Additionally, although the circuit 2000 includes relays 2012, 2014, 2016, it will be appreciated that in other aspects the relay switching functionality may be replicated using solid state switching devices, software, and combinations thereof. In certain aspects, for example, instructions stored and executed in the microcontroller 2034 may be used to control solid state switched outputs of the microcontroller 2034. In such aspects, switches 2004, 2006 may be connected to digital inputs of the microcontroller 2034.

Figure 104:
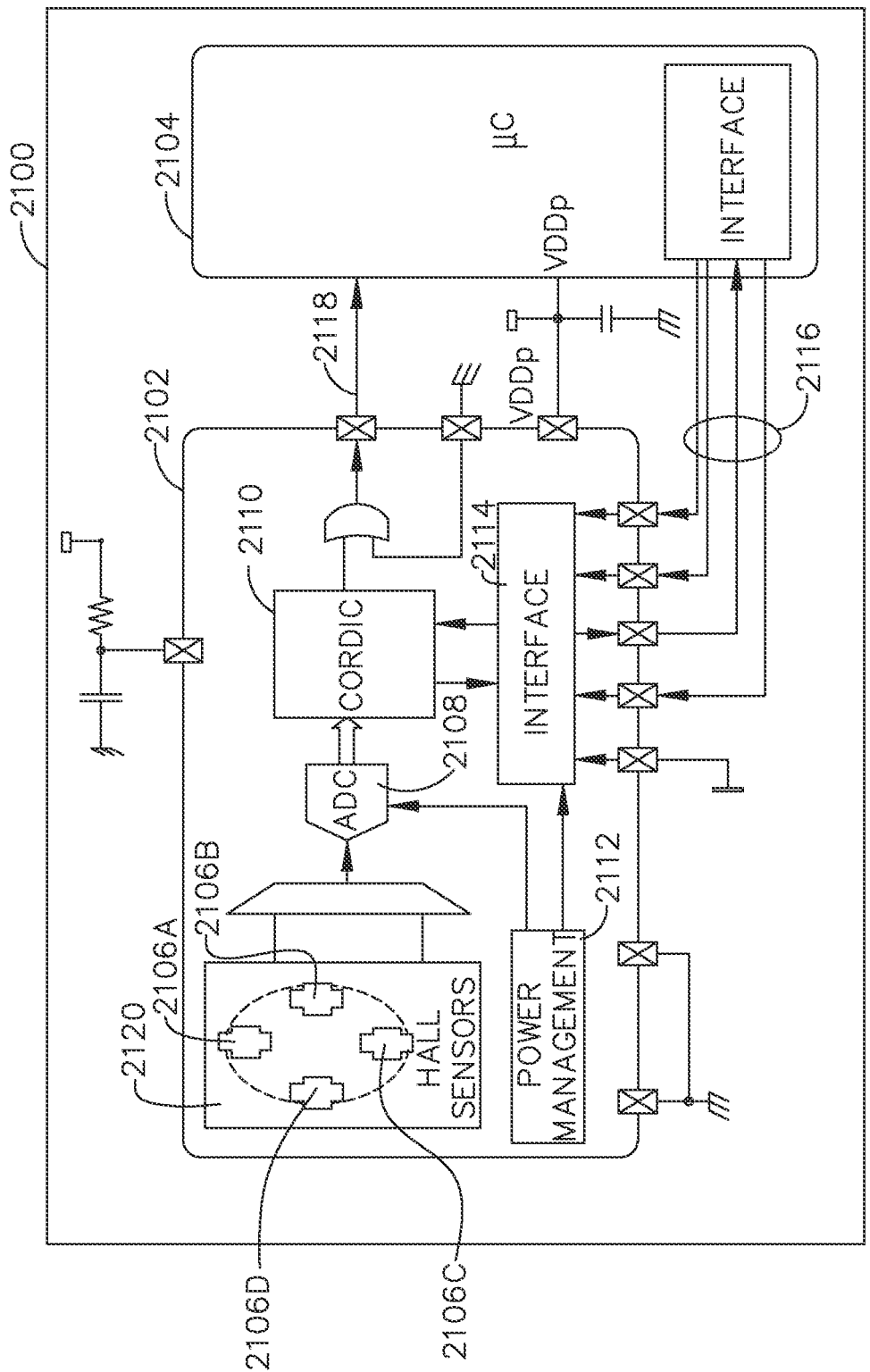
FIG. 104 is a schematic diagram of a position sensor of a surgical instrument.

FIG. 104 illustrates a schematic diagram of a position sensor 2102 of a surgical instrument 100, according to one aspect of the present disclosure. The position sensor 2102 may be implemented as an AS5055EQFT single-chip magnetic rotary position sensor available from Austria Microsystems, AG. The position sensor 2102 is interfaced with the controller 2104 to provide an absolute positioning system 2100. The position sensor 2102 is a low-voltage and low-power component and includes four Hall effect elements 2106A, 2106B, 2106C, 2106D in an area 2120 of the position sensor 2102 that is located above a magnet that is coupled to a component of the surgical instrument 100. The magnet can be coupled to, for example, a drive shaft of the motor driving the first force/rotation transmitting/converting assembly 240, the proximal drive shaft 212 of the first force/rotation transmitting/converting assembly 240, or a gear assembly that is rotatably driven by the clamping member 550 as the clamping member 550 is translated. In other words, the magnet can be coupled to a component of the surgical instrument 100 such that the angular position of the magnet with respect to the Hall effect elements 2106A, 2106B, 2106C, 2106D corresponds to a longitudinal position of, for example, the clamping member 550. A high-resolution ADC 2108 and a smart power management controller 2112 are also provided on the chip. A CORDIC processor 2110 (for Coordinate Rotation Digital Computer), also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface such as an SPI interface 2114 to the controller 2104. The position sensor 2102 provides 12 or 14 bits of resolution. The position sensor 2102 may be an AS5055 chip provided in a small QFN 16-pin 4×4×0.85 mm package.

The Hall effect elements 2106A, 2106B, 2106C, 2106D are located directly above the rotating magnet (not shown). The Hall effect is a well-known effect and for expediency will not be described in detail herein; however, generally, the Hall effect produces a voltage difference (the Hall voltage) across an electrical conductor transverse to an electric current in the conductor and a magnetic field perpendicular to the current. A Hall coefficient is defined as the ratio of the induced electric field to the product of the current density and the applied magnetic field. It is a characteristic of the material from which the conductor is made, since its value depends on the type, number, and properties of the charge carriers that constitute the current. In the AS5055 position sensor 2102, the Hall effect elements 2106A, 2106B, 2106C, 2106D are capable producing a voltage signal that is indicative of the absolute position of the magnet 1202 in terms of the angle over a single revolution of the magnet 1202. This value of the angle, which is unique position signal, is calculated by the CORDIC processor 2110 is stored onboard the AS5055 position sensor 2102 in a register or memory. The value of the angle that is indicative of the position of the magnet 1202 over one revolution is provided to the controller 2104 in a variety of techniques, for example, upon power up or upon request by the controller 2104.

The AS5055 position sensor 2102 requires only a few external components to operate when connected to the controller 2104. Six wires are needed for a simple application using a single power supply: two wires for power and four wires 2116 for the SPI interface 2114 with the controller 2104. A seventh connection can be added in order to send an interrupt to the controller 2104 to inform that a new valid angle can be read. Upon power-up, the AS5055 position sensor 2102 performs a full power-up sequence including one angle measurement. The completion of this cycle is indicated as an INT output 2118, and the angle value is stored in an internal register. Once this output is set, the AS5055 position sensor 2102 suspends to sleep mode. The controller 2104 can respond to the INT request at the INT output 2118 by reading the angle value from the AS5055 position sensor 2102 over the SPI interface 2114. Once the angle value is read by the controller 2104, the INT output 2118 is cleared again. Sending a "read angle" command by the SPI interface 2114 by the controller 2104 to the position sensor 2102 also automatically powers up the chip and starts another angle measurement. As soon as the controller 2104 has completed reading of the angle value, the INT output 2118 is cleared and a new result is stored in the angle register. The completion of the angle measurement is again indicated by setting the INT output 2118 and a corresponding flag in the status register.

Due to the measurement principle of the AS5055 position sensor 2102, only a single angle measurement is performed in very short time (~600 μs) after each power-up sequence. As soon as the measurement of one angle is completed, the AS5055 position sensor 2102 suspends to power-down state. An on-chip filtering of the angle value by digital averaging is not implemented, as this would require more than one angle measurement and, consequently, a longer power-up time that is not desired in low-power applications. The angle jitter can be reduced by averaging of several angle samples in the controller 2104. For example, an averaging of four samples reduces the jitter by 6 dB (50%).

Figure 105:
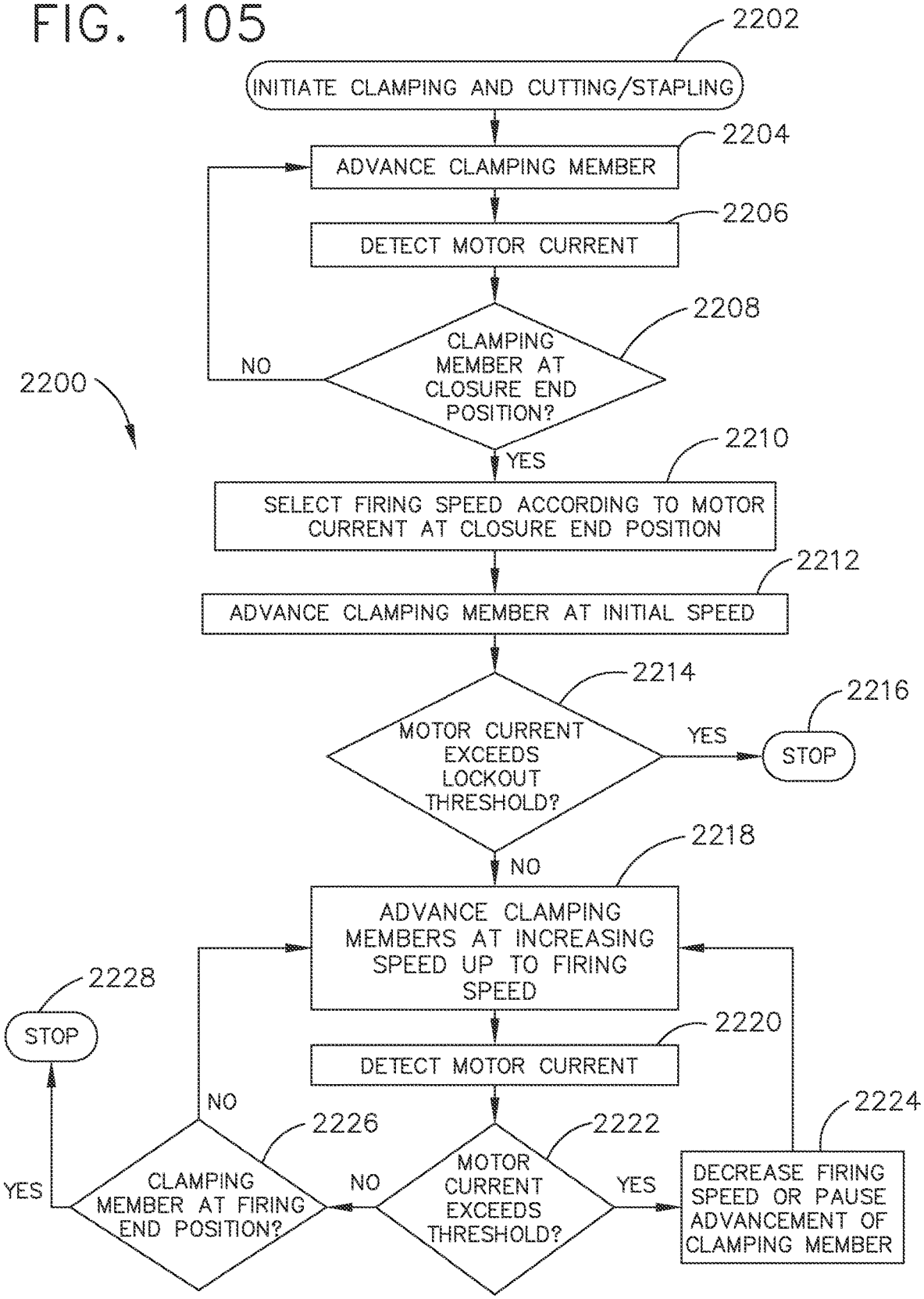
FIG. 105 is a logic flow diagram of a process for monitoring a motor current of a surgical instrument.

FIG. 105 illustrates a logic flow diagram of a process 2200 for monitoring a motor current of a surgical instrument 100, according to one aspect of the present disclosure. In the following description of the process 2200, reference should also be made to FIGS. 102-104, which depict various sensor assemblies utilized by the process 2200, and FIGS. 106-107, which depict various firing strokes of the clamping member 550 executed according to the process 2200. The presently described process 2200 can be executed by a controller, which includes the control circuit depicted in FIGS. 102-103, the microcontroller 2104 of FIG. 104, or another control circuit and/or processor that is executing logic and/or instructions stored in a memory of the surgical instrument 100. The process 2200 begins to be executed when the clamping and cutting/stapling operations of the end effector 500 are initiated 2202.

Figure 106:
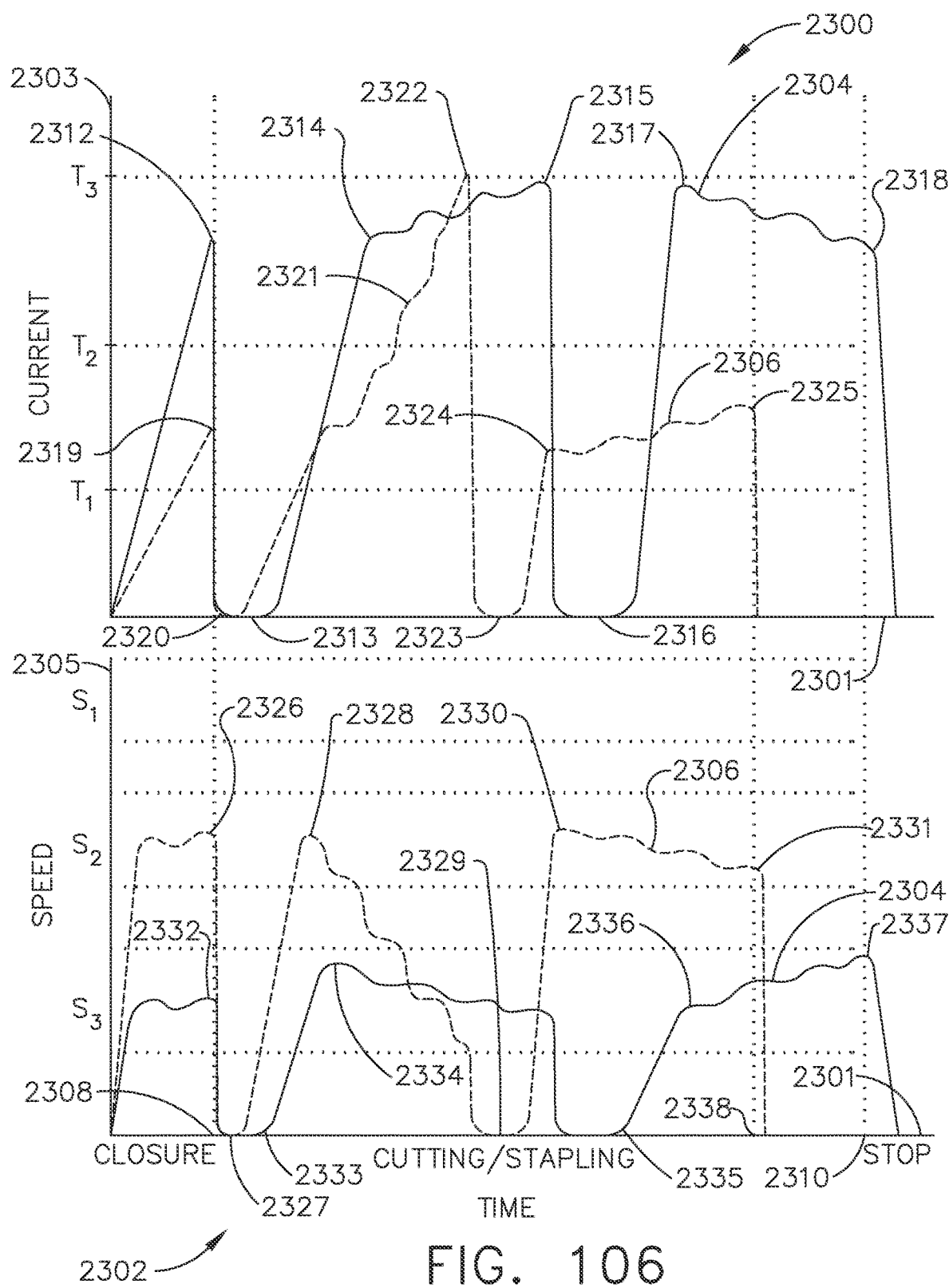
FIG. 106 is a pair of graphs of various clamping member strokes executed per the logic depicted in FIG. 105.
Figure 107:
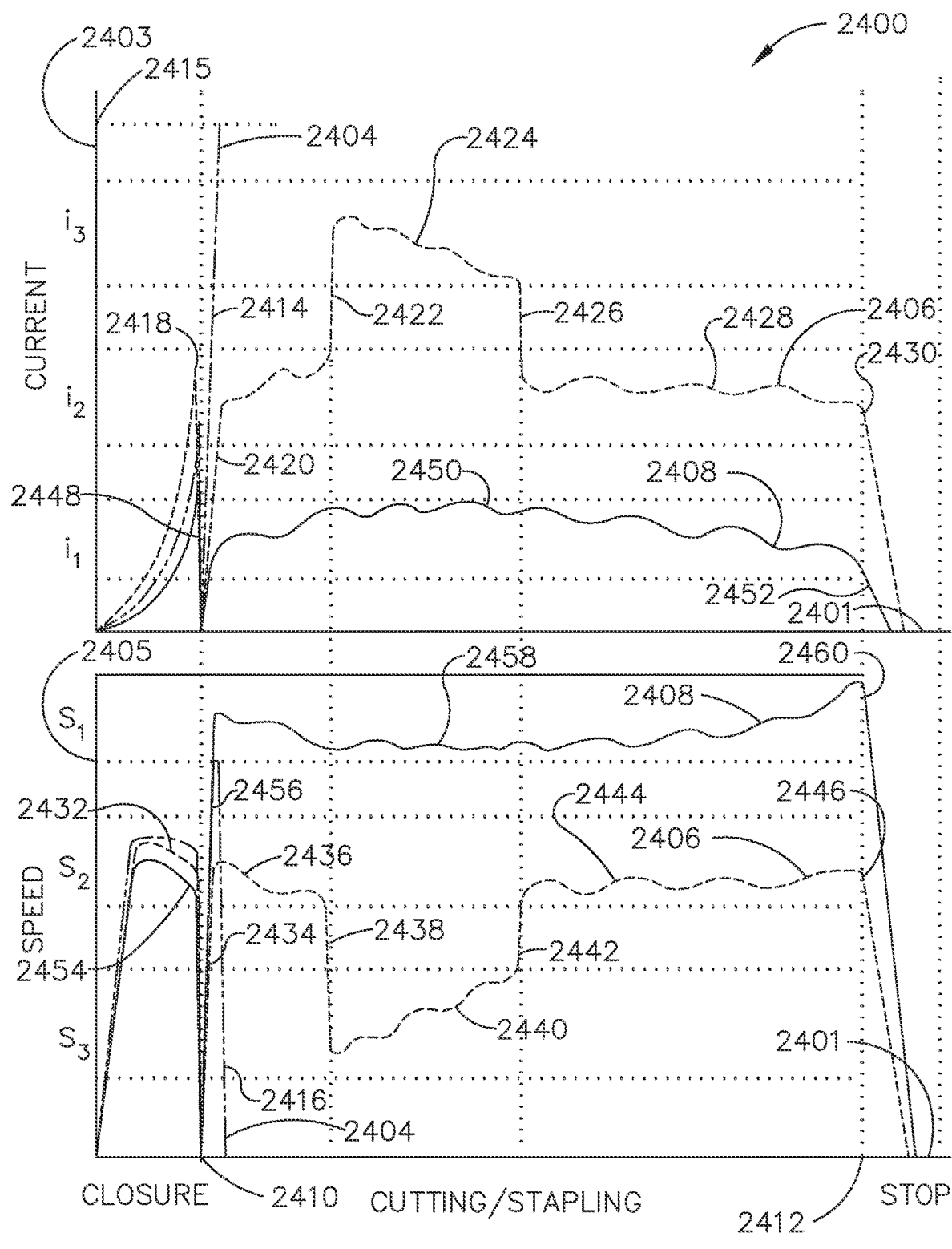
FIG. 107 is a pair of graphs of various clamping member strokes executed per the logic depicted in FIG. 105.

Accordingly, the process 2200 executed by the controller advances 2204 the clamping member 550 from a first or proximal position by energizing the motor 2010 to which the clamping member 550 is operably connected. The advancement of the clamping member 550 between a first or proximal position and a second or distal position can be referred to as a stroke or a firing stroke. During the course of a full stroke of the clamping member 550, the clamping member 550 will clamp the end effector 500 and then cut and/or staple tissue held thereby. The stroke of the clamping member 550 can be represented, for example, as a graph where the x-axis corresponds to the distance or time over which the clamping member 550 has advanced, as depicted in FIGS. 106-107. The actions effectuated by the clamping member 550 can correspond to positions or zones defined within the stroke of the clamping member 550. For example, there can be a position in the stroke where the clamping member 550 has closed the end effector 500 and is thereafter cutting and/or stapling tissue. As another example, there can be a position in the stroke of the clamping member 550 where the clamping member 550 is no longer ejecting staples or cutting tissue. The controller can also take various actions according to the position of the clamping member 550. For example, there can be a position where the speed at which the clamping member 550 is driven is controlled or changed by a controller. These positions or zones can refer to actual physical positions at which the clamping member is located or relative positions within the stroke of the clamping member. The positions or zones can alternatively be represented as times in the stroke of the clamping member 550, as depicted in FIG. 106.

As the clamping member 550 is advanced 2204, the controller detects 2206 the motor current via, for example, the current sensor 2018. The controller then determines 2208 whether the clamping member 550 is at the closure end position. In one example, the controller can determine 2208 whether the clamping member is at the closure end position via the position sensor 2102. The closure end position corresponds to the location in the firing stroke of the clamping member 550 after the clamping member 550 has closed the end effector 500 and is thereafter cutting tissue and/or firing staples as the clamping member 550 continues to advance distally. In some aspects, the controller can retrieve the closure end position from a memory and then compare the stored closure end position to the detected position of the clamping member 550 to determine if the detected position matches or exceeds the stored closure end position. In other aspects, the controller can determine the closure end position by, for example, monitoring for a peak in the motor current. If the clamping member 550 is not at the closure end position, the process 2200 proceeds along the NO branch and the controller continues causing the motor 2010 to advance 2204 the clamping member 550. The process 2200 continues this loop until the clamping member 550 is located at the closure end position.

If the controller determines 2208 that the clamping member 550 is located at or beyond the closure end position, the process 2200 proceeds along the YES branch and the controller selects 2210 the target firing speed at which the clamping member 550 is to be driven by the motor 2010 according to the value of the motor current at the closure end position. The level of motor current required to close the end effector 500 can be indicative of various properties of the clamped tissue. For example, the value of the motor current at the closure end position can correspond to the thickness of the clamped tissue because the force exerted by the clamping member 550 to clamp tissue is proportional to the thickness of the tissue. As the force exerted by the clamping member 550 or the torque exerted by the motor 2010 is proportional to the current drawn by the motor 2010, the level of the motor current at the closure end position thus corresponds to the thickness of the clamped tissue. It can be desirable to set the target firing speed at which the clamping member 550 is driven according to the thickness of the clamped tissue because advancing the clamping member 550 too quickly through thick tissue can cause improper staple formation and increase the strain on the motor 2010. As another example, the level of motor current can also correspond to the anatomical type of the clamped tissue (e.g., lung tissue, gastrointestinal tissue, or cardiac tissue) because the physical resistance exerted on the cutting surface 554 driven by the clamping member 550 can vary for different tissue types. In some aspects, the controller can compare the sensed value of the motor current at the closure end position to a range of motor current values and then determine whether the sensed motor current has exceeded one or more thresholds or falls within one or more zones of the range. The controller can then select 2210 the target firing speed for the clamping member 550 as a particular value or set a tolerance threshold for the target firing speed including a range of values, which correspond to where the sensed motor current lies within the range.

After selecting 2210 the target firing speed, the controller then causes the clamping member 550 to advance 2212 at an initial speed. The initial speed and the length of time or distance over which the clamping member 550 is advanced at the initial speed can be set values that are retrieved by the controller from a memory or calculated values that are determined by the controller as a function of the tissue thickness. In some aspects, the controller lacks this step of the process 2200 and instead simply proceeds to advance the clamping member 550 at the determined target speed. The initial speed can be a value that is less than the target firing speed. In other words, the controller can cause the motor 2010 to initially advance the clamping member 550 at a lower speed in a first zone or portion of the firing strike relative to a subsequent portion or zone of the firing stroke. In some aspects, the value of the initial speed can be zero or nearly zero. It can be desirable to advance 2212 the clamping member 550 at a lower speed initially in order to allow the fluid to drain from the tissue clamped at the end effector 500. Fluid drains from clamped tissue due to the mechanical forces exerted on the tissue by the end effector 500. In one aspect, the length of time or distance that the clamping member 550 is advanced at the initial speed can vary according to the thickness of the clamped tissue.

During the portion of the firing stroke of the clamping member 550 directly following the closure end position, the controller further determines 2214 whether the motor current exceeds a maximum or lockout threshold. The controller can retrieve the lockout threshold from a memory. The sensed motor current exceeding the lockout threshold indicates that the clamping member 550 is not being advanced distally from the closure end position. The clamping member 550 can be prevented from advancing distally in the portion of its firing stroke immediately following the closure end position for a variety of reasons, such as if the end effector 500 lacks a staple cartridge assembly 700. If the motor current exceeds the lockout threshold, the process 2200 proceeds along the YES branch and stops 2216 in order to reduce strain on the motor 2010. The controller can thereafter cause the surgical instrument 100 to display an alert to the operator or take other such actions.

If the motor current does not exceed the lockout threshold, the process 2200 proceeds along the NO branch the controller then causes the clamping member 550 to advance 2218 at an increasing rate of speed until the speed reaches the target speed value or is within the target speed range (which is a function of the tissue thickness). In some aspects, the rate at which the controller causes the motor 2010 to drive the clamping member 550 to increase the speed of the clamping member 550 is a set or predetermined rate. In other aspects, the rate at which the speed of the clamping member 550 is increased is a function of one or more parameters, such as the tissue thickness. In other words, the controller could be configured to cause the speed of the clamping member 550 to increase more slowly for thicker tissue or increase more quickly for thinner tissue.

As the clamping member 550 is advanced distally (i.e., fired), the controller detects 2220 the motor current. The controller accordingly determines 2222 whether the sensed motor current exceeds a threshold value. In one example, the threshold value can be retrieved by the controller from a memory for comparison to the detected 2220 motor current. This threshold can be the same or different than the lockout threshold described above. Furthermore, the threshold can correspond to the tissue thickness, for example. In some aspects, if the controller determines 2222 that the motor current has exceeded the determined threshold, then the process 2200 proceeds along the YES branch and the controller decreases 2224 the firing speed of the clamping member 550. In other aspects, if the controller determines 2222 that the motor current has exceeded the determined threshold, then the process 2200 proceeds along the YES branch and the controller pauses 2224 the clamping member 550 at its current position in its firing stroke. Decreasing the firing speed of or pausing 2224 the clamping member 550 reduces the torque experienced by the motor 2010 (to zero, in the case of pausing the clamping member 550). After a particular length of time or after the clamping member 550 had advanced a particular distance (in the case where the clamping member 550 is slowed, not paused), the process 2200 loops back and the controller again causes the clamping member 550 to advance 2218. The elapsed time or distance before which the controller begins causing the clamping member 550 to increase in speed can be a set value or can be a function of a tissue parameter (e.g., the tissue thickness).

If the controller determines 2222 that the clamping member 550 has not exceeded a threshold, the process 2200 proceeds along the NO branch and the controller then determines 2226 whether the clamping member 550 is located at the firing end position. The firing end position corresponds to the distal point reached by the clamping member 550 in its firing stroke to cut tissue and/or fire staples from the end effector 500. If the clamping member 550 has not reached the firing end position, the process 2200 proceeds along the NO branch and loops back. The controller then continues to advance 2218 the clamping member 550 (and increase its speed, as appropriate) and detects 2220 the motor current during the course of the firing stroke to determine 2222 whether the motor current exceeds the threshold. The controller continues this loop until it determines 2226 that the clamping member 550 is located at the firing end position. If the controller determines 2226 that the clamping member 550 is located at the firing end position, the process 2200 proceeds along the YES branch and then stops 2228.

To provide further explanation regarding the function(s) described above that the controller is configured to execute, the process 2200 will be discussed in terms of several example firing strokes depicted in FIGS. 106-107. FIG. 106 illustrates a first graph 2300 and a second graph 2302, each of which depict a first firing stroke 2304 and a second firing stroke 2306 of the clamping member 550. The first graph 2300 depicts motor current 2303 versus time 2301 and the second graph 2302 depicts clamping member speed 2305 versus time 2301 for the example firing strokes 2304, 2306 of the clamping member 550. The time 2301 axis is delineated into a "CLOSURE" zone, a "CUTTING/STAPLING" zone, and a "STOP" zone, which indicates the action(s) that the clamping member 550 is effectuating in each respective portion of its firing stroke. In combination, the first graph 2300 and the second graph 2302 illustrate the relationship between motor current 2303 and clamping member speed 2305 for different firing strokes 2304, 2306 and the resulting actions taken by a controller executing the process 2200 depicted in FIG. 105.

As discussed above in connection with FIG. 105, the controller executing the process 2200 can be configured to select 2210 the firing speed at which the clamping member 550 is to be driven according to the motor current at the closure end position 2308. In other words, the controller is configured to select 2210 a firing speed of the clamping member 550 that is appropriate for or that otherwise corresponds to the thickness of the clamped tissue, as indicated by the motor current at the closure end position 2308. In one aspect, the controller selects the firing speed of the clamping member 550 according to where the sensed motor current at the closure end position 2308 falls within a range of values. In some aspects, this can be expressed as whether the motor current at the closure end position 2308 has surpassed one or more thresholds in a range of motor current values. In other aspects, this can be expressed as whether the motor current at the closure end position 2308 falls within a particular zone or zones in a range of motor current values.

In the depicted aspect, there are a first threshold $T_1$, a second threshold $T_2$, and a third threshold $T_3$, which can demarcate zones corresponding to thin tissue, medium tissue, and thick tissue, respectively. In other words, if the motor current at the closure end position 2308 is below $T_1$, then the tissue can be considered to be thin because relatively little torque was exerted by the motor 2010 to clamp the end effector 500 on the tissue. Accordingly, if the motor current at the closure end position 2308 has exceeded $T_1$, but is below $T_2$, then the tissue can be considered to be of medium, normal, or expected thickness. Accordingly, if the motor current at the closure end position 2308 has exceeded $T_2$, but is below $T_3$, then the tissue can be considered to thick because the motor 2010 was required to exert a high degree of torque to clamp the tissue. If the motor current at the closure end position 2308 exceed $T_3$, then the tissue can be considered to be too thick to cut and staple or may have been clamped improperly. In that case, the process 2200 can display a warning to the operator and/or lockout the surgical instrument 100 from advancing the clamping member 550 further. The depiction of three thresholds $T_1, T_2, T_3$ is simply illustrative and the process 2200 can incorporate any number of thresholds, however. The speed at which the clamping member 550 is to be driven can be selected by the process 2200 executed by the controller to correspond to the relative tissue thickness, which is indicated by the motor current at the closure end position 2308. In the depicted aspect, there are a first speed zone $S_1$ that is selected if the motor current does not exceed $T_1$, a second speed zone $S_2$ that is selected if the motor current falls between $T_1$ and $T_2$, and a third speed zone $S_3$ that is selected if the motor current falls between $T_2$ and $T_3$. The first speed zone $S_1$ to the third speed zone $S_3$ correspond to increasingly slower speeds. It can be desirable to drive the clamping member 550 at a faster rate through thinner tissue because thin tissue provides little resistance to proper staple formation and thus the operation can be completed more quickly without sacrificing staple quality. Conversely, it can be desirable to drive the clamping member 550 at a slower rate through thicker tissue because staples may not be formed properly in thicker tissue if the sled 712 (FIG. 10) is driven too quickly by the clamping member 550. Driving the sled 712 at a slower rate thus ensures that the staples fully pierce the tissue and are fully formed against the anvil plate 620 (FIG. 10).

The first firing stroke 2304 and the second firing stroke 2306 are examples where the controller determines 2222 that the motor current exceeds a threshold during the course of the clamping member firing stroke and then pauses 2224 the clamping member 550. For example, in the first firing stroke 2304 the closure motor current 2312 at the closure end position 2308 has exceed the second threshold $T_2$; therefore, the controller selects the slowest speed zone $S_3$ as the target speed at which the clamping member 550 is to be driven during the cutting/stapling phase of the firing stroke. In the second firing stroke 2306 the closure motor current 2319 at the closure end position 2308 has exceed the first threshold $T_1$; therefore, the controller selects the medium speed zone $S_2$ as the target speed at which the clamping member 550 is to be driven during the cutting/stapling phase of the firing stroke. The speed zones $S_1$, $S_2$, $S_3$ set the upper and lower tolerance thresholds for the speed at which the clamping member 550 is driven by the motor 2010. If the speed of the clamping member 550 exceeds the upper and lower limits of the speed zone $S_1$, $S_2$, $S_3$ selected by the controller, then the controller can be configured to take various actions, such as controlling the motor 2010 to increase or decrease the speed at which the clamping member 550 is driven or adjusting the electrical energy supplied to the motor 2010. In other words, the speed zones $S_1$, $S_2$, $S_3$ represent ranges of acceptable speeds in which the speed at which the clamping member 550 is actually translated can vary without causing the controller to take corrective action. It should be appreciated that although the target speed zones $S_1$, $S_2$, $S_3$ are depicted as ranges in the second graph 2302, they could alternatively be discrete values. In general, it can be desirable to set tolerance ranges for the speed at which the clamping member 550 is advancing because the speed will naturally vary during a firing stroke because tissue is not uniform in thickness, the clamping member 550 tends to slow as the sled 712 ejects staples (which are spaced from each other), and the tissue cutting surface 554 (FIG. 10) may be advancing through different types of tissue with different physical properties.

Continuing the description of the first firing stroke 2304, after the closure end position 2308 the controller causes the speed at which the clamping member 550 is advanced to drop from the closure speed 2332 to an initial speed 2333, which may be lower than the selected target speed (and in some cases is zero). The initial speed 2333 corresponds to a low initial motor current 2313. The controller then gradually increases the speed at which the clamping member 550 is driven to a target speed 2334 that is within the target speed range $S_3$ previously selected by the controller. As the clamping member speed increases, the motor current likewise increases 2314. If the clamping member 550 does not encounter any abnormal resistance from the tissue as the tissue cutting surface 554 is driven therethrough, the clamping member speed will thus be maintained within the target speed range $S_3$ through the firing stroke until the stop position 2310. However, in this example, the speed instead begins decreasing thereafter. As the speed decreases, the motor current increases until it peaks 2315 and reaches the maximum threshold $T_3$. The clamping member speed dropping while the motor current is simultaneously increasing indicates that the tissue cutting surface 554 driven by the clamping member 550 is encountering thicker than expected tissue or there is otherwise an error that is causing the torque on the motor 2010 to increase unexpectedly. When unexpectedly thick tissue is encountered, the torque on the motor 2010 can increase while the clamping member speed is, at best, maintained or, in this case, falls. When the motor current meets or exceeds the maximum threshold $T_3$ (at peak 2315), the controller reduces or cuts 2316 the current to the motor 2010, which cause the clamping member speed to drop 2335 to a lower speed or, in some aspects, to zero (i.e., the clamping member 550 is paused). After a period of time, the controller re-energizes the motor 2010 and gradually increases 2317 the motor current in order to cause the speed at which the clamping member 550 is driven to gradually increase to a target speed 2336 within the target speed range $S_3$. As long as the motor current does not re-exceed the maximum threshold $T_3$, the clamping member 550 continues to advance until it reaches the stop position 2310. At that point, the controller causes the motor current to drop 2318 to zero and the clamping member speed likewise drops 2337 to zero as the clamping member slows to a stop due to the motor 2010 being de-energized.

A similar series of events described above with respect to the first firing stroke 2304 occurs with respect to the second firing stroke 2306, except that the controller selects the target speed range as $S_2$ because the closure motor current 2319 only exceeded the first threshold $T_1$ at the closure end position 2308. As with the first firing stroke 2304, after the closure end position 2308 the controller causes the speed at which the clamping member 550 is advanced to drop from the closure speed 2326 to an initial speed 2327. The controller then gradually increases the speed at which the clamping member 550 is driven to a target speed 2328 that is within the target speed range $S_2$ previously selected by the controller. As the clamping member speed increases, the motor current likewise increases 2321. As with the first firing stroke 3406, the speed begins decreasing and the motor current increases until it peaks 2322 and reaches the maximum threshold $T_3$. As the motor current meets or exceeds the maximum threshold $T_3$ (at peak 2322), the controller reduces or cuts 2323 the current to the motor 2010, which cause the clamping member speed to drop 2329 to a lower speed or, in some aspects, to zero (i.e., the clamping member 550 is paused). After a period of time, the controller re-energizes the motor 2010 and gradually increases 2324 the motor current to increase the clamping member speed a target speed 2330 within the target speed range $S_2$. The time delay prior to the controller re-energizing the motor can vary for different conditions encountered during the firing stroke. As can be noted from either the first graph 2300 or the second graph 2302, the length of time that the current is cut 2316 in the first firing stroke 2304 is greater than the length of time that the current is cut 2323 in the second firing stroke 2306. In some aspects, the length of the pause (or the length of time at which the clamping member 550 is driven at a lower or initial speed) can be a function of the tissue thickness. For example, the controller can pause the advancement of the clamping member 550 longer for thicker tissue. The controller continues to advance the clamping member 550 until it reaches the stop position 2338. At that point, the controller causes the motor current to drop 2325 to zero and the clamping member speed likewise drops 2331 to zero as the clamping member slows to a stop due to the motor 2010 being de-energized. As can further be noted, the stop position 2338, 2310 can vary. In some aspects, the location of the stop position 2338, 2310 can vary according to the length of the cartridge body 702 present into the end effector 500. In other aspects, the location of the stop position 2338, 2310 can be set by the operator of the surgical instrument 100 to a shorter (i.e., more proximal) position than the maximum stop position.

FIG. 107 illustrates a third graph 2400 and a fourth graph 2402, each of which depict a third firing stroke 2404, a fourth firing stroke 2406, and a fifth firing stroke 2408 of the clamping member 550. The third graph 2400 depicts motor current 2403 versus clamping member displacement distance 2401 and the fourth graph 2402 depicts clamping member speed 2405 versus displacement distance 2401 for the example firing strokes 2404, 2406, 2408 of the clamping member 550. The displacement distance 2401 axis is delineated into a "CLOSURE" zone, a "CUTTING/STAPLING" zone, and a "STOP" zone, which indicates the action(s) that the clamping member 550 is driving in each respective portion of its firing stroke. In combination, the third graph 2400 and the fourth graph 2402 illustrate the relationship between motor current 2403 and clamping member speed 2405 for different firing strokes 2404, 2406, 2408 and the resulting actions taken by a controller executing the process 2200 depicted in FIG. 105.

As discussed above in connection with FIG. 105, the controller executing the process 2200 can be configured to select 2210 the firing speed at which the clamping member 550 is to be driven according to the motor current at the closure end position 2410. In other words, the controller is configured to select 2210 a firing speed for the clamping member 550 that is appropriate for or that otherwise corresponds to the thickness of the clamped tissue, as indicated by the motor current at the closure end position 2410. In one aspect, the controller selects the firing speed of the clamping member 550 according to where the sensed motor current at the closure end position 2410 falls within a range of values. In some aspects, this can be expressed as whether the motor current at the closure end position 2410 has surpassed one or more thresholds in a range of motor current values. In other aspects, this can be expressed as whether the motor current at the closure end position 2410 falls within a particular zone or zones in a range of motor current values. In the depicted aspect, the motor current 2403 includes a first zone $i_1$, a second zone $i_2$, and a third zone $i_3$. The zones may or may not be contiguous with each other. The depiction of three zones $i_1$, $i_2$, $i_3$ along the axis of the motor current 2403 is simply illustrative and the process 2200 can incorporate any number of thresholds, however.

As also discussed above in connection with FIG. 105, the process 2200 executed by the controller can be configured to determine 2214 whether the motor current exceeds a lockout threshold 2415. The third firing stroke 2404 represents an example firing stroke wherein the controller determines 2214 that the lockout threshold 2415 is exceeded. In the third firing stroke 2404, the motor current spikes 2414 in the portion of the firing stroke immediately following the closure end position 2410, reaching or exceeding the lockout threshold 2415, as the clamping member speed sharply drops 2416 to zero. In other words, the motor current increases sharply with minimal or no corresponding movement of the clamping member 550. When the motor current reaches the lockout threshold 2415, the process 2200 executed by the controller stops 2216 and the controller can display a warning to the operator and/or lockout the surgical instrument 100 from firing the clamping member 550. In one example, the spike 2414 in the motor current exhibited by the third firing stroke 2404 directly after the closure end position 2410 can be indicative of a cartridge 702 not being present or being improperly loaded in the end effector 500.

The fourth firing stroke 2406 is an example where controller determines 2222 that the motor current exceeds a threshold during the course of the clamping member stroke and then decreases 2224 the speed of the clamping member 550. In the fourth firing stroke 2406, the closure motor current 2418 falls within the $i_2$ zone; therefore, the controller selects $S_2$ as the target speed range 2436. After the closure end position 2410, the controller causes the clamping member speed to decrease from the closure speed 2432 to an initial speed 2434. The controller then causes the displacement member speed to increase from the initial speed 2434 to a target speed 2436 in the selected speed range $S_2$. It should be noted that the initial speed 2434 can be a set value or a range of values. The motor current correspondingly increases 2420 as the displacement member speed increases. As the clamping member 550 continues advancing in the fourth firing stroke 2406, the clamping member 550 hits a point where the motor current sharply increases 2422 such that it exceeds a threshold demarcated by the upper boundary of the $i_2$ zone. The sharp increase 2422 in the motor current is indicative of the cutting surface 554 being driven through an unexpectedly thick portion of the clamped tissue. In this example, there are multiple thresholds (demarcated by the boundaries of the current zones $i_1$, $i_2$, $i_3$) that the controller compares the sensed motor current against to determine 2222 whether to decrease 2224 the displacement member speed or pause the clamping member 550. This is in contrast to the first firing stroke 2304 and the second firing stroke 2306 where the controller only took action (i.e., paused the clamping member 550 in the particular examples) when the motor current reached or exceeded a singular maximum threshold ($T_3$). When the motor current exceeds the threshold, the controller decreases 2438 the clamping member speed from the original speed range $S_2$ to the lower speed range $S_3$. The controller then causes the motor 2010 to advance the clamping member 550 at the lower speed 2440. As the clamping member 550 advances at the lower speed range $S_3$, the motor current continues 2424 in the higher current range $i_3$ until it sharply decreases 2426 past the lower boundary of the $i_3$ current zone. The sharp decrease 2426 in the motor current is indicative of the cutting surface 554 being driven through a thinner portion of the clamped tissue because less current is required to advance the clamping member 550 at the target speed. When the motor current reaches or exceeds the threshold represented by this lower boundary, the controller then causes the motor 2010 to increase 2442 the clamping member speed from the lower speed range $S_3$ back to the original speed range $S_2$. Through the remaining portion of the fourth firing stroke 2406, the displacement member speed continues 2444 within the target speed range $S_2$ (with the motor current likewise continuing 2428 with its respective range $i_2$) until the clamping member 550 reaches the firing end position 2412. When the clamping member 550 reaches the firing end position 2412, the controller cuts 2430 the motor current and the clamping member speed correspondingly drops 2446 to zero as the motor 2010 is de-energized.

The fifth firing stroke 2408 represents a firing stroke wherein the clamping member 550 is driven through clamped tissue lacking any significant variations in thickness. In the fifth firing stroke 2408, the closure motor current 2448 falls within the $i_1$ zone; therefore, the controller selects $S_1$ as the target speed range 2458. After the closure end position 2410, the controller causes the clamping member speed to decrease from the closure speed 2454 to an initial speed 2456. The controller then causes the displacement member speed to increase from the initial speed 2456 to a target speed 2458 in the selected speed range $S_3$. In the present example, the clamping member 550 maintains its speed within the target speed 2458 for the entire length of the firing stroke. The motor current is likewise maintained 2450 within the boundaries of the current zone $i_1$. In other words, the clamping member 550 does not encounter any portions of tissue that is appreciably thicker or thinner relative to the expected tissue thickness (i.e., the tissue thickness indicated by the closure motor current 2418) as the clamping member 550 advances from the closure end position 2410 to the firing end position 2412. When the clamping member 550 reaches the firing end position 2412, the controller cuts 2452 the motor current, which causes the clamping member speed to drop 2460 to zero as the motor 2010 is de-energized.

Figure 108:
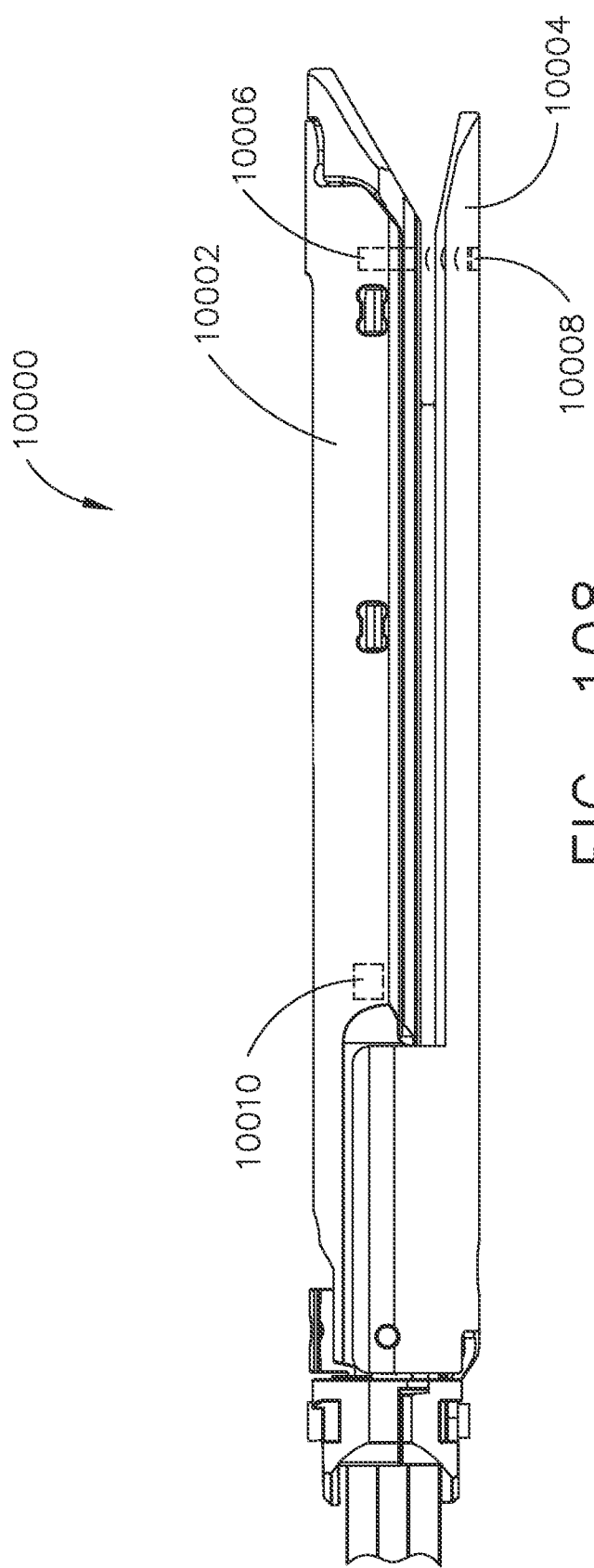
FIG. 108 is a diagram of an end effector including a gap sensor and a cartridge identity sensor.
Figure 109:
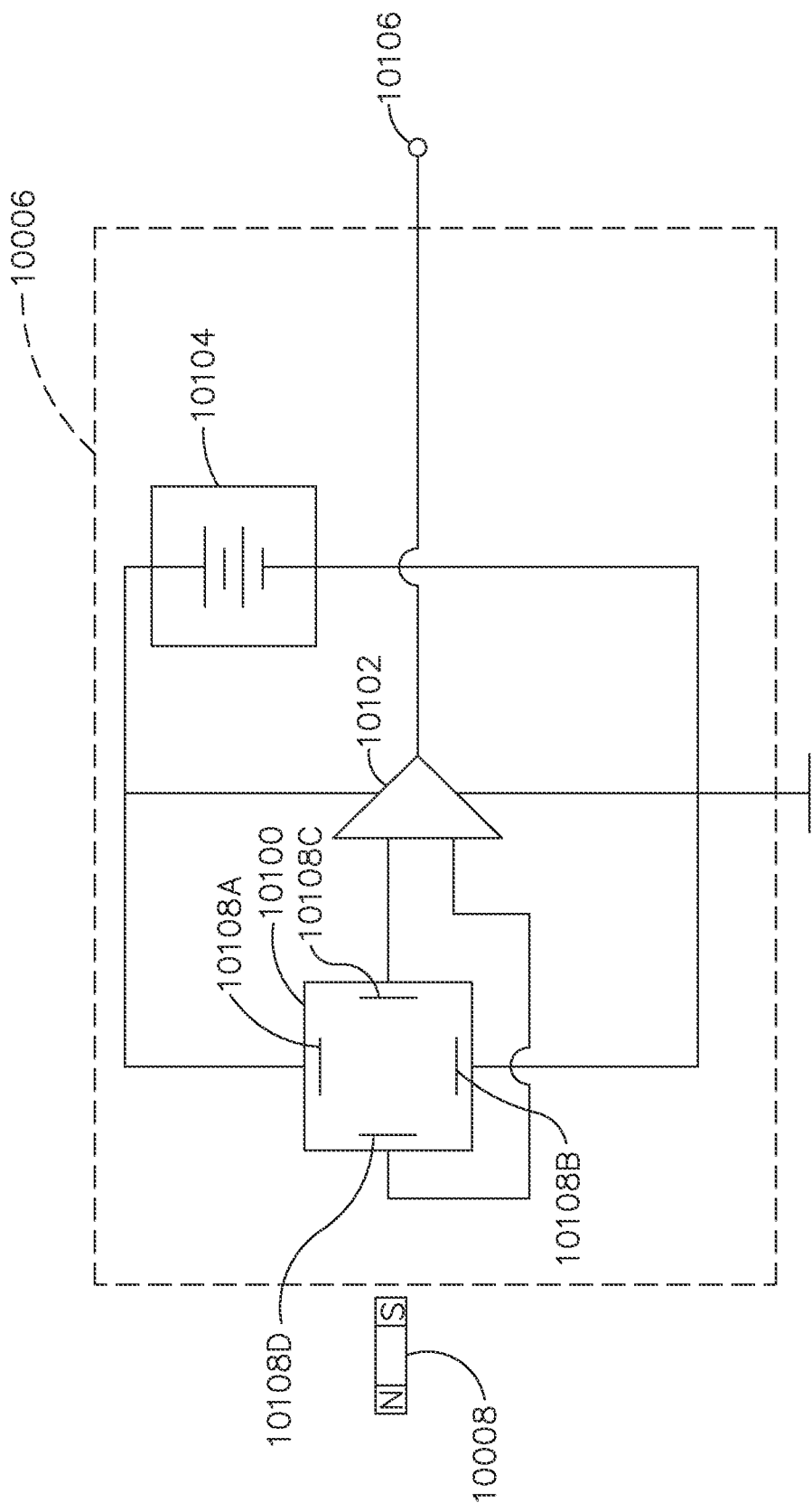
FIG. 109 is a schematic diagram of a Hall effect sensor.

FIG. 108 illustrates a diagram of an end effector 10000 including a gap sensor 10006 and a cartridge identity sensor 10010, according to one aspect of the present disclosure. The gap sensor 10006 is configured to sense the gap or distance between the first jaw member 10004 (i.e., the anvil assembly 610) and the second jaw member 10006 (i.e., the cartridge assembly 700) by sensing the relative position of a magnet 10008. The position sensor 10006 can include a Hall effect sensor, among other sensors configured to detect the relative distance between components. In one aspect depicted in FIG. 109, the position sensor 10006 comprises a Hall element 10100, an amplifier 10102, and a power source 10104. The Hall element comprises a first input terminal 10108A and a second input terminal 10108B. The first and second input terminals 10108A, 10108B are configured to receive a constant input current from the power source 10104. When no magnetic field is present, the input current enters the first input terminal 10108A and exits the second input terminal 10108B with no loss of voltage potential to either side of the Hall element 10100. As a magnetic field is applied to the Hall element 10100, such as, for example, by magnet 10008, a voltage potential is formed at the sides of the Hall element 10100 due to the deflection of electrons flowing through the Hall element 10100. A first output terminal 10108C and a second output terminal 10108D are located at opposite sides of the Hall element 10100. The first and second output terminals 10108C, 10108D provide the voltage potential caused by the magnetic field to the amplifier 10102. The amplifier 10102 amplifies the voltage potential experienced by the Hall element 10100 and outputs the amplified voltage to an output terminal 10106. Therefore, the output of the position sensor 10006 corresponds to the relative distance of the magnet 10008 to the Hall element 10100. Detecting the distance between the jaw members 10006, 10008 can be beneficial because this distance corresponds to the thickness of the grasped tissue when the end effector 10000 is clamped. Therefore, sensing the distance between the jaw member 10006, 10008 can be used in lieu of, or in addition to, determining the tissue thickness from the motor current to clamp the end effector 10000, as described above.

Referring back to FIG. 108, the cartridge identity sensor 10010 is configured to sense the type or identity of a cartridge 702 present in the end effector 10000. In one aspect where the end effector 10000 is a MULU with replaceable cartridges 702, the cartridge identity sensor 10010 includes a receiver that is configured to receive a signal (e.g., a RF signal) transmitted from the cartridge 702. In another aspect where the end effector 10000 is a MULU, the cartridge identity sensor 10010 includes an electrical contact that is configured to contact a corresponding electrical contact of the cartridge 702 when the cartridge 702 is inserted into the end effector 10000. Upon the cartridge 702 being inserted, the cartridge 702 transmits a signal through the electrically connected electrical contacts, which is received by a controller of the surgical instrument 100 to identity the cartridge 702.

Figure 110:
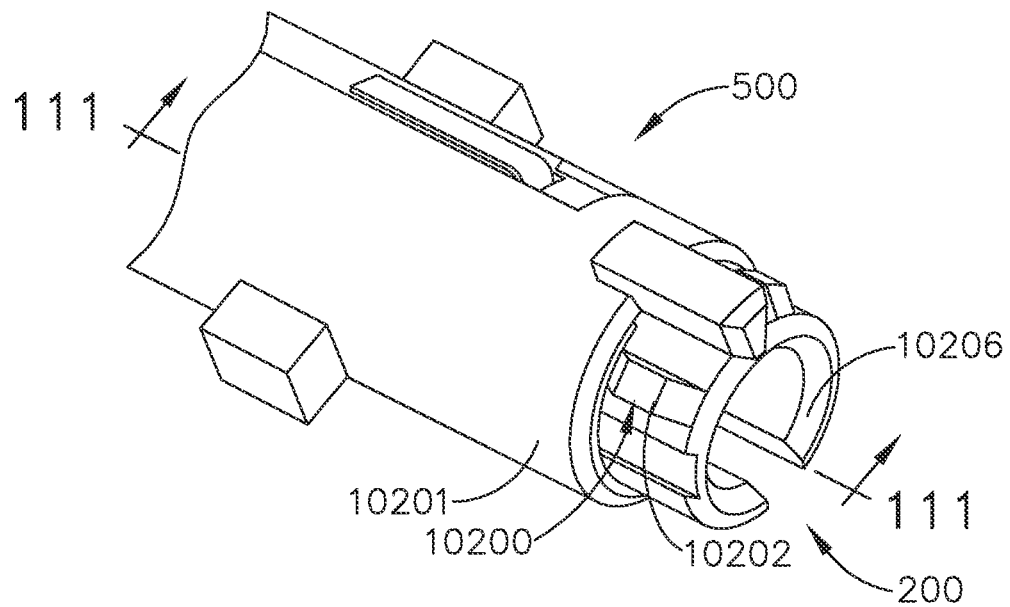
FIG. 110 is a cutaway view of the end effector partially joined to the distal end of the adapter.
Figure 111:
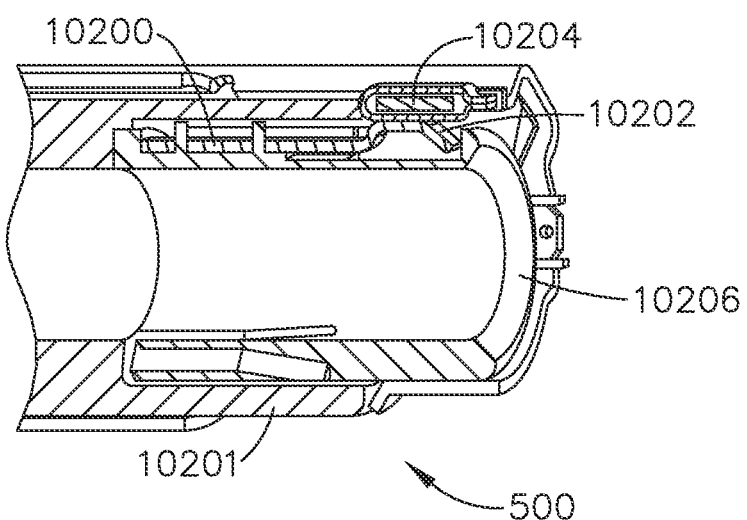
FIG. 111 is a sectional of the end effector joined to the distal end of the adapter along the longitudinal axis thereof.

In another aspect where the end effector 10000 is a SULU, the cartridge identity sensor 10010 is configured to detect when the end effector 10000 is mated to the adapter 200. In this aspect depicted in FIGS. 110-111, the terminal end 10206 of the adapter 200 includes one or more electrical contacts 10200, which each include a bent portion 10202. The end effector 500 further includes a memory disposed within or on the end effector housing 10201. The memory includes a memory chip and one or more electrical contacts 10204 electrically connected to the memory chip. The memory chip is configured to store one or more parameters relating to the end effector 500. The parameters can include a serial number of the end effector 500, a type of the end effector 500 and/or the cartridge 702 therein, a size of end effector 500 and/or the cartridge 702 therein, a staple size, information identifying whether the end effector 500 has been fired, a length of the end effector 500 and/or the cartridge 702 therein, maximum number of uses of the end effector 500, and combinations thereof. When the end effector 500 is mated to the adapter 200, the end effector electrical contacts 10204 engaged the adapter electrical contacts 10200. The memory chip is configured to communicate the presence of the end effector 500 and one or more of the parameters of the end effector 500 described herein, via electrical contacts 10200, 100204, upon engagement of the end effector 500 with the adapter 200.

Figure 112:
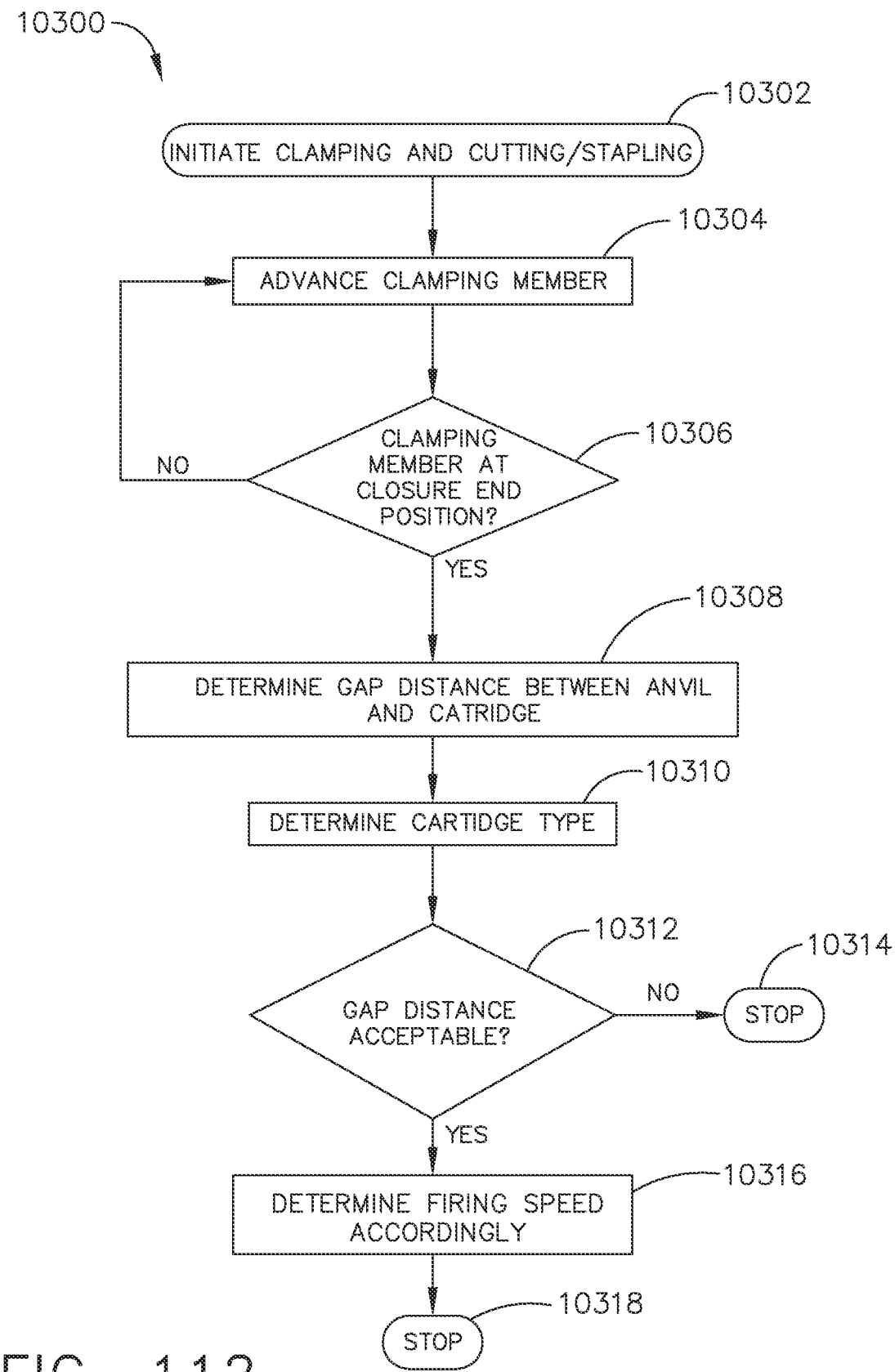
FIG. 112 is a logic flow diagram of a process for selecting an initial speed at which to fire the clamping member.

FIG. 112 illustrates a logic flow diagram of a process 10300 for selecting an initial speed at which to fire the clamping member 550, according to one aspect of the present disclosure. In the following description of the process 10300, reference should also be made to FIGS. 108-111, which depict various sensor assemblies utilized by the process 10300, and FIG. 113, which depicts various firing strokes of the clamping member 550 executed according to the process 10300. The presently described process 10300 can be executed by a controller, which includes the control circuit depicted in FIGS. 102-103, the microcontroller 2104 of FIG. 104, or another control circuit and/or processor that is executing logic and/or instructions stored in a memory of the surgical instrument 100. The process 10300 begins to be executed when the clamping and cutting/stapling operations of the end effector 500 are initiated 10302.

Accordingly, the process 10300 executed by the controller first advances 10304 the clamping member 550 by energizing the motor 2010 to which the clamping member 550 is operably connected. The controller then determines 10306 whether the clamping member 550 is at the closure end position. In one example, the controller can determine 10306 whether the clamping member 550 is at the closure end position via the position sensor 2102 (FIG. 104). The closure end position corresponds to the location in the firing stroke of the clamping member 550 after the clamping member 550 has closed the end effector 500 and is thereafter cutting tissue and/or firing staples. In some aspects, the controller can retrieve the closure end position from a memory and then compare the known closure end position to the sensed position of the clamping member 550. In other aspects, the controller can determine the closure end position by monitoring for a peak in the motor current. If the clamping member 550 is not at the closure end position, the process 10300 proceeds along the NO branch and the controller continues causing the motor 2010 to advance 10304 the clamping member 550. The process 2200 continues this loop until the clamping member 550 is located at or beyond the closure end position.

If the controller determines 10306 that the clamping member 550 is located at or beyond the closure end position in its firing stroke, the process 10300 proceeds along the YES branch and then determines 10308 the gap distance between the anvil assembly 610 and the cartridge assembly 700. In one example, the controller determines 10308 the gap distance via the gap sensor 10006. The controller then determines 10310 the type or identity of the cartridge 702 and/or the end effector 500. In one example, the controller determines 10310 the type or identity of the cartridge 702 via the cartridge identity sensor 10100. The cartridge then determines 10312 whether the gap distance is acceptable for the sensed cartridge type. Different types of cartridges 702 have different acceptable tolerance ranges; therefore, a gap distance between the anvil assembly 610 and the cartridge assembly 700 that is suitable (i.e., within operational tolerances) for one type of cartridge 702 may not be suitable for another type of cartridge 702. If the controller determines that the gap distance is not suitable for the given cartridge type, the process 10300 proceeds along the NO branch and stops 10314. In that case, the process 10300 can display a warning to the operator and/or lockout the surgical instrument 100 from firing the clamping member 550.

If the controller determines that the gap distance is suitable for the given cartridge type, the process 10300 proceeds along the YES branch and next determines 10316 the target firing speed for the clamping member 550 according to the sensed gap distance and the sensed cartridge type. In one aspect, the controller can select a target firing speed according to whether the sensed gap distance exceeds one or more thresholds or falls within one or more zones within a range of gap distances that are particular to a given cartridge type. In other words, different cartridge types may have different tolerance ranges for the speeds at which the clamping member 550 can be advanced for different thicknesses of the clamped tissue. Across cartridge types, the controller can be configured to generally select slower firing speeds for thicker tissue and faster firing speeds for thinner tissue; however, whether a given thickness of tissue is considered to be relatively thick or relatively thin will vary according to the cartridge type. After determining 10316 the appropriate target firing speed, the process 10300 stops 10318.

Figure 113:
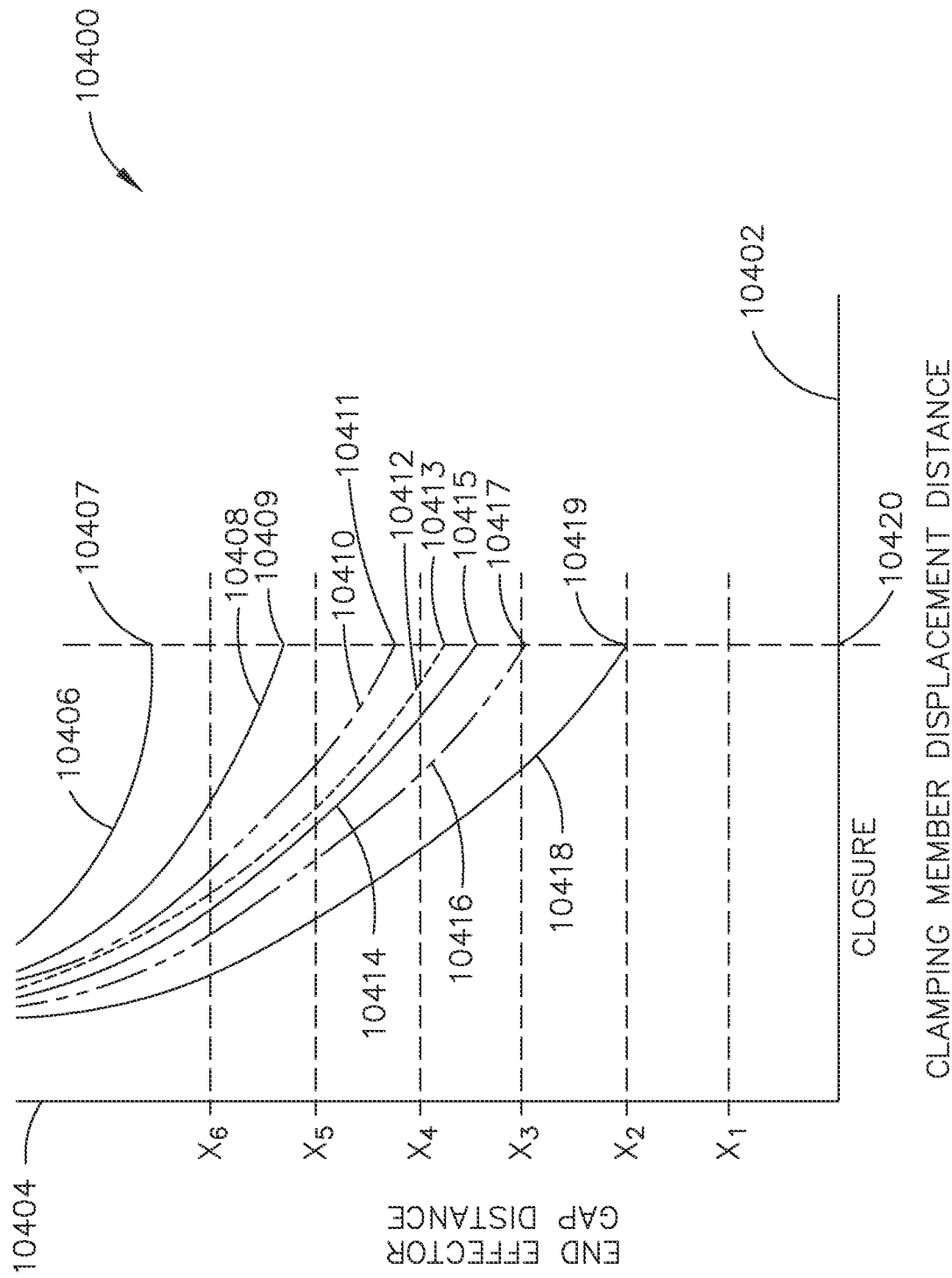
FIG. 113 is a graph of various clamping member strokes executed per the logic illustrated in FIG. 112.

To provide further explanation regarding the function(s) described above that the controller is configured to execute, the process 10300 will be discussed in terms of several example firing strokes depicted in FIG. 113. FIG. 113 illustrates a graph 10400 that depicts several firing strokes 10406, 10408, 10410, 10412, 10414, 10416, 10418 of the clamping member 550 corresponding to different cartridge types. In the graph 10400, the first firing stroke 10406, the second firing stroke 10408, the fifth firing stroke 10414, and the seventh firing stroke 10418 correspond to a first cartridge type; the third firing stroke 10410 and the sixth firing stroke 10416 correspond to a second cartridge type; and the fourth firing stroke 10412 corresponds to a third cartridge type. The graph 10400 depicts the gap distance 10404 of the end effector 500 versus the displacement distance 10402 of the clamping member 550. The resulting actions taken by a controller executing the process 10300 (i.e., determining 10316 the firing speed) depends upon gap distance 10404 at the closure end position 10420 for the cartridge type of each firing stroke. The graph 10400 also depicts a variety of thresholds $x_1 \ldots x_6$ along the gap distance 10404 axis that delineate zones therebetween. The sequentially increasing thresholds $x_1 \ldots x_6$ can correspond to increasingly larger values of the gap distance 10404. Each cartridge type does not necessarily utilize all of the depicted thresholds $x_1 \ldots x_6$ and different cartridge types can use the same or different thresholds $x_1 \ldots x_6$ and/or zones, as will be discussed below. Furthermore, although six thresholds $x_1 \ldots x_6$ are depicted, the process 10300 executed by the controller can utilize any number of thresholds and/or zones in practice.

For the first cartridge type, the thresholds $x_6$, $x_5$, and $x_3$ define the zones that determine the firing speed selected by the controller. For example, at the closure end position 10420 the first firing stroke 10406 is located at a position 10407 exceeding $x_6$. Exceeding the $x_6$ threshold corresponds to the clamped tissue being too thick to cut and staple for the given cartridge type or having been clamped improperly. In this case, the controller can display a warning to the operator and/or lockout the surgical instrument 100 from firing the clamping member 550. The second firing stroke 10408 is located at a position 10409 in a zone between $x_6$ and $x_5$ at the closure end position 10420, which corresponds to a large gap or thick tissue for the given cartridge type. Therefore, the controller can select a slower firing speed for the clamping member 550. The fifth firing stroke 10414 is located at a position 10415 in a zone between $x_5$ and $x_3$ at the closure end position 10420, which corresponds to a medium gap or medium, normal, or expected tissue thickness for the given cartridge type. Therefore, the controller can select a medium or normal firing speed for the clamping member 550. The seventh firing stroke 10418 is located at a position 10419 in a zone below $x_3$ at the closure end position 10420, which corresponds to a small gap or thin tissue for the given cartridge type. Therefore, the controller can select a fast firing speed for the clamping member 550.

The relevant thresholds can vary for different cartridge types. For the second cartridge type, the $x_4$ threshold delineates zones defining a fast firing speed and a normal firing speed. For example, the third firing stroke 10410 is located at a position 10411 in a zone above $x_4$ at the closure end position 10420, which corresponds to a medium gap or a medium, normal, or expected tissue thickness for the given cartridge type. Therefore, the controller can select a medium or normal firing speed for the clamping member 550. The sixth firing stroke 10416 is located at a position 10417 in a zone below $x_4$ at the closure end position 10420, which corresponds to a small gap or thin tissue for the given cartridge type. Therefore, the controller can select a fast firing speed for the clamping member 550.

The relevant thresholds can also be shared between different cartridge types. For the third cartridge type, the $x_4$ threshold delineates zones defining a fast firing speed and a normal firing speed (as with the second cartridge type of the third firing stroke 10410 and the sixth firing stroke 10416). For example, the fourth firing stroke 10412 is located at a position 10413 in a zone below $x_4$ at the closure end position 10420, which corresponds to a small gap or thin tissue for the given cartridge type. Therefore, the controller will select a fast firing speed for the clamping member 550.

In sum, the process 10300 executed by the controller can select the appropriate firing speed for the clamping member 550 during the cutting/stapling portion of its firing stroke according to where the sensed gap distance between the anvil assembly 610 and the cartridge assembly 700 falls relative to various tolerance ranges, which may be unique to each cartridge type. The process 10300 thus allows the controller to customize the speed at which the clamping member 550 is fired to cut and/or staple tissue according to the thickness of the clamped tissue and the cartridge type.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

Figure 114:
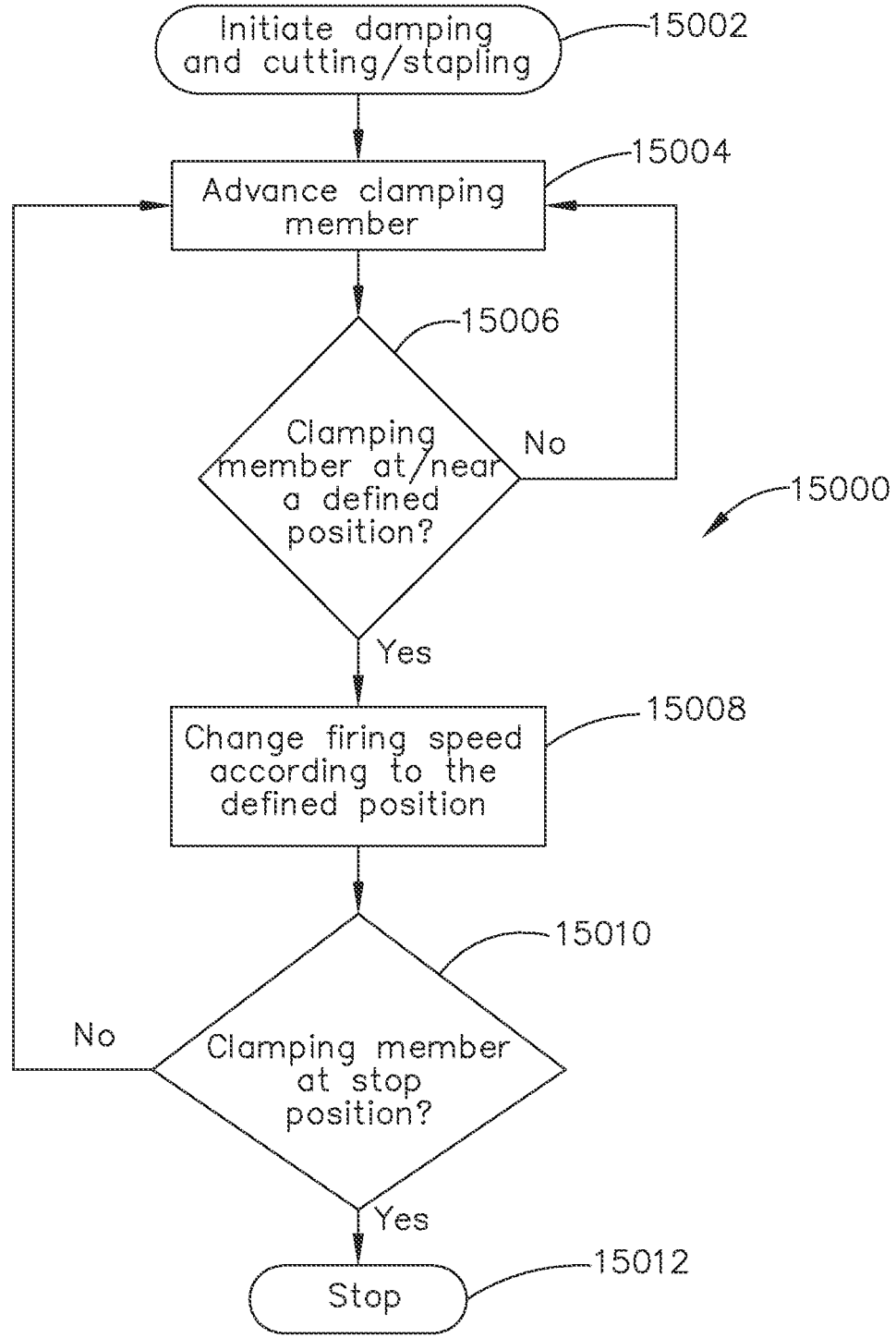
FIG. 114 is a logic flow diagram of a process for controlling a speed of a clamping member during a firing stroke.

FIG. 114 illustrates a logic flow diagram of a process 15000 for controlling a speed of a clamping member 550 during a firing stroke, according to one aspect of the present disclosure. In the following description of the process 15000, reference should also be made to FIGS. 102-104, which depict various sensor assemblies utilized by the process 15000, and FIG. 116, which depicts various firing strokes of the clamping member 550 executed according to the process 15000. The presently described process 15000 can be executed by a controller, which includes the control circuit depicted in FIGS. 102-103, the microcontroller 2104 of FIG. 104, or another control circuit and/or processor that is executing logic and/or instructions stored in a memory of the surgical instrument 100. The process 15000 begins to be executed when the clamping and cutting/stapling operations of the end effector 500 are initiated 15002.

Figure 116:
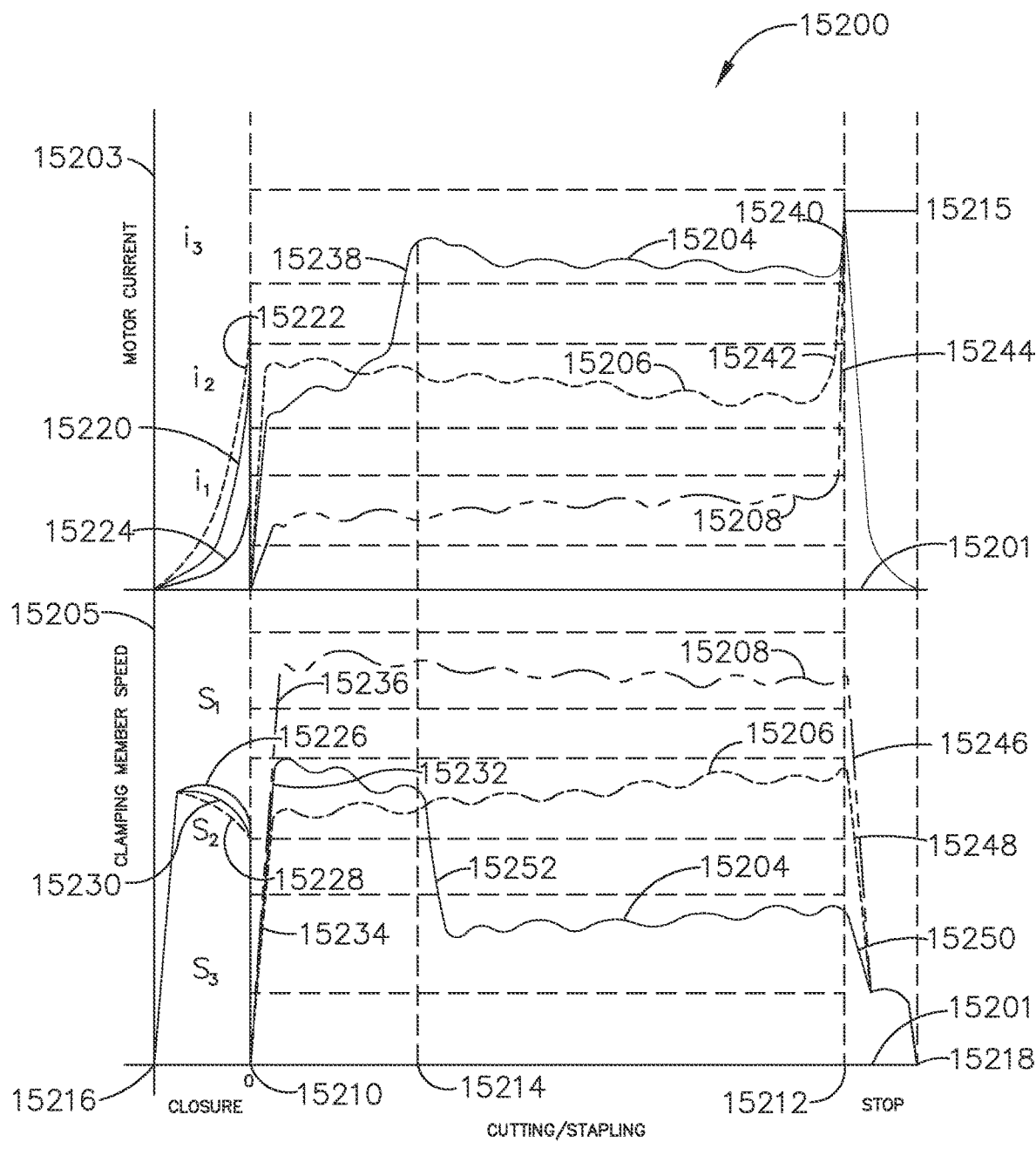
FIG. 116 is a graph of various clamping member firing strokes executed per the logic depicted in FIGS. 114 and 115.
Figure 117:
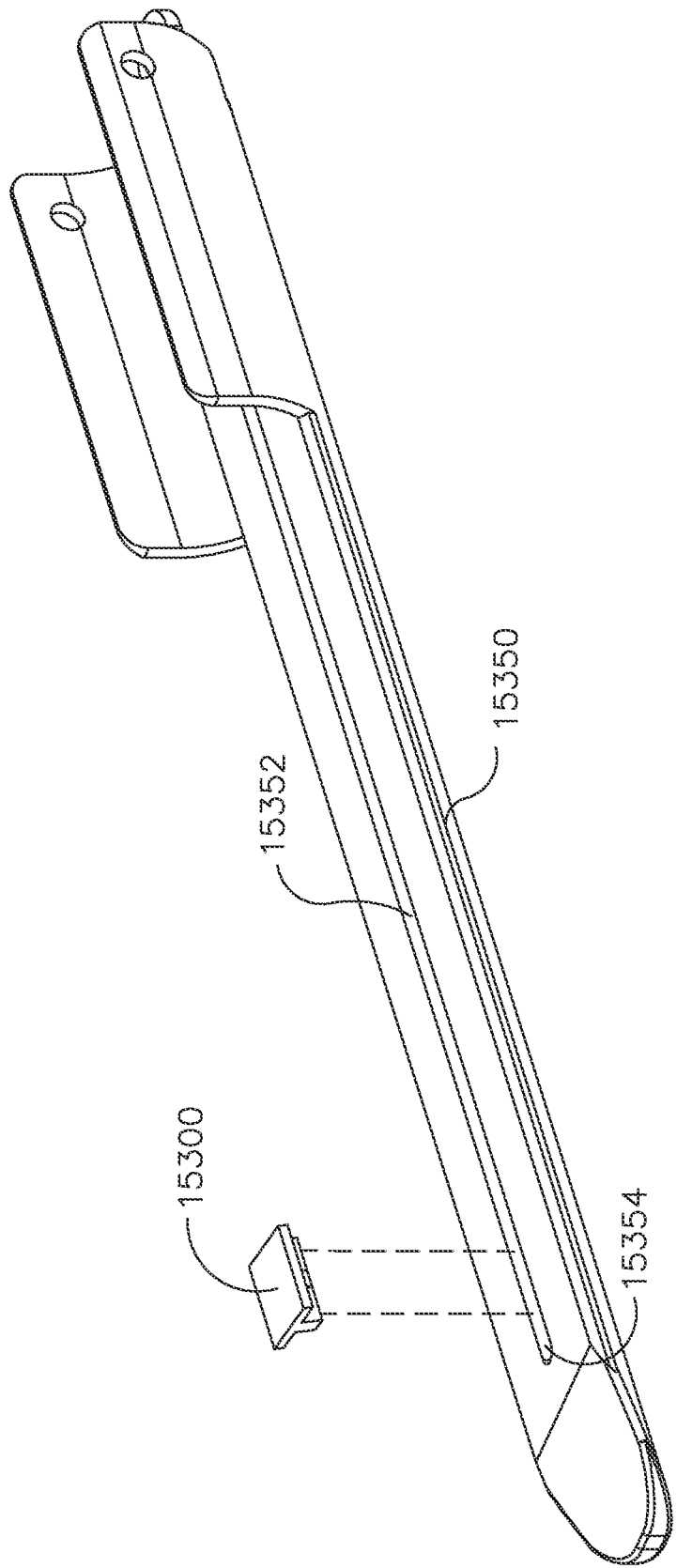
FIG. 117 is an exploded view of an anvil including a slot stop member.
Figure 118:
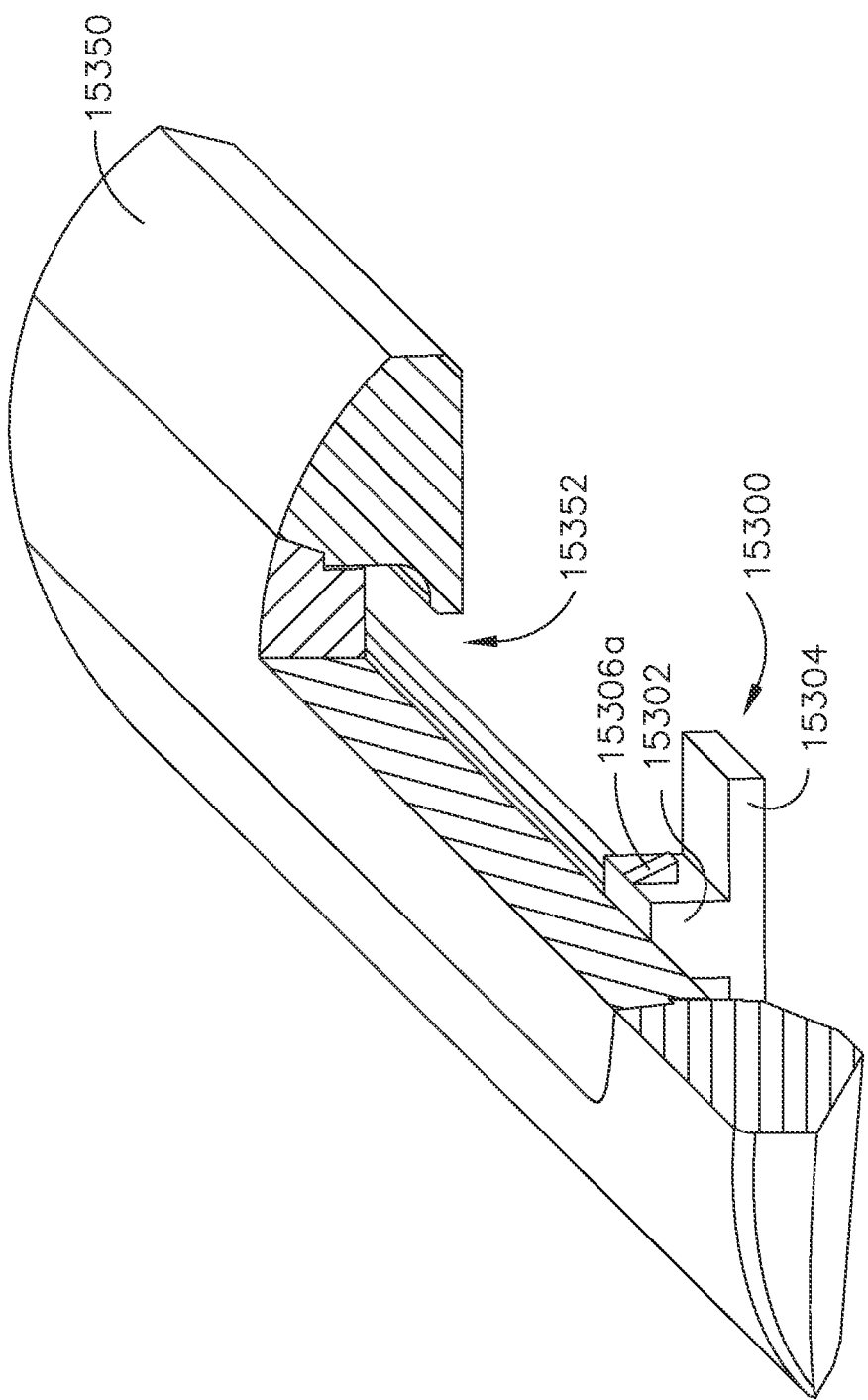
FIG. 118 is a partial cutaway view of an anvil including a slot stop member.
Figure 119:
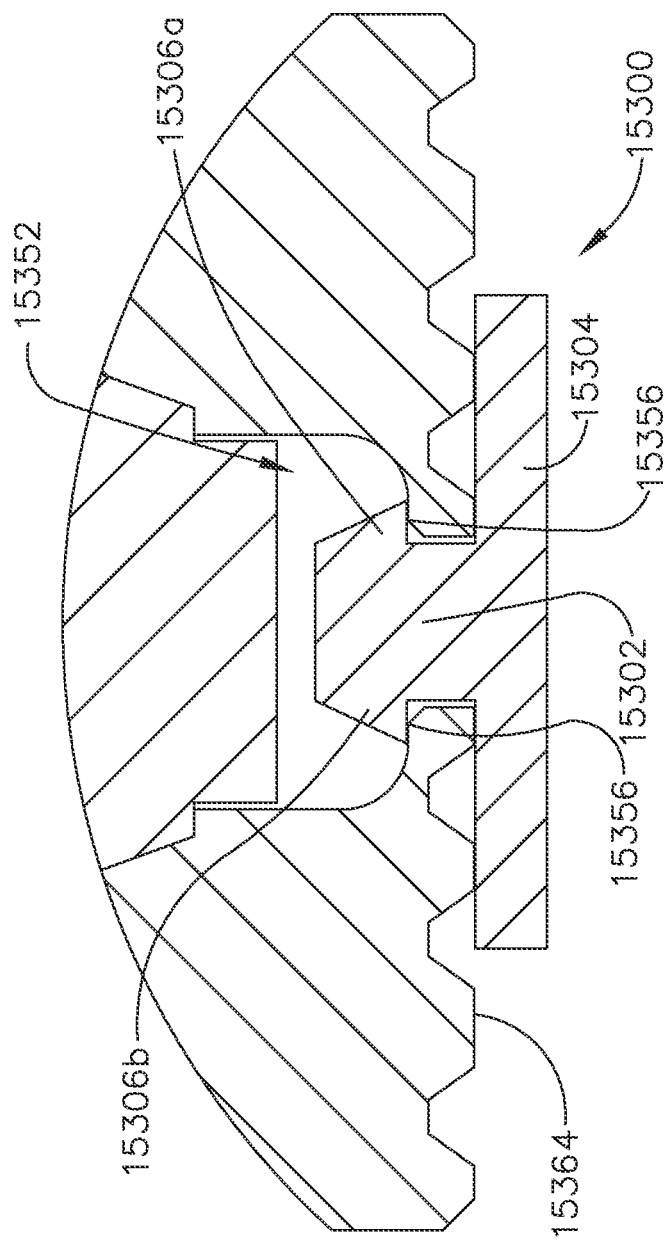
Figure 120:
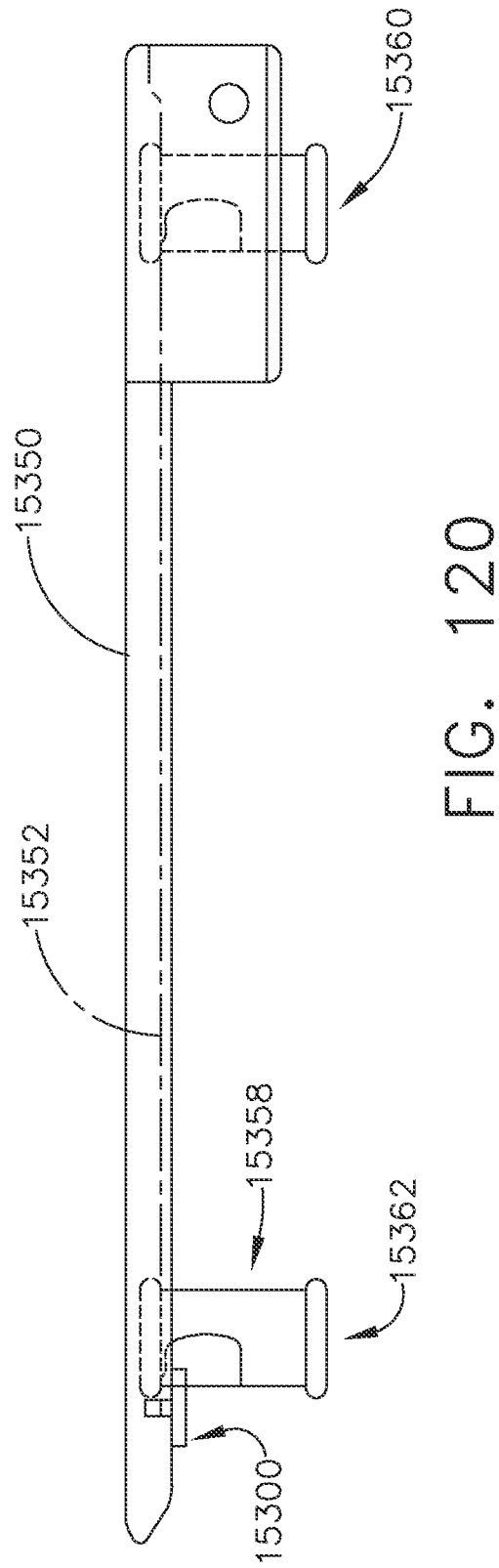

Accordingly, the process 15000 executed by the controller advances 15004 the clamping member 550 from a first or proximal position by energizing the motor 2010 to which the clamping member 550 is operably connected. The advancement of the clamping member 550 between a first or proximal position and a second or distal position can be referred to as a stroke or a firing stroke. During the course of a full stroke of the clamping member 550, the clamping member 550 will clamp the end effector 500 and then cut and/or staple tissue held thereby. The stroke of the clamping member 550 can be represented, for example, as a graph where the x-axis corresponds to the distance or time over which the clamping member 550 has advanced, as depicted in FIG. 116. The actions effectuated by the clamping member 550 can correspond to positions or zones defined within the stroke of the clamping member 550. For example, there can be a position in the stroke where the clamping member 550 has closed the end effector 500 and is thereafter cutting and/or stapling tissue. As another example, there can be a position in the stroke of the clamping member 550 where the clamping member 550 is no longer ejecting staples or cutting tissue. The controller can also take various actions according to the position of the clamping member 550. For example, there can be a position where the speed at which the clamping member 550 is driven is controlled or changed by a controller. These positions or zones can refer to actual physical positions at which the clamping member is located or relative positions within the stroke of the clamping member. The positions or zones can alternatively be represented as times in the stroke of the clamping member 550.

As the clamping member 550 is advanced 15004, the controller determines 15006 whether the clamping member 550 is at or near (i.e., within a tolerance of) a defined position in the firing stroke of the clamping member 550. A defined position is a pre-defined location in the firing stroke of the clamping member 550 where the controller is configured to increase the clamping member speed (i.e., step up the motor 2010) or decrease the clamping member speed (i.e., step down the motor 2010). There can be zero, one, or multiple defined positions in the process 15000 executed by the controller. The defined positions can be located at or near the proximal or distal ends of the firing stroke or can be located at any intermediate position therebetween. In some aspects, the closure end position and the firing end position are defined positions wherein the controller can be configured, for example, to slow the speed at which the clamping member 550 is being driven by the motor 2010. The closure end position corresponds to the location in the firing stroke of the clamping member 550 after the clamping member 550 has closed the end effector 500 and is thereafter cutting tissue and/or firing staples. In one example, slowing the clamping member 550 as it approaches the closure end position can be useful in order to prevent the clamping member 550 from inadvertently colliding with a lockout stop when there is no staple cartridge present in the end effector 500. The firing end position corresponds to the distal point reached by the clamping member 550 in its firing stroke to cut tissue and/or fire staples from the end effector 500. In one example, slowing the clamping member 550 as it approaches the firing end position can be useful in order to prevent the clamping member 550 from inadvertently colliding with the distal end of the anvil elongated slot 622. In yet another aspect, the firing stroke of the clamping member 550 includes an intermediate defined position positioned between the closure end position and the firing end position where the controller is configured to drive the clamping member 550 at a faster speed.

In some aspects, the controller determines 15006 whether the clamping member 550 is approaching or located at a defined position by detecting the present position of the clamping member 550 (e.g., via the position sensor 2102), retrieving one or more stored positions from a memory, and then comparing the detected position to the one or more stored positions to determine if the detected position matches or is within a tolerance distance from at least one of the stored positions. In other aspects, the controller determines 15006 whether the clamping member 550 is approaching or located at a defined position by sensing the motor current and determining whether the sensed motor current or the rate of change of the sensed motor current has exceeded a particular threshold (as described below in FIG. 115). If the controller determines 15006 that the clamping member 550 is not located at a defined position, the process 15000 proceeds along the NO branch and loops back to continue advancing 15004 the clamping member 550.

If the controller determines 15006 that the clamping member 550 is located at (or within a tolerance of) a defined position, the process 15000 proceeds along the YES branch and then changes 15008 the clamping member speed in the manner dictated by the particular defined position. When the controller determines 15006 that the clamping member 550 is located at or near a defined position, the controller can retrieve the manner in which the clamping member speed is to be changed (e.g., whether the speed is to be increased or decreased, a particular value or speed range to which the speed is to be set, or a function for calculating a value or speed range to which the speed is to be set) from a memory that stores each how the clamping member speed is to be changed in association with each of the stored positions. The controller then controls the motor 2010 to increase or decrease the speed at which the clamping member 550 is driven accordingly.

The controller then determines 15010 whether the clamping member 550 is located at a stop position. The controller can determine 15010 the location of the clamping member 550 in the same manner described above, namely via a position sensor 2102 or sensing the motor current relative to one or more thresholds. If the clamping member 550 is located at the stop position, then the process 15000 proceeds along the YES branch and stops 15012. When the process 15000 executed by the controller stops 15012, the controller can take various actions, such as cutting the current to the motor 2010 or displaying a notification to the user that the clamping member 550 has stopped. If the clamping member 550 is not located at the stop position, then the process 15000 proceeds along the NO branch and continues to advance 15004 the clamping member 552. This loop continues until the clamping member 550 reaches the stop position and the process 15000 stops 15012.

Figure 115:
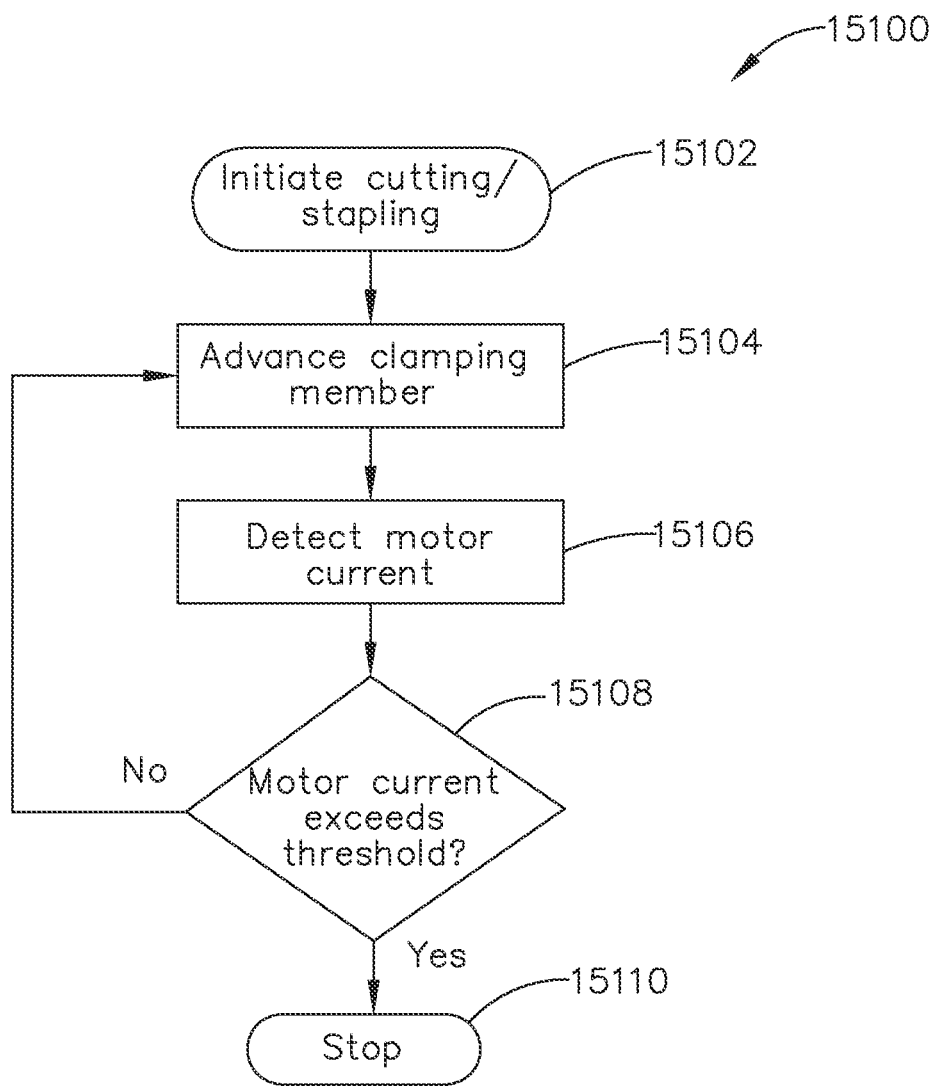
FIG. 115 is a logic flow diagram of a process for detecting a defined position according to motor current.

FIG. 115 illustrates a logic flow diagram of a process 15100 for detecting a defined position according to motor current, according to one aspect of the present disclosure. In the following description of the process 15100, reference should also be made to FIGS. 102-104, which depict various sensor assemblies utilized by the process 15100, and FIG. 116, which depicts various firing strokes of the clamping member 550 executed according to the process 15100. The presently described process 15100 can be executed by a controller, which includes the control circuit depicted in FIGS. 102-103, the microcontroller 2104 of FIG. 104, or another control circuit and/or processor that is executing logic and/or instructions stored in a memory of the surgical instrument 100. The process 15100 begins to be executed when the cutting/stapling operation of the end effector 500 is initiated 15102.

As the controller controls the motor 2010 to advance 15104 the clamping member 550, the controller monitors or detects 15106 the motor current (e.g., via the current sensor 2018). Further, the controller determines 15108 whether the detected motor current or the rate of change of the detected motor current is greater than or equal to a particular threshold value that is indicative of the firing end position in the stroke of the clamping member 550. In other words, the controller determines 15108 whether the motor current spikes or peaks above a certain level, either by comparing the value of the motor current or the rate of change of the motor current to a particular threshold. Because the motor current tends to sharply increase above a particular threshold as the clamping member 550 approaches certain positions, such as the closure end position and the firing end position, the controller can be configured to monitor the motor current for an indicative increase in the motor current and then take action to slow the clamping member 550 or otherwise prevent the clamping member 550 as it approaches these positions. Slowing the clamping member 550 in this manner can prevent the clamping member 550 from sharply contacting the distal ends of the anvil assembly 610 and/or cartridge assembly 700. In some aspects, the controller can be configured to cross-reference the detected motor current with a position detected from a position sensor 2102 to confirm that the clamping member 550 is located at or near a position where it would be expected for the motor current to increase or decrease in the manner that is being detected. If the controller determines 15108 that the motor current has not exceeded the threshold, the process 15100 proceeds along the NO branch and continues advancing 15104 the clamping member 550. If the controller determines 15108 that the motor current has exceed the end of stroke threshold, the process 15100 proceeds along the YES branch and the process 15100 stops 15110. In some aspects, when the process 15100 stops 15110 the controller de-energizes the motor 2010.

To provide further explanation regarding the function(s) described above that the controller is configured to execute, the processes 15000, 15100 will be discussed in terms of several example firing strokes depicted in FIG. 116. FIG. 116 illustrates a first graph 15200 and a second graph 15202, each of which depict a first firing stroke 15204, a second firing stroke 15206, and a third firing stroke 15208 of the clamping member 550 between an initial or proximal position 15216 and an end or distal position 15218. The first graph 15200 depicts motor current 15203 versus clamping member displacement distance 15201 and the second graph 2302 depicts clamping member speed 15205 versus clamping member displacement distance 15201 for the example firing strokes 15204, 15206, 15206 of the clamping member 550. The displacement distance 15201 axis is delineated into a "CLOSURE" zone, a "CUTTING/STAPLING" zone, and a "STOP" zone, which indicates the action(s) that the clamping member 550 is effectuating in each respective portion of its firing stroke. In combination, the first graph 15200 and the second graph 15202 illustrate the relationship between motor current 15203 and clamping member speed 15205 for different firing strokes 15204, 15206, 15208 and the resulting actions taken by a controller executing the processes 15000, 15100 depicted in FIGS. 114-115.

For each of the firing strokes 15204, 15206, 15208, as the displacement member 550 advances from the initial position 15216 to the closure end position 15210 the motor current sharply increases 15220, 15222, 15224. In one example, the controller executing the process 15000 depicted in FIG. 114 can detect this sharp increase 15220, 15222, 15224 in the motor current by sensing when the rate of change in the motor current for each of the firing strokes 15204, 15206, 15208 exceeds a threshold, as depicted in FIG. 116. The process 15000 then decreases 15226, 15228, 15230 the speed of the clamping member 550 accordingly as it reaches the closure end position 15210. As the clamping member 550 advances past the closure end position 15210, the controller increases 15232, 15234, 15236 the speed at which the clamping member 550 is driven until the clamping member 550 is driven within a particular speed range $S_1$, $S_2$, $S_3$. In one example, the controller increases 15232, 15234, 15236 the speed at which the clamping member 550 is driven until the clamping member 550 is driven within a speed range $S_1$, $S_2$, $S_3$ corresponding to the thickness of the tissue clamped at the end effector 500.

In some aspects, such with the second and third firing strokes 15206, 15208, the clamping member 550 is thereafter driven at a consistent speed or within a consistent speed range. In other aspects, such as with the first firing stroke 15204, the controller is configured to control the motor 2010 to drive the clamping member 550 at varying speeds to account for varying tissue properties. For example, in the first firing stroke 15204 the motor current increases 15238 as the clamping member 550 approaches an intermediate position 15214, potentially due to the cutting surface 554 of the clamping member 550 encountering increasingly thick tissue. In response, the controller can be configured to decrease 15252 the speed at which the clamping member 550 is driven in order to prevent the motor current from continuing to increase. Decreasing 15252 the clamping member speed reduces the current drawn by the motor 2010 because it lowers the torque on the motor 2010. In some aspects, the controller can be configured to change the maximum acceptable current or torque limits on the motor 2010 in response to detected conditions. For example, in the first firing stroke 15204 the first or initial maximum acceptable current limit of the motor 2010 is delineated by the upper bound of the current range $i_2$ that was selected by the controller in accordance with the clamped tissue thickness. However, when the motor current 15238 increases as the clamping member 550 approaches the intermediate position 15214, the controller can be configured to upwardly adjust the maximum motor current to a second maximum acceptable current limit delineated by the upper bound of the current range $i_3$.

As the clamping member 550 approaches the firing end position 15212 the motor current sharply increases 15240, 15242, 15244 for each of the firing strokes 15204, 15206, 15208 until it reaches a threshold 15215. The controller executing the process 15000 depicted in FIG. 114 can detect that the motor current has reached or surpassed this threshold 15215, which is indicative of the clamping member 550 approaching the firing end position 15212. The process 15000 then decreases 15246, 15248, 15250 the speed of the clamping member 550 accordingly in each of the firing strokes 15204, 15206, 15208 and the clamping member 550 slows as it reaches the stop position 15218 (i.e., the distal most position of its firing stroke). When the clamping member 550 reaches the stop position 15218, the processes 15000, 15100 can stop and the controller can take various actions, such as displaying an alert to the operator of the surgical instrument 100 indicating that the clamping, cutting, and/or stapling by the surgical instrument 100 has been completed.

In some aspects, the surgical instrument 100 includes stops that are configured to prevent the clamping member 550 (or another component of the firing drive system) from becoming damaged by inadvertently colliding with the anvil assembly 610 and/or the cartridge assembly 700 at the end of its firing stroke. The stops can be constructed from materials that are deformable, bendable, or configured to strain elastically in order to absorb or attenuate the forces from the clamping member 550 as it is advanced to the terminal position of its firing stroke. The stops can be utilized in combination with, or in lieu of, a controller executing a process, such as the process 15100 depicted in FIG. 115, to detect the firing stroke end position and then slow and/or stop the clamping member 550 accordingly.

FIGS. 117-120 illustrate various views of a stop member 15300 that is engaged with the elongated slot 15352 of the anvil plate 15350. In the depicted aspect, the stop member 15300 includes a vertical stem or body 15302, a base 15304 extending orthogonally from the body 15302, and one or more flanges 15306a, 15306b. The base 15304 extends across the surface 15364 of the anvil plate 15350. The flanges 15306a, 15306b bear against the interior surface of the shelf 15356 of the elongated slot 15352 and the base 15304 bears against the surface 15364, which secures the stop member 15300 within the elongated slot 15352 and thus prevents the stop member 15300 from being withdrawn therefrom. The stop member 15300 can be positioned at or adjacently to the distal end 15354 of the elongated slot 15352 and serve as a physical obstruction or barrier preventing the clamping member 15358 from colliding with the distal end 15354 during the stroke of the clamping member 15358 as it translates from a first or proximal position 15360 to a second or distal position 15362.

FIGS. 121-122 illustrate longitudinal sectional views of an end effector 15454 and a drive assembly including a stop member 15400. In one aspect, the surgical instrument 100 includes one or more projections 15450 extending from the shaft assembly 203 (FIG. 1) or the end effector 15454. In the depicted aspect, the projections 15450 extend outwardly from the proximal portion of the end effector 15454, adjacent to the pivot joint 15452. The drive beam 15402 includes one or more stop members 15400 extending generally orthogonally therefrom that are configured to contact the projections 15450. The stop members 15400 are rigidly connected to the drive beam 15402 such that the drive beam 15402 is prevented from being advanced further distally when the stop members 15400 contact the projections 15450. The stop members 15400 are positioned on the drive beam 15402 such that the clamping member 15404 does not contact the distal end 15458 of the elongated slot 15456 when the stop members 15400 contact the projections 15450. Stated differently, the distance from the distal end 15458 of the elongated slot 15456 to the projections 15450 is larger than the distance between the distal end of the clamping member 15404 and the stop members 15400. The projections 15450 and/or the stop members 15400 can be constructed from deformable materials or materials that are configured to strain elastically.

FIGS. 123-124 illustrate longitudinal sectional views of an end effector 15454 including a stop member 15500 located distally in the elongated slot 15456. In the depicted aspect, the end effector 15454 includes a stop member 15500 located at the distal end 15458 of the elongated slot. In this aspect, the stop member 15500 is located within or occupies the distal end 15458 or the distal end 15458 terminates at the stop member 15500. In either case, the stop member 15500 is positioned such that the clamping member 15404 is configured to contact it when the clamping member 15404 has advanced to the most distal position in its firing stroke. The stop member 15500 can be constructed from deformable materials or materials that are configured to strain elastically.

Referring back to FIG. 21, the adapter 200 can include a locking mechanism 280 that is configured to fix the axial or longitudinal position of the distal drive member 248. In some cases, it may be desirable for the lock mechanism 280 to control a switch or transmit a signal to the controller to indicate that the lock mechanism 280 is engaged and thus that the motor 2010 should not be activated to attempt to drive the distal drive member 248. In one aspect, the adapter 200 include a switch (not shown) that is tripped when the camming member 288 of the locking mechanism 280 cams into the recess 249 of the distal drive member 248. The switch is communicably coupled to the controller of the surgical instrument 100. If the controller determines that the locking mechanism switch has indicated that the locking mechanism 280 is engaged, then the controller can limit or cut current to the motor 2010 in order to prevent the motor 2010 from attempting to drive the locked distal drive member 248. Likewise, when the camming member 288 is withdrawn from the recess 249 of the distal drive member 248, then the switch can be un-tripped or re-tripped to indicate to the controller that the locking mechanism 280 has been disengaged and that the motor 2010 can thus be energized to drive the distal drive member 248. Such an arrangement can be useful in order to, for example, prevent damage to the motor 2010 and/or locking mechanism 280.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S.

patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

What is claimed is:

1. A surgical system, comprising:
   an end effector, comprising:
     a first jaw; and
     a second jaw moveable relative to the first jaw toward a closed configuration;
   a clamp driver movable toward a closure end position;
   a motor operably coupled to the clamp driver; and
   a control circuit comprising a processor and a memory, wherein the control circuit is to:
     advance, by the motor, the clamp driver to the closure end position;
     determine a distance between the first jaw and the second jaw in the closed configuration, wherein the closure end position corresponds to the closed configuration;
     receive a signal indicative of at least one of a staple cartridge identity, type, or characteristic from a corresponding staple cartridge; and
     detect that the distance is acceptable for staple firing by the end effector based on the at least one staple cartridge identity, type, or characteristic.

2. The surgical system of claim 1, wherein detecting that the distance is acceptable for staple firing causes the control circuit to determine a speed at which to move the clamp driver based on the distance and the at least one staple cartridge identity, type, or characteristic.

3. The surgical system of claim 1, wherein the at least one staple cartridge identity, type, or characteristic corresponds to a range of acceptable distances for the staple firing, and wherein detecting that the distance is acceptable is based on the distance being within the range of acceptable distances.

4. The surgical system of claim 1, further comprising a position sensor, wherein the distance is determined by the position sensor.

5. The surgical system of claim 4, wherein the position sensor is a Hall effect sensor, and wherein the distance is determined based on a magnetic field detected by the Hall effect sensor.

6. The surgical system of claim 1, further comprising a staple cartridge sensor, wherein the signal is received by the staple cartridge sensor.

7. The surgical system of claim 6, wherein the staple cartridge sensor comprises at least one of a receiver to receive the signal from the corresponding staple cartridge or an electrical contact to interact with an electrical contact of the corresponding staple cartridge to receive the signal.

8. A surgical system, comprising:
   an end effector, comprising:
     a first jaw; and
     a second jaw moveable relative to the first jaw toward a closed configuration;
   a clamp driver movable toward a closure end position;
   a motor operably coupled to the clamp driver; and
   a control circuit comprising a processor and a memory, wherein the control circuit is to:
     advance, by the motor, the clamp driver to the closure end position;
     determine a distance between the first jaw and the second jaw in the closed configuration, wherein the closure end position corresponds to the closed configuration;

receive a signal indicative of at least one of a staple cartridge identity, type, or characteristic from a corresponding staple cartridge; and detect that the distance is unacceptable for staple firing by the end effector based on the at least one staple cartridge identity, type, or characteristic.

9. The surgical system of claim 8, wherein detecting that the distance is unacceptable for staple firing causes the control circuit to at least one of display a warning to a user of the surgical system or lockout the surgical system from staple firing.

10. The surgical system of claim 8, wherein the at least one staple cartridge identity, type, or characteristic corresponds to a range of acceptable distances for staple firing, and wherein detecting that the distance is unacceptable is based on the distance being outside the range of acceptable distances.

11. The surgical system of claim 8, further comprising a position sensor, wherein the distance is determined by the position sensor.

12. The surgical system of claim 11, wherein the position sensor is a Hall effect sensor, and wherein the distance is determined based on a magnetic field detected by the Hall effect sensor.

13. The surgical system of claim 8, further comprising a staple cartridge sensor, wherein the signal is received by the staple cartridge sensor.

14. The surgical system of claim 13, wherein the staple cartridge sensor comprises at least one of a receiver to receive the signal from the corresponding staple cartridge or an electrical contact to interact with an electrical contact of the corresponding staple cartridge to receive the signal.

15. A surgical system, comprising:
an end effector, comprising:
a first jaw; and
a second jaw moveable relative to the first jaw toward a closed configuration;
a clamp driver movable toward a closure end position;
a motor operably coupled to the clamp driver; and
a control circuit comprising a processor and a memory, wherein the control circuit is to:
advance, by the motor, the clamp driver to the closure end position;
determine a distance between the first jaw and the second jaw in the closed configuration, wherein the closure end position corresponds to the closed configuration;
receive a signal indicative of at least one of a staple cartridge identity, type, or characteristic from a corresponding staple cartridge; and
determine a speed at which to fire the clamp driver based on the distance and the at least one staple cartridge identity, type, or characteristic.

16. The surgical system of claim 15, wherein the speed is determined based on the distance being within a range of distances corresponding to the speed.

17. The surgical system of claim 15, further comprising a position sensor, wherein the distance is determined by the position sensor.

18. The surgical system of claim 17, wherein the position sensor is a Hall effect sensor, and wherein the distance is determined based on a magnetic field detected by the Hall effect sensor.

19. The surgical system of claim 15, further comprising a staple cartridge sensor, wherein the signal is received by the staple cartridge sensor.

20. The surgical system of claim 19, wherein the staple cartridge sensor comprises at least one of a receiver to receive the signal from the staple cartridge or an electrical contact to interact with an electrical contact of the staple cartridge to receive the signal.

* * * * *